(12) United States Patent
Hartmann et al.

(10) Patent No.: US 8,076,068 B2
(45) Date of Patent: Dec. 13, 2011

(54) METHOD FOR DETERMINING IMMUNOSTIMULATORY ACTIVITY OF RNA OLIGONUCLEOTIDES

(75) Inventors: Gunther Hartmann, Bonn (DE); Veit Hornung, Pullach (DE)

(73) Assignee: Gunther Hartmann, Bonn (DE)

( * ) Notice: Subject to any disclaimer, the term of this patent is extended or adjusted under 35 U.S.C. 154(b) by 315 days.

(21) Appl. No.: 12/066,903

(22) PCT Filed: Sep. 14, 2006

(86) PCT No.: PCT/EP2006/008980
§ 371 (c)(1),
(2), (4) Date: Nov. 10, 2008

(87) PCT Pub. No.: WO2007/031322
PCT Pub. Date: Mar. 22, 2007

(65) Prior Publication Data
US 2009/0169529 A1    Jul. 2, 2009

Related U.S. Application Data

(60) Provisional application No. 60/717,323, filed on Sep. 15, 2005.

(30) Foreign Application Priority Data

Sep. 14, 2005 (EP) .................................. 05020020
Dec. 19, 2005 (EP) .................................. 05027778

(51) Int. Cl.
*C12Q 1/68*    (2006.01)
(52) U.S. Cl. ........................................................... 435/6
(58) Field of Classification Search ................... 435/6
See application file for complete search history.

(56) References Cited

U.S. PATENT DOCUMENTS

2003/0125241 A1 *  7/2003  Wissenbach et al. ............. 514/8
2005/0070462 A1 *  3/2005  Schellack et al. ................ 514/7
2006/0025366 A1 *  2/2006  MacLachlan et al. .......... 514/44

FOREIGN PATENT DOCUMENTS

WO    WO 03/086280 A2    10/2003
WO    WO 2004/004743 A1    1/2004
WO    WO 2005/021044 A2    3/2005

OTHER PUBLICATIONS

Barchet et al., "Dendritic cells respond to influenza virus through TLR7- and PKR-independent pathways," Eur J Immunol 35: 236-242, 2005.
Heil et al., "Species-Specific Recognition of Single-Stranded RNA via Toll-like Receptor 7 and 8," Science 303: 1526-1529, Mar. 5, 2004.
Hornung et al., "Sequence-specific potent induction of IFN-α by short interfering RNA in plasmacytoid dendritic cells through TLR7," Nature Medicine 11(3): 263-270, Mar. 2005.
Judge et al., "Sequence-dependent stimulation of the mammalian innate immune response by synthetic siRNA," Nature Biotechnology 23(4): 457-462, Apr. 2005.
Kaberdin, "Probing the substrate specificity of *Escherichia coli* RNase E using a novel oligonucleotide-based assay," Nucleic Acids Research 31(16): 4710-4716, Aug. 15, 2003.
Lochmann et al., "Drug delivery of oligonucleotides by peptides," European Journal of Pharmaceutics and Biopharmaceutics 58: 237-251, 2004.
Schlee et al., "siRNA and isRNA: Two Edges of One Sword," Molecular Therapy 14(4): 463-470, Oct. 2006.
Sioud, "Induction of Inflammatory Cytokines and Interferon Responses by Double-stranded and Single-stranded siRNAs is Sequence-dependent and Requires Endosomal Localization," J Mol Biol 348: 1079-1090, 2005.

* cited by examiner

*Primary Examiner* — Jon E Angell
(74) *Attorney, Agent, or Firm* — Nixon Peabody LLP

(57) ABSTRACT

The present invention provides 4-nucleotide (4mer) RNA motifs that confer immunostimulatory activity, in particular, IFN-α-inducing activity to a RNA oligonucleotide. The present invention also provides RNA oligonucleotides, including siRNA, with high or low immunostimulatory activity. The present invention further provides the use of the RNA oligonucleotides of the invention for therapeutic purposes.

16 Claims, 73 Drawing Sheets

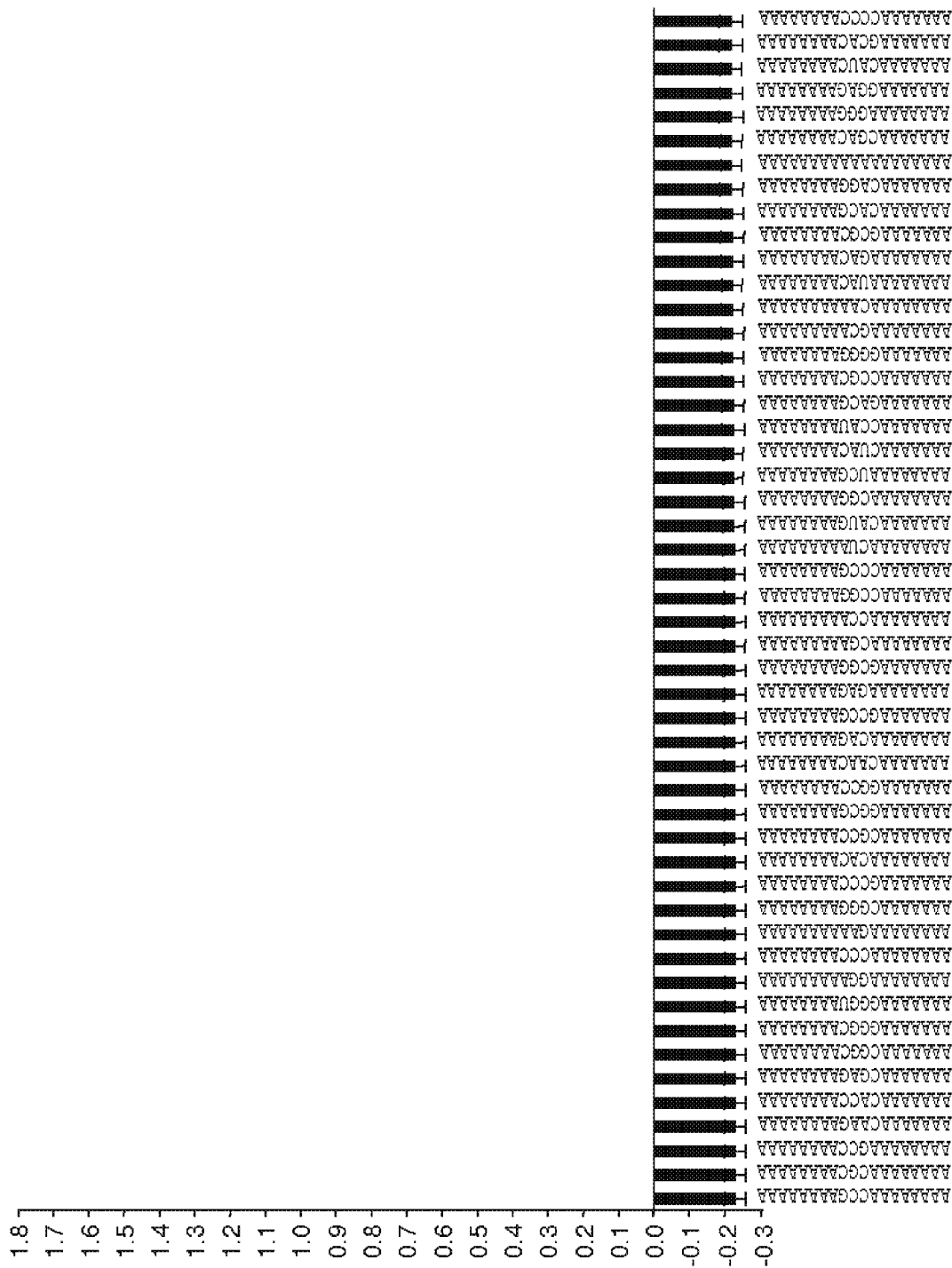

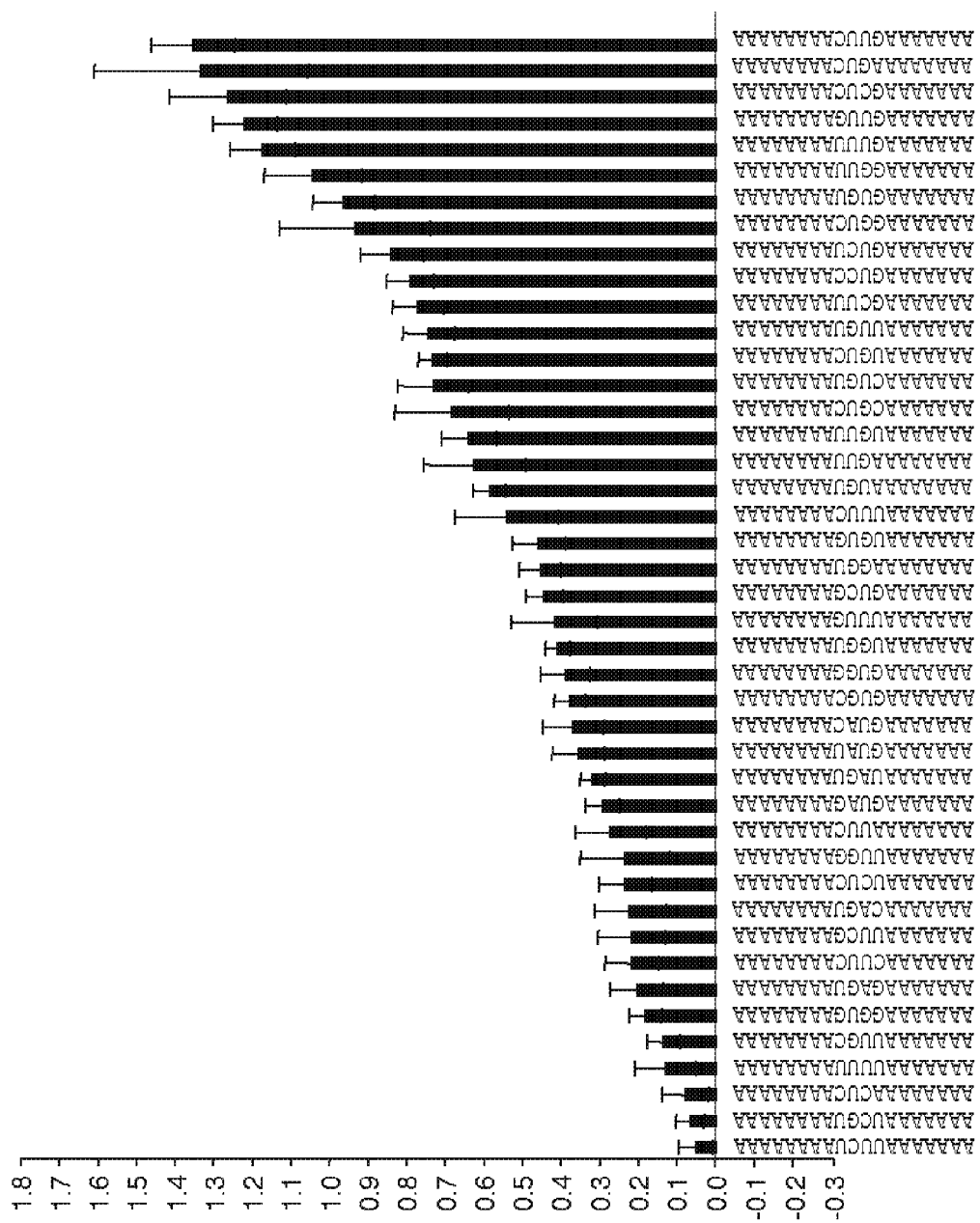

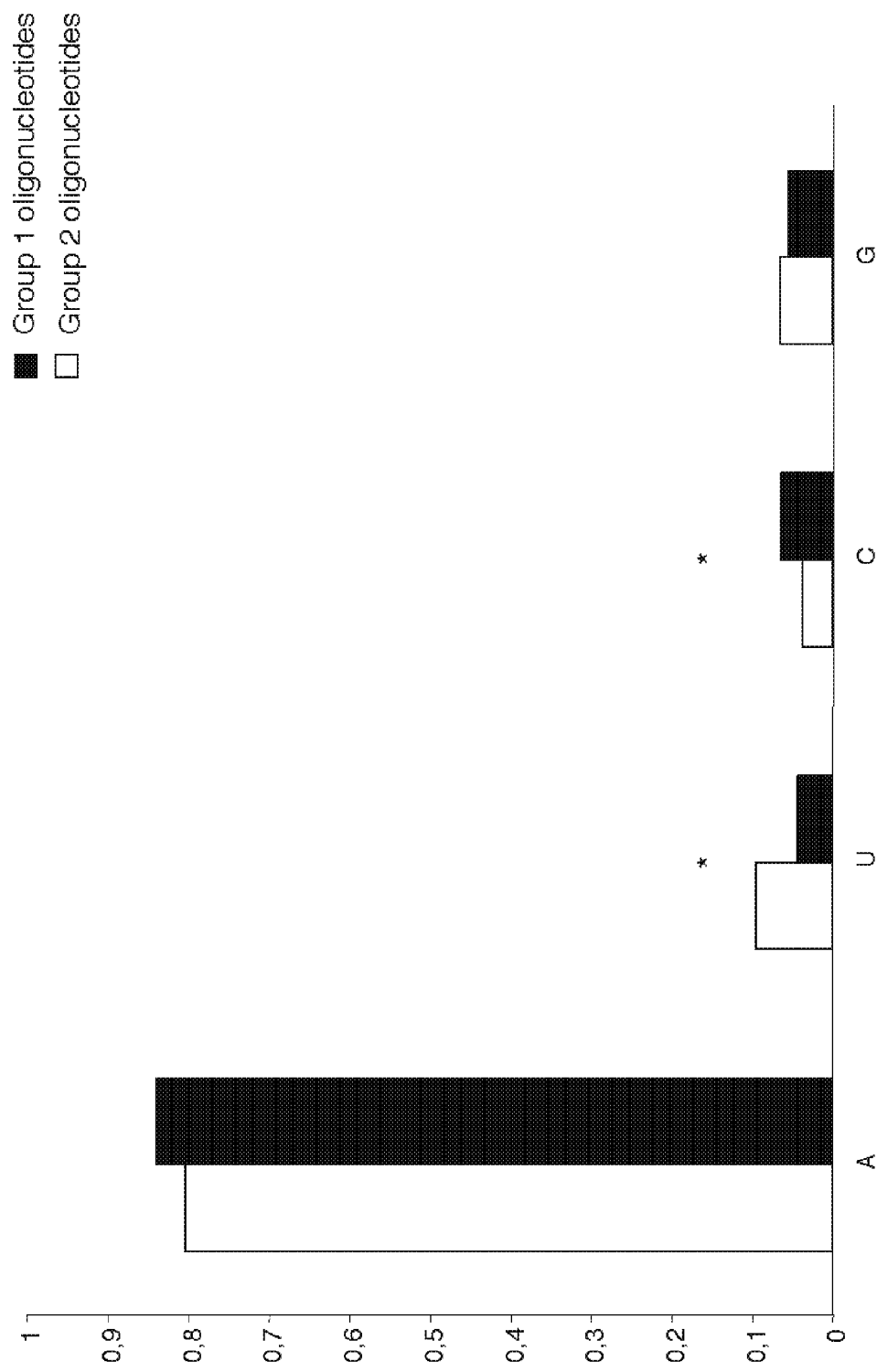

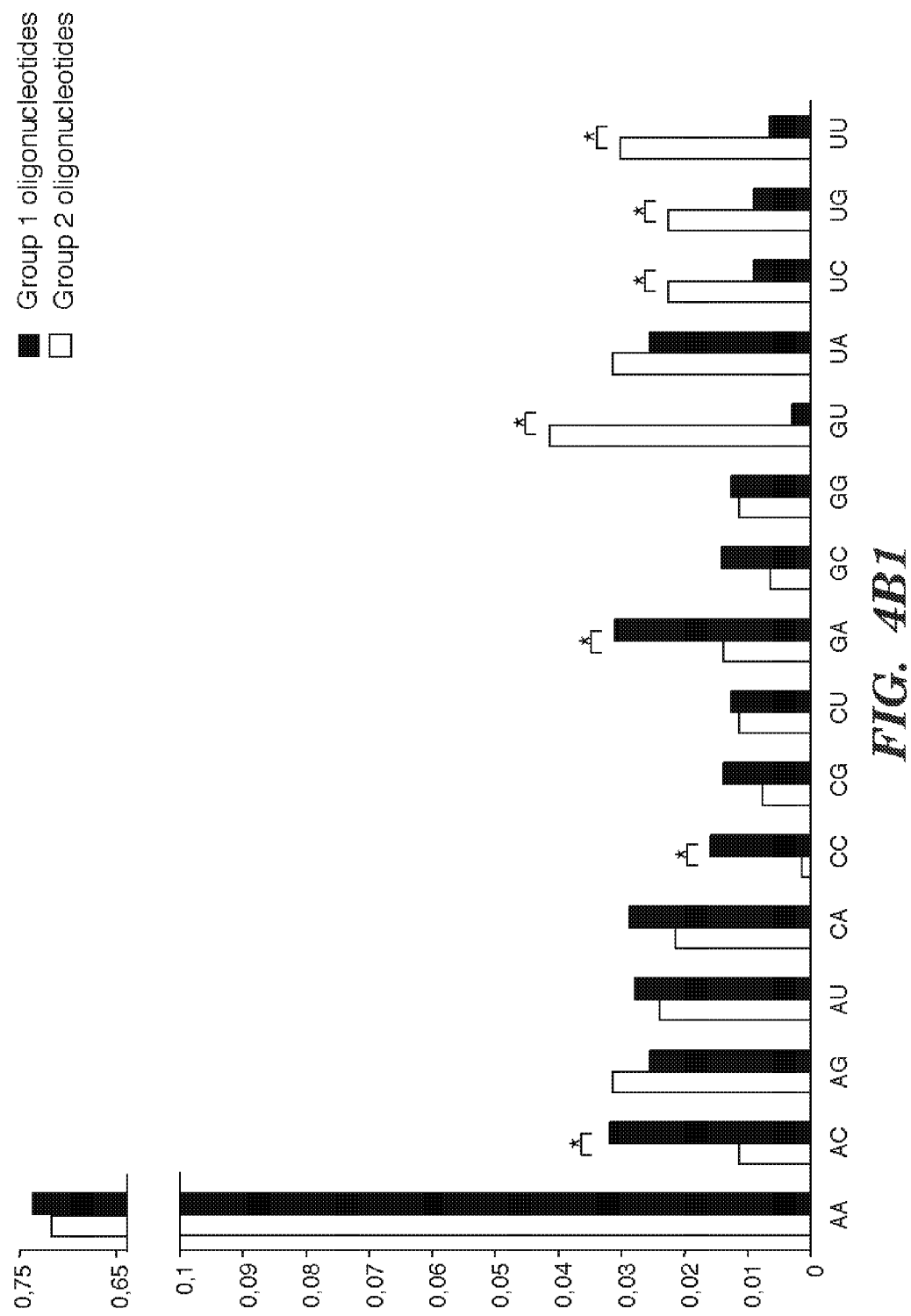
FIG. 4B1

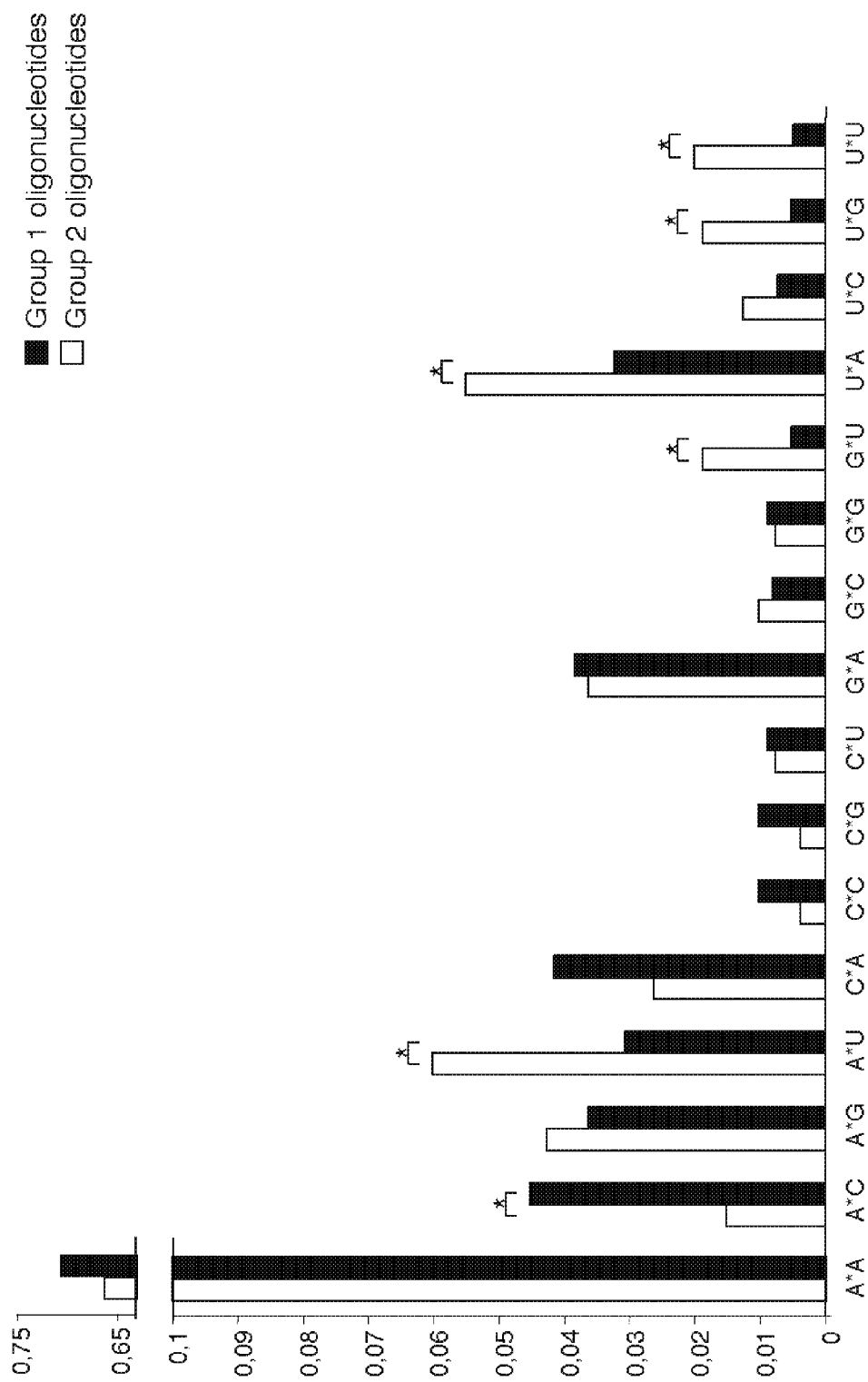
FIG. 4B2

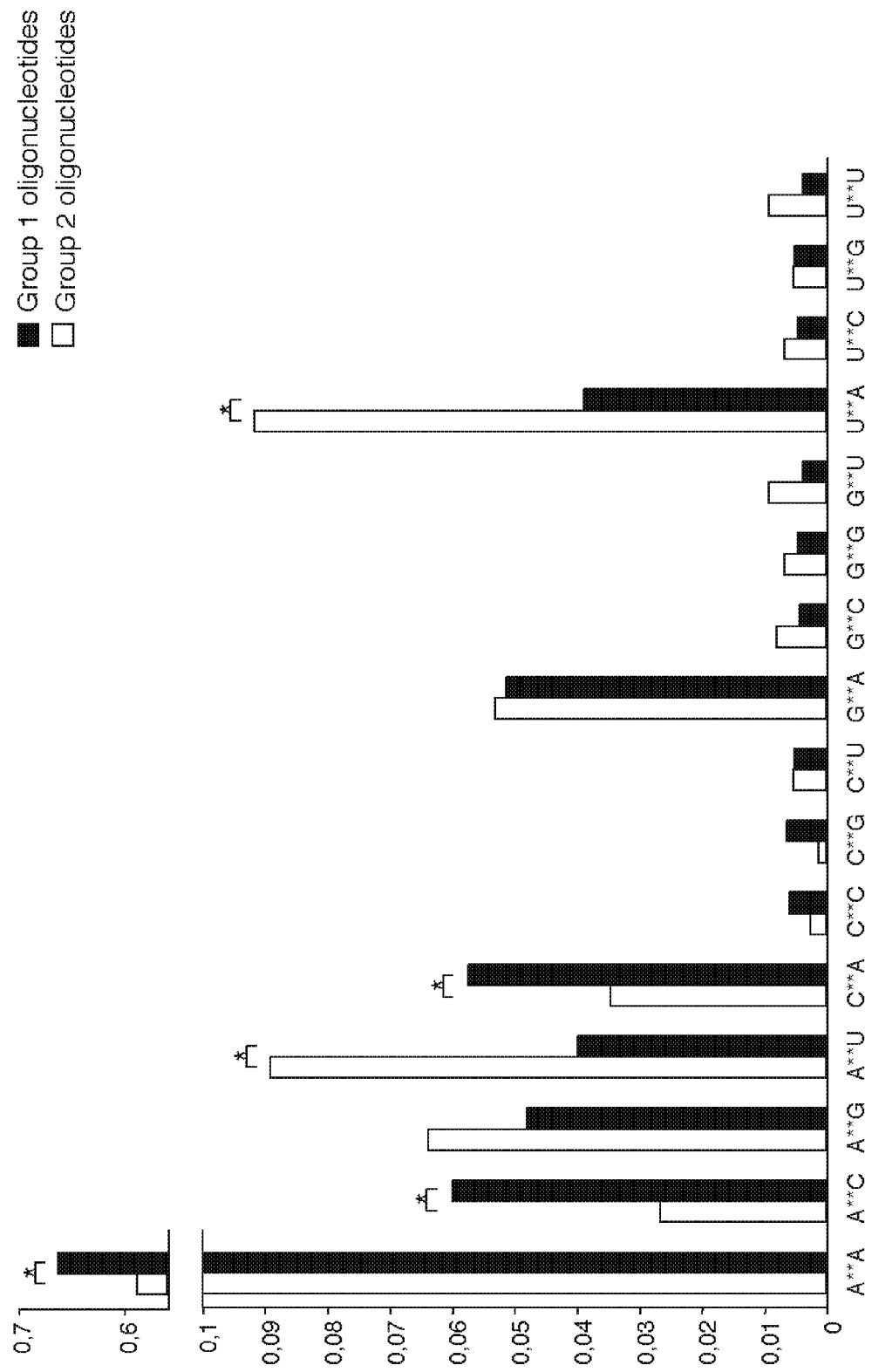
FIG. 4B3

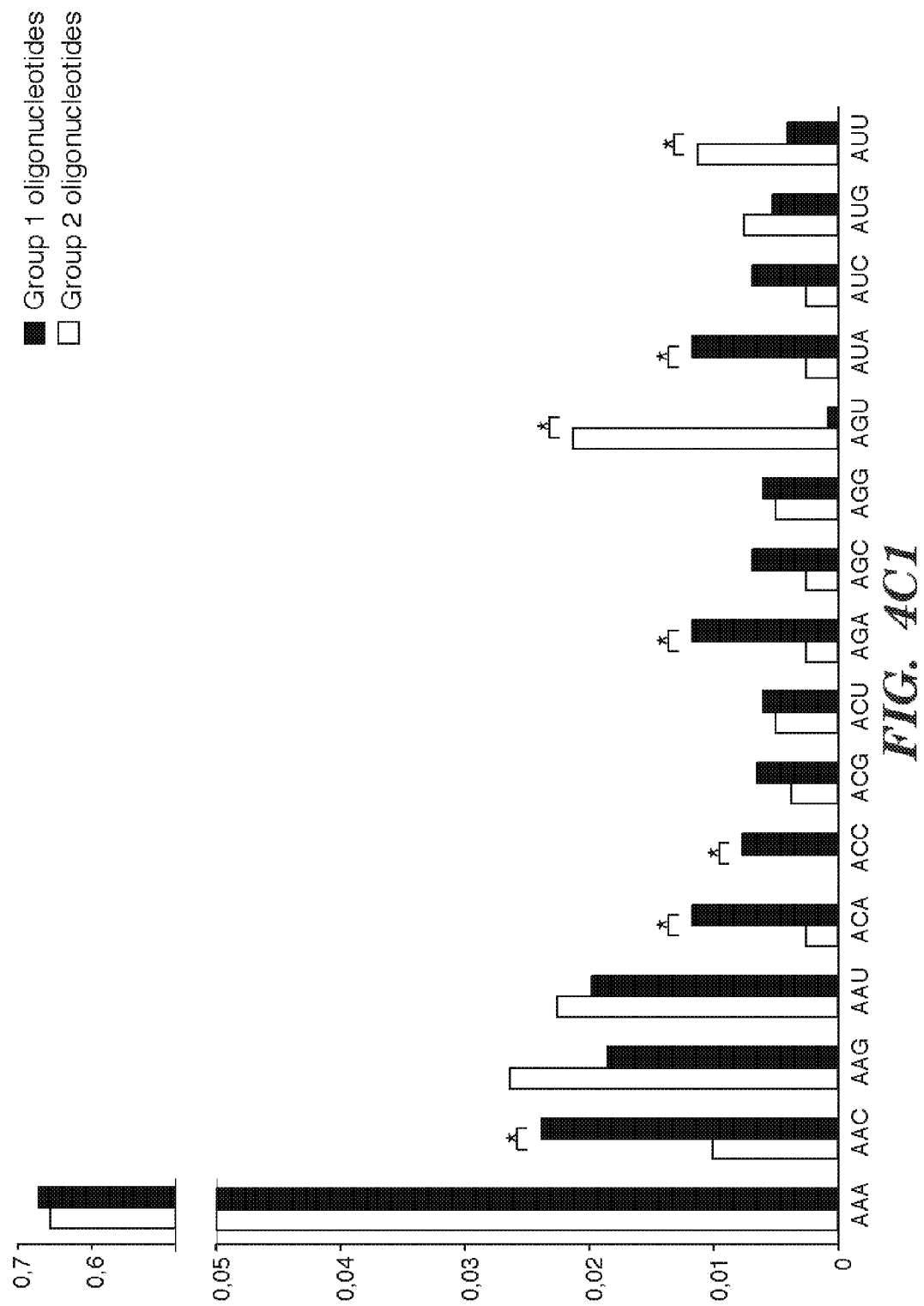
FIG. 4C1

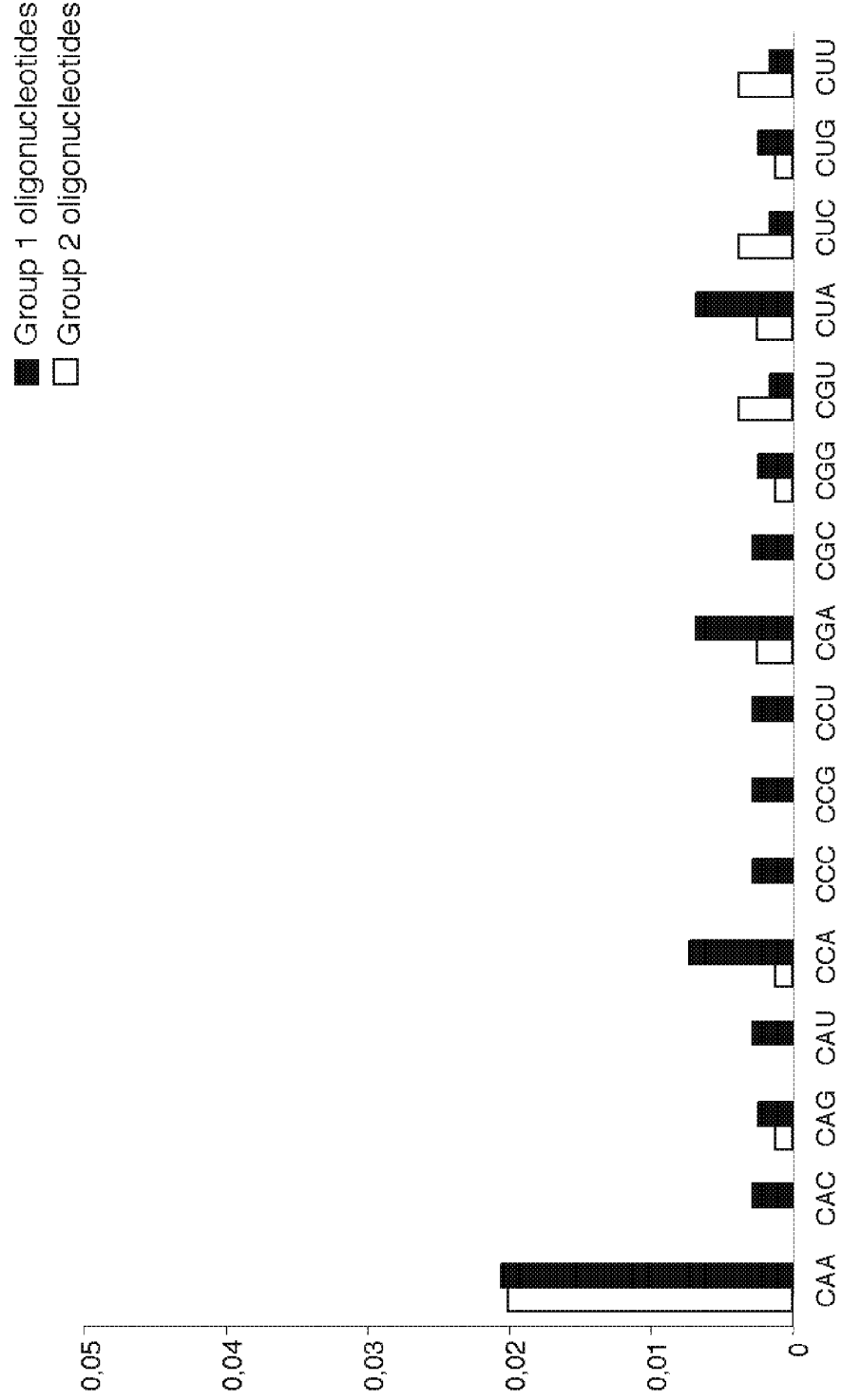
FIG. 4C2

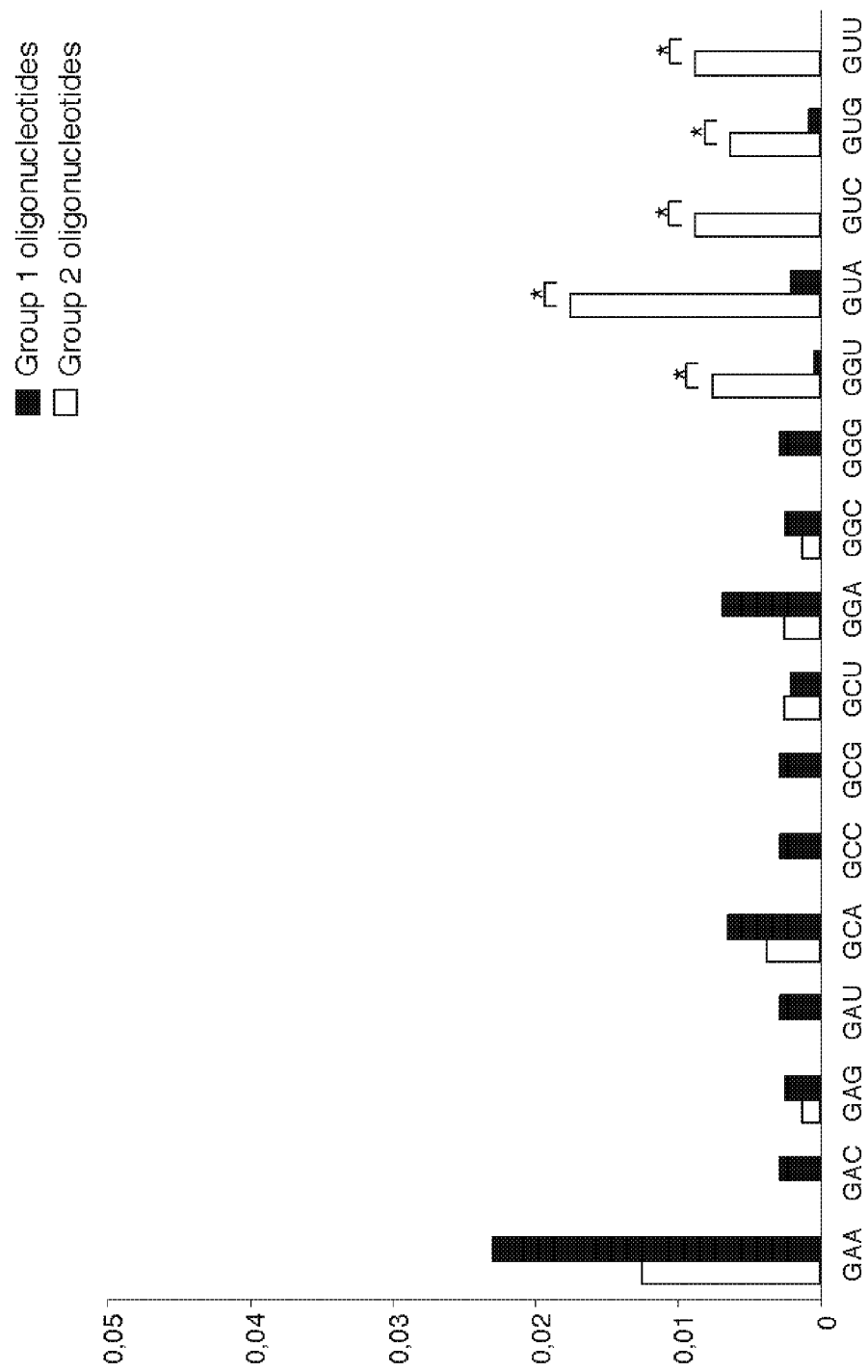
FIG. 4C3

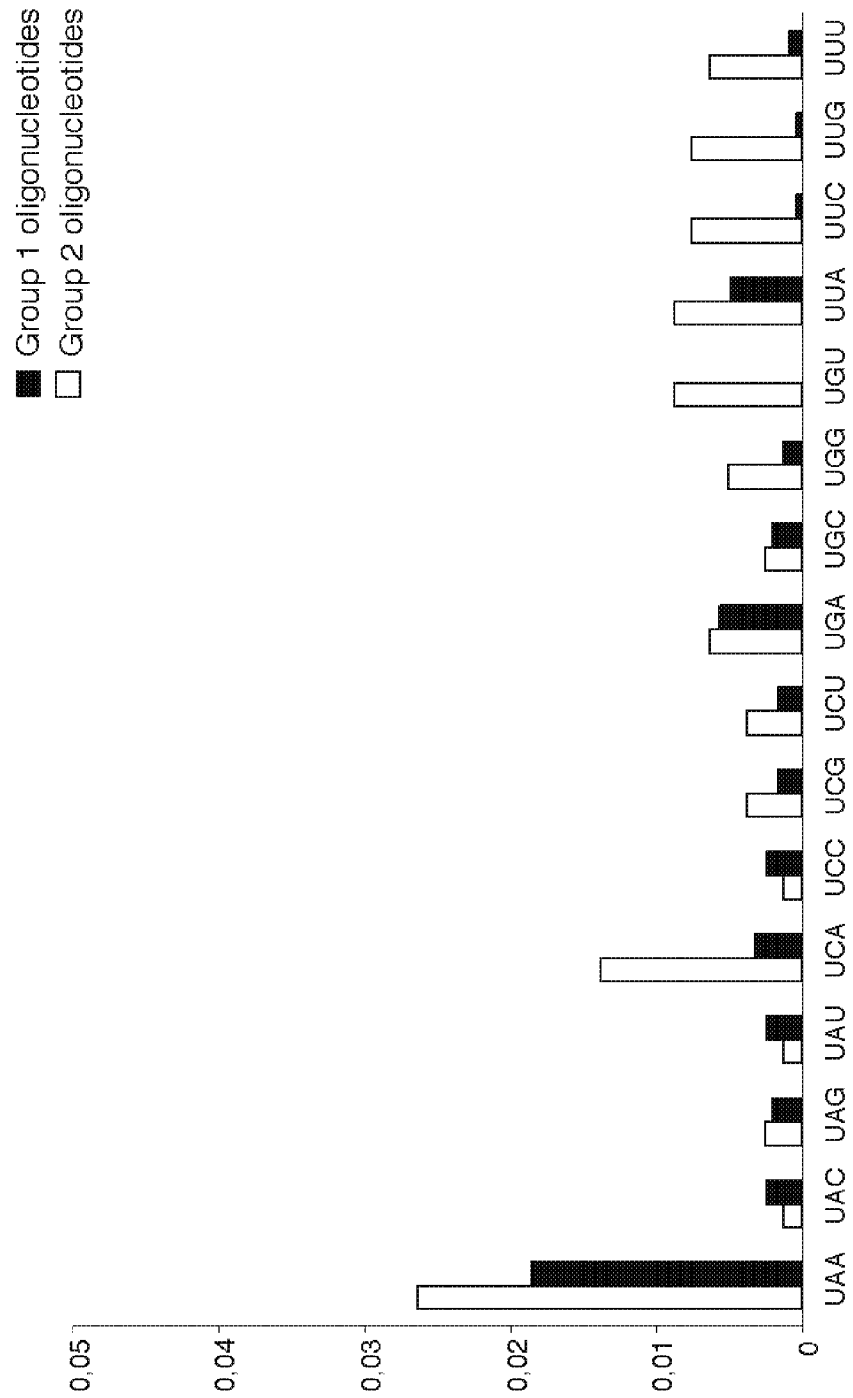
FIG. 4C4

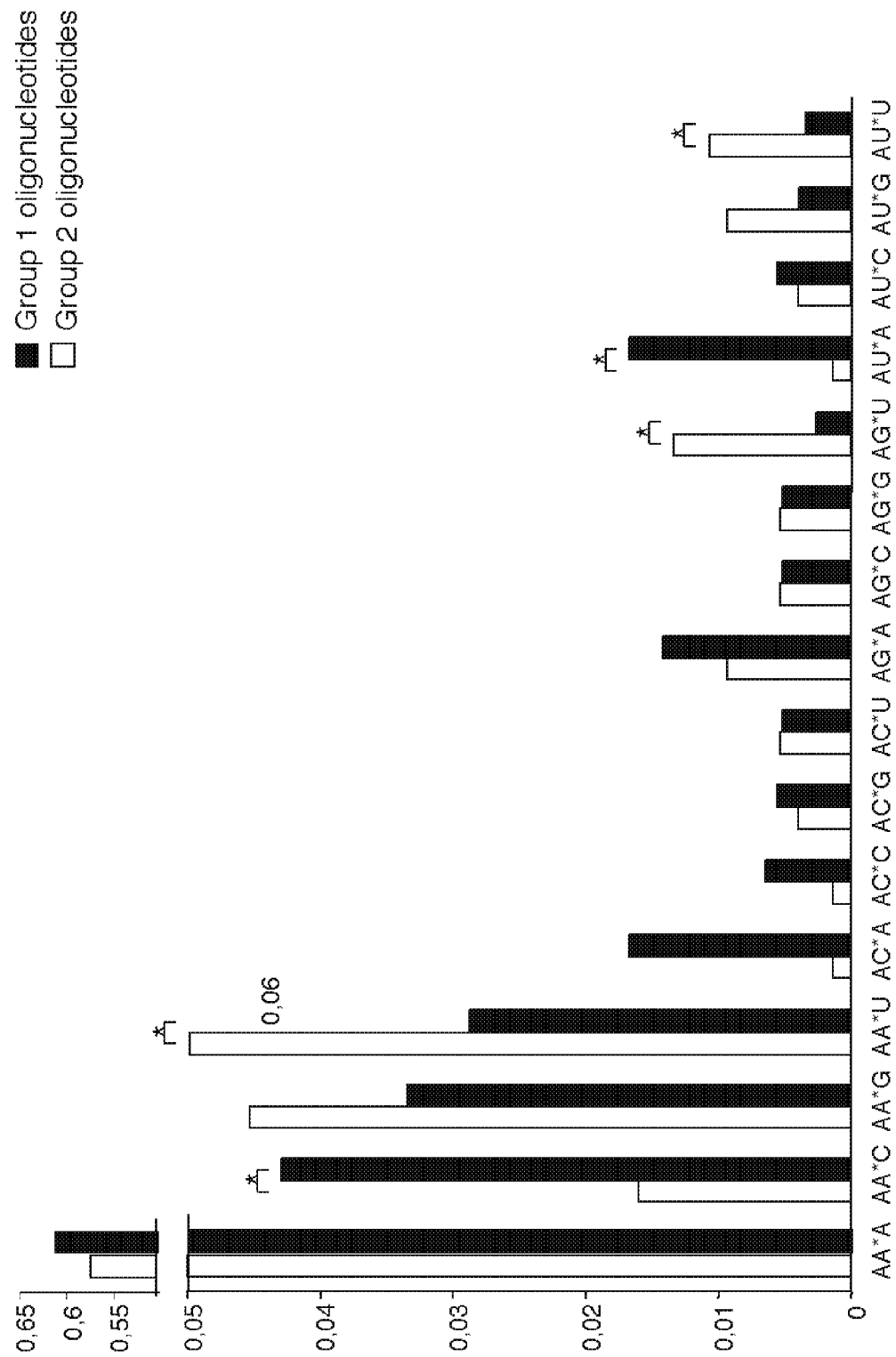
FIG. 4C5

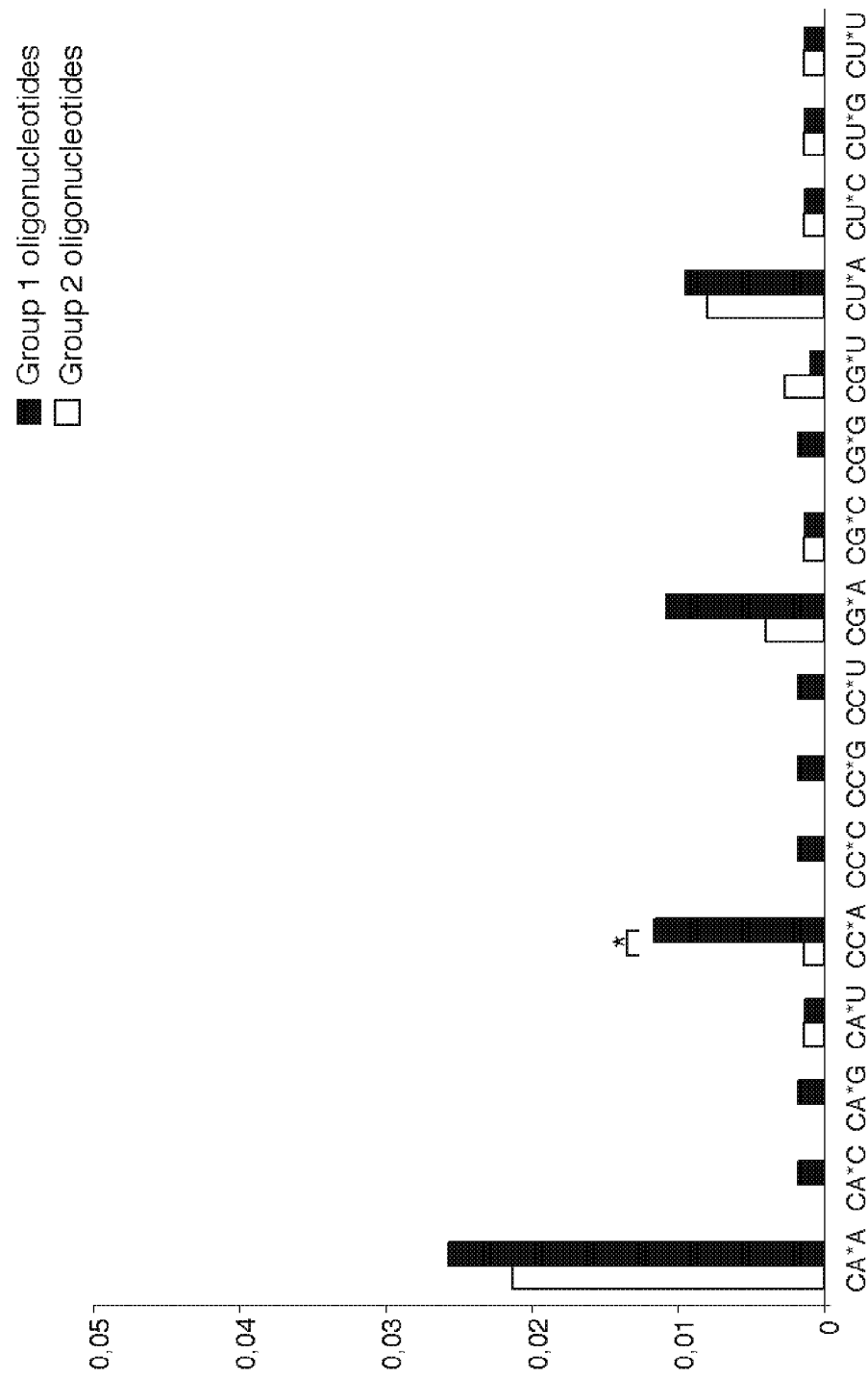
FIG. 4C6

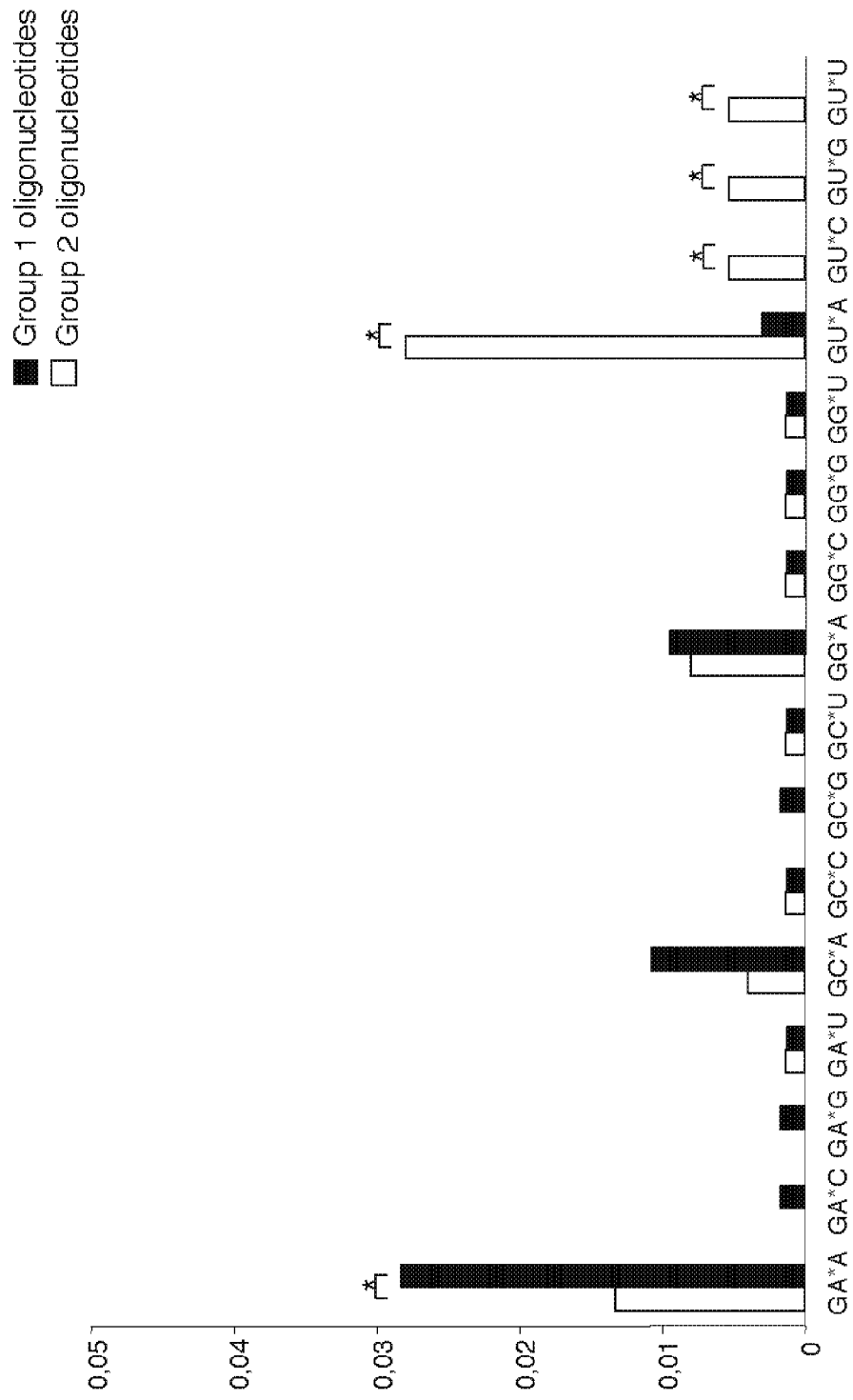
FIG. 4C7

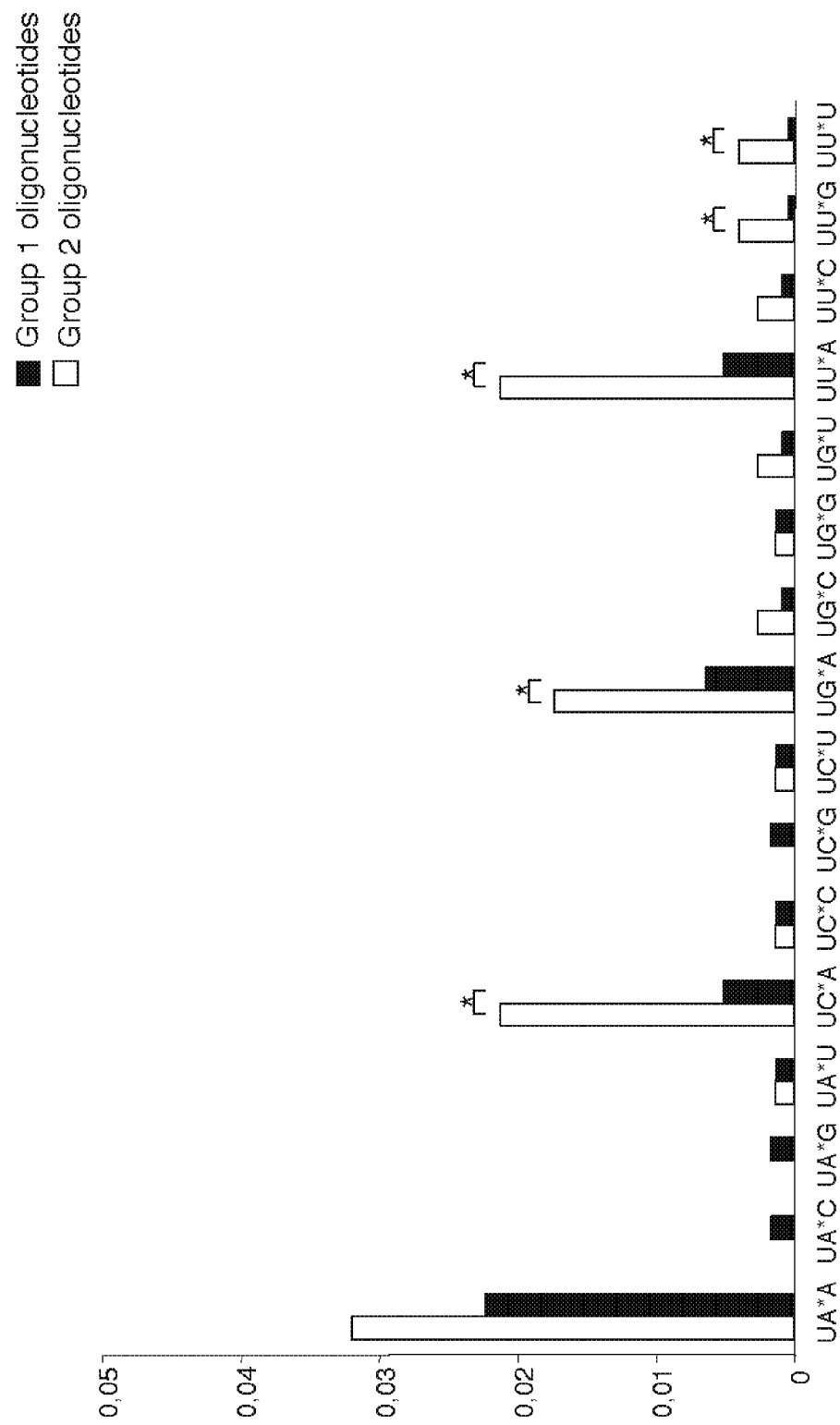
FIG. 4C8

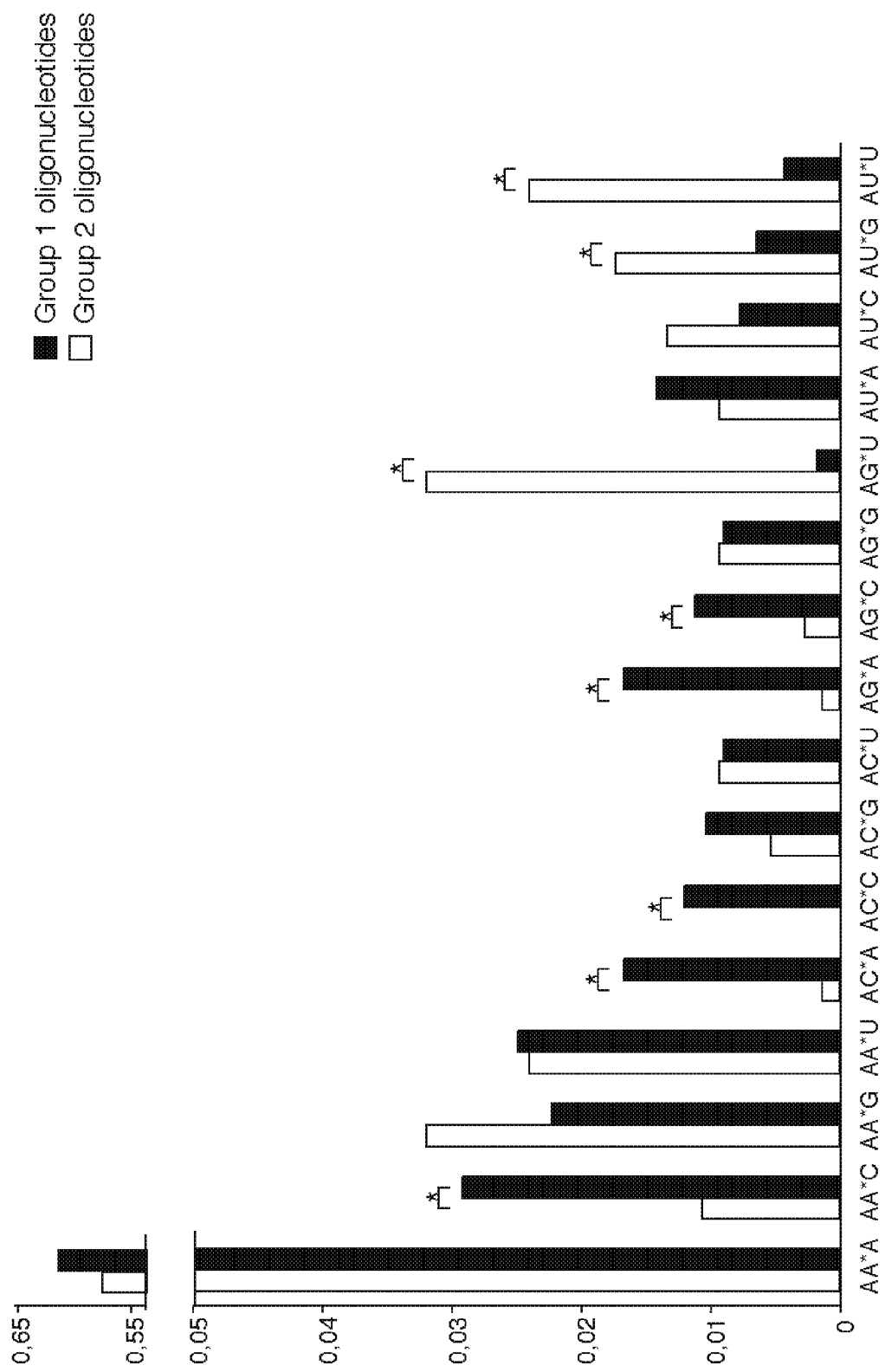
FIG. 4C9

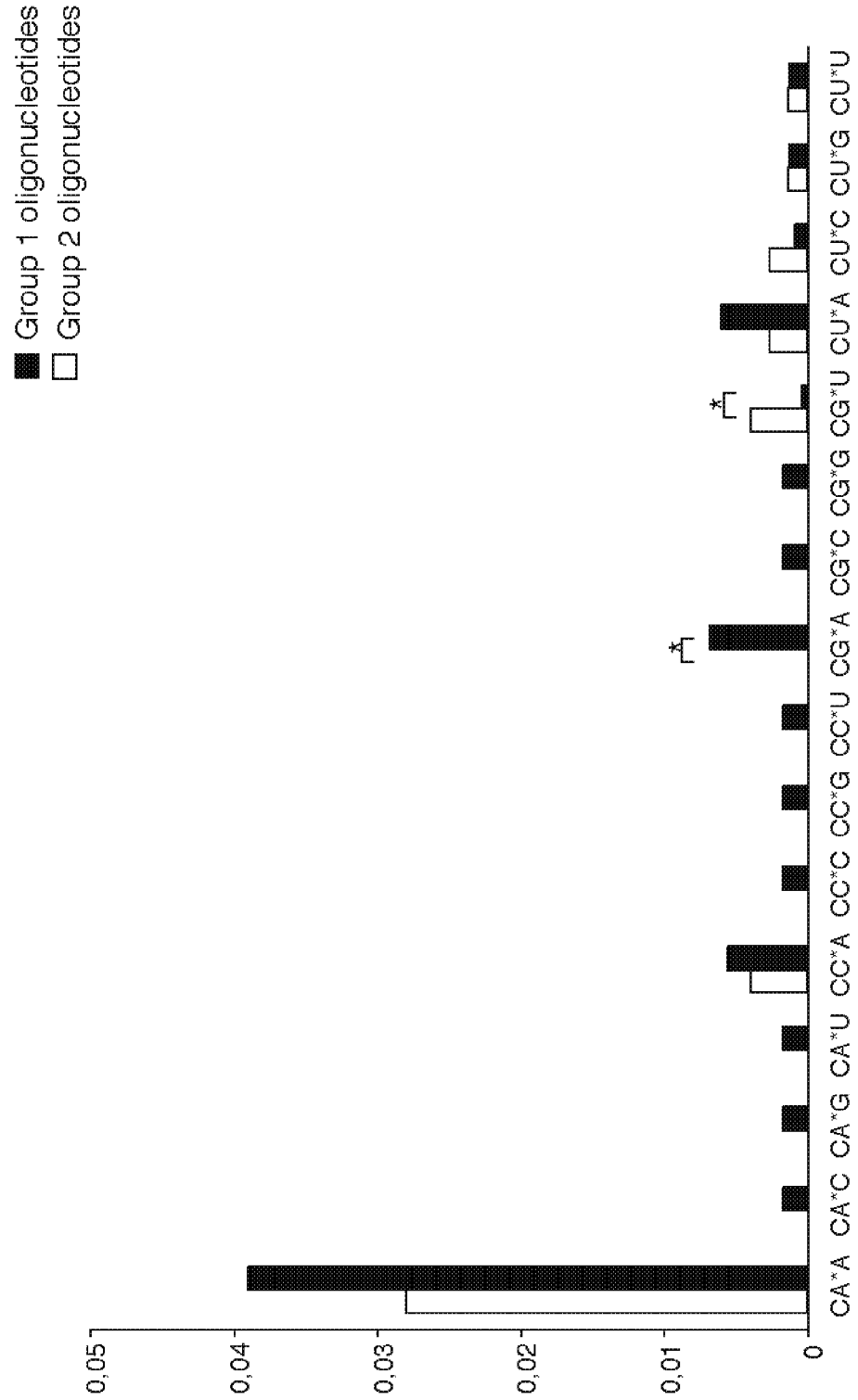
FIG. 4C10

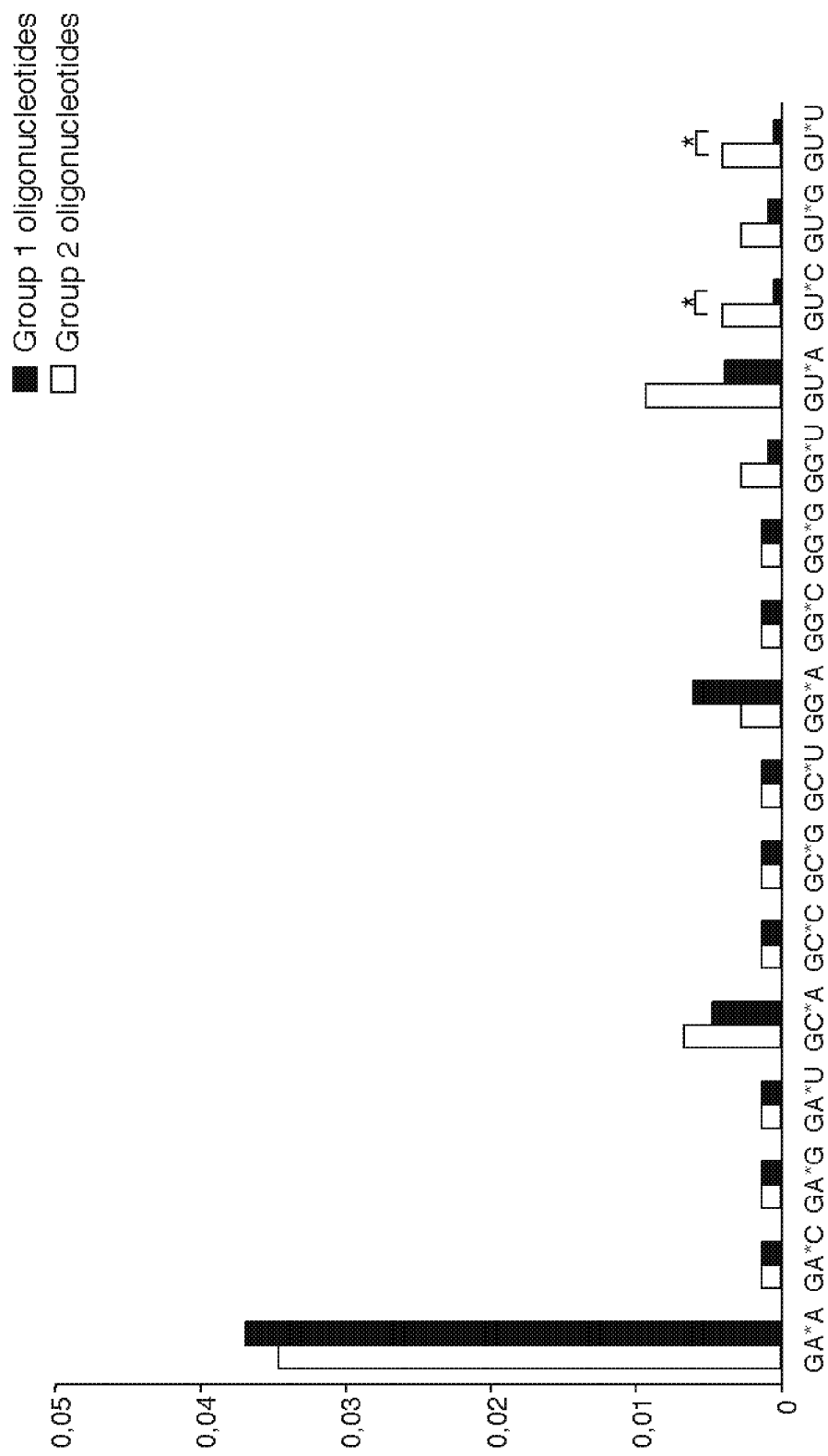
FIG. 4C11

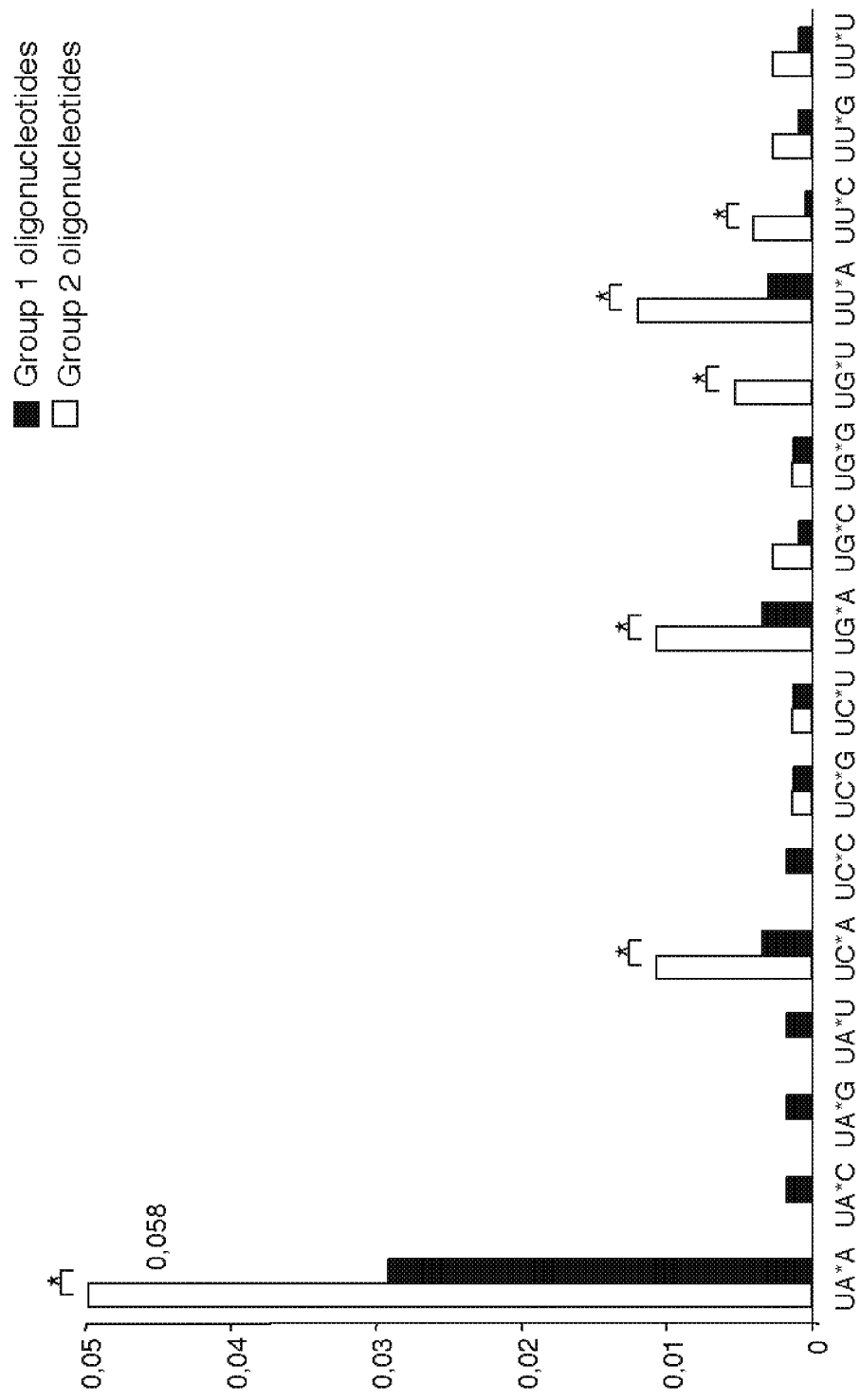
FIG. 4C12

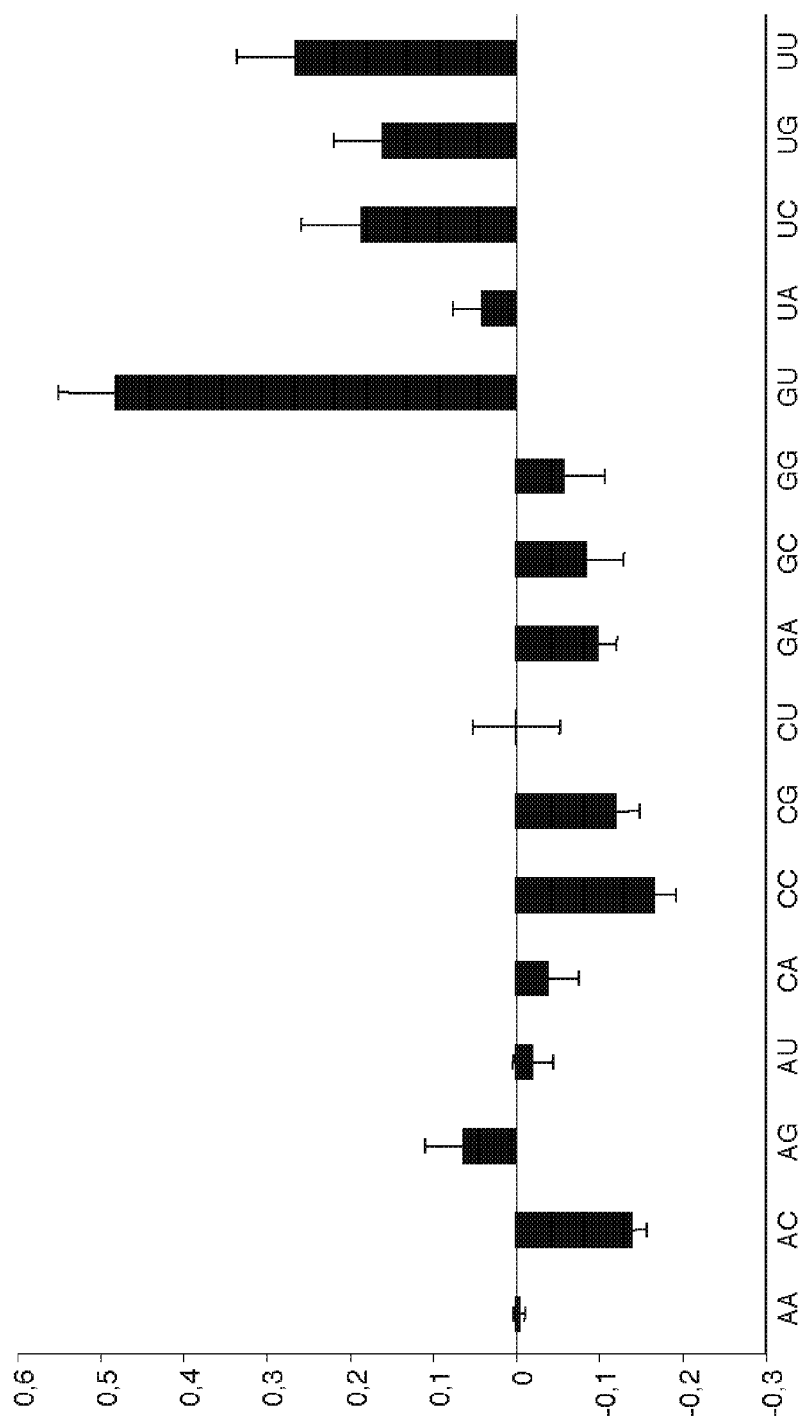
FIG. 5B1

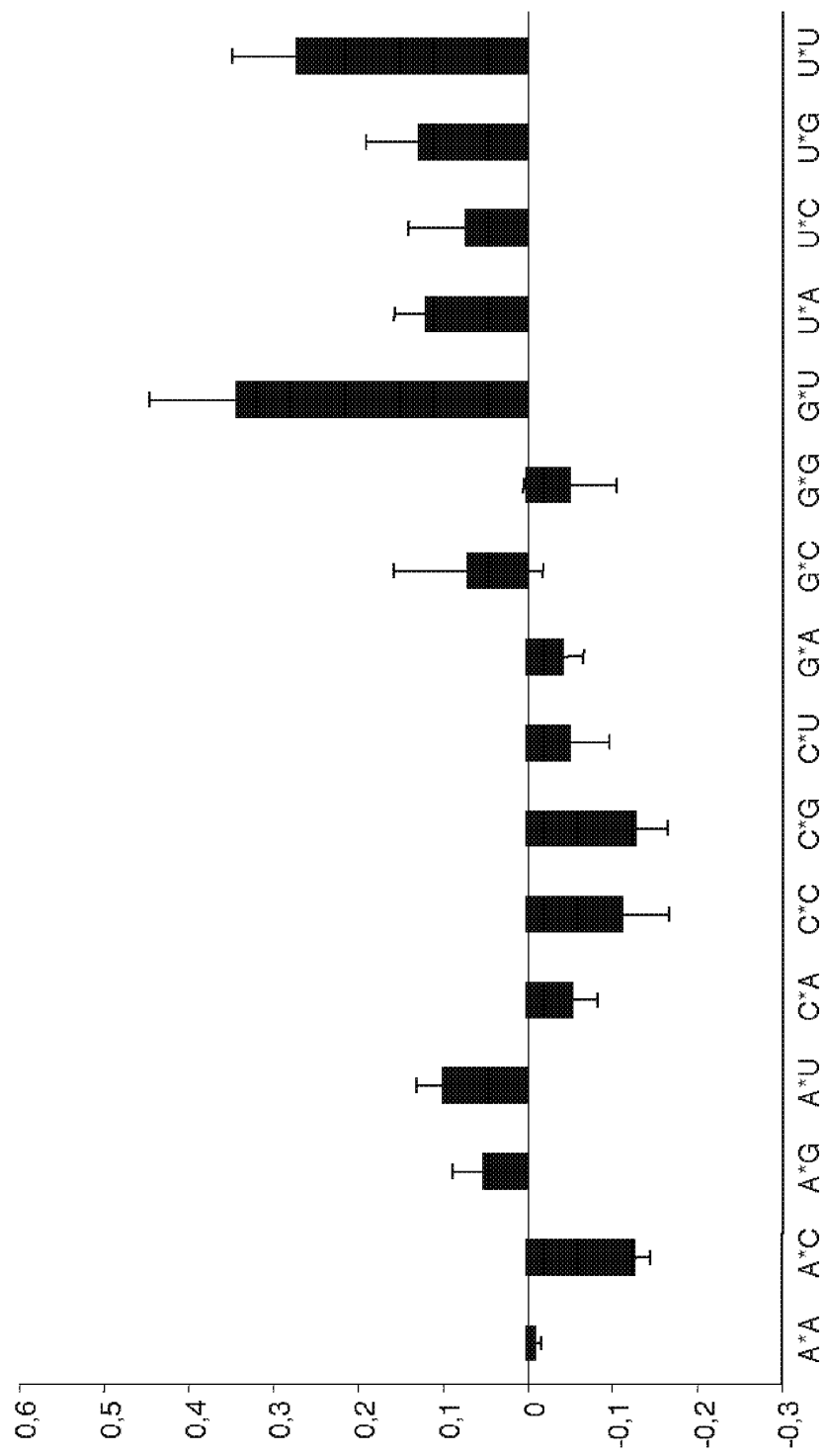
FIG. 5B2

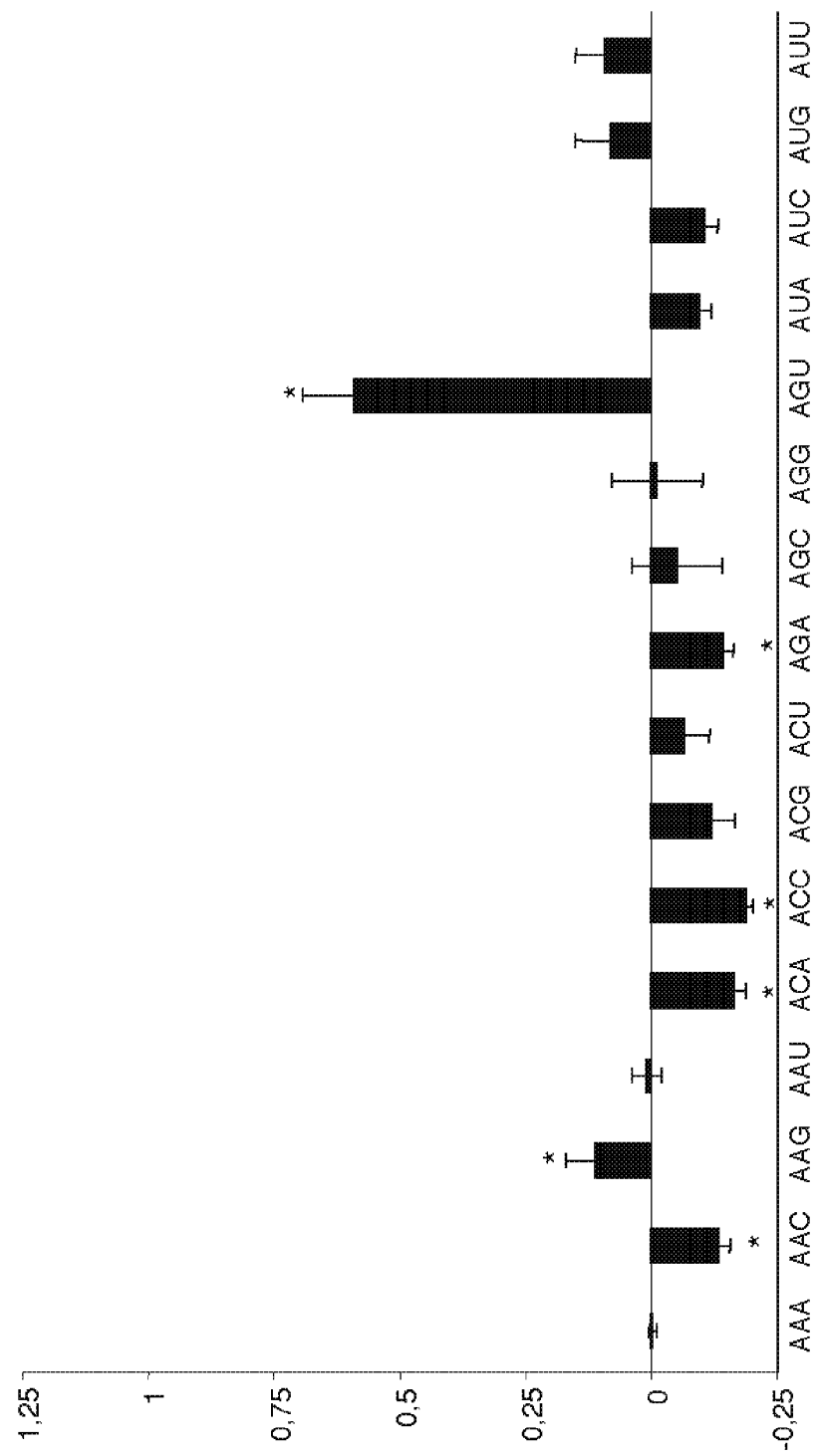
FIG. 5C1

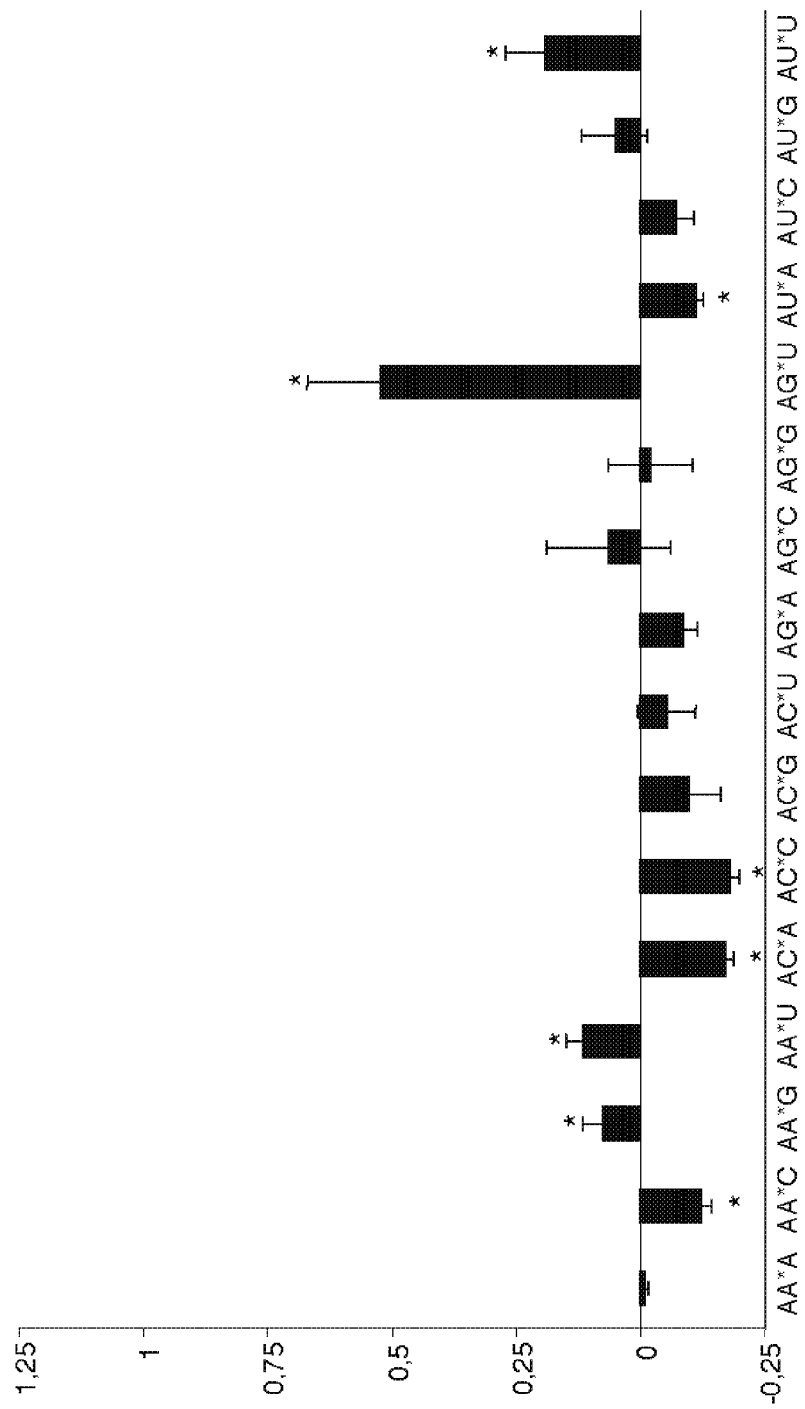
FIG. 5C2

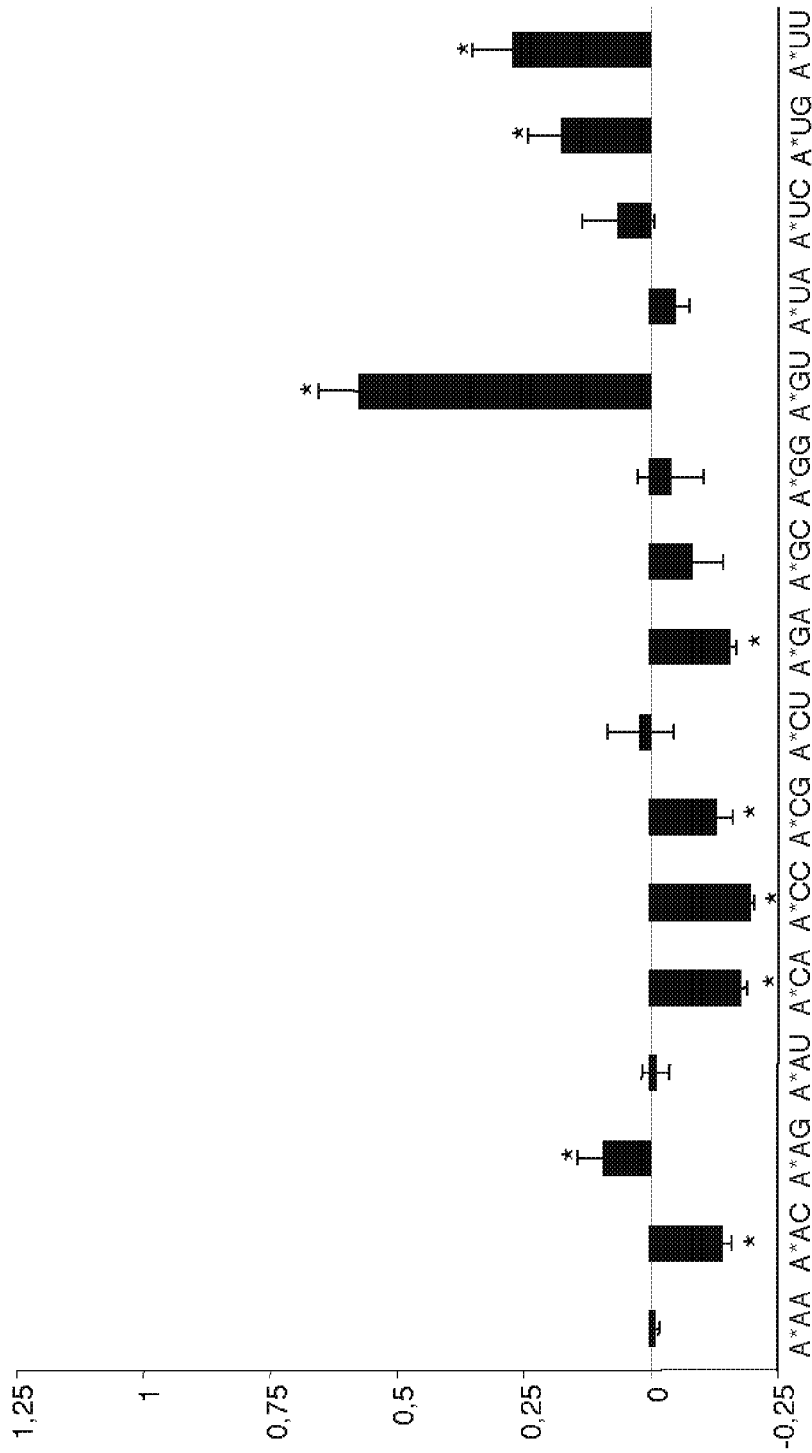
FIG. 5C3

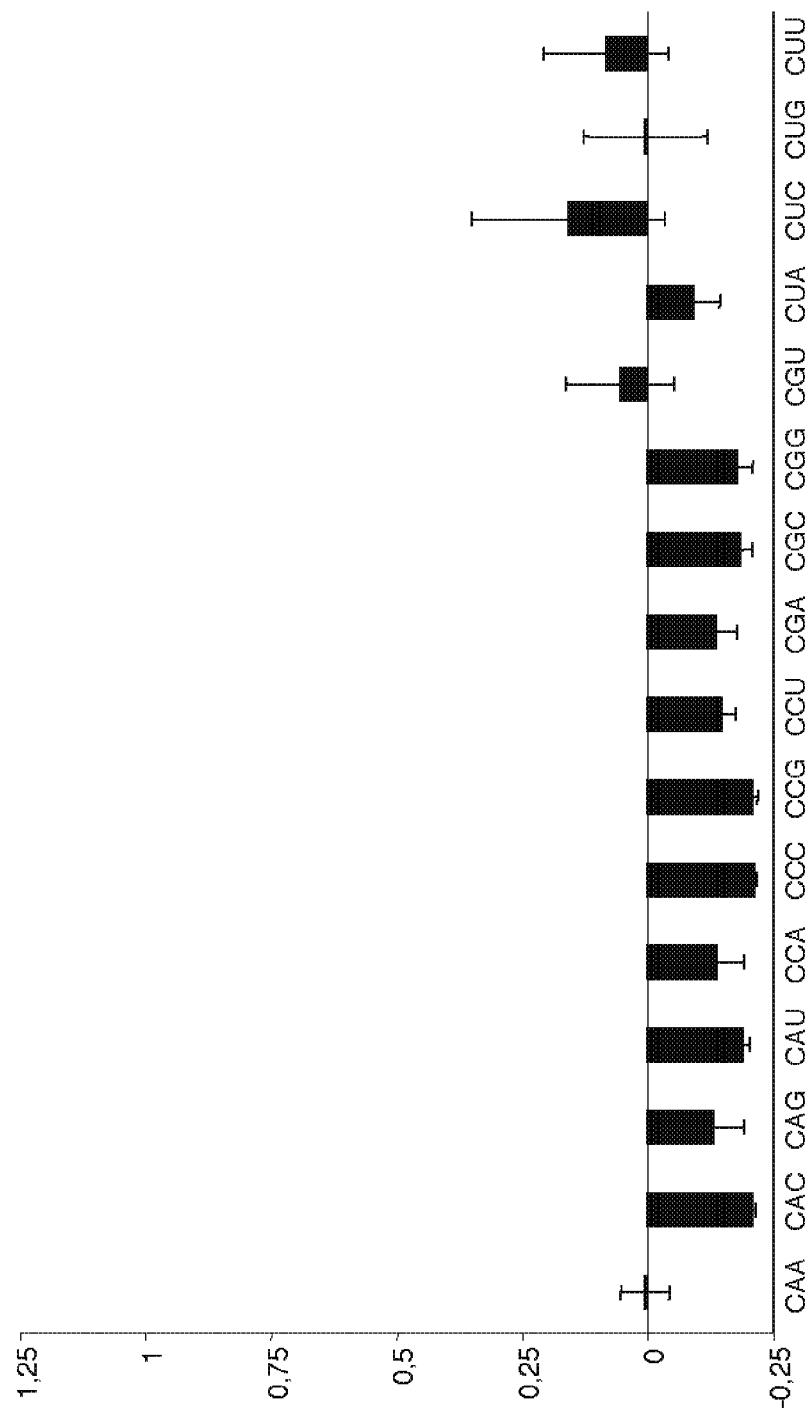
FIG. 5C4

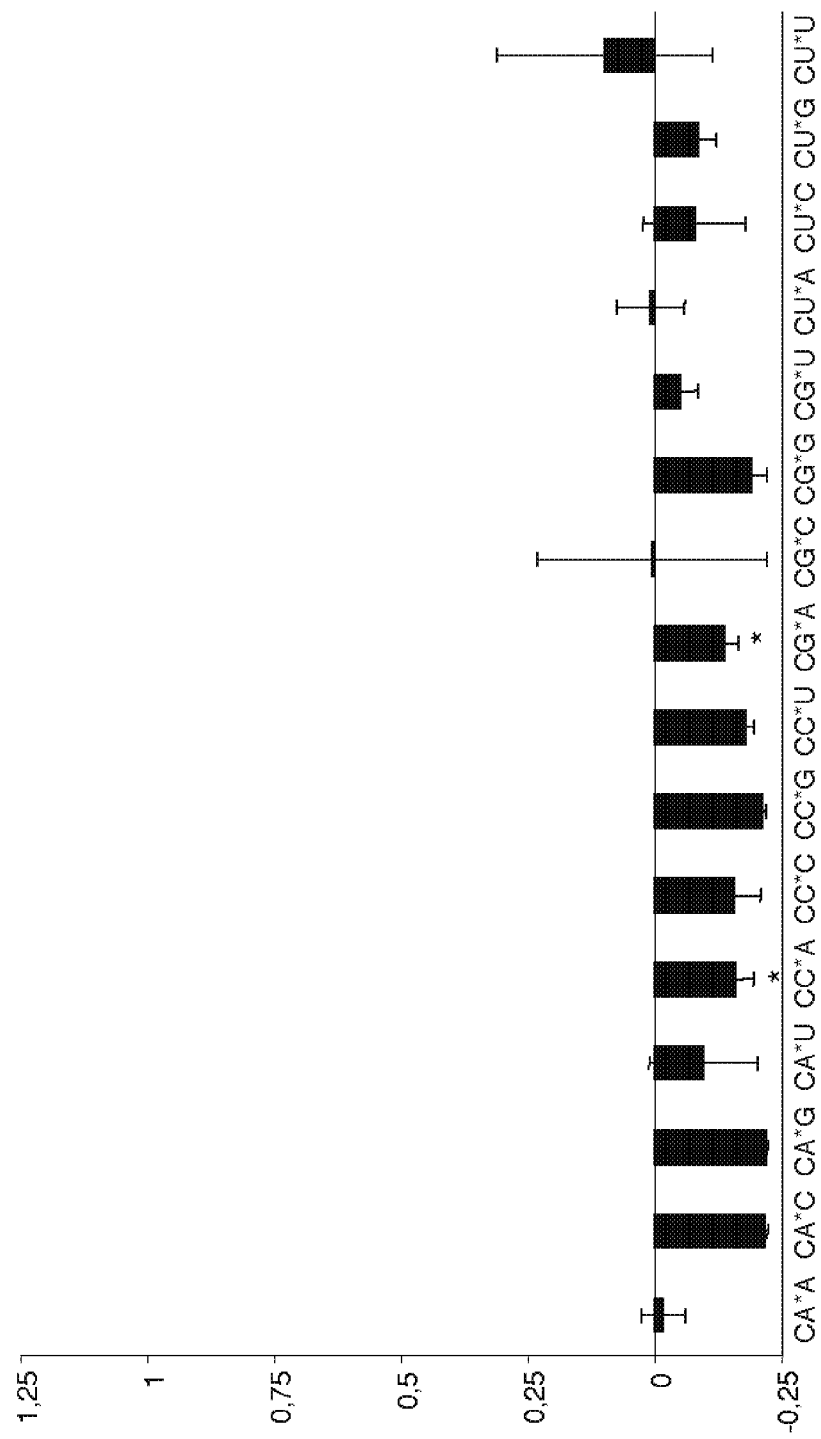
FIG. 5C5

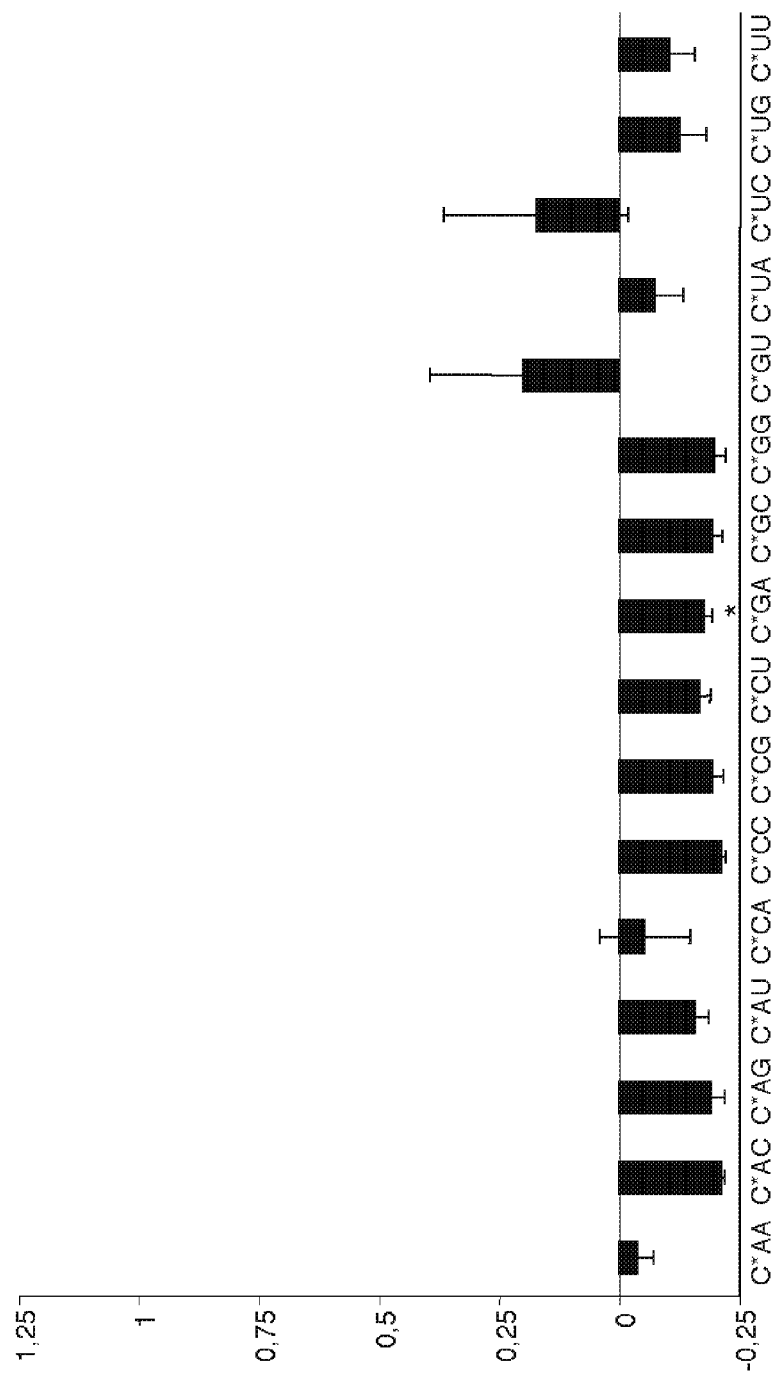
FIG. 5C6

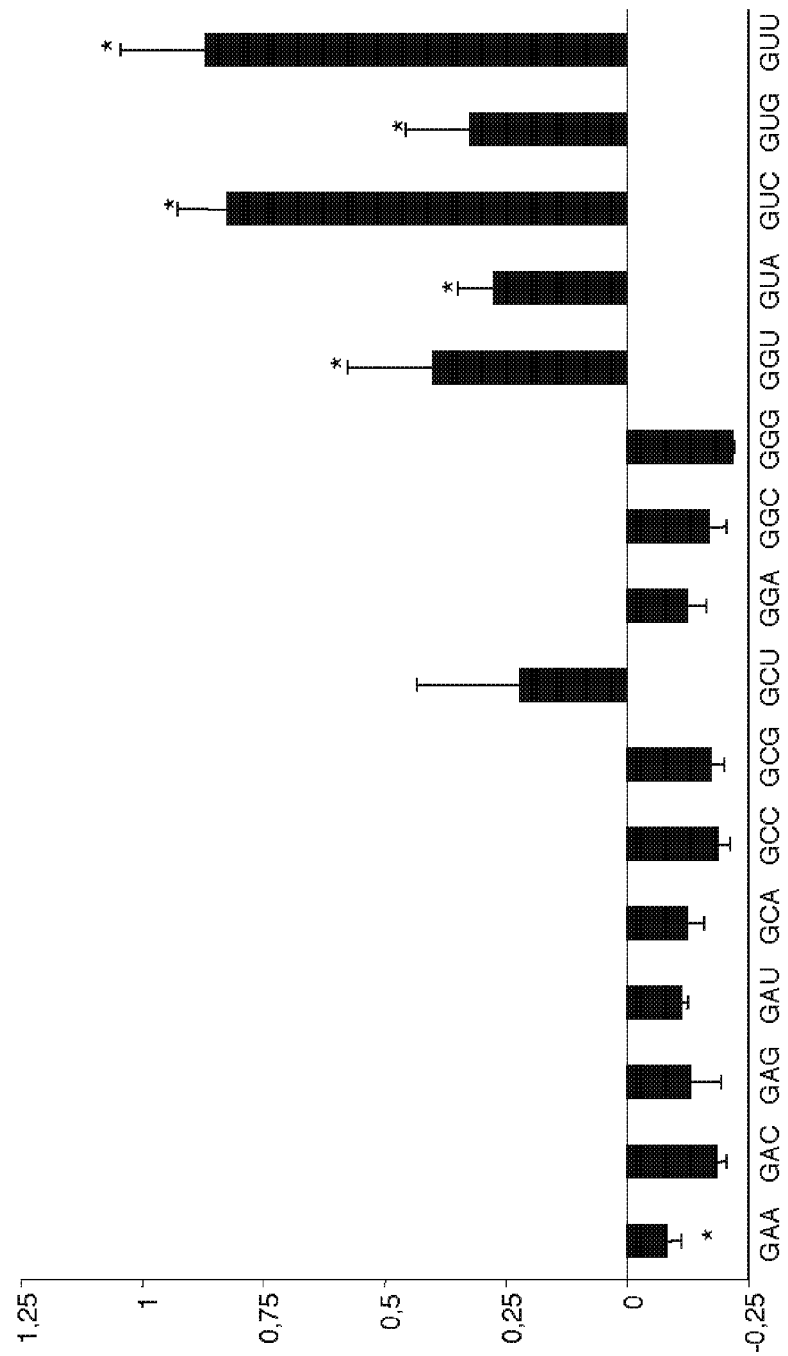
FIG. 5C7

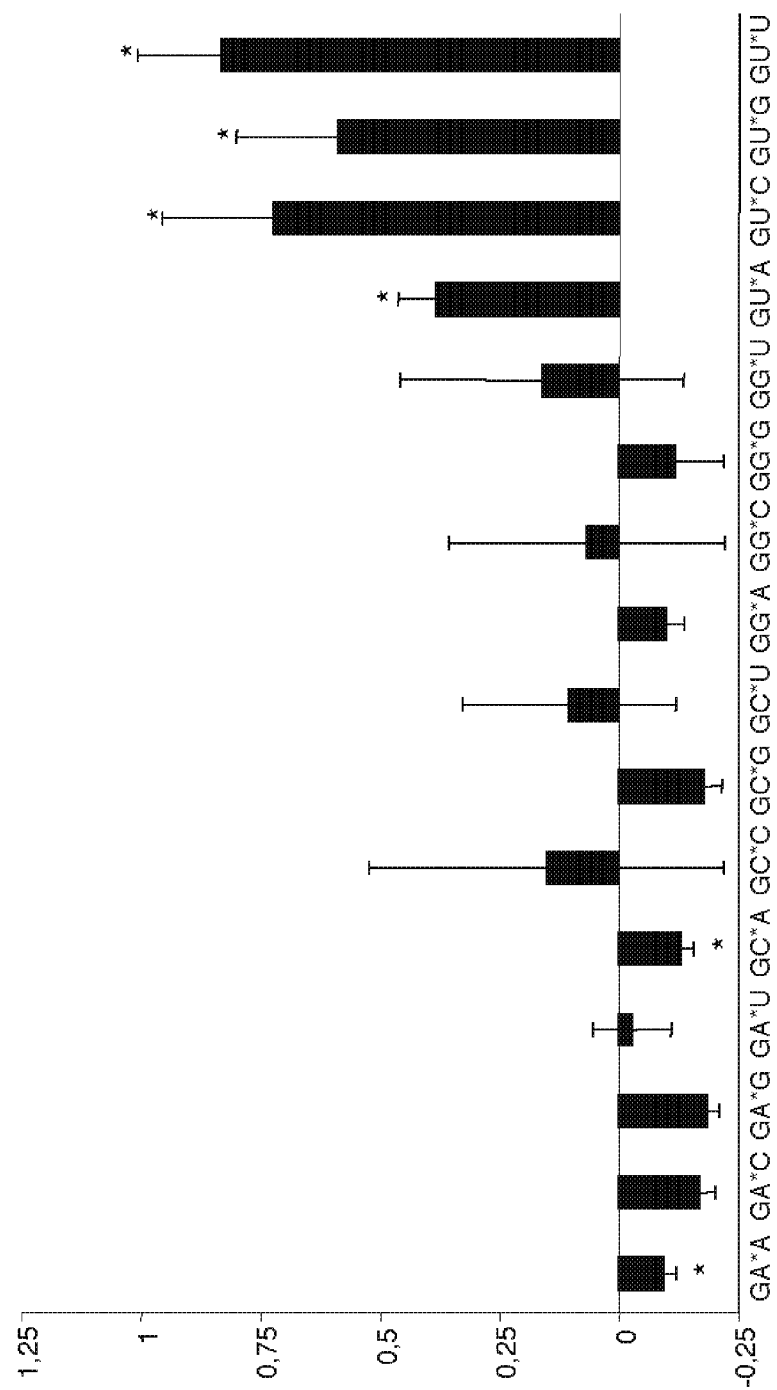
FIG. 5C8

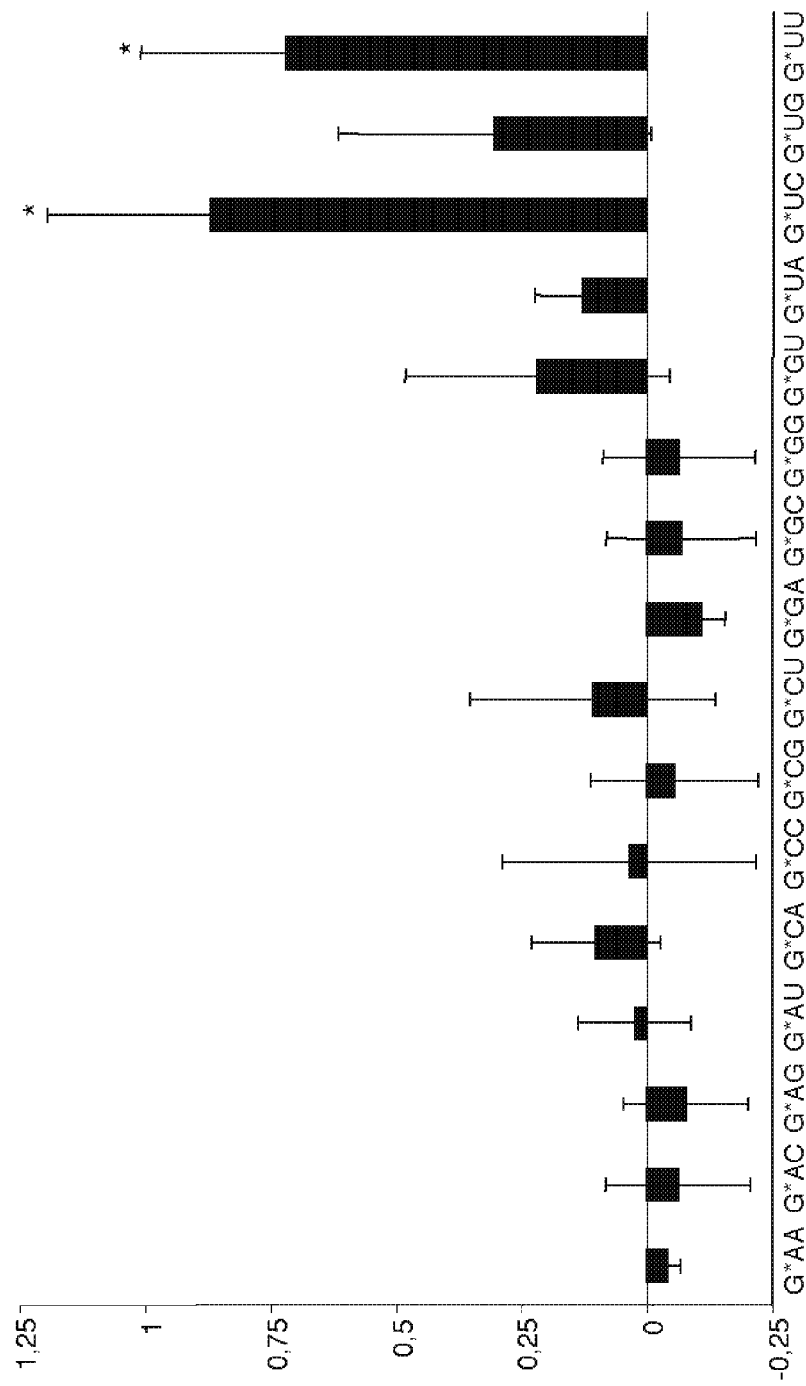
FIG. 5C9

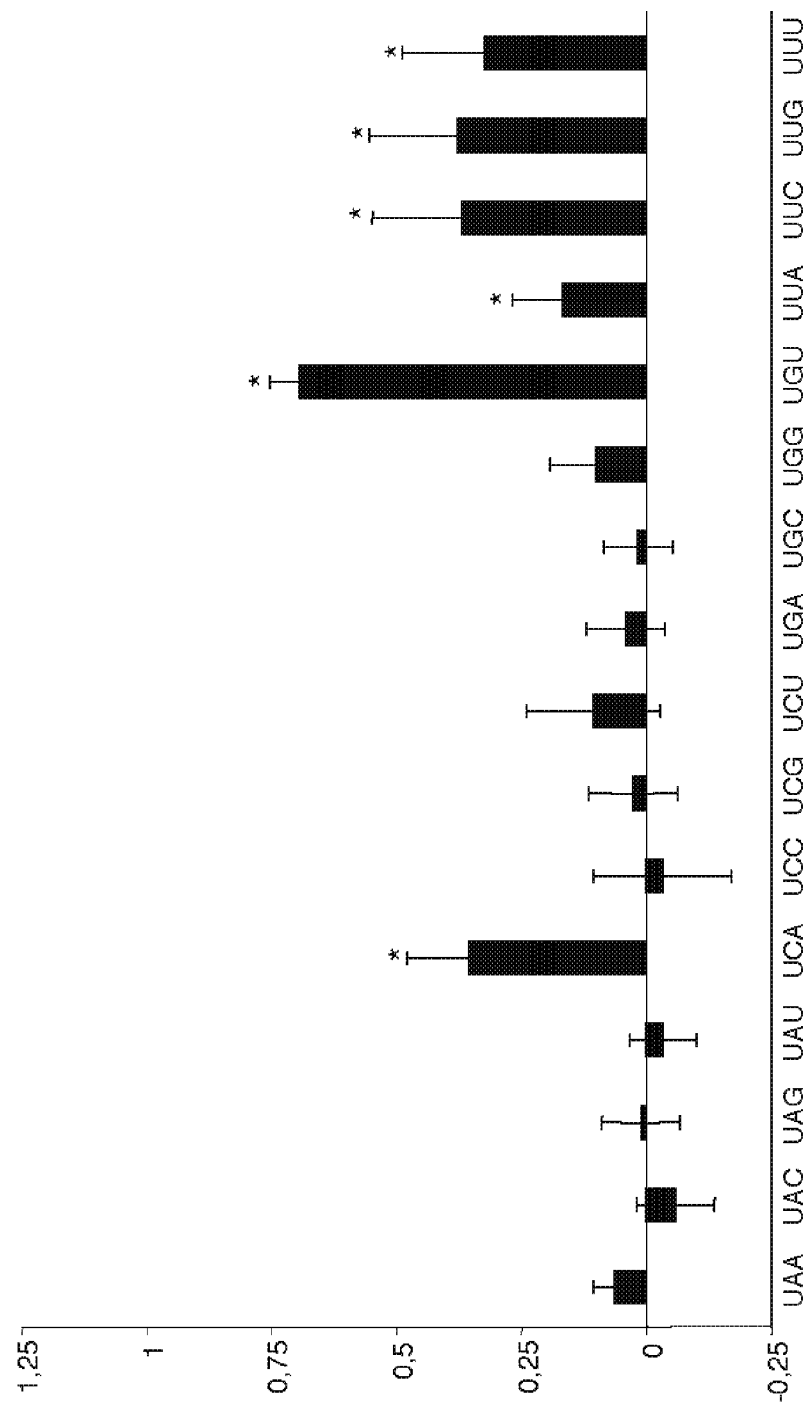
FIG. 5C10

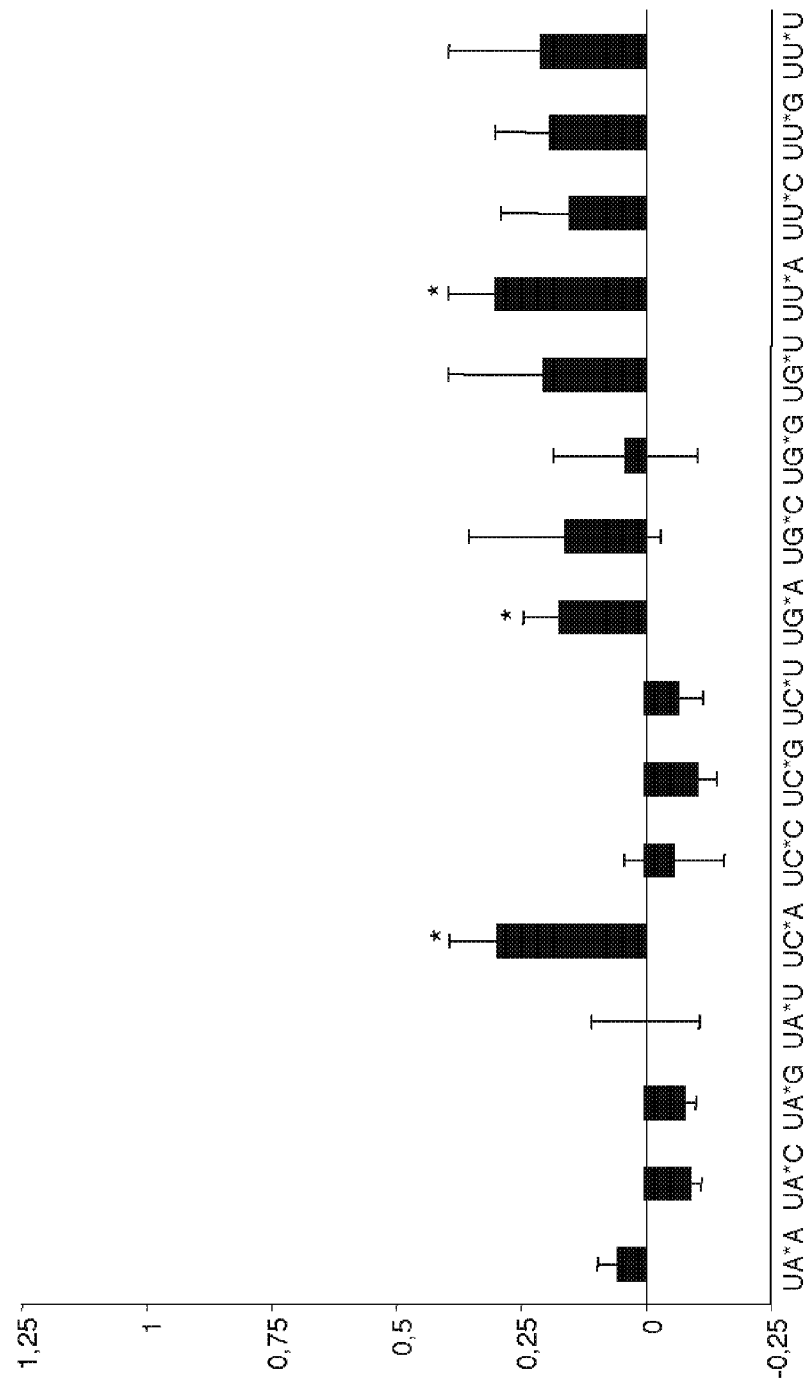
FIG. 5C11

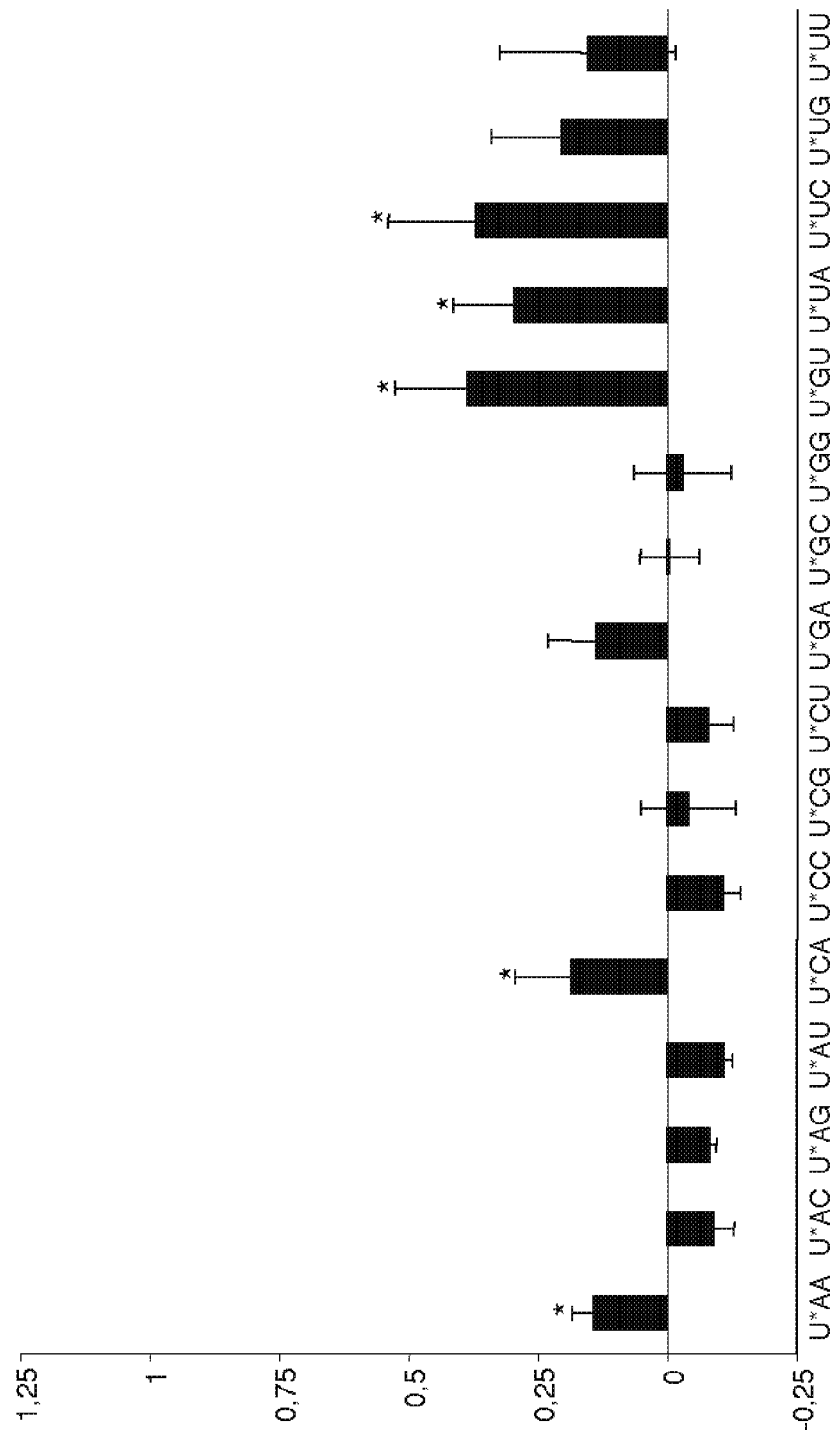
FIG. 5C12

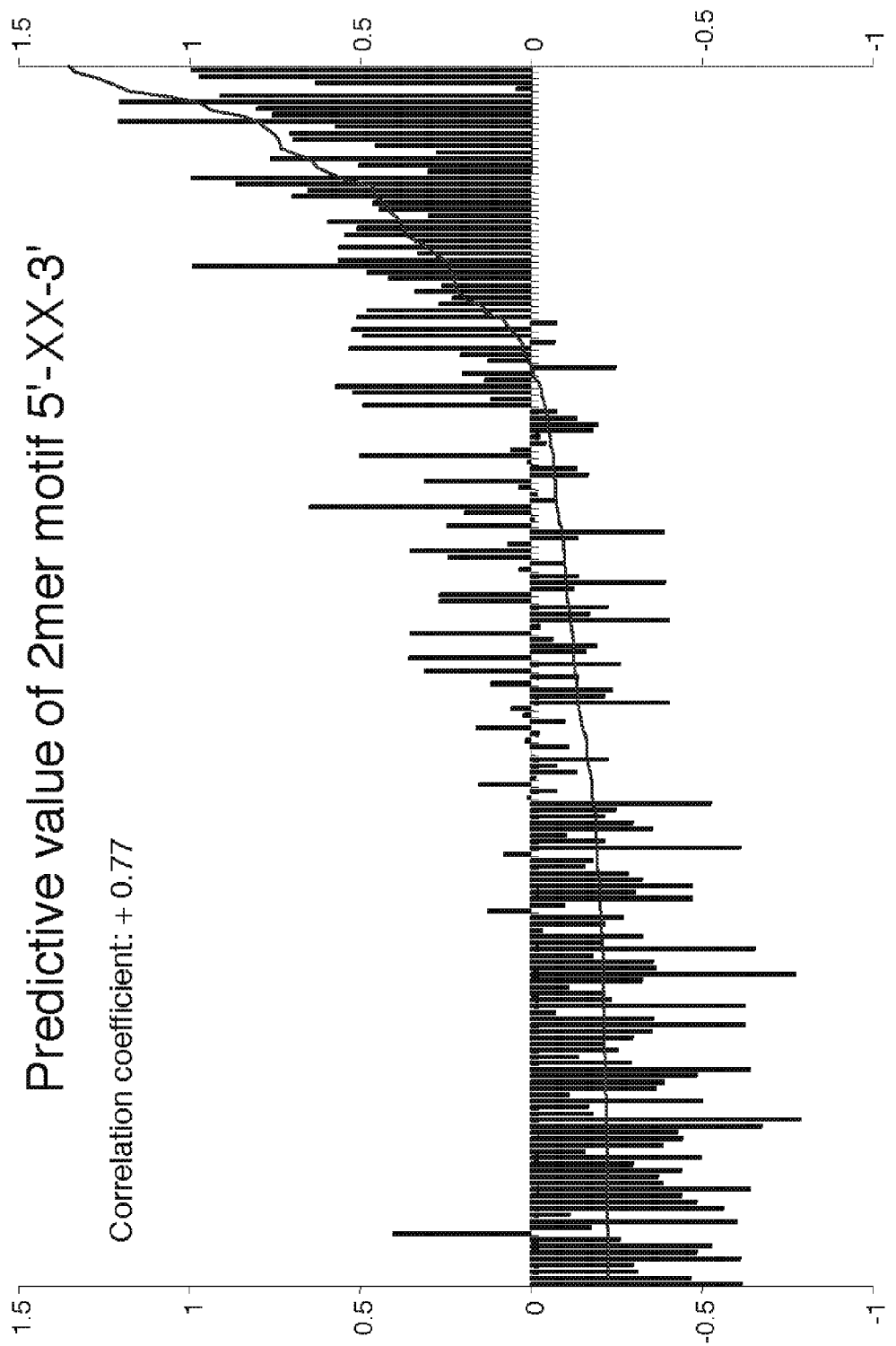
FIG. 6B1

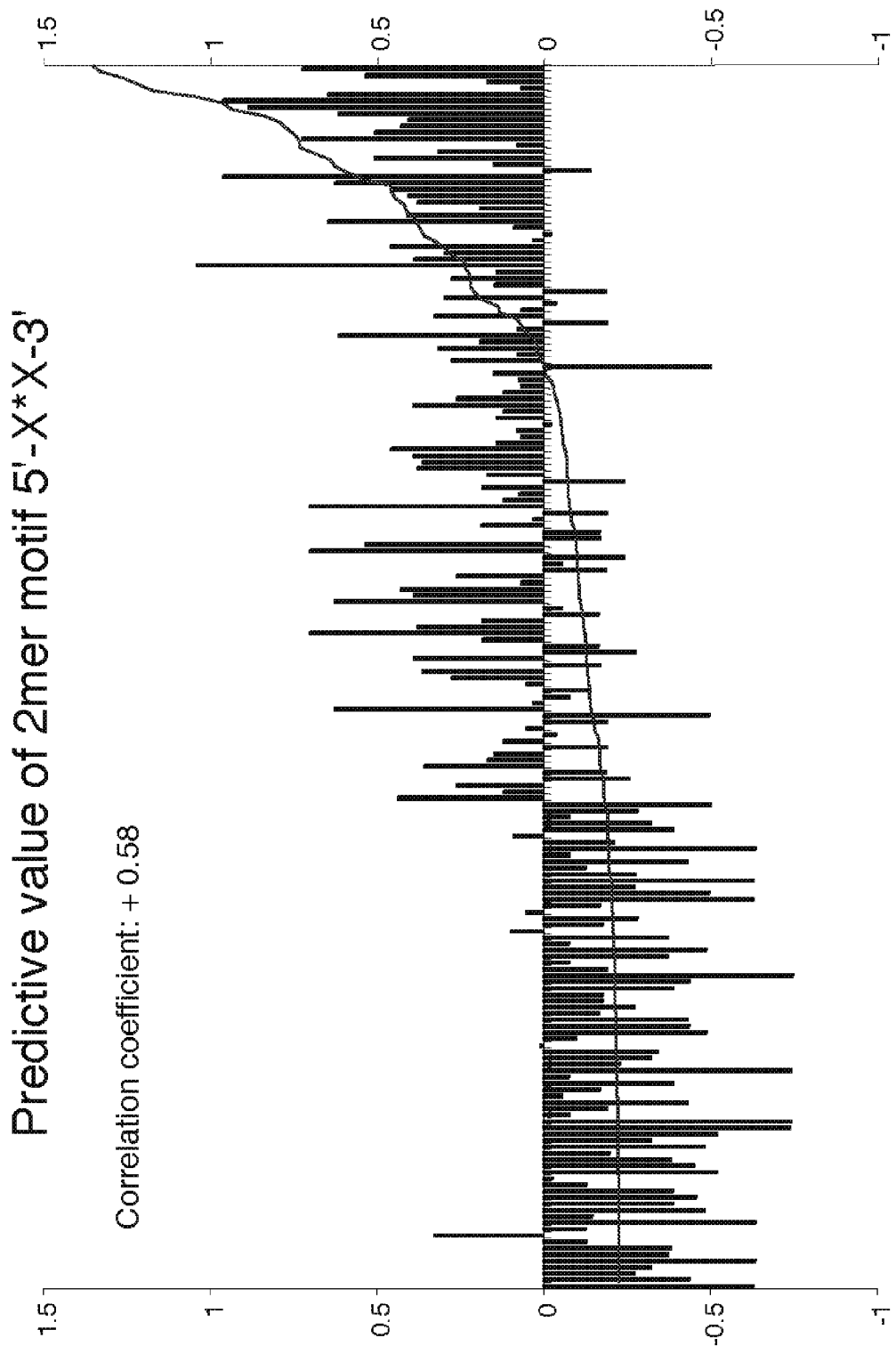
FIG. 6B2

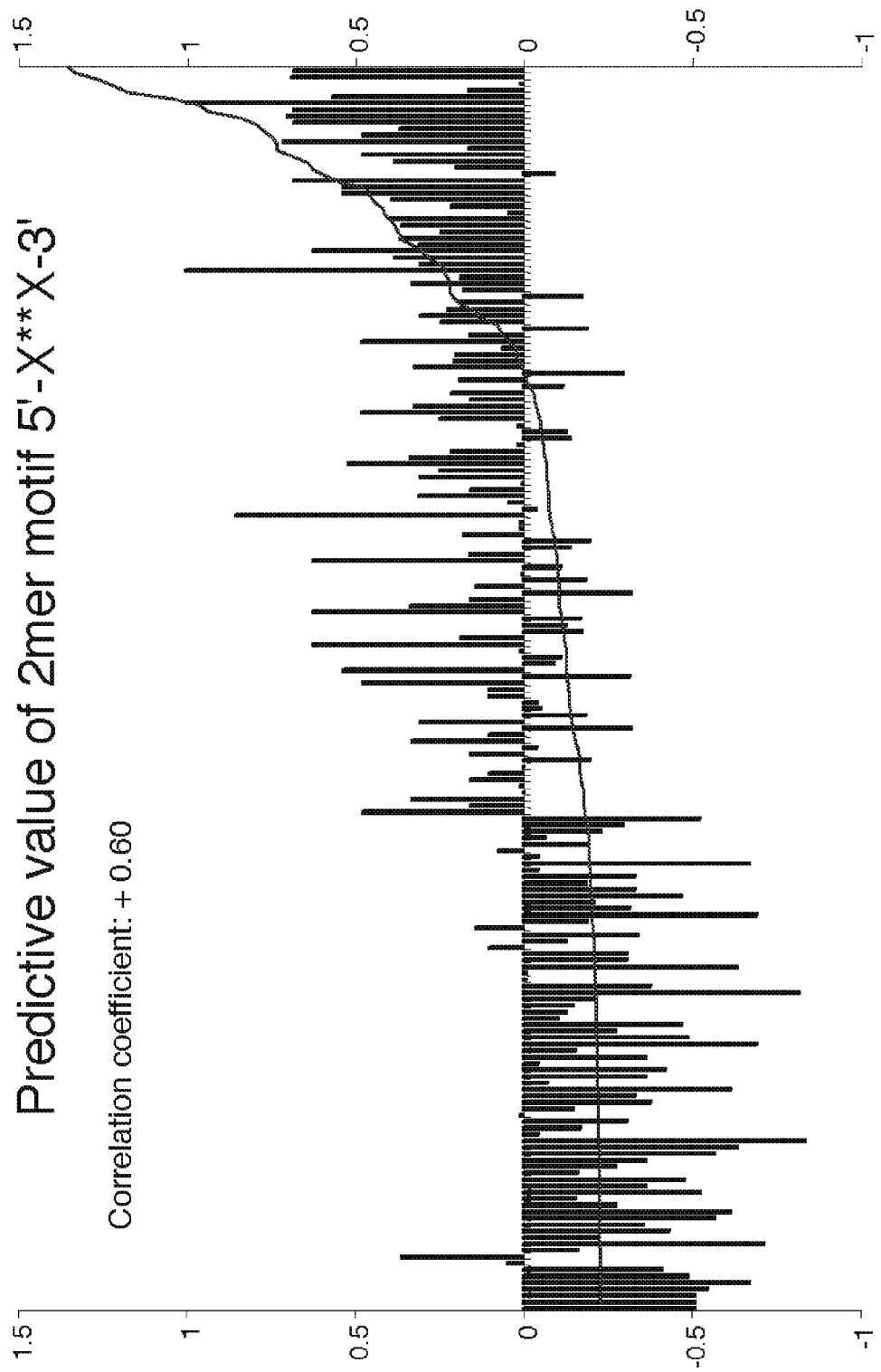
FIG. 6B3

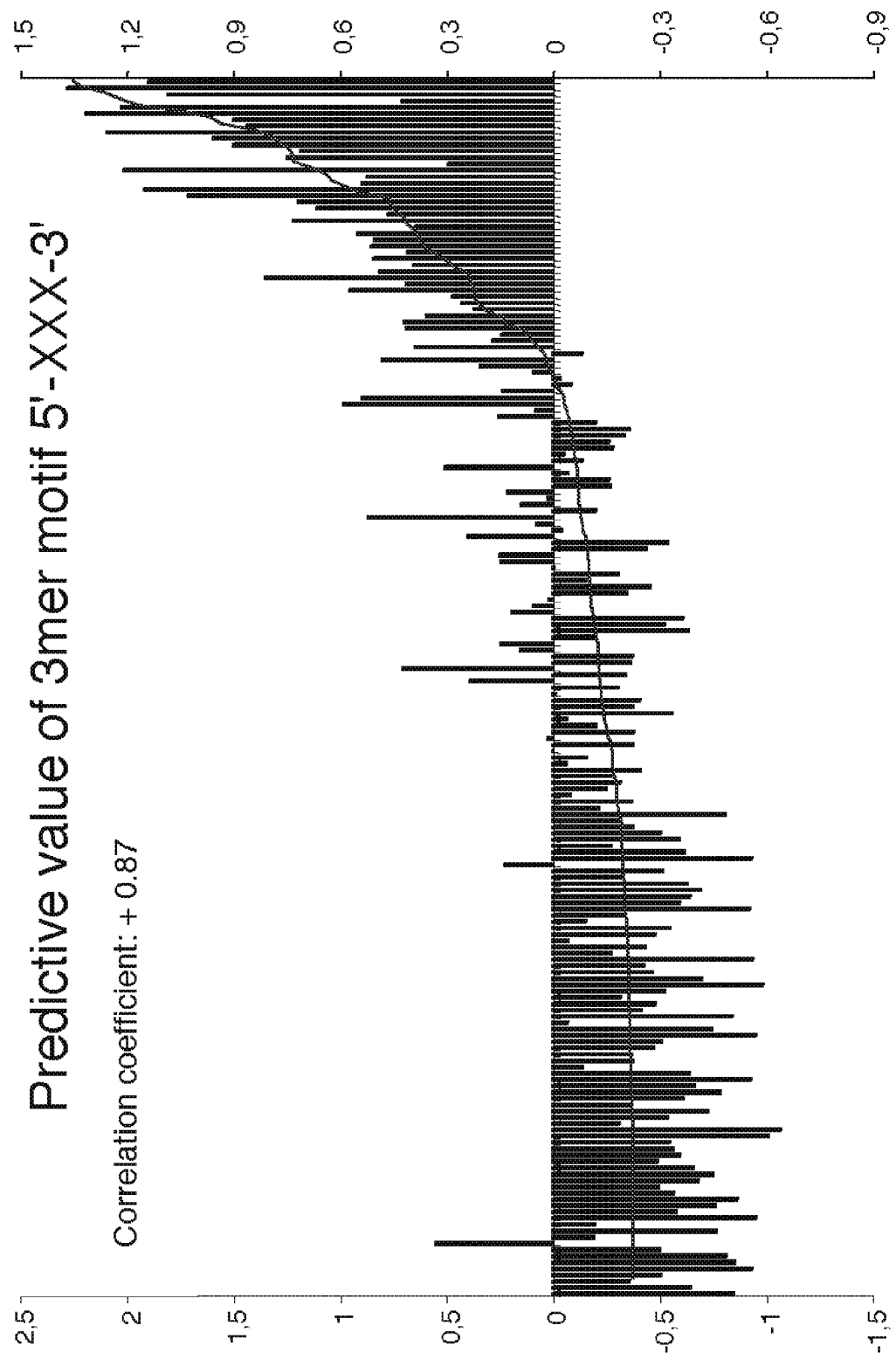
FIG. 6C1

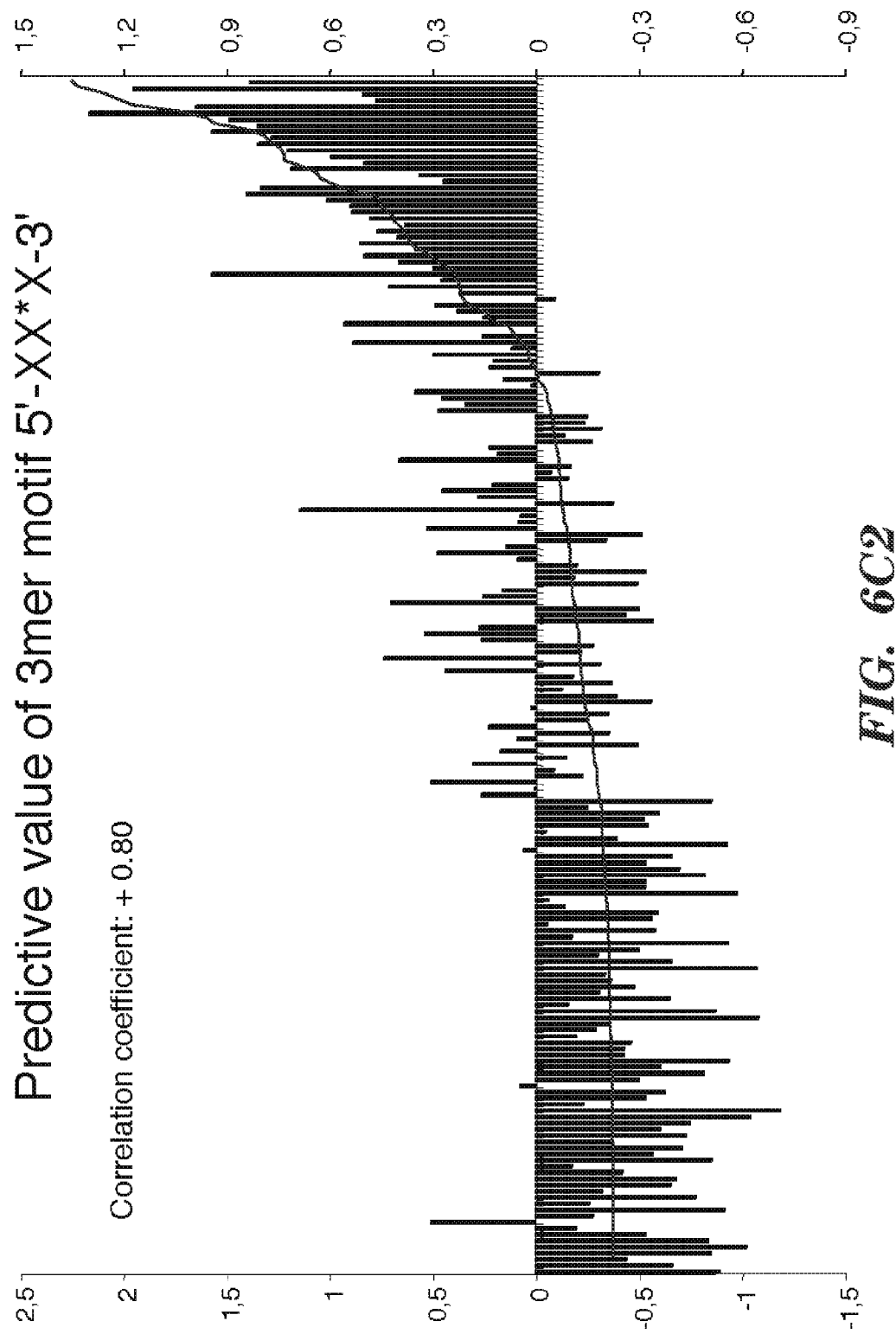
FIG. 6C2

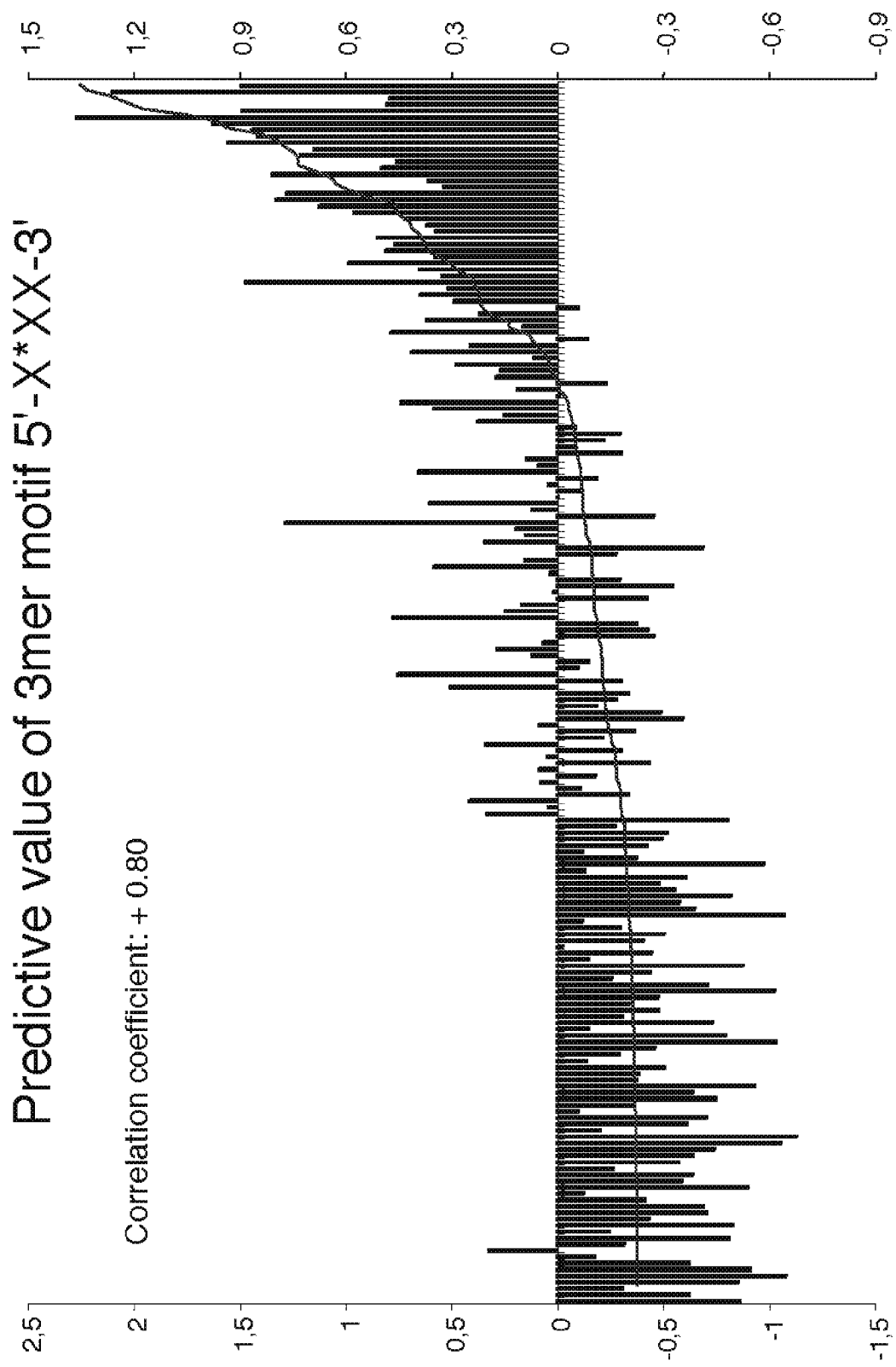
FIG. 6C3

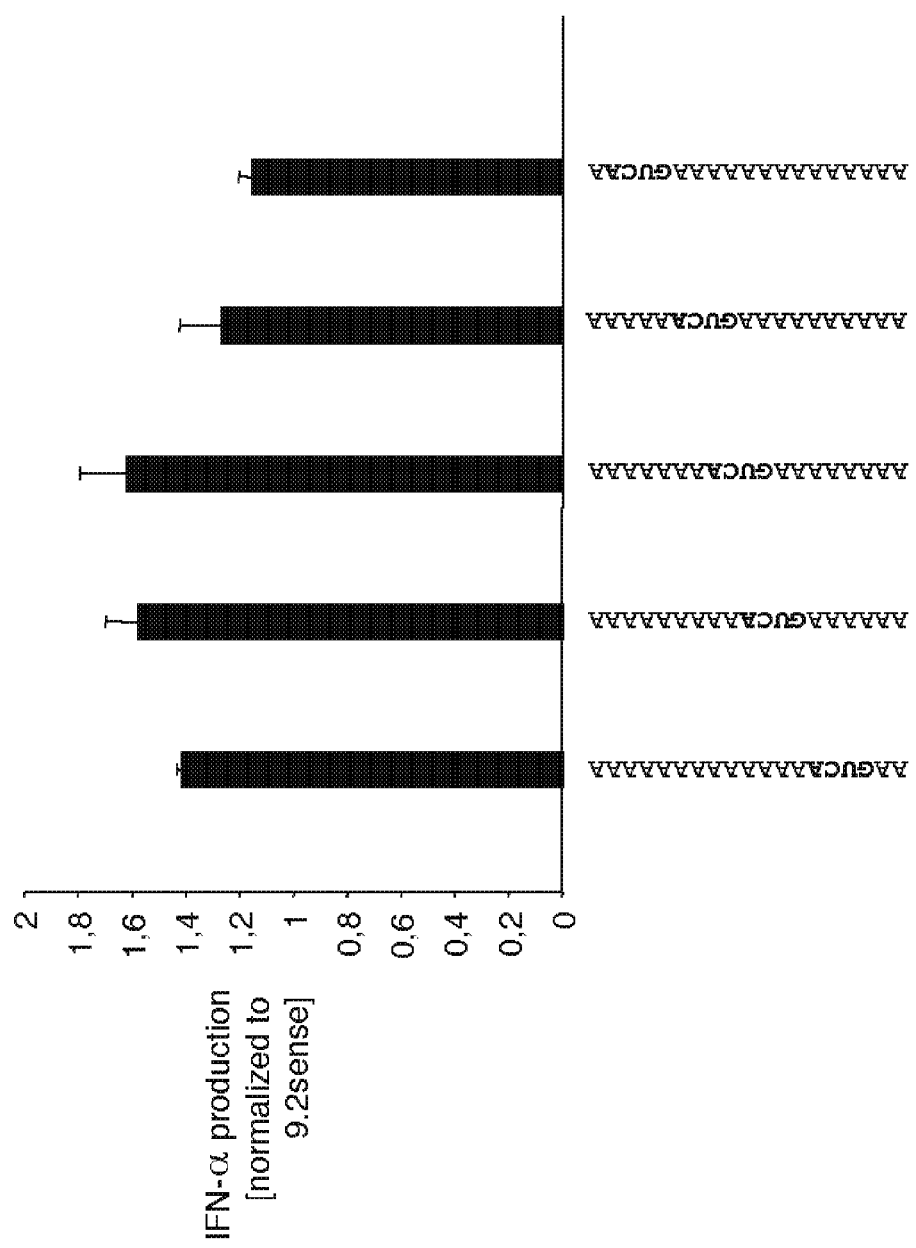

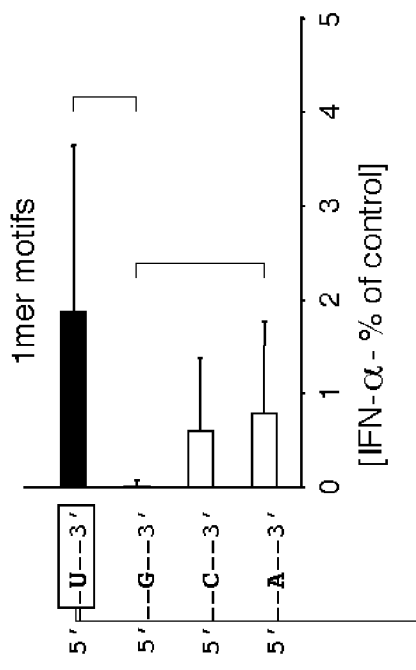
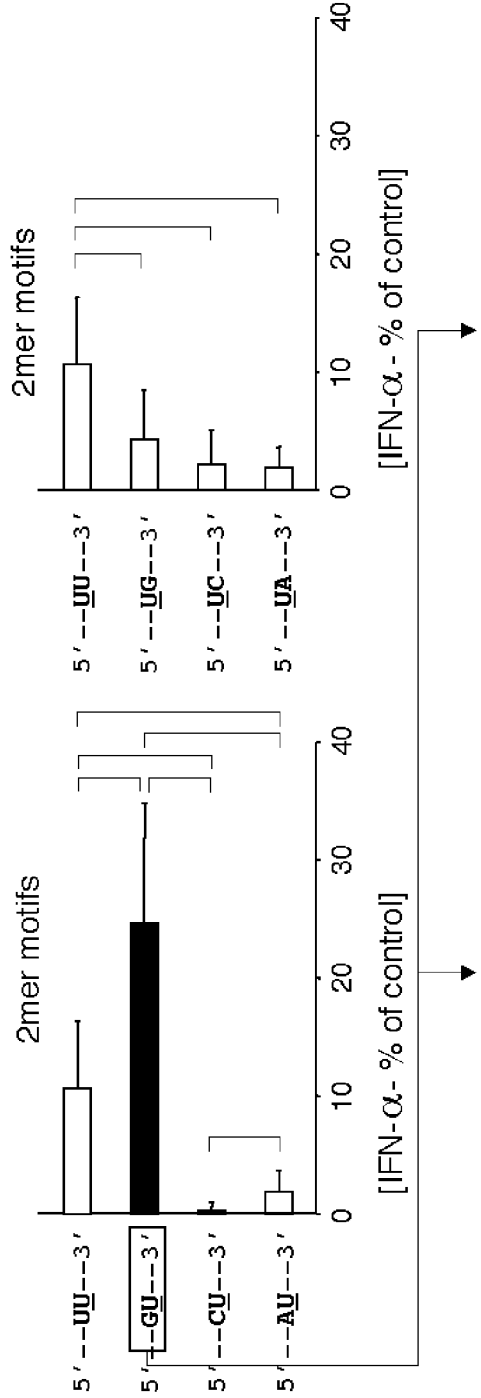
FIG. 9A
FIG. 9B

Alphabetical index for homo sapiens mRNA 1 2 3 4 5 6 7 8 A B C D E F G H I J K L M N O P Q R S T U V

W X Y Z

⬅⬆⬆⬇⬇₁

⬆ Homo sapiens 15 kDa selenoprotein (SEP15), transcript variant 1, mRNA
⬆ Homo sapiens 15 kDa selenoprotein (SEP15), transcript variant 2, mRNA
⬆ Homo sapiens 1-acylglycerol-3-phosphate O-acyltransferase 1 (lysophosphatidic acid acyltransferase, alpha) (AGPAT1), transcript variant 1, mRNA
⬆ Homo sapiens 1-acylglycerol-3-phosphate O-acyltransferase 1 (lysophosphatidic acid acyltransferase, alpha) (AGPAT1), transcript variant 2, mRNA
⬆ Homo sapiens 1-acylglycerol-3-phosphate O-acyltransferase 2 (lysophosphatidic acid acyltransferase, beta) (AGPAT2), transcript variant 1, mRNA

⋮

⬆ Homo sapiens variable charge, X-linked 2 (VCX2), mRNA
⬆ Homo sapiens variable charge, X-linked 3A (VCX3A), mRNA
⬆ Homo sapiens variable charge, Y-linked (VCY), mRNA
⬆ Homo sapiens variable charge, Y-linked 1B (VCY1B), mRNA
⬆ Homo sapiens variably charged X-C (VCX-C), mRNA
⬆ Homo sapiens vascular cell adhesion molecule 1 (VCAM1), transcript variant 1, mRNA
⬆ Homo sapiens vascular cell adhesion molecule 1 (VCAM1), transcript variant 2, mRNA
⬆ Homo sapiens vascular endothelial growth factor (VEGF), transcript variant 1, mRNA
⬆ Homo sapiens vascular endothelial growth factor (VEGF), transcript variant 2, mRNA
⬆ Homo sapiens vascular endothelial growth factor (VEGF), transcript variant 3, mRNA
⬆ Homo sapiens vascular endothelial growth factor (VEGF), transcript variant 4, mRNA
⬆ Homo sapiens vascular endothelial growth factor (VEGF), transcript variant 5, mRNA
⬆ Homo sapiens vascular endothelial growth factor (VEGF), transcript variant 6, mRNA
⬆ Homo sapiens vascular endothelial growth factor (VEGF), transcript variant 7, mRNA
⬆ Homo sapiens vascular endothelial growth factor B (VEGFB), mRNA
⬆ Homo sapiens vascular endothelial growth factor C (VEGFC), mRNA

*FIG. 19A*

PREDICTED IFN-α INDUCTION FOR siRNAS TARGETING hs VEGF TRANSCRIPT VARIANT 1, mRNA
ACESSION NUMBER (NAME OF THE RNA TRANSCRIPT)

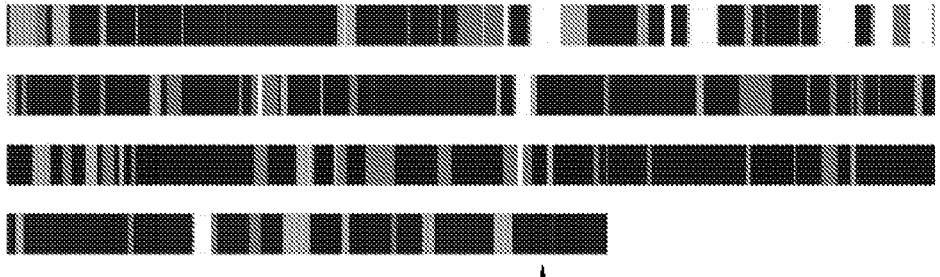

GRAPHICAL DEPICTION OF mRNA:
- ■ BOTH SIRNA STRANDS ABOVE THE THRESHOLD
- ▨ ANTISENSE STRAND BELOW THE THRESHOLD
- ▩ SENSE STRAND THE THRESHOLD
- ☐ BOTH STRANDS BELOW THE THRESHOLD

⬆ Position 00004 of 03665 : value -0,19 (TTGGGGCAGCCGGGTAGCT) - ANTISENSE
Position 00005 of 03665 : value -0,19 (TGGGGCAGCCGGGTAGCTC) - ANTISENSE
Position 00006 of 03665 : value -0,19 (GGGGCAGCCGGGTAGCTCG) - ANTISENSE
Position 00007 of 03665 : value -0,19 (GGGCAGCCGGGTAGCTCGG) - ANTISENSE
Position 00008 of 03665 : value -0,19 (GGCAGCCGGGTAGCTCGGA) - ANTISENSE
Position 00009 of 03665 : value -0,19 (GCAGCCGGGTAGCTCGGAG) - ANTISENSE
Position 00010 of 03665 : value -0,19 (CAGCCGGGTAGCTCGGAGG) - ANTISENSE
Position 00011 of 03665 : value -0,19 (AGCCGGGTAGCTCGGAGGT) - ANTISENSE
Position 00012 of 03665 : value -0,19 (GCCGGGTAGCTCGGAGGTC) - ANTISENSE
Position 00013 of 03665 : value -0,19 (CCGGGTAGCTCGGAGGTCG) - ANTISENSE
Position 00014 of 03665 : value -0,19 (CGGGTAGCTCGGAGGTCGT) - ANTISENSE
Position 00015 of 03665 : value -0,19 (GGGTAGCTCGGAGGTCGTG) - ANTISENSE TO *FIG. 19B (cont.)*

*FIG. 19B*

FROM *FIG. 19B*

Position 00016 of 03665 : value -0,19 (GGTAGCTCGGAGGTCGTGG) - ANTISENSE
Position 00017 of 03665 : value -0,19 (GTAGCTCGGAGGTCGTGGC) - ANTISENSE
Position 00018 of 03665 : value -0,19 (TAGCTCGGAGGTCGTGGCG) - ANTISENSE
Position 00019 of 03665 : value -0,19 (AGCTCGGAGGTCGTGGCGC) - ANTISENSE
Position 00020 of 03665 : value -0,19 (GCTCGGAGGTCGTGGCGCT) - ANTISENSE
Position 00021 of 03665 : value -0,19 (CTCGGAGGTCGTGGCGCTG) - ANTISENSE
Position 00022 of 03665 : value -0,19 (TCGGAGGTCGTGGCGCTGG) - ANTISENSE
Position 00023 of 03665 : value -0,19 (CGGAGGTCGTGGCGCTGGG) - ANTISENSE
Position 00024 of 03665 : value -0,19 (GGAGGTCGTGGCGCTGGGG) - ANTISENSE
Position 00025 of 03665 : value -0,19 (GAGGTCGTGGCGCTGGGGG) - ANTISENSE
Position 00026 of 03665 : value -0,19 (AGGTCGTGGCGCTGGGGGC) - ANTISENSE
Position 00027 of 03665 : value -0,19 (GGTCGTGGCGCTGGGGGCT) - ANTISENSE LIST OF SEQUENCES THAT ARE BELOW THE THRESHOLD:
- POSITION (STARTING BASE OF THE RESPECTIVE SENSE STRAND / TOTAL NUMBER OF BASES)
- VALUE (PREDICTED IFN-α INDUCTION LEVEL FOR THE STRAND BELOW THE THRESHOLD)
- SEQUENCE (BAS SEQUENCE OF THE SENSE STRAND)
- INDICATION WHETHER THE SENSE, THE ANTISENSE OR BOTH STRAND ARE BELOW THE THRESHOLD

SEQUENCE LISTING

<160> NUMBER OF SEQ ID NOS: 390

<210> SEQ ID NO 1
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 1
aaaaaaaaaa aaaaaaaaa                                              19

<210> SEQ ID NO 2
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 2
aaaaaaaaca aaaaaaaaa                                              19

<210> SEQ ID NO 3
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 3
aaaaaaaaga aaaaaaaaa                                              19

```
<210> SEQ ID NO 4
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 4
aaaaaaaaua aaaaaaaaa                                                  19

<210> SEQ ID NO 5
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 5
aaaaaaaacc aaaaaaaaa                                                  19

<210> SEQ ID NO 6
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 6
aaaaaaaacg aaaaaaaaa                                                  19

<210> SEQ ID NO 7
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 7
aaaaaaaacu aaaaaaaaa                                                  19

<210> SEQ ID NO 8
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 8
aaaaaaaagc aaaaaaaaa                                                  19

<210> SEQ ID NO 9
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 9
aaaaaaaagg aaaaaaaaa                                                  19

<210> SEQ ID NO 10
<211> LENGTH: 19
<212> TYPE: RNA
<213> ORGANISM: Artificial
<220> FEATURE:
<223> OTHER INFORMATION: randomized 4 mer motifs on poly A backbone
```

-continued

<400> SEQUENCE: 10
aaaaaaaagu aaaaaaaaa                                                19

<210> SEQ ID NO 11
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 11
aaaaaaaauc aaaaaaaaa                                                19

<210> SEQ ID NO 12
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 12
aaaaaaaaug aaaaaaaaa                                                19

<210> SEQ ID NO 13
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 13
aaaaaaaauu aaaaaaaaa                                                19

<210> SEQ ID NO 14
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 14
aaaaaaaaca caaaaaaaa                                                19

<210> SEQ ID NO 15
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 15
aaaaaaaaca gaaaaaaaa                                                19

<210> SEQ ID NO 16
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 16
aaaaaaaaca uaaaaaaaa                                                19

<210> SEQ ID NO 17
<211> LENGTH: 19

```
<212> TYPE: RNA
<213> ORGANISM: Artificial
<220> FEATURE:
<223> OTHER INFORMATION: randomized 4 mer motifs on poly A backbone

<400> SEQUENCE: 17
aaaaaaaacc caaaaaaaa                                                    19

<210> SEQ ID NO 18
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 18
aaaaaaaacc gaaaaaaaa                                                    19

<210> SEQ ID NO 19
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 19
aaaaaaaacc uaaaaaaaa                                                    19

<210> SEQ ID NO 20
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 20
aaaaaaaacg caaaaaaaa                                                    19

<210> SEQ ID NO 21
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 21
aaaaaaaacg gaaaaaaaa                                                    19

<210> SEQ ID NO 22
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 22
aaaaaaaacg uaaaaaaaa                                                    19

<210> SEQ ID NO 23
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 23
aaaaaaaacu caaaaaaaa                                                    19
```

<210> SEQ ID NO 24
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 24
aaaaaaaacu gaaaaaaaa                                               19

<210> SEQ ID NO 25
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 25
aaaaaaaacu uaaaaaaaa                                               19

<210> SEQ ID NO 26
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 26
aaaaaaaaga caaaaaaaa                                               19

<210> SEQ ID NO 27
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 27
aaaaaaaaga gaaaaaaaa                                               19

<210> SEQ ID NO 28
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 28
aaaaaaaaga uaaaaaaaa                                               19

<210> SEQ ID NO 29
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 29
aaaaaaaagc caaaaaaaa                                               19

<210> SEQ ID NO 30
<211> LENGTH: 19
<212> TYPE: RNA
<213> ORGANISM: Artificial
<220> FEATURE:
<223> OTHER INFORMATION: randomized 4 mer motifs on poly A backbone -continued

<400> SEQUENCE: 30
aaaaaaaagc gaaaaaaaa                                              19

<210> SEQ ID NO 31
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 31
aaaaaaaagc uaaaaaaaa                                              19

<210> SEQ ID NO 32
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 32
aaaaaaaagg caaaaaaaa                                              19

<210> SEQ ID NO 33
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 33
aaaaaaaagg gaaaaaaaa                                              19

<210> SEQ ID NO 34
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 34
aaaaaaaagg uaaaaaaaa                                              19

<210> SEQ ID NO 35
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 35
aaaaaaaagu caaaaaaaa                                              19

<210> SEQ ID NO 36
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 36
aaaaaaaagu gaaaaaaaa                                              19

<210> SEQ ID NO 37
<211> LENGTH: 19

```
<212> TYPE: RNA
<213> ORGANISM: Artificial
<220> FEATURE:
<223> OTHER INFORMATION: randomized 4 mer motifs on poly A backbone

<400> SEQUENCE: 37
aaaaaaaagu uaaaaaaaa                                                      19

<210> SEQ ID NO 38
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 38
aaaaaaaaua caaaaaaaa                                                      19

<210> SEQ ID NO 39
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 39
aaaaaaaaua gaaaaaaaa                                                      19

<210> SEQ ID NO 40
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 40
aaaaaaaaua uaaaaaaaa                                                      19

<210> SEQ ID NO 41
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 41
aaaaaaaauc caaaaaaaa                                                      19

<210> SEQ ID NO 42
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 42
aaaaaaaauc gaaaaaaaa                                                      19

<210> SEQ ID NO 43
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 43
aaaaaaaauc uaaaaaaaa                                                      19
```

```
<210> SEQ ID NO 44
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 44
aaaaaaaaug caaaaaaaa                                              19

<210> SEQ ID NO 45
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 45
aaaaaaaaug gaaaaaaaa                                              19

<210> SEQ ID NO 46
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 46
aaaaaaaaug uaaaaaaaa                                              19

<210> SEQ ID NO 47
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 47
aaaaaaaauu caaaaaaaa                                              19

<210> SEQ ID NO 48
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 48
aaaaaaaauu gaaaaaaaa                                              19

<210> SEQ ID NO 49
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 49
aaaaaaaauu uaaaaaaaa                                              19

<210> SEQ ID NO 50
<211> LENGTH: 19
<212> TYPE: RNA
<213> ORGANISM: Artificial
<220> FEATURE:
<223> OTHER INFORMATION: randomized 4 mer motifs on poly A backbone
```

```
<400> SEQUENCE: 50
aaaaaaacaa caaaaaaaa                                                      19

<210> SEQ ID NO 51
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 51
aaaaaaacaa gaaaaaaaa                                                      19

<210> SEQ ID NO 52
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 52
aaaaaaacaa uaaaaaaaa                                                      19

<210> SEQ ID NO 53
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 53
aaaaaaacac caaaaaaaa                                                      19

<210> SEQ ID NO 54
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 54
aaaaaaacac gaaaaaaaa                                                      19

<210> SEQ ID NO 55
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 55
aaaaaaacac uaaaaaaaa                                                      19

<210> SEQ ID NO 56
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 56
aaaaaaacag caaaaaaaa                                                      19

<210> SEQ ID NO 57
<211> LENGTH: 19
```

```
<212> TYPE: RNA
<213> ORGANISM: Artificial
<220> FEATURE:
<223> OTHER INFORMATION: randomized 4 mer motifs on poly A backbone

<400> SEQUENCE: 57
aaaaaaacag gaaaaaaaa                                                  19

<210> SEQ ID NO 58
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 58
aaaaaaacag uaaaaaaaa                                                  19

<210> SEQ ID NO 59
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 59
aaaaaaacau caaaaaaaa                                                  19

<210> SEQ ID NO 60
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 60
aaaaaaacau gaaaaaaaa                                                  19

<210> SEQ ID NO 61
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 61
aaaaaaacau uaaaaaaaa                                                  19

<210> SEQ ID NO 62
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 62
aaaaaaacca caaaaaaaa                                                  19

<210> SEQ ID NO 63
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 63
aaaaaaacca gaaaaaaaa                                                  19
```

```
<210> SEQ ID NO 64
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 64
aaaaaaacca uaaaaaaa                                                19

<210> SEQ ID NO 65
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 65
aaaaaaaccc caaaaaaa                                                19

<210> SEQ ID NO 66
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 66
aaaaaaaccc gaaaaaaa                                                19

<210> SEQ ID NO 67
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 67
aaaaaaaccc uaaaaaaa                                                19

<210> SEQ ID NO 68
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 68
aaaaaaaccg caaaaaaa                                                19

<210> SEQ ID NO 69
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 69
aaaaaaaccg gaaaaaaa                                                19

<210> SEQ ID NO 70
<211> LENGTH: 19
<212> TYPE: RNA
<213> ORGANISM: Artificial
<220> FEATURE:
<223> OTHER INFORMATION: randomized 4 mer motifs on poly A backbone
```

```
<400> SEQUENCE: 70
aaaaaaaccg uaaaaaaa                                              19

<210> SEQ ID NO 71
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 71
aaaaaaaccu caaaaaaa                                              19

<210> SEQ ID NO 72
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 72
aaaaaaaccu gaaaaaaa                                              19

<210> SEQ ID NO 73
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 73
aaaaaaaccu uaaaaaaa                                              19

<210> SEQ ID NO 74
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 74
aaaaaaacga caaaaaaa                                              19

<210> SEQ ID NO 75
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 75
aaaaaaacga gaaaaaaa                                              19

<210> SEQ ID NO 76
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 76
aaaaaaacga uaaaaaaa                                              19

<210> SEQ ID NO 77
<211> LENGTH: 19
```

```
<212> TYPE: RNA
<213> ORGANISM: Artificial
<220> FEATURE:
<223> OTHER INFORMATION: randomized 4 mer motifs on poly A backbone

<400> SEQUENCE: 77
aaaaaaacgc caaaaaaaa                                              19

<210> SEQ ID NO 78
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 78
aaaaaaacgc gaaaaaaaa                                              19

<210> SEQ ID NO 79
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 79
aaaaaaacgc uaaaaaaaa                                              19

<210> SEQ ID NO 80
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 80
aaaaaaacgg caaaaaaaa                                              19

<210> SEQ ID NO 81
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 81
aaaaaaacgg gaaaaaaaa                                              19

<210> SEQ ID NO 82
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 82
aaaaaaacgg uaaaaaaaa                                              19

<210> SEQ ID NO 83
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 83
aaaaaaacgu caaaaaaaa                                              19
```

<210> SEQ ID NO 84
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 84
aaaaaaacgu gaaaaaaaa                                                19

<210> SEQ ID NO 85
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 85
aaaaaaacgu uaaaaaaaa                                                19

<210> SEQ ID NO 86
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 86
aaaaaaacua caaaaaaaa                                                19

<210> SEQ ID NO 87
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 87
aaaaaaacua gaaaaaaaa                                                19

<210> SEQ ID NO 88
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 88
aaaaaaacua uaaaaaaaa                                                19

<210> SEQ ID NO 89
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 89
aaaaaaacuc caaaaaaaa                                                19

<210> SEQ ID NO 90
<211> LENGTH: 19
<212> TYPE: RNA
<213> ORGANISM: Artificial
<220> FEATURE:
<223> OTHER INFORMATION: randomized 4 mer motifs on poly A backbone

```
<400> SEQUENCE: 90
aaaaaaacuc gaaaaaaa                                                19

<210> SEQ ID NO 91
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 91
aaaaaaacuc uaaaaaaa                                                19

<210> SEQ ID NO 92
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 92
aaaaaaacug caaaaaaa                                                19

<210> SEQ ID NO 93
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 93
aaaaaaacug gaaaaaaa                                                19

<210> SEQ ID NO 94
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 94
aaaaaaacug uaaaaaaa                                                19

<210> SEQ ID NO 95
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 95
aaaaaaacuu caaaaaaa                                                19

<210> SEQ ID NO 96
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 96
aaaaaaacuu gaaaaaaa                                                19

<210> SEQ ID NO 97
<211> LENGTH: 19
```

-continued

<212> TYPE: RNA
<213> ORGANISM: Artificial
<220> FEATURE:
<223> OTHER INFORMATION: randomized 4 mer motifs on poly A backbone

<400> SEQUENCE: 97
aaaaaaacuu uaaaaaaaa                                                19

<210> SEQ ID NO 98
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 98
aaaaaaagaa caaaaaaaa                                                19

<210> SEQ ID NO 99
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 99
aaaaaaagaa gaaaaaaaa                                                19

<210> SEQ ID NO 100
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 100
aaaaaaagaa uaaaaaaaa                                                19

<210> SEQ ID NO 101
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 101
aaaaaaagac caaaaaaaa                                                19

<210> SEQ ID NO 102
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 102
aaaaaaagac gaaaaaaaa                                                19

<210> SEQ ID NO 103
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 103
aaaaaaagac uaaaaaaaa                                                19

<210> SEQ ID NO 104
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 104
aaaaaaagag caaaaaaaa					19

<210> SEQ ID NO 105
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 105
aaaaaaagag gaaaaaaaa					19

<210> SEQ ID NO 106
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 106
aaaaaaagag uaaaaaaaa					19

<210> SEQ ID NO 107
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 107
aaaaaaagau caaaaaaaa					19

<210> SEQ ID NO 108
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 108
aaaaaaagau gaaaaaaaa					19

<210> SEQ ID NO 109
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 109
aaaaaaagau uaaaaaaaa					19

<210> SEQ ID NO 110
<211> LENGTH: 19
<212> TYPE: RNA
<213> ORGANISM: Artificial
<220> FEATURE:
<223> OTHER INFORMATION: randomized 4 mer motifs on poly A backbone -continued

```
<400> SEQUENCE: 110
aaaaaaagca caaaaaaa                                             19

<210> SEQ ID NO 111
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 111
aaaaaaagca gaaaaaaa                                             19

<210> SEQ ID NO 112
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 112
aaaaaaagca uaaaaaaa                                             19

<210> SEQ ID NO 113
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 113
aaaaaaagcc caaaaaaa                                             19

<210> SEQ ID NO 114
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 114
aaaaaaagcc gaaaaaaa                                             19

<210> SEQ ID NO 115
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 115
aaaaaaagcc uaaaaaaa                                             19

<210> SEQ ID NO 116
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 116
aaaaaaagcg caaaaaaa                                             19

<210> SEQ ID NO 117
<211> LENGTH: 19
```

```
<212> TYPE: RNA
<213> ORGANISM: Artificial
<220> FEATURE:
<223> OTHER INFORMATION: randomized 4 mer motifs on poly A backbone

<400> SEQUENCE: 117
aaaaaaagcg gaaaaaaaa                                                19

<210> SEQ ID NO 118
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 118
aaaaaaagcg uaaaaaaaa                                                19

<210> SEQ ID NO 119
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 119
aaaaaaagcu caaaaaaaa                                                19

<210> SEQ ID NO 120
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 120
aaaaaaagcu gaaaaaaaa                                                19

<210> SEQ ID NO 121
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 121
aaaaaaagcu uaaaaaaaa                                                19

<210> SEQ ID NO 122
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 122
aaaaaaagga caaaaaaaa                                                19

<210> SEQ ID NO 123
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 123
aaaaaaagga gaaaaaaaa                                                19
```

<210> SEQ ID NO 124
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 124
aaaaaaagga uaaaaaaa                                                19

<210> SEQ ID NO 125
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 125
aaaaaaaggc caaaaaaa                                                19

<210> SEQ ID NO 126
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 126
aaaaaaaggc gaaaaaaa                                                19

<210> SEQ ID NO 127
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 127
aaaaaaaggc uaaaaaaa                                                19

<210> SEQ ID NO 128
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 128
aaaaaaaggg caaaaaaa                                                19

<210> SEQ ID NO 129
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 129
aaaaaaaggg gaaaaaaa                                                19

<210> SEQ ID NO 130
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 130
aaaaaaaggg uaaaaaaa                                              19

<210> SEQ ID NO 131
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 131
aaaaaaaggu caaaaaaa                                              19

<210> SEQ ID NO 132
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 132
aaaaaaaggu gaaaaaaa                                              19

<210> SEQ ID NO 133
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 133
aaaaaaaggu uaaaaaaa                                              19

<210> SEQ ID NO 134
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 134
aaaaaaagua caaaaaaa                                              19

<210> SEQ ID NO 135
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 135
aaaaaaagua gaaaaaaa                                              19

<210> SEQ ID NO 136
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 136
aaaaaaagua uaaaaaaa                                              19

<210> SEQ ID NO 137
<211> LENGTH: 19

```
<212> TYPE: RNA
<213> ORGANISM: Artificial
<220> FEATURE:
<223> OTHER INFORMATION: randomized 4 mer motifs on poly A backbone

<400> SEQUENCE: 137
aaaaaaaguc caaaaaaaa                                                    19

<210> SEQ ID NO 138
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 138
aaaaaaaguc gaaaaaaaa                                                    19

<210> SEQ ID NO 139
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 139
aaaaaaaguc uaaaaaaaa                                                    19

<210> SEQ ID NO 140
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 140
aaaaaaagug caaaaaaaa                                                    19

<210> SEQ ID NO 141
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 141
aaaaaaagug gaaaaaaaa                                                    19

<210> SEQ ID NO 142
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 142
aaaaaaagug uaaaaaaaa                                                    19

<210> SEQ ID NO 143
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 143
aaaaaaaguu caaaaaaaa                                                    19
```

```
<210> SEQ ID NO 144
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 144
aaaaaaaguu gaaaaaaaa                                                    19

<210> SEQ ID NO 145
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 145
aaaaaaaguu uaaaaaaaa                                                    19

<210> SEQ ID NO 146
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 146
aaaaaaauaa caaaaaaaa                                                    19

<210> SEQ ID NO 147
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 147
aaaaaaauaa gaaaaaaaa                                                    19

<210> SEQ ID NO 148
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 148
aaaaaaauaa uaaaaaaaa                                                    19

<210> SEQ ID NO 149
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 149
aaaaaaauac caaaaaaaa                                                    19

<210> SEQ ID NO 150
<211> LENGTH: 19
<212> TYPE: RNA
<213> ORGANISM: Artificial
<220> FEATURE:
<223> OTHER INFORMATION: randomized 4 mer motifs on poly A backbone
```

```
<400> SEQUENCE: 150
aaaaaaauac gaaaaaaa                                              19

<210> SEQ ID NO 151
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 151
aaaaaaauac uaaaaaaa                                              19

<210> SEQ ID NO 152
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 152
aaaaaaauag caaaaaaa                                              19

<210> SEQ ID NO 153
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 153
aaaaaaauag gaaaaaaa                                              19

<210> SEQ ID NO 154
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 154
aaaaaaauag uaaaaaaa                                              19

<210> SEQ ID NO 155
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 155
aaaaaaauau caaaaaaa                                              19

<210> SEQ ID NO 156
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 156
aaaaaaauau gaaaaaaa                                              19

<210> SEQ ID NO 157
<211> LENGTH: 19
```

```
<212> TYPE: RNA
<213> ORGANISM: Artificial
<220> FEATURE:
<223> OTHER INFORMATION: randomized 4 mer motifs on poly A backbone

<400> SEQUENCE: 157
aaaaaaauau uaaaaaaaa                                               19

<210> SEQ ID NO 158
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 158
aaaaaaauca caaaaaaaa                                               19

<210> SEQ ID NO 159
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 159
aaaaaaauca gaaaaaaaa                                               19

<210> SEQ ID NO 160
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 160
aaaaaaauca uaaaaaaaa                                               19

<210> SEQ ID NO 161
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 161
aaaaaaaucc caaaaaaaa                                               19

<210> SEQ ID NO 162
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 162
aaaaaaaucc gaaaaaaaa                                               19

<210> SEQ ID NO 163
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 163
aaaaaaaucc uaaaaaaaa                                               19
```

```
<210> SEQ ID NO 164
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 164
aaaaaaaucg caaaaaaaa                                                   19

<210> SEQ ID NO 165
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 165
aaaaaaaucg gaaaaaaaa                                                   19

<210> SEQ ID NO 166
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 166
aaaaaaaucg uaaaaaaaa                                                   19

<210> SEQ ID NO 167
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 167
aaaaaaaucu caaaaaaaa                                                   19

<210> SEQ ID NO 168
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 168
aaaaaaaucu gaaaaaaaa                                                   19

<210> SEQ ID NO 169
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 169
aaaaaaaucu uaaaaaaaa                                                   19

<210> SEQ ID NO 170
<211> LENGTH: 19
<212> TYPE: RNA
<213> ORGANISM: Artificial
<220> FEATURE:
<223> OTHER INFORMATION: randomized 4 mer motifs on poly A backbone
```

```
<400> SEQUENCE: 170
aaaaaaauga caaaaaaaa                                              19

<210> SEQ ID NO 171
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 171
aaaaaaauga gaaaaaaaa                                              19

<210> SEQ ID NO 172
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 172
aaaaaaauga uaaaaaaaa                                              19

<210> SEQ ID NO 173
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 173
aaaaaaaugc caaaaaaaa                                              19

<210> SEQ ID NO 174
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 174
aaaaaaaugc gaaaaaaaa                                              19

<210> SEQ ID NO 175
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 175
aaaaaaaugc uaaaaaaaa                                              19

<210> SEQ ID NO 176
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 176
aaaaaaaugg caaaaaaaa                                              19

<210> SEQ ID NO 177
<211> LENGTH: 19
```

```
<212> TYPE: RNA
<213> ORGANISM: Artificial
<220> FEATURE:
<223> OTHER INFORMATION: randomized 4 mer motifs on poly A backbone

<400> SEQUENCE: 177
aaaaaaaugg gaaaaaaaa                                               19

<210> SEQ ID NO 178
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 178
aaaaaaaugg uaaaaaaaa                                               19

<210> SEQ ID NO 179
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 179
aaaaaaaugu caaaaaaaa                                               19

<210> SEQ ID NO 180
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 180
aaaaaaaugu gaaaaaaaa                                               19

<210> SEQ ID NO 181
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 181
aaaaaaaugu uaaaaaaaa                                               19

<210> SEQ ID NO 182
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 182
aaaaaaauua caaaaaaaa                                               19

<210> SEQ ID NO 183
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 183
aaaaaaauua gaaaaaaaa                                               19
```

<210> SEQ ID NO 184
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 184
aaaaaaauua uaaaaaaaa                                                19

<210> SEQ ID NO 185
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 185
aaaaaaauuc caaaaaaaa                                                19

<210> SEQ ID NO 186
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 186
aaaaaaauuc gaaaaaaaa                                                19

<210> SEQ ID NO 187
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 187
aaaaaaauuc uaaaaaaaa                                                19

<210> SEQ ID NO 188
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 188
aaaaaaauug caaaaaaaa                                                19

<210> SEQ ID NO 189
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 189
aaaaaaauug gaaaaaaaa                                                19

<210> SEQ ID NO 190
<211> LENGTH: 19
<212> TYPE: RNA
<213> ORGANISM: Artificial
<220> FEATURE:
<223> OTHER INFORMATION: randomized 4 mer motifs on poly A backbone

```
<400> SEQUENCE: 190
aaaaaaauug uaaaaaaa                                             19

<210> SEQ ID NO 191
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 191
aaaaaaauuu caaaaaaa                                             19

<210> SEQ ID NO 192
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 192
aaaaaaauuu gaaaaaaa                                             19

<210> SEQ ID NO 193
<211> LENGTH: 19
<212> TYPE: RNA
<213> ORGANISM: Artificial
<220> FEATURE:
<223> OTHER INFORMATION: randomized 4 mer motifs on poly A backbone

<400> SEQUENCE: 193
aaaaaaauuu uaaaaaaa                                             19

<210> SEQ ID NO 194
<211> LENGTH: 19
<212> TYPE: RNA
<213> ORGANISM: Artificial
<220> FEATURE:
<223> OTHER INFORMATION: different positions of the GUCA motif on poly A
      backbone

<400> SEQUENCE: 194
aagucaaaaa aaaaaaaa                                             19

<210> SEQ ID NO 195
<211> LENGTH: 19
<212> TYPE: RNA
<213> ORGANISM: Artificial
<220> FEATURE:
<223> OTHER INFORMATION: different positions of the GUCA motif on poly A
      backbone

<400> SEQUENCE: 195
aaaaaaguca aaaaaaaa                                             19

<210> SEQ ID NO 196
<211> LENGTH: 19
<212> TYPE: RNA
<213> ORGANISM: Artificial
<220> FEATURE:
<223> OTHER INFORMATION: different positions of the GUCA motif on poly A
      backbone

<400> SEQUENCE: 196
aaaaaaaagu caaaaaaa                                             19
```

```
<210> SEQ ID NO 197
<211> LENGTH: 19
<212> TYPE: RNA
<213> ORGANISM: Artificial
<220> FEATURE:
<223> OTHER INFORMATION: different positions of the GUCA motif on poly A
      backbone

<400> SEQUENCE: 197
aaaaaaaaaa gucaaaaaa                                                19

<210> SEQ ID NO 198
<211> LENGTH: 19
<212> TYPE: RNA
<213> ORGANISM: Artificial
<220> FEATURE:
<223> OTHER INFORMATION: different positions of the GUCA motif on poly A
      backbone

<400> SEQUENCE: 198
aaaaaaaaaa aaagucaa                                                 19

<210> SEQ ID NO 199
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 199
aaaaaaaagu caaaaaaaa                                                19

<210> SEQ ID NO 200
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 200
aaaaaaaagu cacaaaaaa                                                19

<210> SEQ ID NO 201
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 201
aaaaaaaagu cagaaaaaa                                                19

<210> SEQ ID NO 202
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 202
aaaaaaaagu cauaaaaaa                                                19

<210> SEQ ID NO 203
```

```
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 203
aaaaaaacgu caaaaaaaa                                                       19

<210> SEQ ID NO 204
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 204
aaaaaaacgu cacaaaaaa                                                       19

<210> SEQ ID NO 205
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 205
aaaaaaacgu cagaaaaaa                                                       19

<210> SEQ ID NO 206
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 206
aaaaaaacgu cauaaaaaa                                                       19

<210> SEQ ID NO 207
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 207
aaaaaaaggu caaaaaaaa                                                       19

<210> SEQ ID NO 208
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 208
aaaaaaaggu cacaaaaaa                                                       19

<210> SEQ ID NO 209
<211> LENGTH: 19
<212> TYPE: RNA
```

<210> SEQ ID NO 209
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 209
aaaaaaaggu cagaaaaaa                                           19

<210> SEQ ID NO 210
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 210
aaaaaaaggu cauaaaaaa                                           19

<210> SEQ ID NO 211
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 211
aaaaaaaugu caaaaaaaa                                           19

<210> SEQ ID NO 212
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 212
aaaaaaaugu cacaaaaaa                                           19

<210> SEQ ID NO 213
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 213
aaaaaaaugu cagaaaaaa                                           19

<210> SEQ ID NO 214
<211> LENGTH: 19
<212> TYPE: RNA
<213> ORGANISM: Artificial
<220> FEATURE:
<223> OTHER INFORMATION: single base permutations to the 5' and the 3'
      end of GUCA motif on poly A backbone

<400> SEQUENCE: 214
aaaaaaaugu cauaaaaaa                                           19

<210> SEQ ID NO 215
<211> LENGTH: 19
<212> TYPE: RNA
<213> ORGANISM: Artificial
<220> FEATURE:

-continued

<223> OTHER INFORMATION: sense strand of siRNA specific for human TLR9 with the starting base 1647 (siRNA9.2)

<400> SEQUENCE: 215
agcuuaaccu guccuucaa                                    19

<210> SEQ ID NO 216
<211> LENGTH: 19
<212> TYPE: RNA
<213> ORGANISM: Artificial
<220> FEATURE:
<223> OTHER INFORMATION: poly A modification of the sense strand of siRNA specific for human TLR9 with the starting base 1647 (siRNA9.2)

<400> SEQUENCE: 216
aaaaaaaccu guccuucaa                                    19

<210> SEQ ID NO 217
<211> LENGTH: 19
<212> TYPE: RNA
<213> ORGANISM: Artificial
<220> FEATURE:
<223> OTHER INFORMATION: poly A modification of the sense strand of siRNA specific for human TLR9 with the starting base 1647 (siRNA9.2)

<400> SEQUENCE: 217
aaaaaaaacu guccuucaa                                    19

<210> SEQ ID NO 218
<211> LENGTH: 19
<212> TYPE: RNA
<213> ORGANISM: Artificial
<220> FEATURE:
<223> OTHER INFORMATION: poly A modification of the sense strand of siRNA specific for human TLR9 with the starting base 1647 (siRNA9.2)

<400> SEQUENCE: 218
aaaaaaaaau guccuucaa                                    19

<210> SEQ ID NO 219
<211> LENGTH: 19
<212> TYPE: RNA
<213> ORGANISM: Artificial
<220> FEATURE:
<223> OTHER INFORMATION: poly A modification of the sense strand of siRNA specific for human TLR9 with the starting base 1647 (siRNA9.2)

<400> SEQUENCE: 219
aaaaaaaaaa guccuucaa                                    19

<210> SEQ ID NO 220
<211> LENGTH: 19
<212> TYPE: RNA
<213> ORGANISM: Artificial
<220> FEATURE:
<223> OTHER INFORMATION: poly A modification of the sense strand of siRNA specific for human TLR9 with the starting base 1647 (siRNA9.2)

<400> SEQUENCE: 220
aaaaaaaaaa auccuucaa                                    19

<210> SEQ ID NO 221
<211> LENGTH: 19

```
<212> TYPE: RNA
<213> ORGANISM: Artificial
<220> FEATURE:
<223> OTHER INFORMATION: poly A modification of the sense strand of
      siRNA specific for human TLR9 with the starting base 1647
      (siRNA9.2)

<400> SEQUENCE: 221
aaaaaaaaaa aaccuucaa                                                   19

<210> SEQ ID NO 222
<211> LENGTH: 19
<212> TYPE: RNA
<213> ORGANISM: Artificial
<220> FEATURE:
<223> OTHER INFORMATION: poly A modification of the sense strand of
      siRNA specific for human TLR9 with the starting base 1647
      (siRNA9.2)

<400> SEQUENCE: 222
agcuuaaccu aaaaaaaa                                                    19

<210> SEQ ID NO 223
<211> LENGTH: 19
<212> TYPE: RNA
<213> ORGANISM: Artificial
<220> FEATURE:
<223> OTHER INFORMATION: poly A modification of the sense strand of
      siRNA specific for human TLR9 with the starting base 1647
      (siRNA9.2)

<400> SEQUENCE: 223
agcuuaaccu gaaaaaaa                                                    19

<210> SEQ ID NO 224
<211> LENGTH: 19
<212> TYPE: RNA
<213> ORGANISM: Artificial
<220> FEATURE:
<223> OTHER INFORMATION: poly A modification of the sense strand of
      siRNA specific for human TLR9 with the starting base 1647
      (siRNA9.2)

<400> SEQUENCE: 224
agcuuaaccu guaaaaaaa                                                   19

<210> SEQ ID NO 225
<211> LENGTH: 19
<212> TYPE: RNA
<213> ORGANISM: Artificial
<220> FEATURE:
<223> OTHER INFORMATION: poly A modification of the sense strand of
      siRNA specific for human TLR9 with the starting base 1647
      (siRNA9.2)

<400> SEQUENCE: 225
agcuuaaccu gucaaaaaa                                                   19

<210> SEQ ID NO 226
<211> LENGTH: 19
<212> TYPE: RNA
<213> ORGANISM: Artificial
<220> FEATURE:
<223> OTHER INFORMATION: poly A modification of the sense strand of
      siRNA specific for human TLR9 with the starting base 1647
      (siRNA9.2)

<400> SEQUENCE: 226
agcuuaaccu guccaaaaa                                                   19
```

```
<210> SEQ ID NO 227
<211> LENGTH: 19
<212> TYPE: RNA
<213> ORGANISM: Artificial
<220> FEATURE:
<223> OTHER INFORMATION: poly A modification of the sense strand of
      siRNA specific for human TLR9 with the starting base 1647
      (siRNA9.2)

<400> SEQUENCE: 227
agcuuaaccu guccuaaaa                                                  19

<210> SEQ ID NO 228
<211> LENGTH: 19
<212> TYPE: RNA
<213> ORGANISM: Artificial
<220> FEATURE:
<223> OTHER INFORMATION: poly A modification of the sense strand of
      siRNA specific for human TLR9 with the starting base 1647
      (siRNA9.2)

<400> SEQUENCE: 228
agcuuaaccu guccuuaaa                                                  19

<210> SEQ ID NO 229
<211> LENGTH: 20
<212> TYPE: RNA
<213> ORGANISM: Artificial
<220> FEATURE:
<223> OTHER INFORMATION: ssRNA oligonucleotide "RNA40" (Heil et al.)

<400> SEQUENCE: 229
gcccgucugu ugugugacuc                                                 20

<210> SEQ ID NO 230
<211> LENGTH: 19
<212> TYPE: RNA
<213> ORGANISM: Artificial
<220> FEATURE:
<223> OTHER INFORMATION: sense strand of siRNA specific for human
      beta-Galactosidase (Judge et al.)

<400> SEQUENCE: 230
uugauguguu uagucgcua                                                  19

<210> SEQ ID NO 231
<211> LENGTH: 19
<212> TYPE: RNA
<213> ORGANISM: Artificial
<220> FEATURE:
<223> OTHER INFORMATION: sense strand of siRNA specific for human TLR9
      with the starting base 271

<400> SEQUENCE: 231
caucucuccc ugcucucug                                                  19

<210> SEQ ID NO 232
<211> LENGTH: 19
<212> TYPE: RNA
<213> ORGANISM: Artificial
<220> FEATURE:
<223> OTHER INFORMATION: antisense strand of siRNA specific for human
      TLR9 with the starting base 271

<400> SEQUENCE: 232
cagagagcag ggagagaug                                                  19
```

```
<210> SEQ ID NO 233
<211> LENGTH: 19
<212> TYPE: RNA
<213> ORGANISM: Artificial
<220> FEATURE:
<223> OTHER INFORMATION: sense strand of siRNA specific for human TLR9
      with the starting base 1122

<400> SEQUENCE: 233
ucgccggccu gcaugcccu                                              19

<210> SEQ ID NO 234
<211> LENGTH: 19
<212> TYPE: RNA
<213> ORGANISM: Artificial
<220> FEATURE:
<223> OTHER INFORMATION: antisense strand of siRNA specific for human
      TLR9 with the starting base 1122

<400> SEQUENCE: 234
agggcaugca ggccggcga                                              19

<210> SEQ ID NO 235
<211> LENGTH: 19
<212> TYPE: RNA
<213> ORGANISM: Artificial
<220> FEATURE:
<223> OTHER INFORMATION: sense strand of siRNA specific for human TLR9
      with the starting base 1949

<400> SEQUENCE: 235
gaggcagaug gaggggaga                                              19

<210> SEQ ID NO 236
<211> LENGTH: 19
<212> TYPE: RNA
<213> ORGANISM: Artificial
<220> FEATURE:
<223> OTHER INFORMATION: antisense strand of siRNA specific for human
      TLR9 with the starting base 1949

<400> SEQUENCE: 236
ucuccccucc aucugccuc                                              19

<210> SEQ ID NO 237
<211> LENGTH: 19
<212> TYPE: RNA
<213> ORGANISM: Artificial
<220> FEATURE:
<223> OTHER INFORMATION: sense strand of siRNA specific for human TLR9
      with the starting base 1302

<400> SEQUENCE: 237
aguaucugcu guuguccua                                              19

<210> SEQ ID NO 238
<211> LENGTH: 19
<212> TYPE: RNA
<213> ORGANISM: Artificial
<220> FEATURE:
<223> OTHER INFORMATION: antisense strand of siRNA specific for human
      TLR9 with the starting base 1302

<400> SEQUENCE: 238
uaggacaaca gcagauacu                                              19

<210> SEQ ID NO 239
```

-continued

<211> LENGTH: 19
<212> TYPE: RNA
<213> ORGANISM: Artificial
<220> FEATURE:
<223> OTHER INFORMATION: sense strand of siRNA specific for human TLR9
      with the starting base 1500

<400> SEQUENCE: 239
ugguguugaa ggacaguuc                                                19

<210> SEQ ID NO 240
<211> LENGTH: 19
<212> TYPE: RNA
<213> ORGANISM: Artificial
<220> FEATURE:
<223> OTHER INFORMATION: antisense strand of siRNA specific for human
      TLR9 with the starting base 1500

<400> SEQUENCE: 240
gaacuguccu ucaacacca                                                19

<210> SEQ ID NO 241
<211> LENGTH: 19
<212> TYPE: RNA
<213> ORGANISM: Artificial
<220> FEATURE:
<223> OTHER INFORMATION: sense strand of siRNA specific for human TLR9
      with the starting base 1019

<400> SEQUENCE: 241 aaccgagcu acaacaaca                                                 19

<210> SEQ ID NO 242
<211> LENGTH: 19
<212> TYPE: RNA
<213> ORGANISM: Artificial
<220> FEATURE:
<223> OTHER INFORMATION: antisense strand of siRNA specific for human
      TLR9 with the starting base 1019

<400> SEQUENCE: 242
uguuguugua gcucagguu                                                19

<210> SEQ ID NO 243
<211> LENGTH: 21
<212> TYPE: RNA
<213> ORGANISM: Artificial
<220> FEATURE:
<223> OTHER INFORMATION: example ssRNA oligonucleotide (hairpin
      sequence)

<400> SEQUENCE: 243
gaccuagccu aaaacuaggu c                                             21

<210> SEQ ID NO 244
<211> LENGTH: 17
<212> TYPE: RNA
<213> ORGANISM: Artificial
<220> FEATURE:
<223> OTHER INFORMATION: example ssRNA oligonucleotide (palindromic
      sequence)

<400> SEQUENCE: 244
aaagauccgg aucaaaa                                                  17

<210> SEQ ID NO 245
<211> LENGTH: 19
<212> TYPE: RNA

-continued

```
<213> ORGANISM: Artificial
<220> FEATURE:
<223> OTHER INFORMATION: example ssRNA oligonucleotide (partially double
      stranded sequence 1 example 1)

<400> SEQUENCE: 245
aaaaguucaa agcucaaaa                                                 19

<210> SEQ ID NO 246
<211> LENGTH: 11
<212> TYPE: RNA
<213> ORGANISM: Artificial
<220> FEATURE:
<223> OTHER INFORMATION: example ssRNA oligonucleotide (partially double
      stranded sequence 2 example 1)

<400> SEQUENCE: 246
caaguuucga g                                                         11

<210> SEQ ID NO 247
<211> LENGTH: 33
<212> TYPE: RNA
<213> ORGANISM: Artificial
<220> FEATURE:
<223> OTHER INFORMATION: example ssRNA oligonucleotide (partially double
      stranded sequence 1 example 2)

<400> SEQUENCE: 247
ucaaagucaa aagcucaaag uugaaaguuu aaa                                 33

<210> SEQ ID NO 248
<211> LENGTH: 41
<212> TYPE: RNA
<213> ORGANISM: Artificial
<220> FEATURE:
<223> OTHER INFORMATION: example ssRNA oligonucleotide (partially double
      stranded sequence 2 example 2)

<400> SEQUENCE: 248
gacuugaaaa uuucaguuuu cgaguuuaag uugaaaacuc g                        41

<210> SEQ ID NO 249
<211> LENGTH: 26
<212> TYPE: RNA
<213> ORGANISM: Artificial
<220> FEATURE:
<223> OTHER INFORMATION: example ssRNA oligonucleotide (partially double
      stranded sequence 1 example 3)

<400> SEQUENCE: 249
ucaaagucaa aagcucaaag uugaaa                                         26

<210> SEQ ID NO 250
<211> LENGTH: 31
<212> TYPE: RNA
<213> ORGANISM: Artificial
<220> FEATURE:
<223> OTHER INFORMATION: example ssRNA oligonucleotide (partially double
      stranded sequence 2 example 3)

<400> SEQUENCE: 250
uuucaguuuu cgaguuuaag uugaaaacuc g                                   31

<210> SEQ ID NO 251
<211> LENGTH: 20
<212> TYPE: RNA
<213> ORGANISM: Artificial
<220> FEATURE:
```

<223> OTHER INFORMATION: example ssRNA oligonucleotide (20mer oligo to
      explain the algorithm)

<400> SEQUENCE: 251
cagagcggga ugcguugguc                                                     20

<210> SEQ ID NO 252
<211> LENGTH: 19
<212> TYPE: RNA
<213> ORGANISM: Artificial
<220> FEATURE:
<223> OTHER INFORMATION: disclaimer ssRNA oligonucleotide (Judge et al.
      1)

<400> SEQUENCE: 252
uugauguguu uagucgcua                                                      19

<210> SEQ ID NO 253
<211> LENGTH: 19
<212> TYPE: RNA
<213> ORGANISM: Artificial
<220> FEATURE:
<223> OTHER INFORMATION: disclaimer ssRNA oligonucleotide (Sioud et al.
      1)

<400> SEQUENCE: 253
gcaccacuag uugguuguc                                                      19

<210> SEQ ID NO 254
<211> LENGTH: 19
<212> TYPE: RNA
<213> ORGANISM: Artificial
<220> FEATURE:
<223> OTHER INFORMATION: disclaimer ssRNA oligonucleotide (Sioud et al.
      2)

<400> SEQUENCE: 254
guuguaguug uacuccagc                                                      19

<210> SEQ ID NO 255
<211> LENGTH: 20
<212> TYPE: RNA
<213> ORGANISM: Artificial
<220> FEATURE:
<223> OTHER INFORMATION: disclaimer ssRNA oligonucleotide "RNA40" (Heil
      et al. 1)

<400> SEQUENCE: 255
gcccgucugu ugugugacuc                                                     20

<210> SEQ ID NO 256
<211> LENGTH: 12
<212> TYPE: RNA
<213> ORGANISM: Artificial
<220> FEATURE:
<223> OTHER INFORMATION: disclaimer ssRNA oligonucleotide "RNA40" (Heil
      et al. 2)

<400> SEQUENCE: 256
gucuguugug ug                                                             12

<210> SEQ ID NO 257
<211> LENGTH: 18
<212> TYPE: RNA
<213> ORGANISM: Artificial
<220> FEATURE:
<223> OTHER INFORMATION: disclaimer ssRNA oligonucleotide (patent
      WO 03/086280)

-continued

```
<400> SEQUENCE: 257
guugugguug ugguugug                                                 18

<210> SEQ ID NO 258
<211> LENGTH: 19
<212> TYPE: RNA
<213> ORGANISM: Artificial
<220> FEATURE:
<223> OTHER INFORMATION: example ssRNA oligonucleotide (motif in
      different positions)

<400> SEQUENCE: 258
aaaaaaaguu caaaaaaaa                                                19

<210> SEQ ID NO 259
<211> LENGTH: 19
<212> TYPE: RNA
<213> ORGANISM: Artificial
<220> FEATURE:
<223> OTHER INFORMATION: example ssRNA oligonucleotide (motif in
      different positions)

<400> SEQUENCE: 259
aaaguucaaa aaaaaaaaa                                                19

<210> SEQ ID NO 260
<211> LENGTH: 19
<212> TYPE: RNA
<213> ORGANISM: Artificial
<220> FEATURE:
<223> OTHER INFORMATION: example ssRNA oligonucleotide (motif in
      different positions)

<400> SEQUENCE: 260
aaaaaaaaaa aaguucaaa                                                19

<210> SEQ ID NO 261
<211> LENGTH: 19
<212> TYPE: RNA
<213> ORGANISM: Artificial
<220> FEATURE:
<223> OTHER INFORMATION: example ssRNA oligonucleotide (more than one
      motif)

<400> SEQUENCE: 261
aaaguucaaa aaguucaaa                                                19

<210> SEQ ID NO 262
<211> LENGTH: 19
<212> TYPE: RNA
<213> ORGANISM: Artificial
<220> FEATURE:
<223> OTHER INFORMATION: example ssRNA oligonucleotide (more than one
      motif)

<400> SEQUENCE: 262
guucaaaguu caaaguuca                                                19

<210> SEQ ID NO 263
<211> LENGTH: 19
<212> TYPE: RNA
<213> ORGANISM: Artificial
<220> FEATURE:
<223> OTHER INFORMATION: example ssRNA oligonucleotide (different
      motifs)

<400> SEQUENCE: 263
```

```
aguucaaagu caaaagcuc                                                    19

<210> SEQ ID NO 264
<211> LENGTH: 22
<212> TYPE: RNA
<213> ORGANISM: Artificial
<220> FEATURE:
<223> OTHER INFORMATION: example ssRNA oligonucleotide (different
      motifs)

<400> SEQUENCE: 264
aguucaguuc aagucaaagc uc                                                22

<210> SEQ ID NO 265
<211> LENGTH: 45
<212> TYPE: RNA
<213> ORGANISM: Artificial
<220> FEATURE:
<223> OTHER INFORMATION: example ssRNA oligonucleotide (different
      motifs)

<400> SEQUENCE: 265
aaaguucaaa gucaaaagcu caaaguugaa aguuuaaagg uuaaa                       45

<210> SEQ ID NO 266
<211> LENGTH: 17
<212> TYPE: RNA
<213> ORGANISM: Artificial
<220> FEATURE:
<223> OTHER INFORMATION: example ssRNA oligonucleotide (overlapping
      motifs)

<400> SEQUENCE: 266
aaaaguugcu caaaaaa                                                      17

<210> SEQ ID NO 267
<211> LENGTH: 10
<212> TYPE: RNA
<213> ORGANISM: Artificial
<220> FEATURE:
<223> OTHER INFORMATION: ssRNA oligonucleotide "RNA33" (Heil et al.)

<400> SEQUENCE: 267
guagugugug                                                              10

<210> SEQ ID NO 268
<211> LENGTH: 21
<212> TYPE: RNA
<213> ORGANISM: Artificial
<220> FEATURE:
<223> OTHER INFORMATION: ssRNA oligonucleotide "sense 27" (Sioud et al.)

<400> SEQUENCE: 268
guccgggcag gucuacuuuu u                                                 21

<210> SEQ ID NO 269
<211> LENGTH: 21
<212> TYPE: RNA
<213> ORGANISM: Artificial
<220> FEATURE:
<223> OTHER INFORMATION: ssRNA oligonucleotide "sense 32" (Sioud et al.)

<400> SEQUENCE: 269
gcuggagauc cugaagaacu u                                                 21

<210> SEQ ID NO 270
```

```
<211> LENGTH: 19
<212> TYPE: RNA
<213> ORGANISM: Artificial
<220> FEATURE:
<223> OTHER INFORMATION: ssRNA oligonucleotide "beta-Gal control sense"
      (Judge et al.)

<400> SEQUENCE: 270
uugauguguu uagucgcua                                                19

<210> SEQ ID NO 271
<211> LENGTH: 19
<212> TYPE: RNA
<213> ORGANISM: Artificial
<220> FEATURE:
<223> OTHER INFORMATION: ssRNA oligonucleotide "beta-Gal control
      antisense" (Judge et al.)

<400> SEQUENCE: 271
uagcgacuaa acacaucaa                                                19

<210> SEQ ID NO 272
<211> LENGTH: 19
<212> TYPE: RNA
<213> ORGANISM: Artificial
<220> FEATURE:
<223> OTHER INFORMATION: ssRNA oligonucleotide "5' UTR" (Barchet et al.)

<400> SEQUENCE: 272
aguagaaaca agguaguuu                                                19

<210> SEQ ID NO 273
<211> LENGTH: 19
<212> TYPE: RNA
<213> ORGANISM: Artificial
<220> FEATURE:
<223> OTHER INFORMATION: ssRNA oligonucleotide "3' UTR" (Barchet et al.)

<400> SEQUENCE: 273
uuaacuaccu gcuuuugcu                                                19

<210> SEQ ID NO 274
<211> LENGTH: 42
<212> TYPE: RNA
<213> ORGANISM: Artificial
<220> FEATURE:
<223> OTHER INFORMATION: ssRNA oligonucleotide "5' 3' UTR" (Barchet et
      al.)

<400> SEQUENCE: 274
aguagaaaca agguaguuuu uuguuaacua ccugcuuuug cu                      42

<210> SEQ ID NO 275
<211> LENGTH: 19
<212> TYPE: RNA
<213> ORGANISM: Artificial
<220> FEATURE:
<223> OTHER INFORMATION: ssRNA oligonucleotide "5' UTR U-C replacement"
      (Barchet et al.)

<400> SEQUENCE: 275
agcagaaaca aggcagccc                                                19

<210> SEQ ID NO 276
<211> LENGTH: 19
<212> TYPE: RNA
<213> ORGANISM: Artificial
<220> FEATURE:
```

<223> OTHER INFORMATION: ssRNA oligonucleotide "5' UTR G-C replacement" (Barchet et al.)

<400> SEQUENCE: 276
acuacaaaca accuacuuu 19

<210> SEQ ID NO 277
<211> LENGTH: 19
<212> TYPE: RNA
<213> ORGANISM: Artificial
<220> FEATURE:
<223> OTHER INFORMATION: example ssRNA oligonucleotide (Group A oligos - above threshold)

<400> SEQUENCE: 277
guuuguugcu uugauugcc 19

<210> SEQ ID NO 278
<211> LENGTH: 19
<212> TYPE: RNA
<213> ORGANISM: Artificial
<220> FEATURE:
<223> OTHER INFORMATION: example ssRNA oligonucleotide (Group A oligos - above threshold)

<400> SEQUENCE: 278
uuguaguucg uugcuagug 19

<210> SEQ ID NO 279
<211> LENGTH: 19
<212> TYPE: RNA
<213> ORGANISM: Artificial
<220> FEATURE:
<223> OTHER INFORMATION: example ssRNA oligonucleotide (Group A oligos - above threshold)

<400> SEQUENCE: 279
aguucauggu ggguuguac 19

<210> SEQ ID NO 280
<211> LENGTH: 19
<212> TYPE: RNA
<213> ORGANISM: Artificial
<220> FEATURE:
<223> OTHER INFORMATION: example ssRNA oligonucleotide (Group A oligos - above threshold)

<400> SEQUENCE: 280
uguuuaaguu guucuaccc 19

<210> SEQ ID NO 281
<211> LENGTH: 19
<212> TYPE: RNA
<213> ORGANISM: Artificial
<220> FEATURE:
<223> OTHER INFORMATION: example ssRNA oligonucleotide (Group A oligos - above threshold)

<400> SEQUENCE: 281
aaguuuugau uuuucagua 19

<210> SEQ ID NO 282
<211> LENGTH: 19
<212> TYPE: RNA
<213> ORGANISM: Artificial
<220> FEATURE:
<223> OTHER INFORMATION: example ssRNA oligonucleotide (Group A oligos - above threshold)

```
<400> SEQUENCE: 282
aggcguuugu guucggguu                                                    19

<210> SEQ ID NO 283
<211> LENGTH: 19
<212> TYPE: RNA
<213> ORGANISM: Artificial
<220> FEATURE:
<223> OTHER INFORMATION: example ssRNA oligonucleotide (Group A oligos -
      above threshold)

<400> SEQUENCE: 283
agauguugua ggguguuuu                                                    19

<210> SEQ ID NO 284
<211> LENGTH: 19
<212> TYPE: RNA
<213> ORGANISM: Artificial
<220> FEATURE:
<223> OTHER INFORMATION: example ssRNA oligonucleotide (Group A oligos -
      above threshold)

<400> SEQUENCE: 284
uagugugugu cagugugac                                                    19

<210> SEQ ID NO 285
<211> LENGTH: 19
<212> TYPE: RNA
<213> ORGANISM: Artificial
<220> FEATURE:
<223> OTHER INFORMATION: example ssRNA oligonucleotide (Group A oligos -
      above threshold)

<400> SEQUENCE: 285
gguugcgugu ggaguuguu                                                    19

<210> SEQ ID NO 286
<211> LENGTH: 19
<212> TYPE: RNA
<213> ORGANISM: Artificial
<220> FEATURE:
<223> OTHER INFORMATION: example ssRNA oligonucleotide (Group A oligos -
      above threshold)

<400> SEQUENCE: 286
uguaguuuug uuagaguca                                                    19

<210> SEQ ID NO 287
<211> LENGTH: 19
<212> TYPE: RNA
<213> ORGANISM: Artificial
<220> FEATURE:
<223> OTHER INFORMATION: example ssRNA oligonucleotide (Group A oligos -
      above threshold)

<400> SEQUENCE: 287
gugugguugc uguugucaa                                                    19

<210> SEQ ID NO 288
<211> LENGTH: 19
<212> TYPE: RNA
<213> ORGANISM: Artificial
<220> FEATURE:
<223> OTHER INFORMATION: example ssRNA oligonucleotide (Group B oligos -
      below threshold)

<400> SEQUENCE: 288
```

```
gggaccgaaa gaccagacc                                                      19

<210> SEQ ID NO 289
<211> LENGTH: 19
<212> TYPE: RNA
<213> ORGANISM: Artificial
<220> FEATURE:
<223> OTHER INFORMATION: example ssRNA oligonucleotide (Group B oligos -
      below threshold)

<400> SEQUENCE: 289
uaagacuaga agagacaga                                                      19

<210> SEQ ID NO 290
<211> LENGTH: 19
<212> TYPE: RNA
<213> ORGANISM: Artificial
<220> FEATURE:
<223> OTHER INFORMATION: example ssRNA oligonucleotide (Group B oligos -
      below threshold)

<400> SEQUENCE: 290
agauccgaac caccgacca                                                      19

<210> SEQ ID NO 291
<211> LENGTH: 19
<212> TYPE: RNA
<213> ORGANISM: Artificial
<220> FEATURE:
<223> OTHER INFORMATION: example ssRNA oligonucleotide (Group B oligos -
      below threshold)

<400> SEQUENCE: 291
gaaccagaaa auagagcag                                                      19

<210> SEQ ID NO 292
<211> LENGTH: 19
<212> TYPE: RNA
<213> ORGANISM: Artificial
<220> FEATURE:
<223> OTHER INFORMATION: example ssRNA oligonucleotide (Group B oligos -
      below threshold)

<400> SEQUENCE: 292
cauauaagaa gaccagcca                                                      19

<210> SEQ ID NO 293
<211> LENGTH: 19
<212> TYPE: RNA
<213> ORGANISM: Artificial
<220> FEATURE:
<223> OTHER INFORMATION: example ssRNA oligonucleotide (Group B oligos -
      below threshold)

<400> SEQUENCE: 293
uaagaaccaa cugcuagaa                                                      19

<210> SEQ ID NO 294
<211> LENGTH: 19
<212> TYPE: RNA
<213> ORGANISM: Artificial
<220> FEATURE:
<223> OTHER INFORMATION: example ssRNA oligonucleotide (Group B oligos -
      below threshold)

<400> SEQUENCE: 294
ccccuacaga cagaauacc                                                      19
```

-continued

```
<210> SEQ ID NO 295
<211> LENGTH: 19
<212> TYPE: RNA
<213> ORGANISM: Artificial
<220> FEATURE:
<223> OTHER INFORMATION: example ssRNA oligonucleotide (Group B oligos -
      below threshold)

<400> SEQUENCE: 295
cuggcagaua gauagaagc                                                    19

<210> SEQ ID NO 296
<211> LENGTH: 19
<212> TYPE: RNA
<213> ORGANISM: Artificial
<220> FEATURE:
<223> OTHER INFORMATION: example ssRNA oligonucleotide (Group B oligos -
      below threshold)

<400> SEQUENCE: 296
cuagaccaga acaaucucg                                                    19

<210> SEQ ID NO 297
<211> LENGTH: 19
<212> TYPE: RNA
<213> ORGANISM: Artificial
<220> FEATURE:
<223> OTHER INFORMATION: example ssRNA oligonucleotide (Group B oligos -
      below threshold)

<400> SEQUENCE: 297
uuagagacau aacaacauu                                                    19

<210> SEQ ID NO 298
<211> LENGTH: 19
<212> TYPE: RNA
<213> ORGANISM: Artificial
<220> FEATURE:
<223> OTHER INFORMATION: example ssRNA oligonucleotide (Group B oligos -
      below threshold)

<400> SEQUENCE: 298
ggaccaaacc ucucgacau                                                    19

<210> SEQ ID NO 299
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 299
uaacaaacuc cuaccaaca                                                    19

<210> SEQ ID NO 300
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 300
uguugguagg aguuuguua                                                    19
```

<210> SEQ ID NO 301
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 301
aacaaacucc uaccaacac                                              19

<210> SEQ ID NO 302
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 302
guguugguag gaguuuguu                                              19

<210> SEQ ID NO 303
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 303
uaccaacacu gaccaauaa                                              19

<210> SEQ ID NO 304
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 304
uuauugguca guguuggua                                              19

<210> SEQ ID NO 305
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 305
cuaccaacac ugaccaaua                                              19

<210> SEQ ID NO 306
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 306
uauuggucag uguugguag                                              19

<210> SEQ ID NO 307
<211> LENGTH: 19

```
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 307
accaacacug accaauaaa                                                   19

<210> SEQ ID NO 308
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 308
uuuauugguc aguguuggu                                                   19

<210> SEQ ID NO 309
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 309
acaaacuccu accaacacu                                                   19

<210> SEQ ID NO 310
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 310
aguguuggua ggaguuugu                                                   19

<210> SEQ ID NO 311
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 311
acuccuacca acacugacc                                                   19

<210> SEQ ID NO 312
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 312
ggucaguguu gguaggagu                                                   19

<210> SEQ ID NO 313
<211> LENGTH: 19
<212> TYPE: RNA
<213> ORGANISM: Artificial
```

```
<220> FEATURE:
<223> OTHER INFORMATION: example ssRNA oligonucleotide (Group A siRNA
      oligos targeting human Cyclophilin B - sense strand)

<400> SEQUENCE: 313
ccuaccaaca cugaccaau                                              19

<210> SEQ ID NO 314
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 314
auuggucagu guggguagg                                              19

<210> SEQ ID NO 315
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 315
uccuaccaac acugaccaa                                              19

<210> SEQ ID NO 316
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 316
uuggucagug uugguagga                                              19

<210> SEQ ID NO 317
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 317
aaacuccuac caacacuga                                              19

<210> SEQ ID NO 318
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 318
ucaguguugg uaggaguuu                                              19

<210> SEQ ID NO 319
<211> LENGTH: 19
<212> TYPE: RNA
<213> ORGANISM: Artificial
<220> FEATURE:
<223> OTHER INFORMATION: example ssRNA oligonucleotide (Group A siRNA
```

-continued oligos targeting human Cyclophilin B - sense strand)

<400> SEQUENCE: 319
ccaacacuga ccaauaaaa                                                  19

<210> SEQ ID NO 320
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 320
uuuuauuggu caguguugg                                                  19

<210> SEQ ID NO 321
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 321
caaacuccua ccaacacug                                                  19

<210> SEQ ID NO 322
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 322
caguguuggu aggaguuug                                                  19

<210> SEQ ID NO 323
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 323
aacuccuacc aacacugac                                                  19

<210> SEQ ID NO 324
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 324
gucaguguug guaggaguu                                                  19

<210> SEQ ID NO 325
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

```
<400> SEQUENCE: 325
aacacugacc aauaaaaaa                                                   19

<210> SEQ ID NO 326
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 326 uuuuuauug gucaguguu                                                    19

<210> SEQ ID NO 327
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 327
caacacugac caauaaaaa                                                   19

<210> SEQ ID NO 328
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 328
uuuuuauugg ucaguguug                                                   19

<210> SEQ ID NO 329
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 329
gcuacaaaaa cagcaaauu                                                   19

<210> SEQ ID NO 330
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 330
aauuugcugu uuuuguagc                                                   19

<210> SEQ ID NO 331
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)
```

```
<400> SEQUENCE: 331
ggcuacaaaa acagcaaau                                                      19

<210> SEQ ID NO 332
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 332
auuugcuguu uuguagcc                                                       19

<210> SEQ ID NO 333
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 333
acacugacca auaaaaaaa                                                      19

<210> SEQ ID NO 334
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 334
uuuuuuuauu ggucagugu                                                      19

<210> SEQ ID NO 335
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 335
uggcuacaaa aacagcaaa                                                      19

<210> SEQ ID NO 336
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 336
uuugcuguuu uuguagcca                                                      19

<210> SEQ ID NO 337
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)
```

```
<400> SEQUENCE: 337
guaacaaacu ccuaccaac                                                 19

<210> SEQ ID NO 338
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 338
guugguagga guuuguuac                                                 19

<210> SEQ ID NO 339
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 339
cacugaccaa uaaaaaaaa                                                 19

<210> SEQ ID NO 340
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 340
uuuuuuuuau uggucagug                                                 19

<210> SEQ ID NO 341
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 341
acugaccaau aaaaaaaaa                                                 19

<210> SEQ ID NO 342
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 342
uuuuuuuuua uuggucagu                                                 19

<210> SEQ ID NO 343
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)
```

```
<400> SEQUENCE: 343
uacaaaaaca gcaaauucc                                                19

<210> SEQ ID NO 344
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 344
ggaauuugcu guuuuugua                                                19

<210> SEQ ID NO 345
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 345
cuacaaaaac agcaaauuc                                                19

<210> SEQ ID NO 346
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 346
gaauuugcug uuuuuguag                                                19

<210> SEQ ID NO 347
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 347
aaaauguggg uuuuuuuuu                                                19

<210> SEQ ID NO 348
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 348
aaaaaaaaac ccacauuuu                                                19

<210> SEQ ID NO 349
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)
```

<210> SEQ ID NO 350
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 350
aacuuugcca aacaccaca                                                    19

<210> SEQ ID NO 351
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 351
aaaugugggu uuuuuuuuu                                                    19

<210> SEQ ID NO 352
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 352
aaaaaaaaaa cccacauuu                                                    19

<210> SEQ ID NO 353
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 353
guuuuuuuuu uuuuuaaua                                                    19

<210> SEQ ID NO 354
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 354
uauuaaaaaa aaaaaaaac                                                    19

<210> SEQ ID NO 355
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

-continued

<400> SEQUENCE: 355 aaugugggu uuuuuuuu                                                19

<210> SEQ ID NO 356
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 356
aaaaaaaaaa acccacauu                                              19

<210> SEQ ID NO 357
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 357 gguuuuuuu uuuuuuaau                                               19

<210> SEQ ID NO 358
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 358
auuaaaaaaa aaaaaaacc                                              19

<210> SEQ ID NO 359
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 359
ggguuuuuuu uuuuuuaa                                               19

<210> SEQ ID NO 360
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 360
uuaaaaaaaa aaaaaaccc                                              19

<210> SEQ ID NO 361
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

-continued

<400> SEQUENCE: 361
ugggguuuuu uuuuuuuua                                                    19

<210> SEQ ID NO 362
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 362
uaaaaaaaaa aaaaaccca                                                    19

<210> SEQ ID NO 363
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 363
auguggguuu uuuuuuuu                                                     19

<210> SEQ ID NO 364
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 364
aaaaaaaaaa aacccacau                                                    19

<210> SEQ ID NO 365
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 365 gugggguuuuu uuuuuuuu                                                    19

<210> SEQ ID NO 366
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 366
aaaaaaaaaa aaaacccac                                                    19

<210> SEQ ID NO 367
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - sense strand)

<400> SEQUENCE: 367 ugugggeuuuu uuuuuuuuu                                            19

<210> SEQ ID NO 368
<211> LENGTH: 19
<212> TYPE: RNA
<213> ORGANISM: Artificial
<220> FEATURE:
<223> OTHER INFORMATION: example ssRNA oligonucleotide (Group A siRNA
      oligos targeting human Cyclophilin B - antisense strand)

<400> SEQUENCE: 368
aaaaaaaaaa aaacccaca                                             19

<210> SEQ ID NO 369
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - sense strand)

<400> SEQUENCE: 369
aagaucgagg uggagaagc                                             19

<210> SEQ ID NO 370
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - antisense strand)

<400> SEQUENCE: 370
gcuucuccac cucgaucuu                                             19

<210> SEQ ID NO 371
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - sense strand)

<400> SEQUENCE: 371
agaucgaggu ggagaagcc                                             19

<210> SEQ ID NO 372
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - antisense strand)

<400> SEQUENCE: 372
ggcuucucca ccucgaucu                                             19

<210> SEQ ID NO 373
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - sense strand)

```
<400> SEQUENCE: 373
ccgccgcccu caucgcggg                                                19

<210> SEQ ID NO 374
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - antisense strand)

<400> SEQUENCE: 374
cccgcgauga gggcggcgg                                                19

<210> SEQ ID NO 375
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - sense strand)

<400> SEQUENCE: 375
ccuucugcgg ccgaugaga                                                19

<210> SEQ ID NO 376
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - antisense strand)

<400> SEQUENCE: 376
ucucaucggc cgcagaagg                                                19

<210> SEQ ID NO 377
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - sense strand)

<400> SEQUENCE: 377
cgccgcccuc aucgcgggg                                                19

<210> SEQ ID NO 378
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - antisense strand)

<400> SEQUENCE: 378
ccccgcgaug agggcggcg                                                19

<210> SEQ ID NO 379
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - sense strand)
```

```
<400> SEQUENCE: 379
cuuccugcug cugccggga                                                     19

<210> SEQ ID NO 380
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - antisense strand)

<400> SEQUENCE: 380
ucccggcagc agcaggaag                                                     19

<210> SEQ ID NO 381
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - sense strand)

<400> SEQUENCE: 381
gagcgcuucc ccgaugaga                                                     19

<210> SEQ ID NO 382
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - antisense strand)

<400> SEQUENCE: 382
ucucaucggg gaagcgcuc                                                     19

<210> SEQ ID NO 383
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - sense strand)

<400> SEQUENCE: 383
gccgccgccc ucaucgcgg                                                     19

<210> SEQ ID NO 384
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - antisense strand)

<400> SEQUENCE: 384
ccgcgaugag ggcggcggc                                                     19

<210> SEQ ID NO 385
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - sense strand)
```

```
<400> SEQUENCE: 385
ggcaagaucg agguggaga                                                    19

<210> SEQ ID NO 386
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - antisense strand)

<400> SEQUENCE: 386
ucuccaccuc gaucuugcc                                                    19

<210> SEQ ID NO 387
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - sense strand)

<400> SEQUENCE: 387
ucuuccugcu gcugccggg                                                    19

<210> SEQ ID NO 388
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - antisense strand)

<400> SEQUENCE: 388
cccggcagca gcaggaaga                                                    19

<210> SEQ ID NO 389
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - sense strand)

<400> SEQUENCE: 389
ugccgccgcc cucaucgcg                                                    19

<210> SEQ ID NO 390
<211> LENGTH: 19
<212> TYPE: RNA
<213> ORGANISM: Artificial
<220> FEATURE:
<223> OTHER INFORMATION: example ssRNA oligonucleotide (Group B siRNA
      oligos targeting human Cyclophilin B - antisense strand)

<400> SEQUENCE: 390
cgcgaugagg gcggcggca                                                    19
```

METHOD FOR DETERMINING IMMUNOSTIMULATORY ACTIVITY OF RNA OLIGONUCLEOTIDES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 430168_402USPC_SEQUENCE_LISTING.txt. The text file is 89 KB, was created on Nov. 10, 2008 and is being submitted electronically via EFS-Web.

FIELD OF THE INVENTION

The present invention relates to the field of immunotherapy and drug discovery. The present invention provides a method for determining the immunostimulatory activity of a RNA oligonucleotide. The present invention also provides a method for predicting the immunostimulatory activity of a RNA oligonucleotide. The present invention further provides a method for preparing RNA oligonucleotides with high or low immunostimulatory activity. Moreover, the present invention provides RNA oligonucleotides with immunostimulatory activity and the therapeutic uses thereof. In addition, the present invention provides RNA oligonucleotides with gene silencing activity and with either high or low immunostimulatory activity, the methods of their preparation, and their therapeutic uses.

BACKGROUND OF THE INVENTION

The vertebrate immune system established different ways to detect invading pathogens based on certain characteristics of their microbial nucleic acids. Detection of microbial nucleic acids alerts the immune system to mount the appropriate type of immune response that is required for the defense against the respective type of pathogen detected. Detection of viral nucleic acids leads to the production of type I interferon (IFN), the key cytokine for anti-viral defense. An understanding of how nucleic acids interact with the vertebrate immune system is important for developing different nucleic acid-based therapeutic strategies for the immunotherapy of diseases (Rothenfusser S et al. 2003, *Curr Opin Mol Ther* 5:98-106) and for developing gene-specific therapeutic agents (Tuschl T et al. 2002, *Mol Interv* 2: 158-167).

For the recognition of long dsRNA, two detection modes are known, the serine threonine kinase PKR (Williams B R, 2001, *Sci Signal Transduction Knowledge Environment* 89: RE2; Meurs E F et al. 1992, *J Virol* 66: 5805-5814; Katze M G et al. 1991, *Mol Cell Biol* 11: 5497-5505) and Toll-like receptor (TLR) 3 (Alexopoulou L et al. 2001, *Nature* 413: 732-738). Whereas PKR is located in the cytosol, TLR3 is present in the endosomal compartment (Matsumoto M et al. 2003, *J Immunol* 171: 3154-3162). TLR3 is a member of the Toll-like receptor family that has evolved to detect pathogen-specific molecules (Takeda K et al. 2003, *Annu Rev Immunol* 21: 335-376).

A second characteristic feature of viral nucleic acids used by the immune system to recognize viral infection are CpG motifs found in viral DNA, which are detected via TLR9 (Lund J et al. 2003, *J Exp Med* 198: 513-520; Krug A et al. 2004, *Blood* 103: 1433-1437). CpG motifs are unmethylated CG dinucleotides with certain flanking bases. The frequency of CpG motifs is suppressed in vertebrates, allowing the vertebrate immune system to detect microbial DNA based on such CpG motifs (Krieg A M et al. 1995, *Nature* 374: 546-549; Bauer S et al. 2001, *Proc Natl Acad Sci USA* 98: 9237-9242; Wagner H et al. 2002, *Curr Opin Microbiol* 5: 62-69). Like TLR3, TLR9 is located in the endosomal compartment where it directly binds to CpG motifs (Latz E et al. 2004, *Nat Immunol* 5: 190-198).

In addition to long dsRNA and CpG DNA, two recent publications suggest a third mechanism by which viral nucleic acids are recognized. These studies demonstrate that single-stranded RNA (ssRNA) of ssRNA viruses is detected via TLR7 (mouse and human) and TLR8 (only human) (Diebold S S et al. 2004, *Science* 303: 1529-1531; Heil F et al. 2004, *Science* 303: 1526-1529). Guanine analogues have been identified earlier as specific ligands for TLR7 and TLR8 (Lee J et al. 2003, *Proc Natl Acad Sci USA* 100: 6646-6651; Heil F et al. 2003, *Eur J Immunol* 33: 2987-2997). Like TLR9 (receptor for CpG DNA) (Latz E et al. 2004, *Nat Immunol* 5: 190-198), TLR7 and TLR8 are located in the endosomal membrane (Heil F et al. 2003, *Eur J Immunol* 33: 2987-2997).

Detection of viral nucleic acids leads to the production of type I IFN (IFN-α and IFN-β). The major producer of type I IFN in humans is the plasmacytoid dendritic cell (PDC, also called interferon producing cell, IPC). The plasmacytoid dendritic cell (PDC) is a highly specialized subset of dendritic cells that is thought to function as a sentinel for viral infection and is responsible for the vast amount of type I IFN during viral infection (Asselin-Paturel C et al. 2001, *Nat Immunol* 2: 1144-1150). There is increasing evidence that PDC preferentially use nucleic acid-based molecular patterns to detect viral infection. TLR expression of human and mouse PDC is limited to TLR7 and TLR9 (Krug A et al. 2001, *Eur J Immunol* 31: 3026-3037; Hornung V et al. 2002, *J Immunol* 168: 4531-4537; Edwards A D et al. 2003, *Eur J Immunol* 33: 827-833).

IFN-α was the first type of interferon to be identified and commercialized; it is widely used clinically in the treatment of a variety of tumors (e.g., hairy cell leukemia, cutaneous T cell leukemia, chronic myeloid leukemia, non-Hodgkin's lymphoma, AIDS-related Kaposi's sarcoma, malignant melanoma, multiple myeloma, renal cell carcinoma, bladder cell carcinoma, colon carcinoma, cervical dysplasia) and viral diseases (e.g., chronic hepatitis B, chronic hepatitis C). IFN-α products that are currently in clinical use include the recombinant protein and the highly purified natural protein, both of which have high production costs. Therefore, there is a need for more economical ways of providing IFN-α to patients in need. Furthermore, IFN-α is currently administrated systematically and causes a broad spectrum of side effects (e.g. fatigue, flu-like symptoms, diarrhea). Most alarmingly, IFN-α causes a decrease in bone marrow function which leads to increased susceptibility to life-threatening infections, anemia and bleeding problems. Therefore, there is a need for ways of providing IFN-α in a more localized (i.e., target-specific) matter to reduce the occurrence of side effects.

In addition to inducing an anti-viral interferon response, dsRNA also induces post-transcription gene silencing, a highly conserved anti-viral mechanism known as RNA interference (RNAi). Briefly, the RNA III Dicer enzyme processes dsRNA into short interfering RNA (siRNA) of approximately 22 nucleotides. The antisense strand of the siRNA binds a target mRNA via base pairing and serves as a guide sequence to induce cleavage of the target mRNA by an RNA-induced silencing complex RISC. dsRNA has been an extremely powerful tool in studying gene functions in *C. elegence* and *Drosophila* via gene silencing. However, its use in mammalian cells has been limited because the interferon response it elicits is detrimental to most mammalian cells.

Subsequently, it was found that siRNA was also capable of inducing RNAi, causing degradation of the target mRNA in a sequence-specific manner and it was thought to be short enough to bypass dsRNA-induced nonspecific effects in mammalian cells (Elbashri S M et al. 2001, *Nature* 411:494-498). Since then, siRNA has been widely used as a gene silencing tool in deciphering mammalian gene functions in research and drug discovery, and there has been great interest in its potential in therapeutic applications.

siRNA can be used to reduce or even abolish the expression of disease/disorder-related genes for preventing or treating diseases caused by the expression or overexpression of the disease-related genes. Such diseases include, but are not limited to, infections, metabolic diseases, autoimmune diseases and cancer. However, concern has been raised recently about the potential for siRNA to activate immune responses which may be undesirable for certain indications and thus limit the use of siRNA as a gene silencing agent for therapeutic purposes (Sioud M et al. 2003, Biochem. Biophys. Res. Commun. 312:1220-1225). Therefore, there is a need for methods for predicting the potential of a given siRNA to induce an interferon response and for methods for designing and preparing siRNAs for gene silencing which are devoid of unwanted immunostimulatory activities.

On the other hand, for certain therapeutic applications, for example, the prevention or treatment of cancer and viral infections, immunostimulatory activity may be desirable as an additional functional activity of the siRNA.

In an effort to apply siRNA for the specific downregulation of TLR9 in PDC in our previous publication (Hornung V et al. 2005, *Nat Med* 11: 263-270), we made the surprising observation that, despite the inability of PDC to detect long dsRNA, certain siRNA sequences were potent in vitro inducers of IFN-α in PDC. We found that i) short interfering RNA (siRNA) induces IFN-α in human plasmacytoid dendritic cells when transfected with cationic lipids, ii) this activity of siRNA is sequence-dependent but independent of the G or U content of the siRNA, iii) the immunostimulatory activity of siRNA and the antisense activity are two independent functional activities of siRNA, iv) the immune recognition of siRNA occurs on the single strand level, v) siRNAs containing the 9mer sequence motif 5'-GUCCUUCAA-3' show potent immunostimulatory activity, and vi) such siRNAs induce systemic immune responses in mice, and vii) the induction of immune responses by siRNA requires the presence of TLR7 in mice. Our findings suggest that the 9mer sequence motif 5'-GUCCUUCAA-3' may be a ligand for TLR7.

The natural ligand for TLR7 has not been well defined to date. Guanine analogues have been identified earlier as specific ligands for TLR7 and TLR8 (Lee J et al. 2003, *Proc Natl Acad Sci USA* 100: 6646-6651; Heil F et al. 2003, *Eur J Immunol* 33: 2987-2997), whereas guanosine ribonucleoside or a derivative thereof has been identified as TLR7 ligand in WO03086280.

It is an object of the present invention to identify RNA oligonucleotide motifs for stimulating an immune response, in particular, IFN-α induction. It is also an object of the present invention to identify ligands for activating TLR7 and TLR8. It is another object of the present invention to develop a method for determining the immunostimulatory activity, in particular, the IFN-α-inducing activity, of a RNA oligonucleotide. It is yet another object of the present invention to develop a method for predicting the immunostimulatory activity, in particular, IFN-α-inducing activity, of a RNA oligonucleotide. It is a further object of the invention to develop a method for designing and preparing RNA oligonucleotide having or lacking immunostimulatory activity, in particular, IFN-α-inducing activity. It is also an object of the invention to provide RNA oligonucleotides having high immunostimulatory activity which can be used to induce an immune response, in particular, IFN-α production, in patients in need thereof. It is yet another object of the present invention to provide siRNA molecules that either have or lack immunostimulatory activity which can be used to treat disorders caused by the expression or overexpression of disorder-related genes.

SUMMARY OF THE INVENTION

The present invention provides a method for determining the immunostimulatory activity of a RNA oligonucleotide, a method for predicting the immunostimulatory activity of a RNA oligonucleotide, a method for preparing a RNA oligonucleotide with high or low immunostimulatory activity, and a method for preparing a RNA oligonucleotide with gene silencing activity and with high or low immunostimulatory activity.

The present application also provides an in vitro method for inducing IFN-α production from a mammalian cell, and an in vitro method for activating a dendritic cell.

The present invention further provides a RNA oligonucleotide with immunostimulatory activity, a RNA oligonucleotide with gene silencing activity and with high or low immunostimulatory activity, and the therapeutic uses thereof.

In addition, the present invention provides a pharmaceutical composition comprising one or more of the RNA oligonucleotides of the invention.

BRIEF DESCRIPTION OF THE FIGURES

FIG. 4: The occurrence of 1mer motifs (5'-X-3'), 2mer motifs (5'-XX-3', 5'-X*X-3', 5'-X**X-3') and 3mer motifs (5'-XXX-3', 5'-XX*X-3', 5'-X*XX-3') in ssRNA oligonucleotides with an IFN-a index below the mean IFN-a index (group 1) or above the mean IFN-α index (group 2) was analyzed. The relative occurrence of a given motif within a group of ssRNA oligonucleotides was calculated by dividing the absolute number of occurrences of a given motif within a group through the absolute number of occurrences of all possible motifs within this group. A significant overrepresentation or underrepresentation of a given motif was analyzed using a chi-square test. The null hypothesis of equal distribution within both groups was rejected when the calculated p-value was below 0.05 (significant differences in distribution are indicated by "*"). For all motifs analyzed, relative occurrences are depicted in FIG. 4 for group 1 oligonucleotides (black bars) and for group 2 oligonucleotides (white bars): 1mer motifs 5'-X-3' (FIG. 4A); 2mer motifs 5'-XX-3' (FIG. 4B1), 5'-X*X-3' FIG. (FIG. 4B2), 5'-X**X-3' (FIG. 4B3) and 3mer motifs 5'-XXX-3' (FIG. 4C1-4C4), 5'-XX*X-3' (FIG. 4C5-4C8), 5'-X*XX-3' (FIG. 4C9-4C12).

FIG. 19: Based on the algorithm described in example 17, a computer program was written that applies the algorithm to all possible siRNA duplexes targeting all human RNA transcripts (50421 as of September 2006) as published by the National Center for Biotechnology Information (NCBI). Each entry into the NCBI database (ftp://ftp.ncbi.nih.gov/refseq/H_sapiens/mRNA_Prot/human.rna.fna.gz) of all listed human RNA transcripts was analyzed the following way: A list of all possible 19mer siRNA duplexes targeting a given RNA transcript was generated. Of all siRNA duplexes the IFN-α induction of both the sense and the antisense strand was predicted using the method described in example 17. The obtained data is stored in a database (CD-ROM) and can be retrieved by a search engine. Using the search interface, the user can pick the transcript of interest (alphabetical index of all RNA transcripts targeted by siRNAs) and then adjust the level of threshold to identify siRNA duplexes that are of either low, intermediate or high in immunostimulatory activity (A). For example, using the threshold of 0.11 as described in example 17, a set of siRNA duplexes was identified for *Homo sapiens* vascular endothelial growth factor (VEGF) transcript variant 1 mRNA (NM_001025366.1) with low immunostimulatory activity for both the sense and the antisense strand (B).

DETAILED DESCRIPTION OF THE INVENTION

Definitions

Figure 1:
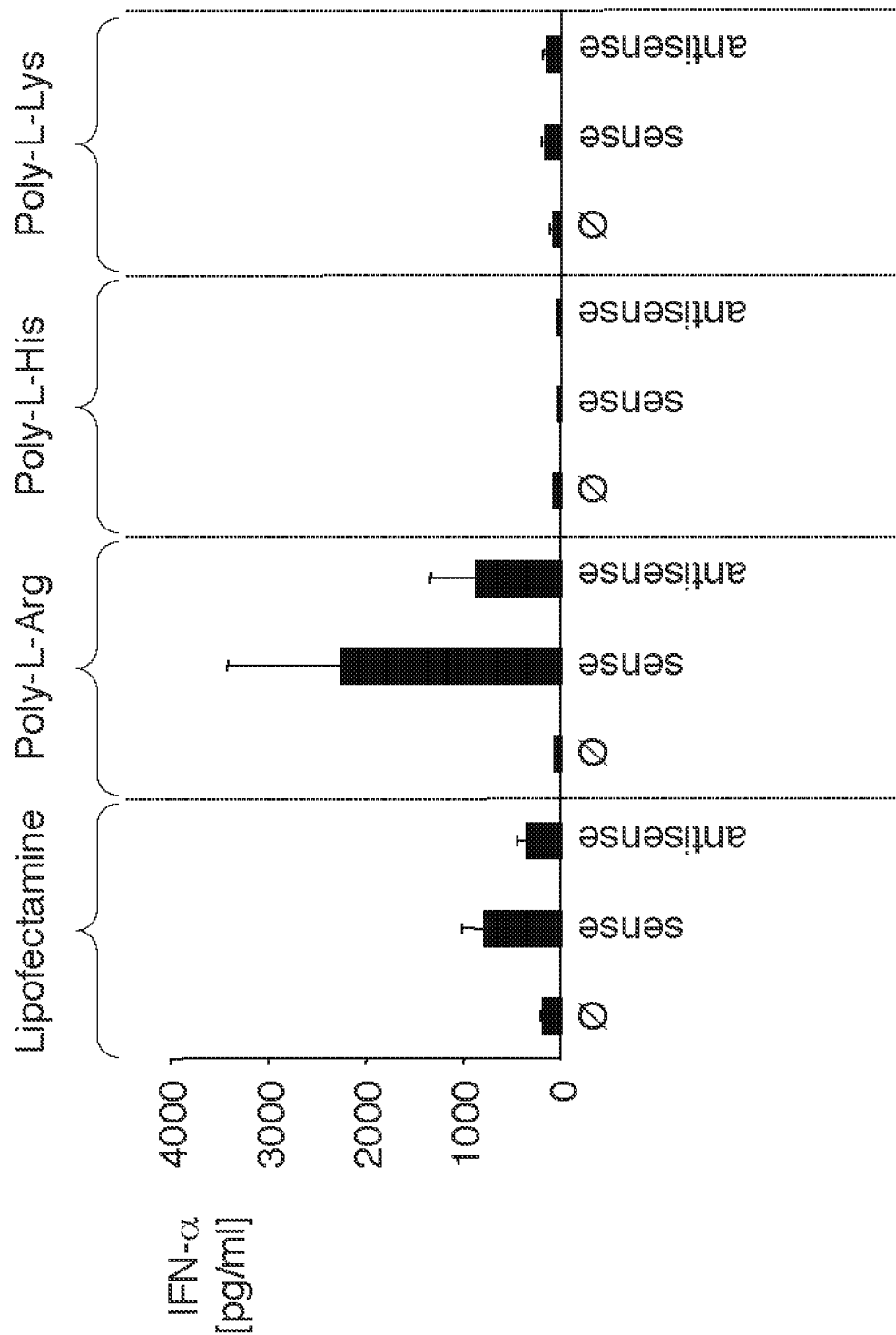
FIG. 1: PBMC of three individual donors were isolated and stimulated with ssRNA oligonucleotides 9.2sense (5'-AGCUUAACCUGUCCUUCAA-3') and 9.2antisense (5'-UUGAAGGACAGGUUAAGCU-3') that were complexed with either Lipofectamine, poly-L-arginine, poly-L-histidine or poly-L-lysine in duplicates. 24 hours after stimulation supernatants were harvested and IFN-α was assessed by ELISA. Data are presented as mean values±SEM.

As used herein, "a" and "an" refers to a group or species of entities, rather than one single individual.

Oligonucleotide

As used herein, the term "oligonucleotide" refers to a polynucleotide formed from a plurality of linked nucleoside units. Such oligonucleotides can be obtained from existing nucleic acid sources, including genomic or cDNA, but are preferably produced by synthetic methods including chemical synthesis, in vitro and in vivo transcription. In preferred embodiments each nucleoside unit includes a heterocyclic base and a pentofuranosyl, trehalose, arabinose, 2'-deoxy-2'-substituted arabinose, 2'-O-substituted arabinose or hexose sugar group. The nucleoside residues can be coupled to each other by any of the numerous known internucleoside linkages. Such internucleoside linkages include, without limitation, phosphodiester, phosphorothioate, phosphorodithioate, pyrophosphate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., $(R_p)$- or $(S_p)$-phosphorothioate, alkylphosphonate, or phosphotriester linkages).

The oligonucleotides of the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside an arabinonucleoside or a 2'-deoxy-2'-substituted-arabinoside.

As used herein, the term "2'-substituted ribonucleoside" or "2'-substituted arabinoside" includes ribonucleosides or arabinonucleoside in which the hydroxyl group at the 2' position of the pentose moiety is substituted to produce a 2'-substituted or 2'-O-substituted ribonucleoside. Preferably, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-O-methylribonucleosides or 2'-O-methylarabinosides and 2'-O-methoxyethylribonucleosides or 2'-O-methoxyethylarabinosides.

The term "2'-substituted ribonucleoside" or "2'-substituted arabinoside" also includes ribonucleosides or arabinonucleosides in which the 2'-hydroxyl group is replaced with a lower alkyl group containing 1-6 saturated or unsaturated carbon atoms, or with an amino or halo group. Examples of such 2'-substituted ribonucleosides or 2'-substituted arabinosides include, without limitation, 2'-amino, 2'-fluoro, 2'-allyl, and 2'-propargyl ribonucleosides or arabinosides.

The term "oligonucleotide" includes hybrid and chimeric oligonucleotides. A "chimeric oligonucleotide" is an oligonucleotide having more than one type of internucleoside linkage. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (see e.g., Pederson et al. U.S. Pat. Nos. 5,635,377 and 5,366,878).

A "hybrid oligonucleotide" is an oligonucleotide having more than one type of nucleoside. One preferred example of such a hybrid oligonucleotide comprises a ribonucleotide or 2'-substituted ribonucleotide region, and a deoxyribonucleotide region (see, e.g., Metelev and Agrawal, U.S. Pat. Nos. 5,652,355, 6,346,614 and 6,143,881).

RNA oligonucleotides discussed herein include otherwise unmodified RNA as well as RNA which have been modified (e.g., to improve efficacy), and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. 1994, *Nucleic Acids Res* 22: 2183-2196. Such rare or unusual RNAs, often termed modified RNAs (apparently because these are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occurs in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. All nucleic acid sequences listed herein are in the 5' to 3' direction unless otherwise indicated.

The RNA oligonucleotide of the invention can be single-stranded, double stranded, or partially double-stranded.

A single-stranded RNA oligonucleotide may contain self-complementary sequences and forms a hairpin. For example, 5'-GACCUAGCCUAAAACUAGGUC-3'. The self-complementary sequence may be a palindromic sequence. For example, 5'AAA<u>GAUCCGGAUC</u>AAAA-3'.

A double stranded RNA oligonucleotide may have one- or two-nucleotide overhang at the 5' or 3' end of one or both strands.

A partially double-stranded RNA oligonucleotide may comprise two strands of the same or different length, wherein the at least one of the strands contains nucleotides outside the complementary sequence. For example, Example 1:
5'-AAAA<u>GUUCAAAGCUC</u>AAAA-3'

3'-<u>CAAGUUUCGAG</u>-5'

Example 2:
5'-UCAAAGUC<u>AAAAGCUCAAAGUUGAAAGUU</u>AAA-3'

3'-GACUUGAAAA<u>UUUCAGUUUUCGAGUUU</u>AAGUUGAAAACUCG-5'

-continued

Example 3:
5'-UCAAAGUCAAAAGCUCAAAGUUGAAA-3'

3'-UUUCAGUUUUCGAGUUUAAGUUGAAAACUCG-5'

The length of a single-stranded RNA oligonucleotide is the number of nucleotides contained in the oligonucleotide.

In the case of a double-stranded or partially double-stranded oligonucleotide, the length of the oligonucleotide is the length of the individual strands. In other words, a partially double-stranded oligonucleotide can have two lengths.

Enhanced Nuclease Resistance

For increased nuclease resistance and/or binding affinity to the target, an oligonucleotide can include, for example, 2'-modified ribose units and/or phosphorothioate linkages and/or pyrophosphate linkages. For example, the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification. "Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Preferred substitutents are 2'-methoxyethyl, 2'-OCH3, 2'-O-allyl, 2'-C-allyl, and 2'-fluoro. To maximize nuclease resistance, the 2' modifications can be used in combination with one or more phosphate linker modifications (e.g., phosphorothioate). The so-called "chimeric" oligonucleotides are those that contain two or more different modifications. The inclusion of furanose sugars in the oligonucleotide backbone can also decrease endonucleolytic cleavage. An oligonucleotide agent can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

Single-stranded RNA oligonucleotides which contain self-complementary sequences and form a hairpin structure have enhanced nuclease resistance compared to single-stranded oligonucleotides which do not.

5'-Phosphate Modifications

The oligonucleotides of the present invention can be 5' phosphorylated or can include a phosphoryl analog at the 5' prime terminus. 5'-phosphate modifications of the antisense strand include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure. Other suitable 5'-phosphate modifications will be known to the skilled person.

Tethered Ligands

The RNA oligonucleotides of the present invention also include those with tethered ligands. The properties of a RNA oligonucleotide, including its pharmacological properties, can be influenced and tailored by the introduction of ligands, e.g. tethered ligands.

The ligands may be coupled, preferably covalently, either directly or indirectly via an intervening tether, to the RNA oligonucleotide. In preferred embodiments, the ligand is attached to the oligonucleotide via an intervening tether.

In preferred embodiments, a ligand alters the distribution, targeting or lifetime of a RNA oligonucleotide into which it is incorporated. In preferred embodiments a ligand provides an enhanced affinity for a selected target, e.g., molecule, cell or cell type, a cellular or organ compartment, tissue, organ or region of the body.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

A wide variety of ligands may be used. Ligands may include agents that allow for the specific targeting of the oligonucleotide; diagnostic compounds or reporter groups which allow for the monitoring of oligonucleotide distribution; cross-linking agents; nuclease-resistance conferring moieties; and natural or unusual nucleobases. General examples include lipophilic molecules, lipids, lectins, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, insulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g. low density lipoprotein (LDL), or albumins, e.g. human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetyl-glucosamine, multivalent mannose, or multivalent fucose. The ligand can be, for example, a lipopolysaccharide, an activator of p38 MAP kinase, or an activator of NF-κB. The ligand can be a substance, e.g., a drug, which can increase the uptake of the oligonucleotide agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one embodiment, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In another embodiment, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another embodiment, the ligand is a cell-permeation agent, preferably a helical cell-permeation agent. Preferably, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

In a preferred embodiment, the ligand is an antibody or a fragment thereof which is specific for a moiety present in a cell to be targeted. The moiety may be a protein, a carbohydrate structure, a polynucleotide, or a combination thereof. The moiety may be secreted, associated with the plasma membrane (e.g., on the extracellular or intracellular surface), cytosolic, associated with intracellular organelles (e.g., ER, Golgi complex, mitochondria, endosome, lysosome, secretory vesicle) or nuclear. The antibody may be monoclonal or polyclonal. The antibody may be chemeric or humanized. The antibody may be a single chain antibody. The antibody fragment may be a Fab fragment, a F(ab')$_2$ fragment, or any fragments that retain the antigen-binding specificity of the intact antibody.

Immunostimulatory Activity

As used herein, "immunostimulatory activity" refers to the capability of a molecule or a composition to induce an immune response. In one aspect, the immunostimulatory activity refers to the type I-IFN-inducing activity, in particular, the IFN-α-inducing activity.

As used herein, "inducing an immune response" means initiating or causing an increase in one or more of B-cell activation, T-cell activation, natural killer cell activation, activation of antigen presenting cells (e.g., B cells, dendritic cells, monocytes and macrophages), cytokine production, chemokine production, specific cell surface marker expression, in particular, expression of co-stimulatory molecules. In one aspect, such an immune response involves the production of type I IFN, in particular, IFN-α, in cells such as PDC.

As used herein, "IFN-α-inducing activity" refers to the capability of a molecule or composition to induce IFN-α production from a cell capable of producing IFN-α. Cells capable of producing IFN-α include, but are not limited to, peripheral blood mononuclear cells (PBMC) (e.g., B cells, dendritic cells (myeloid dendritic cells and plasmacytoid dendritic cells), macrophages, monocytes, natural killer cells, granulocytes), endothelial cells, and cell lines (e.g., THP1; cells transfected with expression vectors for TLR-7 and/or TLR-8 such as CHO cells, COS cells, HEK293 cells). Cells capable of producing IFN-α include those that express TLR7, TLR8, or both TLR7 and TLR8.

Gene Silencing Activity

As used herein, "gene silencing" refers to the downregulation or the abolition of the expression of a target gene. Gene silencing as used herein, occurs at the post-transcriptional level. Gene silencing may be directly or indirectly mediated by siRNA, shRNA and antisense RNA.

Both the antisense-strand of the siRNA and the antisense RNA have complementary to the target mRNA and are the effector strand of the gene silencing activity. The term complementary is well understood by those skilled in the art. For example, A is complementary to T, G is complementary to C, 5'-AG-3' is complementary to 5'-CT-3'.

The degree of complementarity between two oligonucleotides is the percentage of complementary bases in the overlapping region of the two oligonucleotides. The degree of complementarily can be determined manually or automatically by various engines such as BLAST. For example, ATCG has 100% complementarity to CGAT and CGATGG, and 75% complementarity to CGTT and CGTTGG. Furthermore, the degree of complementarity between a RNA oligonucleotide and any sequences present in the public databases (e.g., EMBL, GeneBank) can be determined by the BLAST program.

The degree of complementarity between the antisense strand of the siRNA or the antisense RNA and the target mRNA is at least 80% 81%, 82%, 83%, preferably at least 84%, 85%, 86%, 87%, 88%, more preferably at least 89%, 90%, 91%, 92%, 93%, even more preferably at least 94%, 95%, 96%, 97%, 98%, 99%, and most preferably 100%.

The gene silencing activity of a RNA oligonucleotide can be determined experimentally by methods well known in the art. For Example, the RNA oligonucleotide may be introduced into a cell by a method known in the art such as transfection and transduction; the mRNA level of the target gene can be determined by routine methods such as Northern blot analysis, quantitative PCR, RNase protection assay, and branching DNA; and the protein expression level can be determined by routine methods such as Western blotting, ELISA, and biological activity assays specific to the target protein. Furthermore, the mRNA level of all known and hypothetical genes can be determined at the global level using the microarray technology. Technologies in the field of proteonomics allow for the protein levels of a large number of genes to be determined at the global level as well.

Naked RNA oligonceotide may be transfected into a cell via electroporation. RNA oligonucleotide may be complexed with a complexation agent which facilitates the uptake of the oligonucletide into a cell. Such complexation agents include, but are not limited to cationic lipids (e.g., Lipofectamine, Oligofectamine, DOTAP), cationic peptides, and calcium phosphate.

The gene silencing activity of a RNA oligonucleotide can be predicted by algorithms such as the one disclosed in Reynolds et al. 2004, *Nat Biotechnol* 22:326-330.

siRNA

As used herein, "siRNA" stands for short interfering RNA, and has the same definition as that established in the art. siRNA is double-stranded and is usually between 19 and 27 nucleotide in length. In vivo, siRNA is the product of Dicer activity on long dsRNA. The antisense strand of siRNA is complementary to the target mRNA; it binds the target mRNA and induces RISC-mediated target mRNA degradation. siRNA can be chemically synthesized, produced in vitro by Dicer-mediated enzymatic degradation of long dsRNA, produced by in vitro transcription from linear (e.g. PCR products) or circular templates (e.g., viral or non-viral vectors), or produced by in vivo transcription from viral or non-viral vectors. Commercially available synthetic siRNA usually contain a core of 19 complementary base pairs and a 2-nucleotide (UU or TT) 3' overhang on each strand.

siRNA may be chemically modified to have enhanced stability in vitro (especially in serum-containing media) and in vivo. siRNA may also be chemically modified to have enhanced uptake by cells in vitro and in vivo. Furthermore, siRNA may be linked to tethered ligands to have enhanced target specificity and improved pharmacological properties (such as half-life, clearance, distribution).

shRNA

As used herein, "shRNA" stands for short hairpin RNA and has the same definition as that established in the art. shRNA is processed inside a cell into siRNA which mediates RNAi as described previously. The loop sequence in shRNA is not thought to be involved in RNAi, and it can be of various lengths and sequences. The preferred lengths and sequences of the loop are known to those skilled in the art.

Similar to siRNA, shRNA can be chemically synthesized, produced by in vitro transcription from linear (e.g. PCR products) or circular templates (e.g., viral or non-viral vectors), or produced by in vivo transcription from viral or non-viral vectors.

Antisense RNA

As used herein, "antisense RNA" has the same definition as that established in the art. Antisense RNA is complementary to target mRNA and it thought to interfere with the translation of the target mRNA. Antisense RNA molecules are usually 18-50 nucleotides in length. Antisense RNA may be modified to have enhanced stability, nuclease resistance, target specificity and improved pharmacological properties.

Similar to siRNA and shRNA, antisense RNA can be chemically synthesized, produced by in vitro transcription from linear (e.g. PCR products) or circular templates (e.g., viral or non-viral vectors), or produced by in vivo transcription from viral or non-viral vectors.

Disorder/Disease-related Gene and Antigen

As used herein, "disorder/disease-related gene" refers to a gene that is expressed or overexpressed in a disease/disorder and that is not expressed or expressed in reduced amount under normal condition. For example, a mutant CF gene is expressed in cystic fibrosis patient but not in an individual without cystic fibrosis; ErbB2 (or Her2) is overexpressed in breast cancer cells compared to normal breast cells; a viral gene is expressed in infected cells but not in uninfected cells. The gene product of the disorder/disease-related gene is referred to herein as the "disorder/disease-related antigen".

Mammal

As used herein, the term "mammal" includes, without limitation, rats, mice, cats, dogs, horses, sheep, cattle, cows, pigs, rabbits, non-human primates, and humans.

Technology Platform

The vertebrate immune system established different ways to detect invading pathogens based on certain characteristics of their microbial nucleic acids. Detection of microbial nucleic acids alerts the immune system leading to the appropriate type of immune responses that is required for the defense against the respective type of pathogen detected. Detection of viral nucleic acids leads to the production of type I IFN, the key cytokine for anti-viral defense. While it is well established that the recognition of microbial DNA is sequence-specific, involving the so-called CpG motifs, the optimal motif for the recognition of microbial RNA has not been defined yet. The present application provides a technology platform for identifying the optimal motif for the recognition of microbial RNA and the induction of type I IFN.

The technology platform of the present invention comprises three key features: i) the transfection of peripheral blood mononuclear cells (PBMC) from healthy donors with RNA oligonucleotides; ii) the generation of a RNA oligonucleotide library containing 4mer motifs on a poly adenosine (polyA) backbone; iii) the development of algorithms based on the experimental data generated for the RNA oligonucleotide library to predict the immunostimulatory activity of any given RNA oligonucleotide.

The first key feature of the technology platform is the method of introducing RNA oligonucleotides into PBMC. Naked RNA oligonucleotides are not taken up by the cells to any significant degree. RNA oligonucleotides normally need to form complexes with complexation agent (or transfection agent) in order to be introduced into cells. In the literature, cationic lipids such as lipofectamine or DOTAP are routinely used as complexation agent for the transfection of RNA oligonucleotides. However, RNA-cationic lipid complexes lead to rapid cell death of myeloid cells. Although myeloid cells are not the cellular source of IFN-α within PBMC (the source is PDC), death of myeloid cells in the cell culture negatively affects the reproducibility of IFN-α induction in PBMC. Therefore, the use of cationic lipids is limited to isolated PDC. However, isolated PDC are not suitable for large scale screening assays because PDC make up 0.2-0.6% of the PBMC in a normal individual; it is difficult to obtain enough cells for the assays.

To identify a complexation agent that is suitable for use with PBMC, we compared different types of cationic peptides, poly-His, poly-L-Lys, and poly-L-Arg. Poly-L-Arg was found to provide the most potent support for the immunostimulatory activity of RNA oligonucleotides when compared to other cationic peptides and cationic lipids (FIG. 1). A protocol was then established that allows well-controlled and highly reproducible complex formation between the RNA oligonucleotide and the complexation agent and subsequent RNA transfection into cells. Complex formation could be controlled by salt concentration, phosphate content and incubation time. Complex formation was monitored by the size of complexes and the functional activity over a range of concentrations. The use of poly-L-Arg did not affect the viability of myeloid cells and thus could be applied to PBMC without restrictions.

Figure 2:
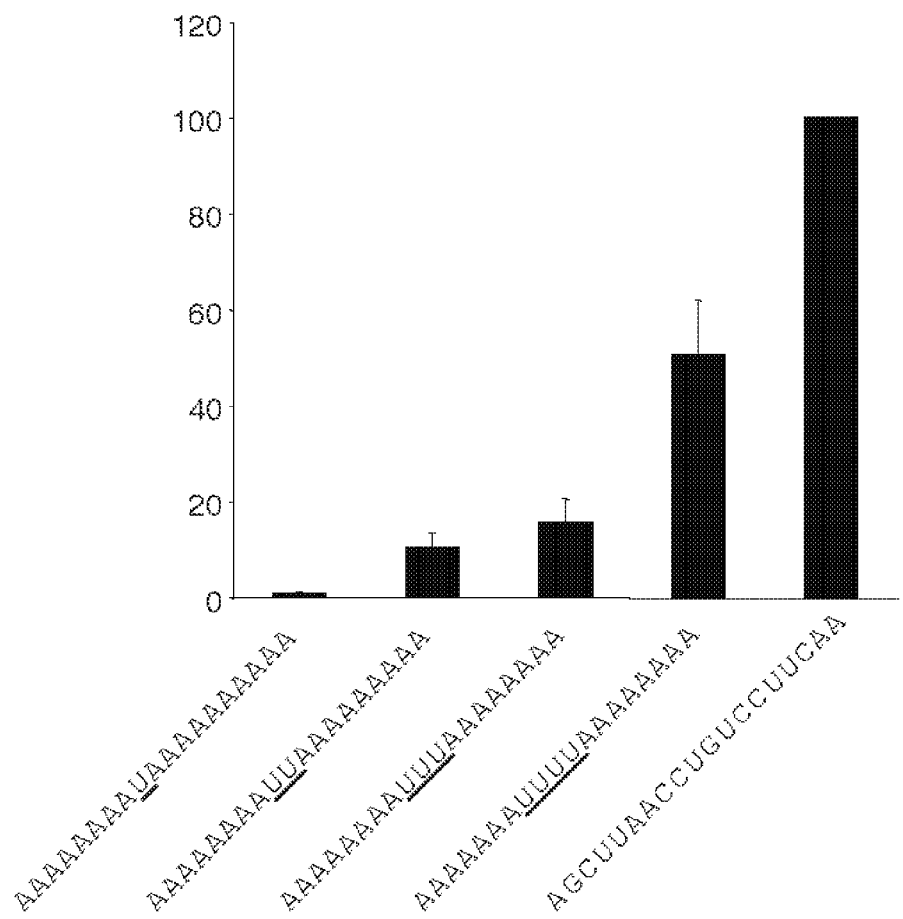
FIG. 2: PBMC of three different healthy donors were isolated and stimulated with poly-L-arginine complexed ssRNA oligonucleotides in duplicates. 44 hours after stimulation IFN-a production was assessed in supernatant via ELISA. For all tested ssRNA oligonucleotides, the mean values of the measured duplicates were normalized to the positive control ssRNA oligonucleotide 9.2sense (5'-AGCUUAACCUGUC-CUUCAA) by dividing the mean value of tested oligonucleotide by the mean value of 9.2sense (=100%). Data from three different donors were summarized and are presented as mean values±SEM.
Figure 7B:
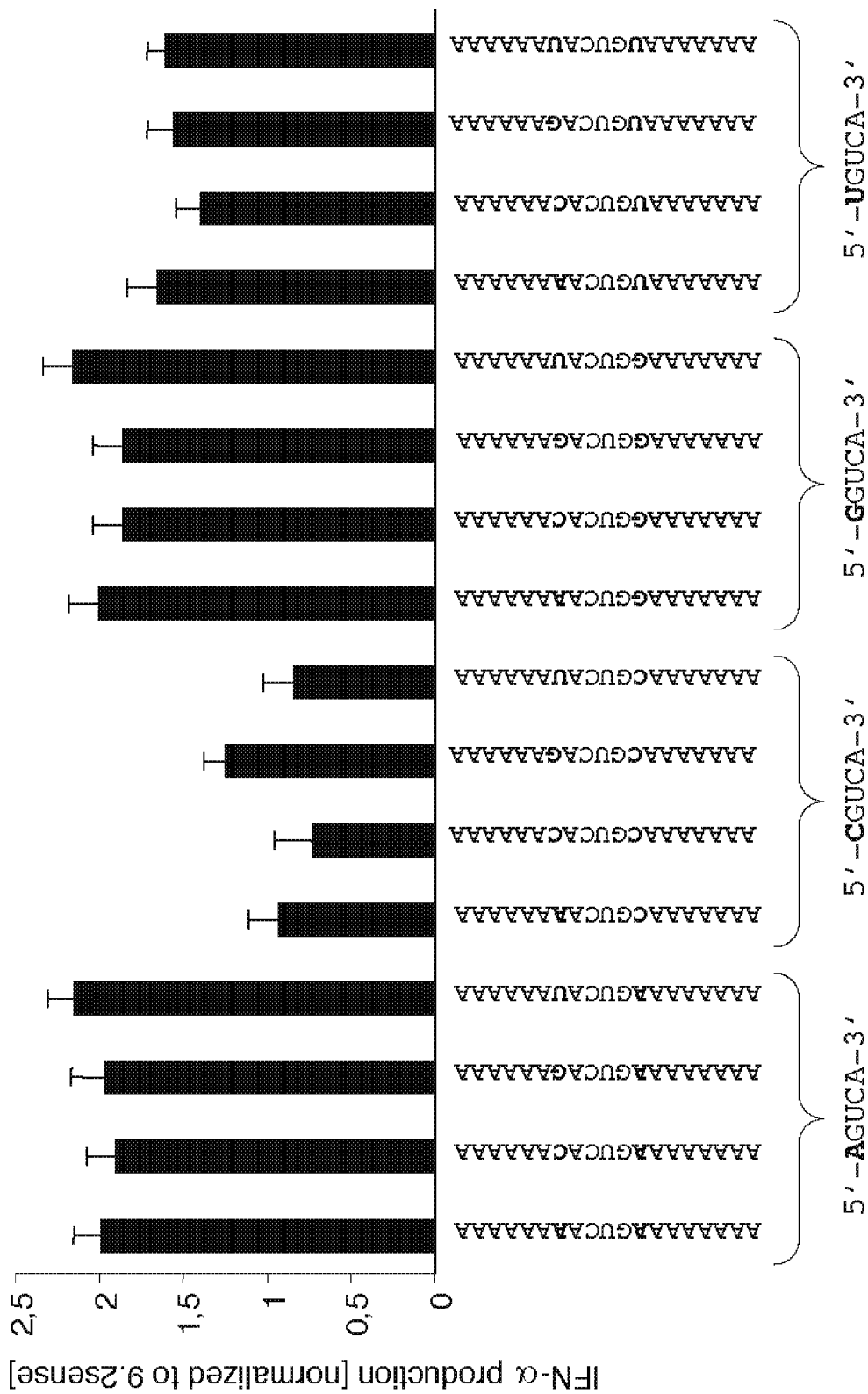
FIG. 7: PBMC from healthy donors were isolated and stimulated with poly-L-arginine complexed ssRNA oligonucleotides in duplicates. 44 hours after stimulation IFN-a production was assessed in supernatant via ELISA. For all tested ssRNA oligonucleotides, the mean values of the measured duplicates were normalized to the positive control ssRNA oligonucleotide 9.2sense (5'-AGCUUAACCUGUCCUUCAA) by dividing the mean value of tested oligonucleotide by the mean value of 9.2sense (=1). A: A panel of ssRNA oligonucleotides was tested with different positions of the 5'-GUCA-3'-motif within the 19mer ssRNA oligonucleotide (see table 4). The 5'-GUCA-3'-motif is indicated by bold letters. Data from two independent donors were summarized and are depicted as mean values±SEM. B/C: 16 ssRNA oligonucleotides, which included all possible oligonucleotides with permutated bases at the flanking positions to the 5'- and the 3'-end of the central 5'-GUCA-3'-motif (table 5), were complexed with poly-L-arginine and used to stimulate PBMC. 44 hours after stimulation IFN-a production was assessed in supernatant via ELISA. Data for all 16 oligonucleotides from three independent donors were summarized as mean values±SEM (B). In addition all 16 oligonucleotides were assorted into groups according to the base preceding or following the central 5'-GUCA-3'-motif (C). On the left side oligonucleotides with a common base preceding the central 5'-GUCA-3'-motif were grouped, whereas on the right side oligonucleotides with a common base following the central 5'-GUCA-3'-motif were grouped. Individual ssRNA oligonucleotide IFN-a data were summarized according to the respective group and are depicted as mean values±SEM. A two-tailed Student's t-test was used to calculate a statistically significant difference between the various groups (p<0.05 is indicated by a "*").

The second key issue of the technology platform was the generation of the RNA oligonucleotide library. An earlier study showed that a minimal length of 19 bases was required for the optimal immunostimulatory activity of an RNA oligonucleotide; furthermore, it showed that poly adenosine (poly A) was completely inactive (Hornung V et al. 2005, *Nat Med* 11:263-270). Therefore, the motif search was performed with a 19mer oligonucleotide on a poly A sequence background. By adding increasing numbers of uridine (U) in the center of such a poly A oligonucleotide, we found that a 4-nucleotide (4-mer) motif in the center was sufficient to confer marked immunostimulatory activity (FIG. 2). Importantly, after identifying the optimal 4mer sequence motifs for inducing IFN-α production, we found that changing the bases flanking the 4mer motifs did not further enhance the immunostimulatory activity of the 4mer motifs (FIG. 7B). The library of 193 RNA oligonucleotides used covered all 256 possible 4mer motifs. The reduction from 258 to 193 was possible because of redundant motifs caused by the poly A flanking regions. In additional studies we found that the exact location of the 4mer motif within the poly A backbone is not critical for the immunostimulatory activity (FIG. 7A).

Figure 8A:
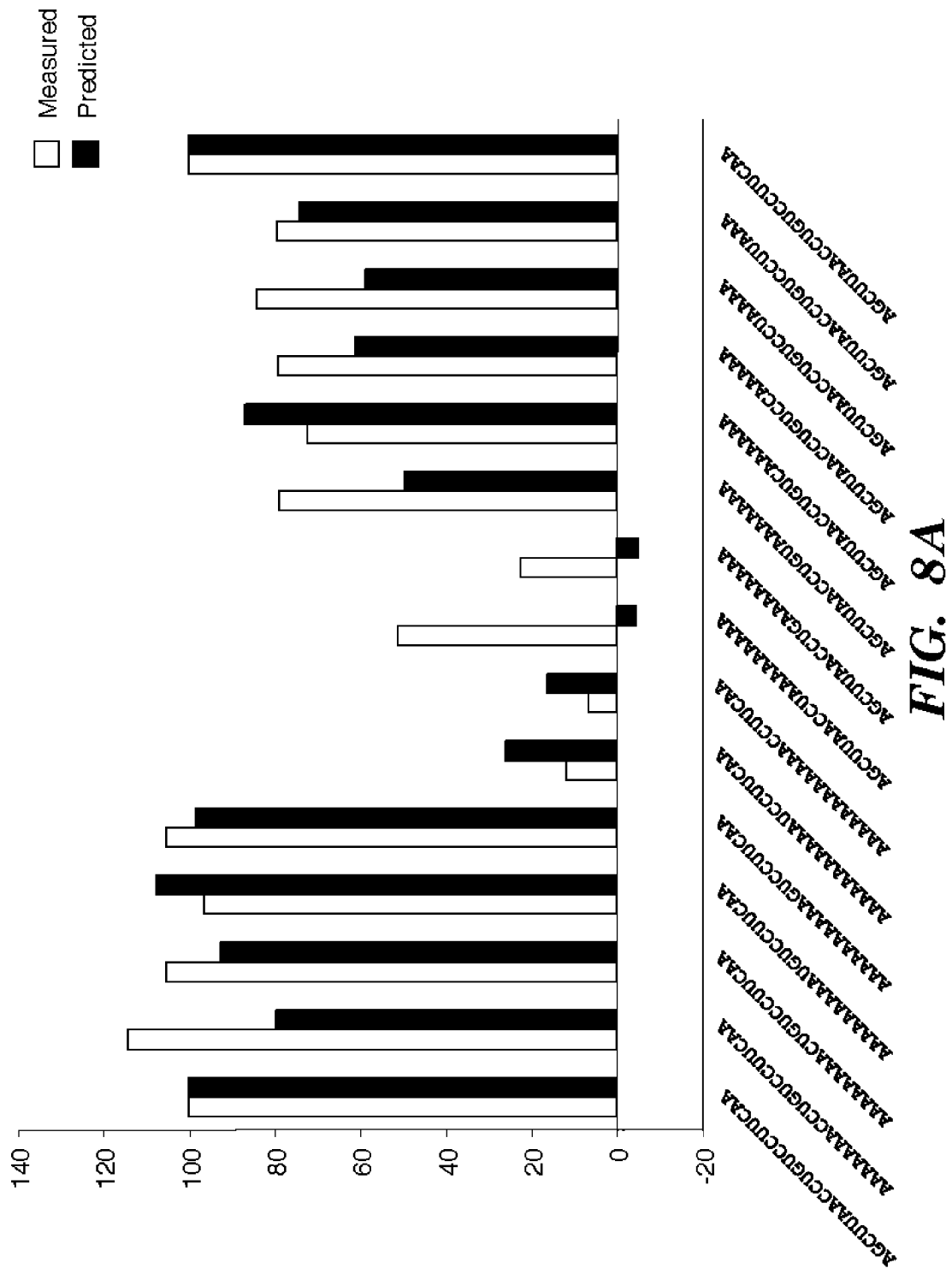
FIG. 8: A: PBMC from two healthy donors were isolated and stimulated with poly-L-arginine complexed ssRNA oligonucleotides (Table 6) in duplicates. 44 hours after stimulation IFN-α production was assessed in supernatant via ELISA. IFN-α data were summarized as mean values and subsequently normalized to the positive control RNA9.2sense (5'-AGCUUAACCUGUCCUUCAA-3'). In addition, respective sequences were analyzed using the IFN-α point score matrix (Table 7) and subsequently normalized to RNA9.2sense. A correlation coefficient of 0.84 was calculated for these two sets of data. Measured IFN-α levels are depicted in white bars, whereas predicted IFN-α scores are shown in black bars (A). Next, IFN-α point score matrix was employed to analyze IFN-α-inducing RNA oligonucleotides that have been described in the literature. Given the fact that in the study performed by Judge et al. (2005, Nat Biotechnol 23:457-462) double-stranded RNA oligonucleotides were tested, a mean value for the individually analyzed single-stranded components was calculated. Data were normalized to the most potent RNA oligonucleotide (=100%) within the respective panel of oligonucleotides (B). For the prediction of single-stranded RNA oligonucleotides reported by Heil et al. (2004 Science 303:1526-1529), the predicted IFN-α point scores are depicted (C).
Figure 8B:
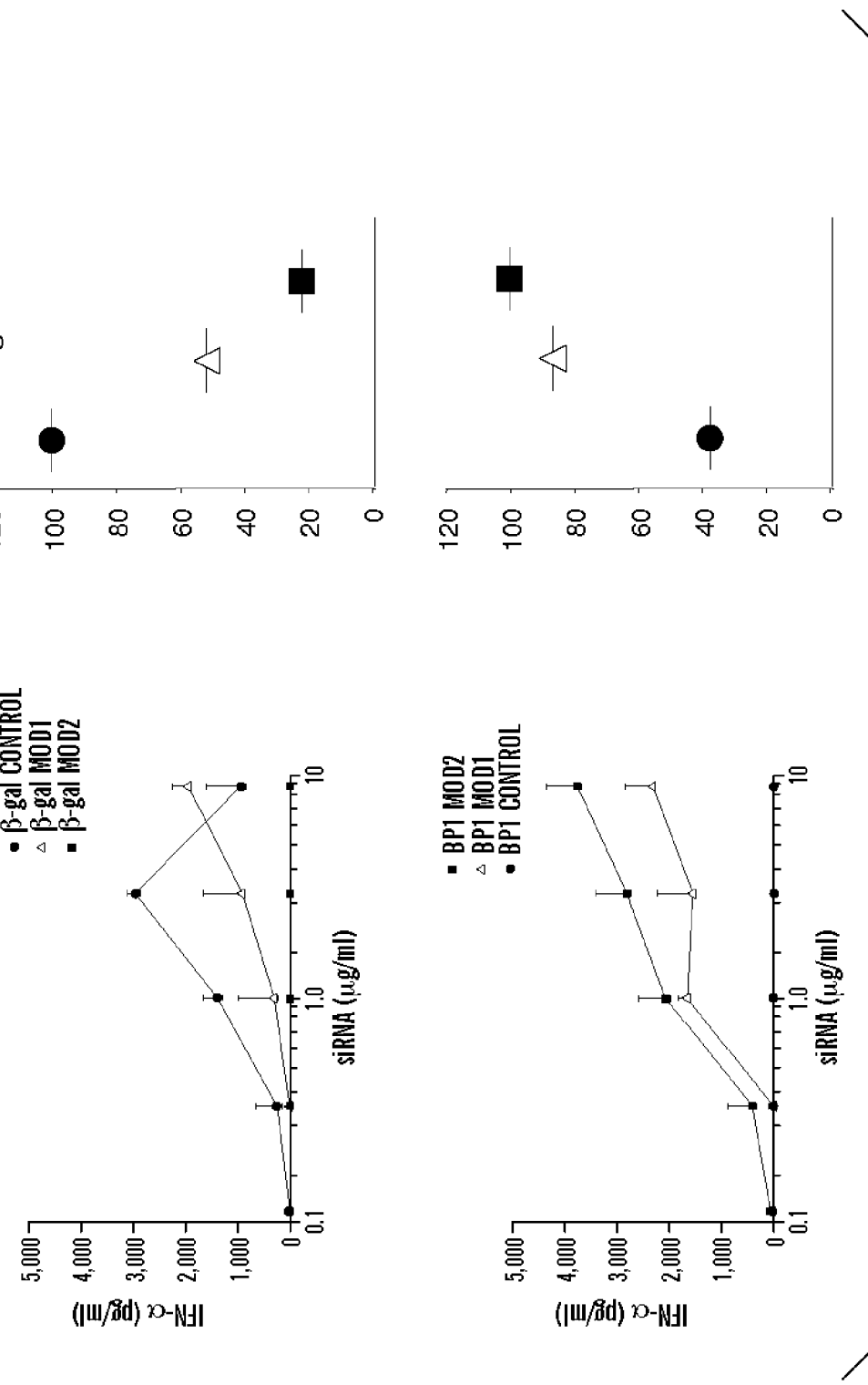
Figure 8C:
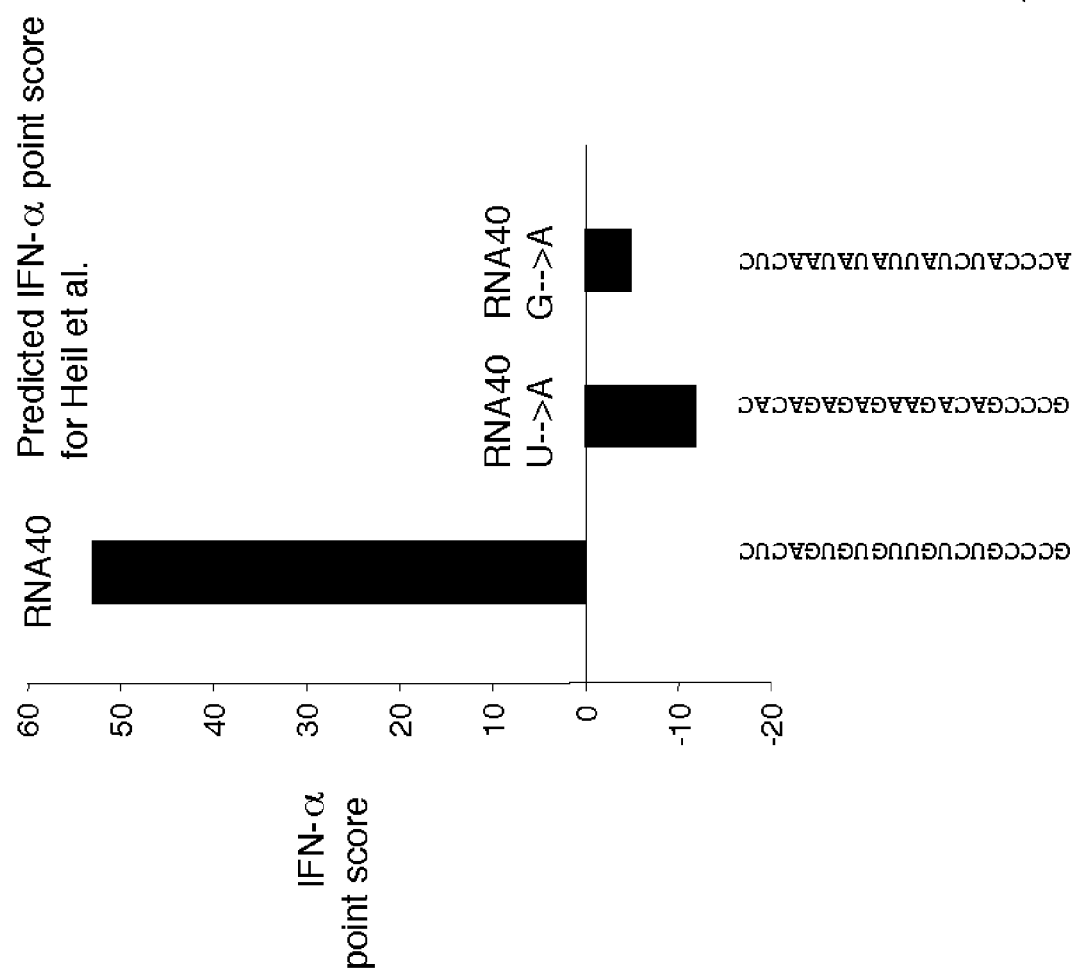

The third key feature of the technology platform was the generation of a data matrix and its mathematical analysis. Algorithms were developed that allowed an excellent prediction of the immunostimulatory activity of RNA oligonucleotides. The frequency of a given 4mer motif at a certain position within an oligonucleotide is only 1:256. Even though the most active 4mer motifs can be used as the core for constructing potent immunostimulatory RNA oligonucleotides, the IFN-α indices of the 4mer motifs are not particularly useful for predicting the activity of a given RNA oligonucleotide, or for designing RNA oligonucleotides with minimal immunostimulatory activity which is desired for an siRNA. Therefore, algorithms were established which based on parts of the 4mer motifs, namely 1, 2 or 3 bases either in a row (XXX) or with spacing (X*XX; XX*X). The highest predictive value was obtained with the algorithm using 3 bases (i.e., 3mer motifs). This 3mer-based algorithm allowed an impressively accurate prediction (correlation coefficient (r)=0.87) of the immunostimulatory activity of the 19mer RNA oligonucleoties carrying 4mer motifs in our library (FIG. 6E) and RNA oligonucleotides previously published in the literature by us and others (FIG. 8A-C).

There are a number of applications for the information generated by our technology platform: a) the 4mer motif data matrix can be used to design oligonucleotides with optimal IFN-α-inducing activity; b) 4mer motifs with minimal IFN-α-inducing activity can be used as the repertoire for selecting potential inhibitory sequence motifs; c) the 3mer-based algorithm (e.g., the IFN-α point score matrix) can be used to predict the immunostimulatory activity of a given RNA oligonucleotide; d) the 3mer-based algorithm (e.g., the IFN-α point score matrix) can be used to design RNA oligonucleotides with maximal immunostimulatory activity and additional sequence requirements for other functionalities such as gene silencing in the case of an siRNA (in this case the use of 4mer motif matrix is not useful since 4mer motifs are not frequent enough); e) the 3mer-based algorithm (e.g., the IFN-α point score matrix) can also be used to design RNA nucleotides with minimal immunostimulatory activity and additional sequence requirements for other functionalities such as gene silencing in the case of an siRNA (in this case the use of 4mer motif matrix is not useful since 4mer motifs are not frequent enough).

In the case of an immunostimulatory RNA, an oligonucleotide containing only one of the most potent 4mer motifs is 80% more active than the most active complex oligonucleotide containing a 9mer motif in the literature (Table 1). In a 19mer oligonucleotide, there is room for several potent 4mer motifs. A 19mer RNA olignucleotide containing more than one potent immunostimulatory 4mer motifs is expected to have even higher activity.

Furthermore, inhibitory motifs may exist that inhibit the immunostimulatory activity of a RNA oligonucleotide as in the case of CpG oligonucleotides. Such inhibitory motifs, by definition, are among the motifs with weak IFN-α-inducing activity. In the field of RNA interference, type I IFN induction usually is unwanted. The 3mer-based algorithm (e.g., the IFN-α point score matrix) described above can be used to select siRNA sequences with minimal immunostimulatory activity. A sequence analysis of cyclophilin B mRNA, one of the best studied targets for siRNA, identifies a number of siRNA sequences for which our algorithm (e.g., the IFN-α point score matrix) predicts minimal type I IFN induction and which still are known to be potent in gene silencing (Reynolds A et al. 2004, *Nat Biotechnol* 22: 326-330). This confirms our previous finding that RNA interference and IFN-α induction are two independent functional activities of a siRNA molecule.

Of note, the motif search performed in the present study focuses on the activity of RNA oligonucleotides to induce IFN-α. From previous studies, it is known that the cellular source of IFN-α within the PBMC is PDC. By analysing the level of IFN-α induction in PBMC, other activities of the RNA oligonucleotides on other cellular subsets of the PBMC, such as myeloid cells, are not addressed. Myeloid cells express TLR8 in addition to TLR7 and thus may show different nucleotide sequence specificities and may be induced to exhibit additional activities than IFN-α production. It therefore needs to be born in mind that ssRNA oligonucleotides are capable of inducing both PDC-dependent (i.e. IFN-α production) and PDC-independent activities (e.g., activation of myeloid cells). In contrast, we found that dsRNA oligonucleotides, such as siRNA, are only recognized by PDC but not myeloid cells. As a result, it is valid to predict the immunological activity of siRNA oligonucleotides based on their ability to induce IFN-α production.

Method for Determining the Immunostimulatory Activity of an RNA Oligonucleotide

The present invention provides a method for determining the immunostimulatory activity, in particular, the IFN-α-inducing activity, of a RNA oligonucleotide, comprising the steps of:

(a) complexing the RNA oligonucleotide with a complexation agent;
(b) contacting a cell with the complexed RNA oligonucleotide, wherein the cell expresses TLR7 or TLR8 or both TLR7 and TLR8; and
(c) determining the amount of IFN-α produced by the cell of step (b), an increase of IFN-α production indicating immunostimulatory activity of the RNA oligonucleotide.

In one embodiment of the invention, the complexation agent is a polycationic peptide, preferably poly-L-arginine (poly-L-Arg). In one embodiment, the polycationic peptide, in particular, poly-L-Arg, is at least 24 amino acids in length. The polycationic peptide, in particular, poly-L Arg, may be a heterogeneous mixture of peptides of different lengths.

The cells expressing TLR7 or TLR8 or both TLR7 or TLR8 include, but are not limited to, peripheral blood mononuclear cells (PBMC), plasmacytoid dendritric cells (PDC), myeloid dendritic cells (MDC), B cells, macrophages, monocytes, natural killer cells, granulocytes, endothelial cells, cell lines such as THP1, and cells containing exogenous DNA which directs the expression of TLR7 or TLR8 or both TLR7 or TLR8 such as transfected CHO, HEK293, and COS cells.

In one embodiment of the invention, the cell is a mammalian cell, preferably a human cell or a cell of human origin.

The RNA oligonucleotide can be single-stranded, double-stranded or partially double-stranded.

Method for Predicting the Immunostimulatory Activity of a RNA Oligonucleotide

The present invention provides a method for predicting the immunostimulatory activity, in particular the IFN-α-inducing activity, of a RNA oligonucleotide, comprising the steps of:
(a) identifying all possible 3-nucleotide (3mer) motifs contained in the oligonucleotide;
(b) assigning an IFN-α point score for each individual 3mer motif;
(c) assigning the sum of the IFN-α point scores of individual 3mer motifs as the IFN-α score of the oligonucleotide; and
(d) assigning to the oligonucleotide a high immunostimulatory activity if the IFN-α score is at least 23, an intermediate immunostimulatory activity if the IFN-α score is between −4 and 23, and a low immunostimulatory activity if the IFN-α score is at most −4, when n=6;
assigning to the oligonucleotide a high immunostimulatory activity if the IFN-α score is at least 26, an intermediate immunostimulatory activity if the IFN-α score is between −4 and 26, and a low immunostimulatory activity if the IFN-α score is at most −4, when n=7;
assigning to the oligonucleotide a high immunostimulatory activity if the IFN-α score is at least 28, an intermediate immunostimulatory activity if the IFN-α score is between −5 and 23, and a low immunostimulatory activity if the IFN-α score is at most −5, when n=8;
assigning to the oligonucleotide a high immunostimulatory activity if the IFN-α score is at least 30, an intermediate immunostimulatory activity if the IFN-α score is between −5 and 30, and a low immunostimulatory activity if the IFN-α score is at most −9, when n=9;
assigning to the oligonucleotide a high immunostimulatory activity if the IFN-α score is at least $1.4909 \times n + 22.014$, an intermediate immunostimulatory activity if the IFN-α score is between $0.005 \times n^2 - 0.2671 \times n - 3.5531$ and $1.4909 \times n + 22.014$, and a low immunostimulatory activity if the IFN-α score is at most $0.005 \times n^2 - 0.2671 \times n - 3.5531$, when n is greater than 9, wherein n is the length of the oligonucleotide.

The present invention also provides a method for assigning the IFN-α score of a RNA oligonucleotide comprising steps (a)-(c) described above.

A single-stranded RNA oligonucleotide of the length n (n≧6) is broken up into all possible 3mer motifs starting a the 5' end. This will result in a total number of n-2 possible 3mer motifs. For example the 20mer ssRNA oligonucleotide 5'-CAGAGCGGGAUGCGUUGGUC-3' can be broken up into the following 18 3mer motifs (5'->3'): CAG, AGA, GAG, AGC, GCG, CGG, GGG, GGA, GAU, AUG, UGC, GCG, CGU, GUU, UUG, UGG, GGU, GUC.

Subsequently, all of the 3mer motifs are checked against the IFN-α point score matrix (Table 7).

TABLE 7

| IFN-α point score matrix | |
|---|---|
| 3mer motif (5'→3') | IFN-α point score |
| ACA | −2 |
| ACC | −2 |
| AGA | −2 |
| AAC | −1 |
| AUA | −1 |
| UGG | +1 |
| GUA | +3 |
| GUG | +3 |
| GGU | +4 |
| UCA | +4 |
| UUC | +4 |
| UUU | +5 |
| AGU | +6 |
| UUG | +6 |
| GUC | +8 |
| UGU | +8 |
| GUU | +9 |

Whenever a 3mer motif is present in the IFN-α point score matrix, the listed point score is added to the so-called predicted IFN-α score of the oligonucleotide analyzed. A 3mer motif which is absent from the IFN-α point score matrix has a point score of 0. Thus the predicted IFN-α score of an oligonucleotide is the sum of IFN-α scores of all 3mer motifs that are present in the IFN-α point score matrix.

For example, for the 20mer ssRNA oligonucleotide 5'-CAGAGCGGGAUGCGUUGGUC-3', a predicted IFN-α score can be calculated as follows:

| 3mer motifs in the 20mer ssRNA | Score in the IFN-α point score matrix | predicted IFN-α score |
| --- | --- | --- |
| CAG | 0 | 0 |
| AGA | (−2) | −2 |
| GAG | 0 | 0 |
| AGC | 0 | 0 |
| GCG | 0 | 0 |
| CGG | 0 | 0 |
| GGG | 0 | 0 |
| GGA | 0 | 0 |
| GAU | 0 | 0 |
| AUG | 0 | 0 |
| UGC | 0 | 0 |
| GCG | 0 | 0 |
| CGU | 0 | 0 |
| GUU | (+9) | +9 |
| UUG | (+6) | +6 |
| UGG | (+1) | +1 |
| GGU | (+4) | +4 |
| GUC | (+8) | +8 |
| Overall |  | +26 |

This method is herein referred to as the "addition method".

The present application further provides an alternative method for predicting the immunostimulatory activity, in particular the IFN-α-inducing activity, of a RNA oligonucleotide, comprising the steps of:
(a) identifying all possible 3-nucleotide (3mer) motifs contained in the oligonucleotide;
(b) assigning an IFN-α point score for each individual 3mer motif according to Table 12A;
(c) assigning the highest individual IFN-α point score as the IFN-α score of the oligonucleotide; and
(d) assigning to the oligonucleotide a high immunostimulatory activity if the IFN-α score is at least 0.58, an intermediate immunostimulatory activity if the IFN-α score is between 0.11 and 0.58, and a low immunostimulatory activity if the IFN-α score is at most 0.11.

The present invention also provides a method for assigning the IFN-α score of a RNA oligonucleotide comprising steps (a)-(c) described above.

This method is herein referred to as the "simplified method".

The IFN-α score of a double-stranded RNA oligonucleotide is the higher of the two IFN-α scores for the two strands.

In the case of a double-stranded or partially double-stranded RNA oligonucleotide, the oligonucleotide is assigned high immunostimulatory activity if at least one of the strands meets the threshold for having high immunostimulatory activity as defined above; the oligonucleotide is assigned low immunostimulatory activity if both strands meet the threshold for having low immunostimulatory activity as defined above. The rest RNA oligonucleotides are assigned intermediate immunostimulatory activity.

Method for Designing and Preparing RNA Oligonucleotides

The present application provides a method for preparing a RNA oligonucleotide having immunostimulatory activity, in particular, high IFN-α-inducing activity, comprising the steps of:
(a) providing candidate oligonucleotide sequence(s);
(b) identifying oligonucleotide sequence(s) with high immunostimulatory activity predicted according to the method of prediction described in the previous section;
(c) preparing the RNA oligonucleotide(s) identified for high immunostimulatory activity in step (b); and
(d) optionally testing the immunostimulatory activity of the RNA oligonucleotide(s) prepared in step (c) according to the method of determination described previously; and
(e) further optionally modifying the oligonucleotide(s) to optimize the immunostimulatory activity.

The present application also provides a method for preparing a RNA oligonucleotide having low immunostimulatory activity, in particular, low IFN-α-inducing activity, comprising the steps of:
(a) providing candidate oligonucleotide sequence(s);
(b) identifying oligonucleotide sequence(s) with low immunostimulatory activity predicted according to the method of prediction described in the previous section;
(c) preparing the RNA oligonucleotide(s) identified for low immunostimulatory activity in step (b); and
(d) optionally testing the RNA oligonucleotide(s) prepared in step (c) for the lack of immunostimulatory activity according to the method of determination described previously; and
(e) further optionally modifying the oligonucleotide(s) to minimize the immunostimulatory activity.

The present invention further provides a method for preparing a RNA oligonucleotide having high immunostimulatory activity, in particular, high IFN-α-inducing activity, comprising the steps of:
(a) providing an oligonucleotide sequence which comprises at least one, preferably at least two, more preferably at least three, even more preferably at least four, of the 4-nucleotide (4-mer) motifs selected from the group consisting of:

GUUC (No. 1),

GUCA (No. 2),

GCUC (No. 3),

GUUG (No. 4),

GUUU (No. 5),

GGUU (No. 6),

GUGU (No. 7),

GGUC (No. 8),

GUCU (No. 9),

GUCC (No. 10),

GCUU (No. 11),

UUGU (No. 12),

UGUC (No. 13),

CUGU (No. 14),

CGUC (No. 15),

UGUU (No. 16),

GUUA (No. 17),

UGUA (No. 18),

UUUC (No. 19),

UGUG (No. 20),

GGUA (No. 21),

GUCG (No. 22),

UUUG (No. 23),

UGGU (No. 24),

GUGG (No. 25),

GUGC (No. 26),

GUAC (No. 27),

GUAU (No. 28),

UAGU (No. 29),

GUAG (No. 30),

UUCA (No. 31),

UUGG (No. 32),

UCUC (No. 33),

CAGU (No. 34),

UUCG (No. 35),

CUUC (No. 36),

GAGU (No. 37),

GGUG (No. 38),

UUGC (No. 39),

UUUU (No. 40),

CUCA (No. 41),

UCGU (No. 42),

UUCU (No. 43),

UGGC (No. 44),

CGUU (No. 45),

CUUG (No. 46),

UUAC (No. 47), wherein the nucleotide sequences of the motifs are 5'→3',
wherein the oligonucleotide is between 6 and 64, preferably between 12 and 50, more preferably between 14 and 40, even more preferably between 16 and 36, and most preferably between 18 and 25 nucleotides in length,
wherein at least one strand of the RNA oligonucleotide has an IFN-α score of at least 23 when n=6; at least 26 when n=7; at least 28 when n=8; at least 30 when n=9; at least $1.4909 \times n+22.014$ when n is greater than 9, wherein the IFN-α score is assigned according to the "addition method" as described above, and wherein n is the length of the oligonucleotide,
or wherein at least one strand of the RNA oligonucleotide has an IFN-α score of at least 0.58, wherein the IFN-α score is assigned according to the "simplified method" as described above,
(b) preparing the RNA oligonucleotide of step (a); and
(c) optionally testing the immunostimulatory activity of the RNA oligonucleotide prepared in step (b) according to the method of determining the immunostimulatory activity as described above; and
(d) further optionally modifying the oligonucleotide to optimize the immunostimulatory activity.

The RNA oligonucleotide can be single-stranded, double-stranded or partially double-stranded.

The RNA oligonucleotide can have other functionalities such as the gene silencing activity.

The methods provided by the present application can be used to prepare immunostimulatory RNA oligonucleotides, siRNA, shRNA or antisense RNA with high or low immunostimulatory activity.

Some of the RNA oligonucleotides which have low immunostimulatory activity, i.e., the non-immunostimulatory oligonucleotides, may in fact have inhibitory activity against immune activation. Such an immunoinhibitory oligonucleotide may be able to prevent immune activation induced by an immunostimulatory oligonucleotide when used in combination.

RNA oligonucleotides can be prepared by methods including, but are not limited to, chemical synthesis, in vitro and in vivo transcription from linear templates (e.g., PCR product) and circular templates (e.g., viral or non-viral vectors).

Method for Preparing siRNA Having High or Low Immunostimulatory Activity

The present invention provides a method for preparing an siRNA having gene silencing activity for a target gene and having immunostimulatory activity, in particular, IFN-α-inducing activity, comprising the steps of:
(a) identifying all potential siRNA antisense sequences for a target mRNA;
(b) identifying antisense sequences that have gene silencing activity;
(c) predicting the immunostimulatory activity for the antisense sequences identified in step (b) and their complementary (i.e., sense) sequences;
(d) identifying siRNA wherein at least one of the sense and antisense sequences has an IFN-α score of at least $1.4909 \times n+31.014$, wherein the IFN-α score is assigned according to the "addition method" described above, wherein n is the length of the sequence and n is between 19 and 25;
(e) decreasing the IFN-α score threshold by 1 if no siRNA is identified in step (d), until at least one siRNA is identified;
(f) preparing the siRNA identified in step (d) or (e);
(g) optionally testing the gene silencing and/or the immunostimulatory activity of the siRNA prepared in (f);
(h) further optionally modify the siRNA prepared in (f) to optimize the gene silencing and/or immunostimulatory activity.

The present invention also provides an alternative method for preparing siRNA with gene silencing activity and immunostimulatory activity, comprising the steps of:
(a) identifying all potential siRNA antisense sequences for a target mRNA;
(b) predicting the immunostimulatory activity for all of the antisense sequences identified in (a) and their complementary (i.e., sense) sequences;
(c) identifying 10 siRNA with the highest IFN-α scores, wherein the IFN-α score is assigned according to the "addition method" described above, wherein the IFN-α score of the siRNA is the higher of the two scores for the sense and the antisense strand;
(d) identifying siRNA with gene silencing activity among the 10 siRNA identified in step (c);

(e) identifying 10 siRNA with the next highest IFN-α scores if no siRNA can be identified in step (d); repeat steps (d) and (e) until at least one siRNA is identified;
(f) preparing the siRNA identified in step (d) or (e);
(g) optionally testing the gene silencing and/or the immunostimulatory activity of the siRNA prepared in (f);
(h) further optionally modify the siRNA prepared in (f) to optimize the gene silencing and/or immunostimulatory activity.

The present invention further provides a method for preparing an siRNA having gene silencing activity for a target gene and having low (or minimal) immunostimulatory activity, in particular, IFN-α-inducing activity, comprising the steps of:
(a) identifying all potential siRNA antisense sequences for a target mRNA;
(b) identifying antisense sequences that have gene silencing activity;
(c) predicting the immunostimulatory activity for the antisense sequences identified in step (b) and their complementary (i.e., sense) sequences;
(d) identifying siRNA wherein both the sense and the antisense sequences have an IFN-α score of at most 0.6075×n−9.9484, wherein the IFN-α score is assigned according to the "addition method" described above, wherein n is the length of the sequence and n is between 19 and 25;
(e) increasing the IFN-α score threshold by 1 if no siRNA is identified in step (b), until at least one siRNA is identified;
(f) preparing the siRNA identified in step (d) or (e);
(g) optionally testing the gene silencing and/or the immunostimulatory activity of the siRNA prepared in (f);
(h) further optionally modify the siRNA prepared in (f) to optimize the gene silencing activity and/or to minimize the immunostimulatory activity.

The present invention also provide an alternative method for preparing siRNA with gene silencing activity and low (or minimal) immunostimulatory activity, comprising the steps of:
(a) identifying all potential siRNA antisense sequences for a target mRNA;
(b) predicting the immunostimulatory activity for all of the antisense sequences identified in (a) and their complementary (i.e., sense) sequences;
(c) identifying 10 siRNA with the lowest IFN-α scores, wherein the IFN-α score is assigned according to the "addition method" described above, wherein the IFN-α score of the siRNA is the higher of the two scores for the sense and the antisense strand;
(d) identifying siRNA with gene silencing activity among the 10 siRNA identified in step (c);
(e) identifying 10 siRNA with the next lowest IFN-α scores if no siRNA can be identified in step (d); repeat steps (d) and (e) until at least one siRNA is identified;
(f) preparing the siRNA identified in step (d) or (e);
(g) optionally testing the gene silencing and/or the immunostimulatory activity of the siRNA prepared in (f);
(h) further optionally modify the siRNA prepared in (f to optimize the gene silencing activity and/or to minimize the immunostimulatory activity.

Candidate siRNA with gene silencing activity for a given gene can be identified using methods known to those skilled in the art, including, but not limited to, commercial engines such as those available from Dharmacon, Qiagen, Invitrogen. Furthermore, the gene silencing activity of an siRNA may be predicted using the algorithm of Reynolds et al. (2004, *Nat Biotechnol* 22:326-330) and may be determined experimentally.

The gene silencing activity of an siRNA can be determined experimentally by methods well known in the art. For Example, the RNA oligonucleotide may be introduced into a cell by a method known in the art such as transfection and transduction; the mRNA level of the target gene can be determined by routine methods such as Northern blot analysis, quantitative PCR, RNase protection assay, and branching DNA; and the protein expression level can be determined by routine methods such as Western blotting, ELISA, and biological activity assays specific to the target protein. Furthermore, the mRNA level of all known and hypothetical genes can be determined at the global level using the microarray technology. Technologies in the field of proteonomics allow for the protein levels of a large number of genes to be determined at the global level as well.

The same methods may be used for preparing an shRNA which comprises the sense and the antisense sequences of an siRNA identified by the above methods and a loop sequence. The preferred loop sequences for shRNA are known to those skilled in the art.

The same methods may also be used for preparing antisense RNA wherein only one strand, the antisense strand, needs to be identified and prepared.

The siRNA, shRNA and antisense RNA can be prepared by methods including, but are not limited to, chemical synthesis, in vitro and in vivo transcription from PCR products and viral or non-viral vectors.

Immunostimulatory RNA oligonucleotides

The present invention provides an immunostimulatory RNA oligonucleotide having immunostimulatory activity, in particular, IFN-α-inducing activity, comprising at least one, preferably at least two, more preferably at least three, even more preferably at least four, even more preferably at least five, and most preferably at least six, of the motifs selected from the group consisting of GUY, GUNY, and GNUY, wherein Y is a pyrimidine (either a U or a C), wherein N is any one of nucleotides A, C, G, and U, and wherein the nucleotide sequences of the motifs are 5'→3'.

In one embodiment, the immunostimulatory RNA oligonucleotide is between 6 and 64, preferably between 12 and 50, more preferably between 14 and 40, even more preferably between 16 and 36, and most preferably between 18 and 25 nucleotides in length.

In a further embodiment, at least one strand of the immunostimulatory RNA oligonucleotide has an IFN-α score of at least 23 when n=6; at least 26 when n=7; at least 28 when n=8; at least 30 when n=9; at least 1.4909×n+22.014 when n is greater than 9, wherein the IFN-α score is assigned according to the "addition method" described above, wherein n is the length of the oligonucleotide, provided that the oligonucleotide of the present invention is not 5'-UUGAUGUGU-UUAGUCGCUA-3' (Judge et al. 2005, *Nat Biotechnol* 23:457-462), 5'-GCACCACUAGUUGGUUGUC-3' (Sioud 2005, *J Mol Biol* 348:1079-1090), 5'-GUUGUAGUU-GUACUCCAGC-3' (Sioud), 5'-GCCCGUCUGUUGU-GUGACUC-3' (Heil et al. 2004 *Science* 303:1526-1529), 5'-GUCUGUUGUGUG-3' (Heil, et al.), 5'-GUUGUGGUU-GUGGUUGUG-3' (WO 03/086280).

In an alternative embodiment, at least one strand of the immunostimulatory RNA oligonucleotide has an IFN-α score of at least 0.58, wherein the IFN-α score is assigned according to the "simplified method" described above, provided that the oligonucleotide of the present invention is not 5'-UUGAUGUGUUUAGUCGCUA-3' (Judge et al. 2005, *Nat Biotechnol* 23:457-462), 5'-GCACCACUAGUUGGUUGUC-3' (Sioud 2005, *J Mol Biol* 348:1079-1090), 5'-GUUGUAGUUGUACUCCAGC-3' (Sioud), 5'-GCCCGUCUGUUGUGUGACUC-3' (Heil et al. 2004 *Science* 303:1526-1529), 5'-GUCUGUUGUGUG-3' (Heil, et al.), 5'-GUUGUGGUUGUGGUUGUG-3' (WO 03/086280).

The present invention further provides an immunostimulatory RNA oligonucleotide having immunostimulatory activity, in particular, IFN-α-inducing activity, comprising at least one, preferably at least two, more preferably at least three, even more preferably at least four, even more preferably at least five, and most preferably at least six, of the 4-nucleotide (4-mer) motifs selected from the group consisting of:

GUUC (No. 1),
GUCA (No. 2),
GCUC (No. 3),
GUUG (No. 4),
GUUU (No. 5),
GGUU (No. 6),
GUGU (No. 7),
GGUC (No. 8),
GUCU (No. 9),
GUCC (No. 10),
GCUU (No. 11),
UUGU (No. 12),
UGUC (No. 13),
CUGU (No. 14),
CGUC (No. 15),
UGUU (No. 16),
GUUA (No. 17),
UGUA (No. 18),
UUUC (No. 19),
UGUG (No. 20),
GGUA (No. 21),
GUCG (No. 22),
UUUG (No. 23),
UGGU (No. 24),
GUGG (No. 25),
GUGC (No. 26),
GUAC (No. 27),
GUAU (No. 28),
UAGU (No. 29),
GUAG (No. 30),
UUCA (No. 31),
UUGG (No. 32),
UCUC (No. 33),
CAGU (No. 34),
UUCG (No. 35),
CUUC (No. 36),
GAGU (No. 37),
GGUG (No. 38),
UUGC (No. 39),
UUUU (No. 40),
CUCA (No. 41),
UCGU (No. 42),
UUCU (No. 43),
UGGC (No. 44),
CGUU (No. 45),
CUUG (No. 46),
UUAC (No. 47), wherein the nucleotide sequences of the motifs are 5'→3',
wherein the oligonucleotide is between 6 and 64, preferably between 12 and 50, more preferably between 14 and 40, even more preferably between 16 and 36, and most preferably between 18 and 25 nucleotides in length,
wherein at least one strand of the RNA oligonucleotide has an IFN-α score of at least 23 when n=6; at least 26 when n=7; at least 28 when n=8; at least 30 when n=9; at least 1.4909× n+22.014 when n is greater than 9, wherein the IFN-α score is assigned according to the "addition method" described above,
or wherein at least one strand of the RNA oligonucleotide has an IFN-α score of at least 0.58, wherein the IFN-α score is assigned according to the "simplified method" described above,
wherein n is the length of the oligonucleotide,
and wherein the oligonucleotide is not 5'-UUGAUGUGUUAGUCGCUA-3' (Judge et al. 2005, *Nat Biotechnol* 23:457-462), 5'-GCACCACUAGUUGGUUGUC-3' (Sioud 2005, *J Mol Biol* 348:1079-1090), 5'-GUUGUAGUUGUACUCCAGC-3' (Sioud), 5'-GCCCGUCUGUUGUGUGACUC-3' (Heil et al. 2004 *Science* 303:1526-1529), 5'-GUCUGUUGUGUG-3' (Heil, et al.), 5'-GUUGUGGUUGUGGUUGUG-3' (WO 03/086280).

In one embodiment, the 4mer motifs are selected from the group consisting of No. 1-19, No. 1-18, No. 1-17, No. 1-16, preferably, No. 1-15, No. 1-14, No. 1-13, No. 1-12, more preferably, No. 1-11, No. 1-10, No. 1-9, No. 1-8, No. 1-7, even more preferably, No. 1-6, No. 1-5, No. 1-4, No. 1-3, most preferably, No. 1-2 of the 4mer motifs.

The immunostimulatory RNA oligonucleotide of the invention may comprise one or more copies of the same 4mer motif, or one or more copies of different 4mer motifs.

The present invention also provide an immunostimulatory RNA oligonucleotide having immunostimulatory, in particular, IFN-α-inducing activity, comprising at least one, preferably at least two, more preferably at least three, even more preferably at least four, even more preferably at least five, most preferably at least six, of the 4mer motifs selected from the group consisting of No. 1-6, preferably No. 1-5, No. 1-4, No. 1-3, more preferably No. 1-2 of the 4mer motifs, wherein the spacer nucleotides which are not part of any of the 4mer motif(s) are identical, and wherein the spacer nucleotide is selected from the group consisting of A, T, C, G and variants and derivatives thereof.

In one embodiment, the spacer nucleotide is A or a derivative thereof.

In one embodiment, the immunostimulatory RNA oligonucleotide of the invention can comprise one or more copies of one type of 4mer motif (e.g., GUUC) on a poly A backbone. Examples of such an oligonucleotide includes, but are not limited to:

```
AAAAAAAGUUCAAAAAAAA
AAAGUUCAAAAAAAAAAAA
AAAAAAAAAAAAGUUCAAA
AAAGUUCAAAAAGUUCAAA
GUUCAAAGUUCAAAGUUCA
```

In another embodiment, the immunostimulatory RNA oligonucleotide of the invention can comprise one or more copies of more than one type of 4mer motif (e.g., GUUC GUCA, GCUC, GUUG, GUUU, GGUU) on a poly A backbone. Examples of such an oligonucleotide includes, but are not limited to:

```
AGUUCAAAGUCAAAAGCUC
AGUUCAGUUCAAGUCAAAGCUC
AAAGUUCAAAGUCAAAAGCUCAAAGUUGAAAGUUUAAAGGUUAAA
```

The more than one 4mer motifs in an immunostimulatory RNA oligonucleotide may overlap. For example, AAAAGUUGCUCAAAAAA.

Examples of immunostimulatory RNA oligonucleotides of the invention include, but are not limited to:

| | |
|---|---|
| aaaguucaaaaaaguucaaa | (SEQ ID NO: 391) |
| aaagucaaaaaaguucaaa | (SEQ ID NO: 392) |
| aaagcucaaaaaaguucaaa | (SEQ ID NO: 393) |
| aaaguugaaaaaaguucaaa | (SEQ ID NO: 394) |
| aaaguuuaaaaaaguucaaa | (SEQ ID NO: 395) |
| aaagguuaaaaaaguucaaa | (SEQ ID NO: 396) |
| aaaguguaaaaaaguucaaa | (SEQ ID NO: 397) |
| aaaggucaaaaaaguucaaa | (SEQ ID NO: 398) |
| aaagucuaaaaaaguucaaa | (SEQ ID NO: 399) |
| aaaguccaaaaaaguucaaa | (SEQ ID NO: 400) |
| aaaguucaaaaaagucaaa | (SEQ ID NO: 401) |
| aaagucaaaaaagucaaa | (SEQ ID NO: 402) |
| aaagcucaaaaaagucaaa | (SEQ ID NO: 403) |
| aaaguugaaaaaagucaaa | (SEQ ID NO: 404) |
| aaaguuuaaaaaagucaaa | (SEQ ID NO: 405) |
| aaagguuaaaaaagucaaa | (SEQ ID NO: 406) |
| aaaguguaaaaaagucaaa | (SEQ ID NO: 407) |
| aaaggucaaaaaagucaaa | (SEQ ID NO: 408) |
| aaagucuaaaaaagucaaa | (SEQ ID NO: 409) |
| aaaguccaaaaaagucaaa | (SEQ ID NO: 410) |
| aaaguucaaaaaagcucaaa | (SEQ ID NO: 411) |
| aaagucaaaaaagcucaaa | (SEQ ID NO: 412) |
| aaagcucaaaaaagcucaaa | (SEQ ID NO: 413) |
| aaaguugaaaaaagcucaaa | (SEQ ID NO: 414) |
| aaaguuuaaaaaagcucaaa | (SEQ ID NO: 415) |
| aaagguuaaaaaagcucaaa | (SEQ ID NO: 416) |
| aaaguguaaaaaagcucaaa | (SEQ ID NO: 417) |
| aaaggucaaaaaagcucaaa | (SEQ ID NO: 418) |
| aaagucuaaaaaagcucaaa | (SEQ ID NO: 419) |
| aaaguccaaaaaagcucaaa | (SEQ ID NO: 420) |
| aaaguucaaaaaaguugaaa | (SEQ ID NO: 421) |
| aaagucaaaaaaguugaaa | (SEQ ID NO: 422) |
| aaagcucaaaaaaguugaaa | (SEQ ID NO: 423) |
| aaaguugaaaaaaguugaaa | (SEQ ID NO: 424) |
| aaaguuuaaaaaaguugaaa | (SEQ ID NO: 425) |
| aaagguuaaaaaaguugaaa | (SEQ ID NO: 426) |
| aaaguguaaaaaaguugaaa | (SEQ ID NO: 427) |
| aaaggucaaaaaaguugaaa | (SEQ ID NO: 428) |
| aaagucuaaaaaaguugaaa | (SEQ ID NO: 429) |
| aaaguccaaaaaaguugaaa | (SEQ ID NO: 430) |
| aaaguucaaaaaaguuuaaa | (SEQ ID NO: 431) |
| aaagucaaaaaaguuuaaa | (SEQ ID NO: 432) |
| aaagcucaaaaaaguuuaaa | (SEQ ID NO: 433) |
| aaaguugaaaaaaguuuaaa | (SEQ ID NO: 434) |
| aaaguuuaaaaaaguuuaaa | (SEQ ID NO: 435) |
| aaagguuaaaaaaguuuaaa | (SEQ ID NO: 436) |
| aaaguguaaaaaaguuuaaa | (SEQ ID NO: 437) |
| aaaggucaaaaaaguuuaaa | (SEQ ID NO: 438) |
| aaagucuaaaaaaguuuaaa | (SEQ ID NO: 439) |
| aaaguccaaaaaaguuuaaa | (SEQ ID NO: 440) |
| aaaguucaaaaaagguuaaa | (SEQ ID NO: 441) |
| aaagucaaaaaagguuaaa | (SEQ ID NO: 442) |
| aaagcucaaaaaagguuaaa | (SEQ ID NO: 443) |
| aaaguugaaaaaagguuaaa | (SEQ ID NO: 444) |
| aaaguuuaaaaaagguuaaa | (SEQ ID NO: 445) |

| | |
|---|---|
| aaagguuaaaaaagguuaaa | (SEQ ID NO: 446) |
| aaaguguaaaaaagguuaaa | (SEQ ID NO: 447) |
| aaaggucaaaaaagguuaaa | (SEQ ID NO: 448) |
| aaagucuaaaaaagguuaaa | (SEQ ID NO: 449) |
| aaaguccaaaaaagguuaaa | (SEQ ID NO: 450) |
| aaaguucaaaaaaguguaaa | (SEQ ID NO: 451) |
| aaagucaaaaaaaguguaaa | (SEQ ID NO: 452) |
| aaagcucaaaaaaguguaaa | (SEQ ID NO: 453) |
| aaaguugaaaaaaguguaaa | (SEQ ID NO: 454) |
| aaaguuuaaaaaaguguaaa | (SEQ ID NO: 455) |
| aaagguuaaaaaaguguaaa | (SEQ ID NO: 456) |
| aaaguguaaaaaaguguaaa | (SEQ ID NO: 457) |
| aaaggucaaaaaaguguaaa | (SEQ ID NO: 458) |
| aaagucuaaaaaaguguaaa | (SEQ ID NO: 459) |
| aaaguccaaaaaaguguaaa | (SEQ ID NO: 460) |
| aaaguucaaaaaaggucaaa | (SEQ ID NO: 461) |
| aaagucaaaaaaaggucaaa | (SEQ ID NO: 462) |
| aaagcucaaaaaaggucaaa | (SEQ ID NO: 463) |
| aaaguugaaaaaaggucaaa | (SEQ ID NO: 464) |
| aaaguuuaaaaaaggucaaa | (SEQ ID NO: 465) |
| aaagguuaaaaaaggucaaa | (SEQ ID NO: 466) |
| aaaguguaaaaaaggucaaa | (SEQ ID NO: 467) |
| aaaggucaaaaaaggucaaa | (SEQ ID NO: 468) |
| aaagucuaaaaaaggucaaa | (SEQ ID NO: 469) |
| aaaguccaaaaaaggucaaa | (SEQ ID NO: 470) |
| aaaguucaaaaaagucuaaa | (SEQ ID NO: 471) |
| aaagucaaaaaaagucuaaa | (SEQ ID NO: 472) |
| aaagcucaaaaaagucuaaa | (SEQ ID NO: 473) |
| aaaguugaaaaaagucuaaa | (SEQ ID NO: 474) |
| aaaguuuaaaaaagucuaaa | (SEQ ID NO: 475) |
| aaagguuaaaaaagucuaaa | (SEQ ID NO: 476) |
| aaaguguaaaaaagucuaaa | (SEQ ID NO: 477) |
| aaaggucaaaaaagucuaaa | (SEQ ID NO: 478) |
| aaagucuaaaaaagucuaaa | (SEQ ID NO: 479) |
| aaaguccaaaaaagucuaaa | (SEQ ID NO: 480) |
| aaaguucaaaaaaguccaaa | (SEQ ID NO: 481) |
| aaagucaaaaaaaguccaaa | (SEQ ID NO: 482) |
| aaagcucaaaaaaguccaaa | (SEQ ID NO: 483) |
| aaaguugaaaaaaguccaaa | (SEQ ID NO: 484) |
| aaaguuuaaaaaaguccaaa | (SEQ ID NO: 485) |
| aaagguuaaaaaaguccaaa | (SEQ ID NO: 486) |
| aaaguguaaaaaaguccaaa | (SEQ ID NO: 487) |
| aaaggucaaaaaaguccaaa | (SEQ ID NO: 488) |
| aaagucuaaaaaaguccaaa | (SEQ ID NO: 489) |
| aaaguccaaaaaaguccaaa | (SEQ ID NO: 490) |

In one embodiment, immunostimulatory RNA oligonucleotide of the invention does not have gene silencing activity for any known mammalian gene.

The immunostimulatory RNA oligonucleotide of the invention may be single-stranded, single-stranded containing a self-complementary sequence and can form a hairpin structure, double-stranded, or partially double-stranded.

Furthermore, the immunostimulatory RNA oligonucleotide of the invention may be covalently linked to one or more lipophilic groups which enhance the stability and the activity and facilitate the delivery of the RNA oligonucleotides.

As used herein, the term "lipophilic" or "lipophilic group" broadly refers to any compound or chemical moiety having an affinity for lipids. Lipophilic groups encompass compounds of many different types, including those having aromatic, aliphatic or alicyclic characteristics, and combinations thereof.

In specific embodiments, the lipophilic group is an aliphatic, alicyclic, or polyalicyclic substance, such as a steroid (e.g., sterol) or a branched aliphatic hydrocarbon. The lipophilic group generally comprises a hydrocarbon chain, which may be cyclic or acyclic. The hydrocarbon chain may comprise various substituents and/or at least one heteroatom, such as an oxygen atom. Such lipophilic aliphatic moieties include, without limitation, saturated or unsaturated fatty acids, waxes (e.g., monohydric alcohol esters of fatty acids and fatty diamides), terpenes (e.g., the $C_{10}$ terpenes, $C_{15}$ sesquiterpenes, $C_{20}$ diterpenes, $C_{30}$ triterpenes, and $C_{40}$ tetraterpenes), and other polyalicyclic hydrocarbons.

The lipophilic group may be attached by any method known in the art, including via a functional grouping present in or introduced into the RNA oligonucleotide, such as a hydroxy group (e.g., —CO—CH$_2$—OH). Conjugation of the RNA oligonucleotide and the lipophilic group may occur, for example, through formation of an ether or a carboxylic or carbamoyl ester linkage between the hydroxy and an alkyl group R—, an alkanoyl group RCO— or a substituted carbamoyl group KNHCO—. The alkyl group R may be cyclic (e.g., cyclohexyl) or acyclic (e.g., straight-chained or branched; and saturated or unsaturated). Alkyl group R may be a butyl, pentyl, hexyl, heptyl, octyl, nonyl, decyl, undecyl, dodecyl, tridecyl, tetradecyl, pentadecyl, hexadecyl, heptadecyl or octadecyl group, or the like. Preferably, the lipophilic group is conjugated to the 5'-hydroxyl group of the terminal nucleotide. In a preferred embodiment, the lipophilic group is 12-hydroxydodeconoic acid bisdecylamide.

In another embodiment, the lipophilic group is a steroid, such as sterol. Steroids are polycyclic compounds containing a perhydro-1,2-cyclopentanophenanthrene ring system. Steroids include, without limitation, bile acids (e.g., cholic acid, deoxycholic acid and dehydrocholic acid), cortisone, digoxigenin, testosterone, cholesterol and cationic steroids, such as cortisone.

In a preferred embodiment, the lipophilic group is cholesterol or a derivative thereof. A "cholesterol derivative" refers to a compound derived from cholesterol, for example by substitution, addition or removal of substituents. The steroid may be attached to the RNA oligonucleotide by any method known in the art. In a preferred embodiment, the liphophilic group is cholesteryl (6-hydroxyhexyl) carbamate.

In another embodiment, the lipophilic group is an aromatic moiety. In this context, the term "aromatic" refers broadly to mono- and polyaromatic hydrocarbons. Aromatic groups include, without limitation, $C_6$-$C_{14}$ aryl moieties comprising one to three aromatic rings, which may be optionally substituted; "aralkyl" or "arylalkyl" groups comprising an aryl group covalently linked to an alkyl group, either of which may independently be optionally substituted or unsubstituted; and "heteroaryl" groups. As used herein, the term "heteroaryl" refers to groups having 5 to 14 ring atoms, preferably 5, 6, 9, or 10 ring atoms; having 6, 10, or 14π electrons shared in a cyclic array; and having, in addition to carbon atoms, between one and about three heteroatoms selected from the group consisting of nitrogen (N), oxygen (O), and sulfur (S).

As used herein, a "substituted" alkyl, cycloalkyl, aryl, heteroaryl, or heterocyclic group is one having between one and about four, preferably between one and about three, more preferably one or two, non-hydrogen substituents. Suitable substituents include, without limitation, halo, hydroxy, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

The lipophilic group can be covalently linked directly or indirectly via a linker to the RNA oligonucleotide. The covalent linkage may or may not comprise a phosphodiester group. And the linker may be of various lengths. The preferred lengths of the linker are known to those skilled in the art and may be determined experimentally.

In one embodiment, the lipophilic group is covalently linked to the 5' end of at least one strand of the RNA oligonucleotide.

In addition, the immunostimulatory oligonucleotide of the invention may be coupled to a solid support. By "coupled" it is meant that the oligonucleotide is covalently or non-covalently, directly or indirectly, linked to the solid support. Suitable solid supports include, but are not limited to, silicon wafers, synthetic polymer support such as polystyrene, polypropylene, polyglycidylmethacrylate, substituted polystyrene (e.g., aminated or carboxylated polystyrene, polyacrlamides, polyamides, polyvinylchlorides, etc.), glass, agarose, nitrocellulose, nylon and gelatin nanoparticles. Solid support may enhance the stability and the activity of the oligonucleotide, especially short oligonucleotides less than 16 nucleotides in length.

Immunostimulatory RNA Oligonucleotide Conjugates

The present invention also provides immunomodulatory RNA oligonucleotide conjugates, comprising an immunomodulatory RNA oligonucleotide and an antigen conjugated to the oligonucleotide. In some embodiments, the antigen is conjugated to the oligonucleotide at a position other than its 3' end. In some embodiments, the antigen produces a vaccine effect.

The antigen is preferably selected from the group consisting of disease/disorder-related antigens. The disorder may be a cancer, a dermatological disorder, an immune disorder, a metabolic disorder, a neurological disorder, an ocular disease, an infection, or other hereditary and non-hereditary disorders. The antigen may be a protein, a polypeptide, a peptide, a carbohydrate, or a combination thereof.

The immunostimulatory RNA oligonucleotide may be covalently linked to the antigen, or it is otherwise operatively associated with the antigen. As used herein, the term "operatively associated with" refers to any association that maintains the activity of both the oligonucleotide and the antigen. Non-limiting examples of such operative associations include being part of the same liposome or other such delivery vehicle or reagent. In embodiments wherein the oligonucleotide agent is covalently linked to the antigen, such covalent linkage preferably is at any position on the oligonucleotide that does not interfere with the immunostimulatory activity of the oligonucleotide.

RNA Oligonucleotide with Gene Silencing Activity

The present invention provides a RNA oligonucleotide with gene silencing activity.

In one embodiment, the RNA oligonucleotide has both gene silencing activity and immunostimulatory activity, wherein at least one strand of the oligonucleotide has an IFN-α score of at least $1.4909 \times n + 31.014$, wherein the IFN-α score is assigned according to the "addition method" described above, wherein n is the length of the oligonucleotide.

In an alternative embodiment, the RNA oligonucleotide has both gene silencing activity and immunostimulatory activity, wherein at least one strand of the oligonucleotide has an IFN-α score of at least 0.58, wherein the IFN-α score is assigned according to the "simplified method" described above.

In another embodiment, the RNA oligonucleotide has gene silencing activity and low/minimal immunostimulatory activity, wherein all strand(s) of the oligonucleotide has (have) an IFN-α score of at most $0.6075 \times n - 9.9484$, wherein the IFN-α score is assigned according to the "addition method" described above, wherein n is the length of the oligonucleotide.

In an alternative embodiment, the RNA oligonucleotide has gene silencing activity and low/minimal immunostimulatory activity, wherein all strand(s) of the oligonucleotide has(have) an IFN-α score of at most 0.11, wherein the IFN-α score is assigned according to the "simplified method" described above.

The RNA oligonucleotide may be an siRNA, an shRNA or an antisense RNA. The siRNA is between 14 and 25 nucleotides in length; the shRNA is between 30 and 70 nucleotides in length; and the antisese RNA is between 14 and 50 nucleotides in length.

In the case of an immunostimulatory siRNA, the gene silencing activity resides on the antisense strands which is complementary to the target mRNA, whereas the immunostimulatory activity may reside on either the sense or the antisesen strand. In a preferred embodiment, the immunostimulatory activity resides on the sense strand; i.e., the sense strand has an IFN-α score of at least $1.4909 \times n + 31.014$ when the IFN-α score is assigned according to the "addition method" described above or the sense strand has and IFN-α score of at least 0.58 when the IFN-α score is assigned according to the "simplified method" described above.

In the case of an shRNA, the molecule is processed inside a cell to yield a siRNA molecule and the loop (linker) sequence. Therefore, the IFN-α score needs to be calculated not only for the intact molecule (a single-stranded RNA), but also for both strands of the resulting siRNA molecule and the single-stranded loop sequence. The shRNA is considered to have high immunostimulatory activity if at least one of the above-mentioned entities has an IFN-α score above the threshold of $1.4909 \times n + 31.014$ according to the "addition method" or 0.58 according to the "simplified method"; the molecule is considered to have low immunostimulatory activity if all of the entities mentioned above have an IFN-α score below the threshold of 0.6075×n−9.9484 according to the "addition method" or 0.11 according to the "simplified method". The gene silencing activity resides in the sequence that corresponds to the antisense strand of the siRNA; whereas the immunostimulatory activity may reside in any part of the molecule. In a preferred embodiment, the immunostimulatory activity resides in the portion of an shRNA that corresponds to the sense strand of the corresponding siRNA or in the loop sequence; i.e., said portion has an IFN-a score of at least 1.4909×n+31.014 according to the "addition method" or 0.58 according to the "simplified method".

In the case of an immunostimulatory antisense RNA, the immunostimulatory activity and the gene silencing activity have to reside on the same strand.

The gene silencing RNA oligonucleotide of the invention may be covalently linked to one or more lipophilic groups which enhance the stability and the activity and facilitate the delivery of the RNA oligonucleotides.

Pharmaceutical Compositions

The present invention provides pharmaceutical compositions comprising one or more of the RNA oligonucleotides of the invention and a pharmaceutically acceptable carrier. The more than one RNA oligonucleotides may have the same, similar, or different functionalities including, but are not limited to immunostimulatory activity and gene silencing activity.

For example, a RNA oligonucleotide having immunostimulatory activity but lacking gene silencing activity may be combined with a RNA oligonucleotide having gene silencing activity and low immunostimulatory activity in a pharmaceutical composition to achieve both immune activation and gene silencing. Such a combination composition may be useful for treating disorders such as cancers and viral infections. Such a combination composition may be necessary when the two activities cannot be optimized on a single RNA oligonucleotide.

In one embodiment, the pharmaceutical composition further comprises a RNA complexation agent. In a preferred embodiment, the complexation agent is a polycationic peptide, preferably poly-L-arginine (poly-L-Arg). In a preferred embodiment, the polycationic peptide, in particular, poly-L-Arg, is at least 24 amino acids in length. The polycationic peptide, in particular, poly-L Arg, may be a heterogeneous mixture of peptides of different lengths.

The pharmaceutical composition of the invention may further comprises another agent such as an agent that stabilizes the RNA oligonucleotide(s), e.g., a protein that complexes with the oligonucleotide agent to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

The pharmaceutical composition of the present invention can further comprise one or more additional pharmaceutically active (or therapeutic) agents which are selected from the group consisting of agents that are used for the treatment of cancer, dermatological disorders, immune disorders, metabolic disorders, neurological disorders, ocular diseases, infections, and other hereditary and non-hereditary disorders in a mammal.

In certain embodiments, the additional pharmaceutically active agent is selected from the group consisting of immunostimulatory RNA oligonucleotides, immunostimulatory DNA oligonucleotides, cytokines, chemokines, growth factors, antibiotics, anti-angiogenic factors, chemotherapeutic agents, anti-viral agents, anti-fungal agents, anti-parasitic agents, and antibodies. In one embodiment, the additional pharmaceutically active agent is natural or recombinant IFN-α polypeptide, or a CpG-containing or non-CpG-containing DNA oligonucleotide capable of inducing IFN-α (see e.g., WO 01/22990, WO 03/101375). In another embodiment, the additional pharmaceutically active agent is natural or recombinant IL-12, or an immunostimulatory RNA oligonucleotide capable inducing IL-12 (see e.g. our co-pending application; Sugiyama et al. 2005, *J Immunol* 174:2273-2279). In yet another embodiment, the additional pharmaceutically active agent is an anti-angiogenic factor such as vasostatin or an anti-VEGF antibody. In certain embodiments, the additional pharmaceutically active agent is a cancer-specific agent such as Herceptin®, Rituxan®, Gleevec®, Iressa®.

A formulated oligonucleotide composition can assume a variety of states. In some examples, the composition is at least partially crystalline, uniformly crystalline, and/or anhydrous (e.g., less than 80, 50, 30, 20, or 10% water). In another example, the oligonucleotide agent is in an aqueous phase, e.g., in a solution that includes water, this form being the preferred form for administration via inhalation.

The aqueous phase or the crystalline compositions can be incorporated into a delivery vehicle, e.g., a liposome (particularly for the aqueous phase), or a particle (e.g., a microparticle as can be appropriate for a crystalline composition). Generally, the oligonucleotide composition is formulated in a manner that is compatible with the intended method of administration.

The pharmaceutical compositions encompassed by the invention may be administered by any means known in the art including, but not limited to, oral or parenteral routes, including intravenous, intramuscular, intraperitoneal, subcutaneous, transdermal, airway (aerosol), ocular, rectal, vaginal, and topical (including buccal and sublingual) administration. In preferred embodiments, the pharmaceutical compositions are administered by intravenous or intraparenteral infusion or injection. The pharmaceutical compositions can also be administered intraparenchymally, intrathecally, and/or by stereotactic injection.

For oral administration, the oligonucleotide agent useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of oligonucleotide agent in the cells that harbor the target gene or virus. Such substances include, for example, micellar structures, such as liposomes or capsids, as described below. Although microinjection, lipofection, viruses, viroids, capsids, capsoids, or other auxiliary agents are required to introduce oligonucleotide agent into cell cultures, surprisingly these methods and agents are not necessary for uptake of oligonucleotide agent in vivo. The oligonucleotide agent of the present invention are particularly advantageous in that they do not require the use of an auxiliary agent to mediate uptake of the oligonucleotide agent into the cell, many of which agents are toxic or associated with deleterious side effects. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions can also include encapsulated formulations to protect the oligonucleotide agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075.

In general, a suitable dose of a RNA oligonucleotide will be in the range of 0.001 to 500 milligrams per kilogram body weight of the recipient per day (e.g., about 1 microgram per kilogram to about 500 milligrams per kilogram, about 100 micrograms per kilogram to about 100 milligrams per kilogram, about 1 milligrams per kilogram to about 75 milligrams per kilogram, about 10 micrograms per kilogram to about 50 milligrams per kilogram, or about 1 microgram per kilogram to about 50 micrograms per kilogram). The pharmaceutical composition may be administered once per day, or the oligonucleotide agent may be administered as two, three, four, five, six or more sub-doses at appropriate intervals throughout the day. In that case, the oligonucleotide agent contained in each sub-dose must be correspondingly smaller in order to achieve the total daily dosage. The dosage unit can also be compounded for delivery over several days, e.g., using a conventional sustained release formulation which provides sustained release of the oligonucleotide agent over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the infection or disease/disorder, previous treatments, the general health and/or age of the subject, and other diseases/disorders present. Moreover, treatment of a subject with a therapeutically effective amount of a composition can include a single treatment or a series of treatments. Estimates of effective dosages and in vivo half-lives for the individual RNA oligonucleotide agent encompassed by the invention can be made using conventional methodologies or on the basis of in vivo testing using an appropriate animal model, as described elsewhere herein.

Toxicity and therapeutic efficacy of the RNA oligonucleotide and the pharmaceutical composition of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. oligonucleotide agents that exhibit high therapeutic indices are preferred.

The data obtained from cell culture assays and animal studies can be used in formulating a range of dosage for use in humans. The dosages of compositions of the invention are preferably within a range of circulating concentrations that include the ED50 with little or no toxicity. The dosage may vary within this range depending upon the dosage form employed and the route of administration utilized. For any oligonucleotide agent used in the method of the invention, the therapeutically effective dose can be estimated initially from cell culture assays. A dose may be formulated in animal models to achieve a circulating plasma concentration range of the oligonucleotide agent or, when appropriate, of the polypeptide product of a target sequence (e.g., achieving a decreased concentration of the polypeptide) that includes the IC50 (i.e., the concentration of the test oligonucleotide agent which achieves a half-maximal inhibition of symptoms) as determined in cell culture. Such information can be used to more accurately determine useful doses in humans. Levels in plasma may be measured, for example, by high performance liquid chromatography.

The administering physician can adjust the amount and timing of the administration of the pharmaceutical composition of the invention on the basis of results observed using standard measures of efficacy known in the art or described herein.

Use of the RNA Oligonucleotide for Inducing an Immune Response

The present application provides the use of the immunostimulatory RNA oligonucleotide of the invention for the preparation of a pharmaceutical composition for inducing an immune response in a mammal.

Inducing an immune response means initiating or causing an increase in one or more of B-cell activation, T-cell activation, natural killer cell activation, activation of antigen presenting cells (e.g., B cells, dendritic cells, monocytes and macrophages), cytokine production, chemokine production, specific cell surface marker expression, in particular, expression of co-stimulatory molecules. In one aspect, such an immune response involves the production of type I IFN, in particular, IFN-α, in cells such as PDC.

Use of the RNA Oligonucleotide for Treating Diseases/Disorders

The present invention provides the use of the immunostimulatory RNA oligonucleotide of the invention for the preparation of a pharmaceutical composition for preventing and/or treating a disorder selected from immune disorders, infections, and cancers in a mammal, wherein the induction of an immune response is beneficial to the mammal.

The present invention also provides the use of the RNA oligonucleotide of the invention which has both immunostimulatory activity and gene silencing activity for the preparation of a pharmaceutical composition for preventing and/or treating a disorder selected from infections and cancers in a mammal, wherein the induction of an immune response together with the downregulation of a disorder-related gene are beneficial to the mammal.

The present invention further provides the use of the RNA oligonucleotide of the invention which has gene silencing activity and low/minimal immunostimulatory activity for the preparation of a pharmaceutical composition for preventing and/or treating a disorder in a mammal caused by the expression or overexpression of a disorder-related gene, wherein the induction of an immune disorder it to be avoided. The disorder may be selected from cancer, dermatological disorders, immune disorders, metabolic disorders, neurological disorders, ocular diseases, infections, and other hereditary and non-hereditary disorders.

The immune disorders include, but are not limited to, allergy, autoimmune disorders, inflammatory disorders, and immunodeficiency.

Allergies include, but are not limited to, food allergies and respiratory allergies.

Autoimmune diseases include, but are not limited to, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis.

Inflammatory disorders include, without limitation, airway inflammation which includes, without limitation, asthma.

Immunodeficiencies include, but are not limited to, spontaneous immunodeficiency, acquired immunodeficiency (including AIDS), drug-induced immunodeficiency (such as that induced by immunosuppressants used in transplantation and chemotherapeutic agents used for treating cancer).

In one embodiment, the immune disorders include those caused by pathological Th2 responses.

The infections include, but are not limited to viral infections, bacterial infections, anthrax, parasitic infections, fungal infections and prion infection.

Viral infections include, but are not limited to, infection by hepatitis C, hepatitis B, herpes simplex virus (HSV), HIV-AIDS, poliovirus, and smallpox virus. Examples of (+) strand RNA viruses which can be targeted for inhibition include, without limitation, picornaviruses, caliciviruses, nodaviruses, coronaviruses, arteriviruses, flaviviruses, and togaviruses. Examples of picornaviruses include enterovirus (poliovirus 1), rhinovirus (human rhinovirus 1A), hepatovirus (hepatitis A virus), cardiovirus (encephalomyocarditis virus), aphthovirus (foot-and-mouth disease virus O), and parechovirus (human echovirus 22). Examples of caliciviruses include vesiculovirus (swine vesicular exanthema virus), lagovirus (rabbit hemorrhagic disease virus), "Norwalk-like viruses" (Norwalk virus), "Sapporo-like viruses" (Sapporo virus), and "hepatitis E-like viruses" (hepatitis E virus). Betanodavirus (striped jack nervous necrosis virus) is the representative nodavirus. Coronaviruses include coronavirus (avian infections bronchitis virus) and torovirus (Berne virus). Arterivirus (equine arteritis virus) is the representative arteriviridus. Togavirises include alphavirus (Sindbis virus) and rubivirus (Rubella virus). Finally, the flaviviruses include flavivirus (Yellow fever virus), pestivirus (bovine diarrhea virus), and hepacivirus (hepatitis C virus).

In certain embodiments, the viral infections are selected from chronic hepatitis B, chronic hepatitis C, HIV infection, RSV infection, HSV infection, VSV infection, CMV infection, and influenza infection.

Cancers include, but are not limited to biliary tract cancer, brain cancer, breast cancer, cervical cancer, choriocarcinoma, colon cancer, endometrial cancer, esophageal cancer, gastric cancer, intraepithelial neoplasm, leukemia, lymphoma, liver cancer, lung cancer, melanoma, myelomas, neuroblastoma, oral cancer, ovarian cancer, pancreatic cancer, prostate cancer, rectal cancer, sarcoma, skin cancer, testicular cancer, thyroid cancer and renal cancer.

In certain embodiments, cancers are selected from hairy cell leukemia, chronic myelogenous leukemia, cutaneous T-cell leukemia, chronic myeloid leukemia, non-Hodgkin's lymphoma, multiple myeloma, follicular lymphoma, malignant melanoma, squamous cell carcinoma, renal cell carcinoma, prostate carcinoma, bladder cell carcinoma, breast carcinoma, ovarian carcinoma, non-small cell lung cancer, small cell lung cancer, hepatocellular carcinoma, basaliom, colon carcinoma, cervical dysplasia, and Kaposi's sarcoma (AIDS-related and non-AIDS related).

Dermatological disorders include, but are not limited to, psoriasis, acne, rosacea, eczema, molluscum contagious, seborrheic keratosis, actinic keratosis, verruca vulgaris.

Metabolic disorders include, but are not limited to, diabetes and obesity.

Ocular diseases include, but are not limited to, age-related macular degeneration.

Neurological disorders include, but are not limited to, Alzeimer' disease, Huntington's disease, Parkinson's disease, and spinal cord injury.

Hereditary diseases include, but are not limited to, cystic fibrosis.

In one embodiment, the pharmaceutical composition is for administration selected from the group consisting of airway, oral, ocular, parenteral (including intraveneous, intradermal, intramuscular, intraperitoneal, and subcutaneous), rectal, vaginal and topical (including buccal and sublingual) administration.

In another embodiment, the pharmaceutical composition is for use in combination with one or more treatments of disorders selected from treatments for cancer, dermatological disorders, immune disorders, metabolic disorders, neurological disorders, ocular diseases, infections, and other hereditary and non-hereditary disorders in a mammal. Such treatments include, but are not limited to, surgery, chemotherapy, radiation therapy, and the administration of pharmaceutically active (or therapeutic) agents such as immunostimulatory RNA oligonucleotides, immunostimulatory DNA oligonucleotides, cytokines, chemokines, growth factors, antibiotics, anti-angiogenic factors, chemotherapeutic agents, antiviral agents, anti-fungal agents, anti-parasitic agents, and antibodies.

In one embodiment, pharmaceutically active agent is natural or recombinant IFN-α polypeptide, or a CpG-containing or non-CpG-containing DNA oligonucleotide capable of inducing IFN-α (see e.g., WO 01/22990, WO 03/101375). In another embodiment, the pharmaceutically active agent is natural or recombinant IL-12, or an immunostimulatory RNA oligonucleotide capable inducing IL-12 (see e.g. our co-pending application; Sugiyama et al. 2005, *J Immunol* 174:2273-2279). In yet another embodiment, the pharmaceutically active agent is an anti-angiogenic factor such as vasostatin or an anti-VEGF antibody. In certain embodiments, the pharmaceutically active agent is a cancer-specific agent such as Herceptin, Rituxan, Gleevec, Iressa.

Mammals include, but are not limited to, rats, mice, cats, dogs, horses, sheep, cattle, cows, pigs, rabbits, non-human primates, and humans. In a preferred embodiment, the mammal is human.

In Vitro Method for Inducing IFN-α Production

The present invention provides an in vitro method of inducing IFN-α production in a mammalian cell, comprising the steps of:

(a) complexing an immunostimulatory RNA oligonucleotide of the invention with a complexation agent; and (b) contacting the cell with the complex prepared in step (a).

The mammalian cell is capable of producing IFN-α. In one embodiment, the mammalian cell expresses TLR7, TLR8, or both TLR7 and TLR8. The mammalian cells include, but are not limited to, peripheral blood mononuclear cells (PBMC), plasmacytoid dendritric cells (PDC), myeloid dendritic cells (MDC), B cells, macrophages, monocytes, natural killer cells, granulocytes, endothelial cells, cell lines such as THP1, and cells containing exogenous DNA which directs the expression of TLR7 or TLR8 or both TLR7 or TLR8 such as transfected CHO, HEK293 or COS cells.

In one embodiment of the invention, the complexation agent is a polycationic peptide, preferably poly-L-arginine (poly-L-Arg). In one embodiment, the polycationic peptide, in particular, poly-L-Arg, is at least 24 amino acids in length. The polycationic peptide, in particular, poly-L Arg, may be a heterogeneous mixture of peptides of different lengths.

In a preferred embodiment, the mammal is human.

In Vitro Method for Activating Mammalian Dendritic Cells

The present application provides an in vitro method of activating mammalian dendritic cells, comprising the steps of:

(a) complexing an immunostimulatory RNA oligonucleotide of the invention with a complexation agent;

(b) contacting dendritic cells isolated from a donor mammal with the complexed RNA oligonucleotide; and (c) contacting the dendritic cells with an antigen.

In one embodiment of the invention, the complexation agent is a polycationic peptide, preferably poly-L-arginine (poly-L-Arg). In one embodiment, the polycationic peptide, in particular, poly-L-Arg, is at least 24 amino acids in length. The polycationic peptide, in particular, poly-L Arg, may be a heterogeneous mixture of peptides of different lengths.

In one embodiment, the antigen is a disease/disorder-related antigen. The disorder may be a cancer, a dermatological disorder, an immune disorder, a metabolic disorder, a neurological disorder, an ocular disease, an infection, or other hereditary and non-hereditary disorders. The antigen may be a protein, a polypeptide, a peptide, a carbohydrate, or a combination thereof.

The present invention further provides the use of the in vitro activated dendritic cells for the preparation of a medicament for inducing an immune response in a mammal, wherein the in vitro activated dendritic cells are for transfer into a recipient that is the same or different from the donor.

In a preferred embodiment, the mammal is human.

The present invention is illustrated by the following examples.

EXAMPLES

Example 1

Stimulation of PBMC Using Poly-L-arginine-complexed Single-stranded RNA Oligonucleotides First we sought to develop an assay system for the comparison of the IFN-a inducing capacity of single-stranded RNA (ssRNA) oligonucleotides on a large scale. Peripheral blood mononuclear cells (PBMC) were selected as a biological system that is relevant for future clinical application. Within PBMC, the plasmacytoid dendritic cell (PDC) is responsible for IFN-α production upon stimulation with ssRNA oligonucleotides. In order to stimulate IFN-α production in PDC, ssRNA oligonucleotides require transfection. While cationic lipids such as lipofectamine are well-established to support IFN-α production in isolated PDC, the induction of IFN-α in PBMC was not satisfactory. In order to improve transfection of RNA in PBMC we tested a number of cationic polypeptides including poly-L-Lys, poly-His and poly-L-Arg. Among these three, poly-L-Arg (14 kD) was the most potent polycationic peptide and was even more potent than the cationic lipid lipofectamine to support the stimulatory activity of an established immunostimulatory RNA oligonucleotide (RNA9.2sense) (FIG. 1). Within PBMC, the source of IFN-α production were found to be PDC, since PDC depletion abrogated IFN-α production (data not shown). Importantly, poly-L-Arg complexation maintained the same sequence dependency (sense versus antisense strand) of ssRNA oligonucleotide-mediated IFN-α induction that was previously seen for lipofectamine (Homung et al. 2005, *Nat Med* 11:263-270). This experimental system was found to be robust, since adding different concentrations of RNA oligonucleotide from 80% to 120% had little effect on the amount of IFN-α induced. This is in marked contrast to the use of cationic lipids that require exact adjustment of the net charges to avoid cytotoxicity. Together these data indicated that poly-L-Arg complexation is an effective and reliable system to screen for ssRNA oligonucleotide-induced IFN-α production in PBMC.

The experimental procedures are described in more detail in the following:

PBMC Isolation

Human PBMC were prepared from whole blood donated by young healthy donors. PBMC were obtained from whole blood by Ficoll-Hypaque density gradient centrifugation (Biochrom, Berlin, Germany). PBMC were cultured in RPMI-Medium (Biochrom, Berlin, Germany) supplemented with human AB-Serum (2 vol %, Firma, Germany) at a density of $2 \times 10^6$ PBMC/ml. Subsequently PBMC were plated into 96-well flat bottom wells at 200 µl/well. Cells were kept on ice until stimulation.

Resuspension and Annealing of ssRNA Oligonucleotides

Lyophilized ssRNA oligonucleotides (Eurogentec, Belgium) were resuspended in sterile, RNase free water at a concentration of 620 µg/ml. Subsequently 40 µl of the ssRNA oligonucleotides, 40 µl sterile, RNase free water and 20 µl 5× annealing buffer (50 mM Tris-HCl, pH 8.0, 100 mM NaCl, 5 mM EDTA) were combined. This resulted in a final volume of 100 µl with a final concentration of the ssRNA oligonucleotide of 248 µg/ml. Subsequently the solution was incubated at 95° C. for 2 minutes and cooled down to 20° C. with a linear decrease in temperature in 60 minutes (−1.25° C./1 minute). The solution was then stored at −80° C. prior to usage (ssRNA oligonucleotide stock solution).

Stimulation

If not otherwise indicated, ssRNA oligonucleotides were complexed using the polycationic polymer Poly-L-arginine Hydrochloride with a molecular weight of 5.000-15.000 (Prod. Number: P4663, Sigma, Munich, Germany). Lyophilized Poly-L-arginine Hydrochloride was dissolved in sterile, RNase free water at a concentration of 2000 µg/ml (Poly-L-arginine stock solution) and subsequently aliquoted and stored at a temperature of −20° C. ssRNA oligonucleotides were complexed using the following protocol:

1. The poly-L-arginine stock solution and the ssRNA oligonucleotide stock solution are thawed to 4° C.
2. Poly-L-arginine is diluted in Phosphate buffered saline to a concentration of 24 µg/ml (1:83.3 dilution from 2000 µg/ml stock solution).
3. Immediately the ssRNA oligonucleotide is added to a final concentration of 14.8 µg/ml (1:16.6 dilution from 248 µg/ml stock solution).
4. Subsequently, the solution is mixed thoroughly by vortexing for 10 seconds.
5. Next, 15 µl of this solution is added immediately to 200 µl PBMC in the 96-well flat bottom plate. The final concentration of poly-L-arginine is 1.67 µg/ml, whereas the final concentration of the ssRNA oligonucleotide is 1.03 µg/ml.

Throughout all procedures the temperature was kept between 20-25° C. On all 96-well plates PBMC from three individual donors were plated, whereas eleven different ssRNA oligonucleotides were tested. In addition, on each plate the ssRNA oligonucleotide 9.2 sense (5'-AGCUUAAC-CUGUCCUUCAA-3') was included as a positive control. All tested ssRNA oligonucleotides were run in duplicates. After stimulation cells were cultured at 37° C./5% CO2 for 44 hours.

ELISA

After 44 hours of cell culture supernatants were collected and stored in three individual aliquots at −80° C. Prior to ELISA-procedures frozen supernatants were thawed at 20-25° C. for two hours. To measure IFN-a the IFN-a module set Bender MedSystems (Prod. Number: BMS216MST, Graz, Austria) was used. This ELISA detects most of IFN-α isoforms at a detection range of 8-500 pg/ml. All ELISA procedures were performed according to manufacturer's recommendations.

Example 2

Rational Design of a 4mer-motif Library to Screen for Potent Motifs Within ssRNA Previous experiments have shown that a minimal length of 19 bases is required for maximal IFN-α induction by ssRNA oligonucleotides. Since poly adenosine oligonucleotides proved to be inactive in terms of IFN-a induction, we decided to generate a ssRNA oligonucleotide library by placing putative motifs into the center of poly adenosine RNA oligonucleotides. In a first set of experiments we determined the minimal length of a motif for IFN-α induction in our system. We designed a panel of 19mer poly-adenosine ssRNA oligonucleotides with increasing numbers of uracil in the center: 5'-U-3', 5'-UU-3', 5'-UUU-3' and 5'-UUUU-3'. These oligonucleotides were compared to the previously published standard ssRNA oligonucleotide RNA9.2sense (5'-AGCU-UAACCUGUCCUUCAA-3'): while the 1mer motif 5'-U-3' hardly induced IFN-α (0.8% of RNA9.2sense), considerable amounts of IFN-a were observed for the 2mer motif 5'-UU-3' (10.6% of RNA9.2sense), the 3mer motif 5'-UUU-3' (15.7% of RNA9.2sense) and the 4mer motif 5'-UUUU-3' (50.5% of RNA9.2sense) (FIG. 2). Since the largest increment of IFN-a induction was seen between the 3mer and 4mer motif, we generated a library of ssRNA oligonucleotides comprising all possible 4mer motifs in the centre of a poly adenosine oligonucleotide. In view of the fact that the flanking adenosine residues can be part of a 4mer RNA sequence motif, only 193 ssRNA oligonucleotides (table 1) were needed to cover all 256 possible 4mer motifs.

Example 3

Generation and Processing of Raw Data

All 193 ssRNA oligonucleotides were tested on PBMC of six individual healthy donors using poly-L-Arg for complexation. At 44 hours after stimulation with RNA oligonucleotides, supernatants were collected and IFN-α production was measured by ELISA. Prior to statistical analysis the raw data were processed as follows: for each cell culture plate the mean IFN-α value of the experimental duplicates for each tested ssRNA oligonucleotide were normalized to the ssRNA oligonucleotide RNA9.2sense (5'-AGCUUAACCUGUC-CUUCAA-3'). This standard RNA oligonucleotide was included as a positive control on all cell culture plates. Normalization was performed by calculating the ratio of IFN-α induced by the tested oligonucleotide and IFN-a induced by the standard oligonucleotide RNA9.2sense. Thus, for each tested oligonucleotide in an individual donor a mean ratio of IFN-a induction was obtained. In the following, this mean of the ratios is referred to as IFN-a index (one value of IFN-a index per donor). For example testing ssRNA oligonucleotide ANP144 (5'-AAAAAAAGUUGAAAAAAAA-3') in donor 1 gave the mean of the two raw values of the duplicates (IFN-α in supernatant) of 2024 pg/ml, whereas the control oligonucleotide RNA9.2sense (5'-AGCUUAACCUGUC-CUUCAA-3') resulted in 1256 pg/ml. The corresponding IFN-α index of oligonucleotide ANP144 for donor 1 was calculated to be 1.61 (=2024 pg/ml divided by 1256 pg/ml).

Figure 3B:
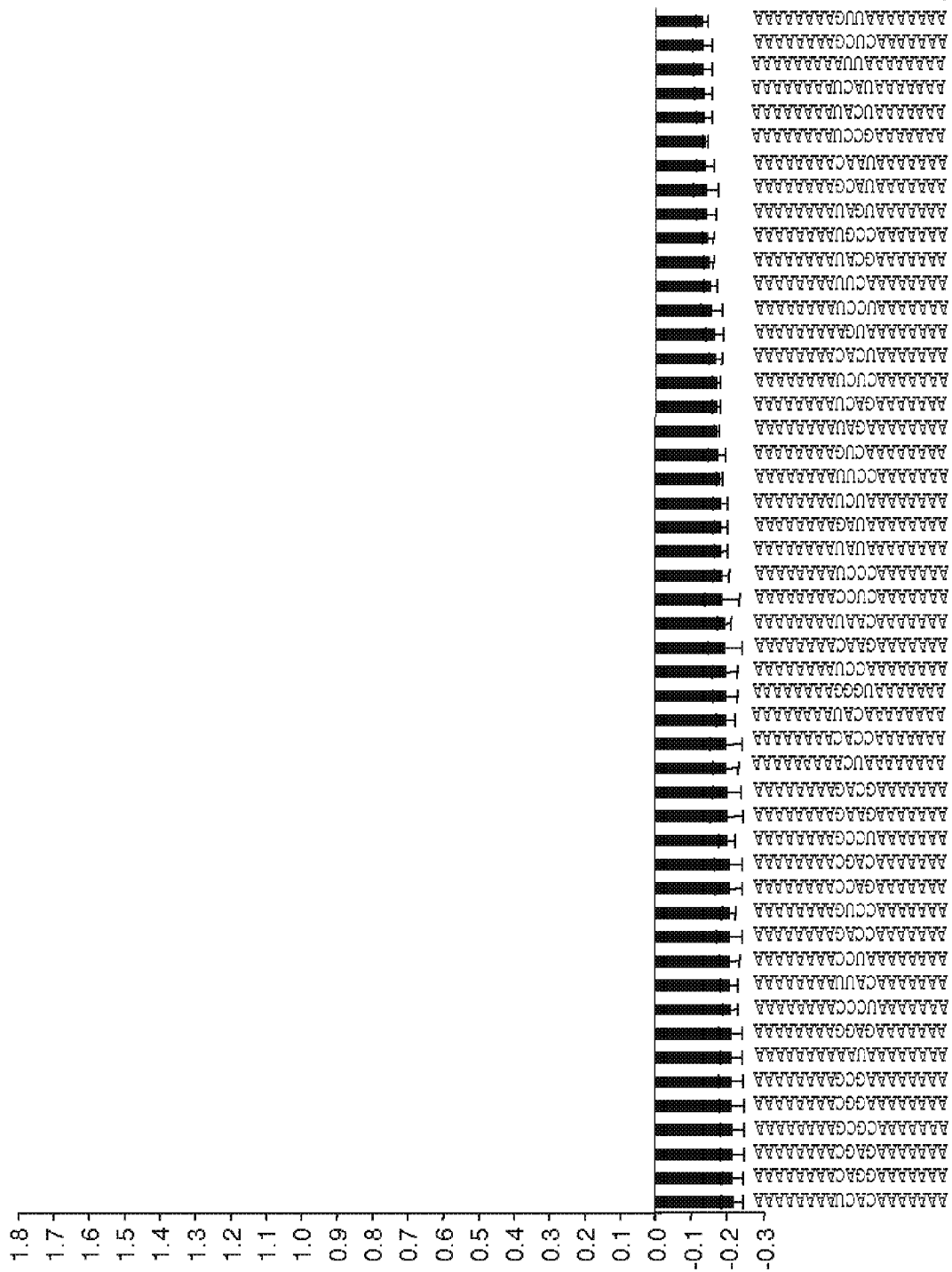
FIG. 3: PBMC of six different healthy donors were isolated and stimulated with poly-L-arginine complexed ssRNA oligonucleotides in duplicates. 44 hours after stimulation IFN-a production was assessed in supernatant via ELISA. For all tested ssRNA oligonucleotides, the mean values of the measured duplicates were normalized to the positive control ssRNA oligonucleotide 9.2sense (5'-AGCUUAACCUGUC-CUUCAA) by dividing the mean value of tested oligonucleotide by the mean value of 9.2sense (=IFN-a index of a given oligonucleotide). Next, all individual IFN-a indices were adjusted to the mean value of all IFN-a indices by subtracting the mean value of all IFN-a indices from the individual IFN-a index of a given oligonucleotide (=adjusted IFN-a index). Data from six individual donors were summarized and were assorted in ascending order displaying the corresponding SEM. In addition, a statistical analysis was performed to assess a putative significant difference for the adjusted IFN-α indices of all top thirty ssRNA oligonucleotides. A two-tailed Student's t-test was employed to calculate the p-value off all possible ssRNA oligonucleotide combinations. A p-value >0.01 and <0.05 is depicted by a black box, whereas a p-value <0.01 is depicted as a grey box.
Figure 3E:
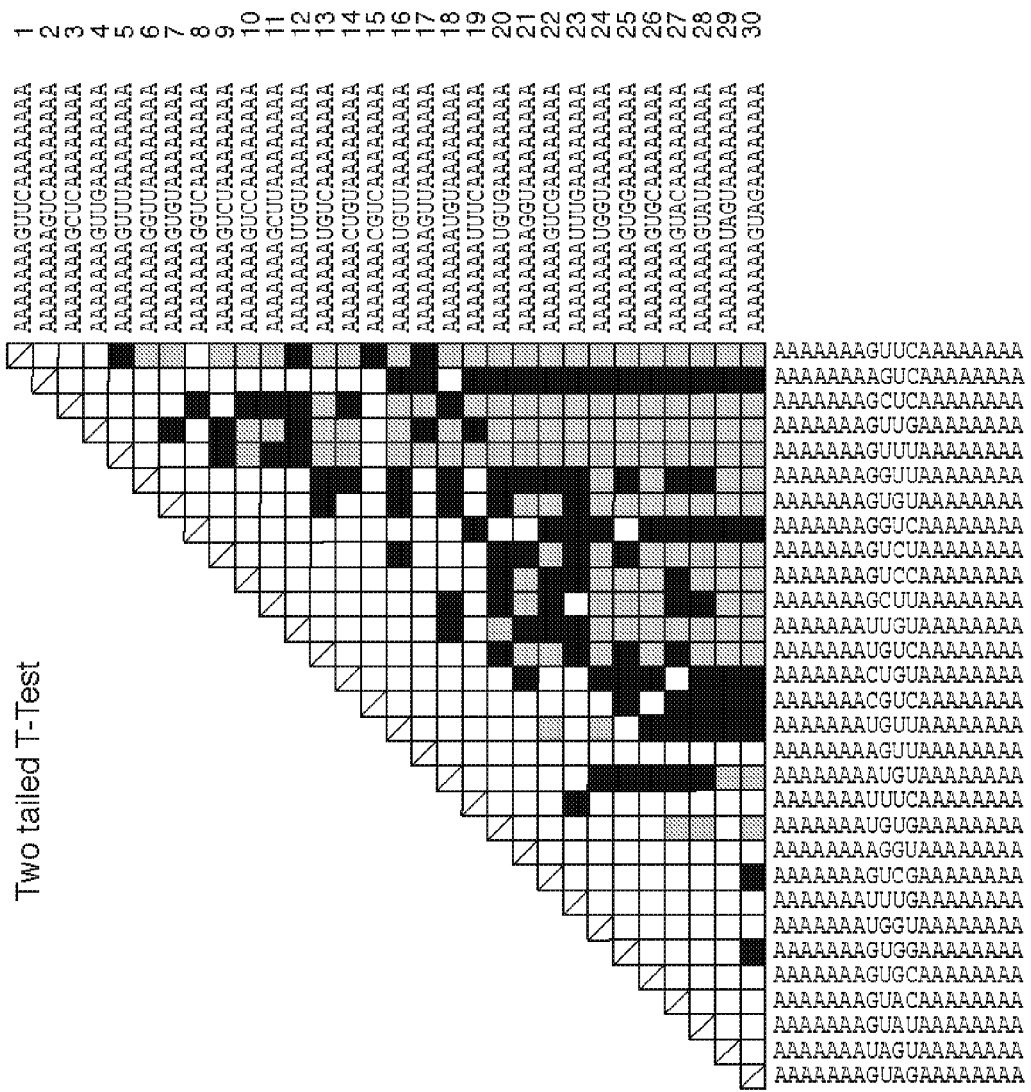

Next, the means of all IFN-α indices for every individual donor were calculated. Then the adjusted IFN-α indices were calculated as IFN-α index minus the mean of all IFN-α indices of one individual donor. For example ssRNA oligonucleotide ANP144 of donor 1 (5'-AAAAAAAG-UUGAAAAAAAA-3') had an IFN-α index of 1.61, whereas the mean of all IFN-a indices of donor 1 was 0.37. The adjusted IFN-a index of ANP144 was calculated: 1.61minus 0.37=1.24 (=substracting 0.37 from). The adjusted IFN-α indices from all six donors were summarized by calculating the means and the corresponding standard error of mean. The data are depicted in ascending order (FIG. 3A, B, C, D). The adjusted IFN-a indices of the top thirty ssRNA oligonucleotides of all six donors were compared using a two-tailed Student's t-test (FIG. 3E). For most combinations tested, a significant difference was observed when the interval between the analyzed pairs was at least six or seven places in the assortment.

The ssRNA oligonucleotides were split into two groups: group 1 (table 2) comprising all ssRNA oligonucleotides with an IFN-α index that lower than the mean IFN-α index off all ssRNA oligonucleotides (or in other words with a mean of the adjusted IFN-α index below 0) (table 1), and group 2 (table 3) comprising all ssRNA oligonucleotides with an IFN-a index higher than the mean IFN-α index off all tested ssRNA oligonucleotides (or in other words with a mean of the adjusted IFN-α index below 0) (table 1). Thus group 1 contained all ssRNA oligonucleotides with an adjusted IFN-α index below 0, whereas group 2 contained all ssRNA oligonucleotides with an adjusted IFN-a index above 0. Group 1 consisted of 148 ssRNA oligonucleotides (75%), whereas group 2 consisted of 45 ssRNA oligonucleotides (25%).

Example 4

Analyzing the Predictive Value of 1mer, 2mer and 3mer Motifs within the 4mer Motif Matrix Next the frequency of 1 mer motifs (5'-X-3'), 2mer motifs (5'-XX-3', 5'-X*X-3', 5'-X**X-3') and 3mer motifs (5'-XXX-3', 5'-XX*X-3', 5'-X*XX-3') in ssRNA oligonucleotides with an IFN-a index below the mean IFN-a index (group 1) and above the mean IFN-α index (group 2) was analyzed. Multiple occurrences of a motif within one single ssRNA oligonucleotide was accounted for. For example, the motif 5'-GU-3' is present twice in the ssRNA oligonucleotide ANP142 (5'-AAAAAAAGUGUAAAAAAAA-3', group 2). Consequently the ssRNA oligonucleotide ANP142 contributed two counts for motif 5'-GU-3' within group 2. In order to compare the distribution of a specific motif between the two groups, the relative occurrence of a specific motif was calculated (ratio of the absolute number of occurrence of a specific motif over the total number of occurrence of all motifs). For example the motif 5'-GU-3' was found 7 times in group 1 (total number of 5'-XX-3'-motifs in group 1:2482) and 33 times in group 2 (total number of 5'-XX-3'-motifs in group 2:799). Thus the calculated relative occurrence for motif 5'-GU-3' in group 1 was 0.0028, whereas the respective relative occurrence for group 2 was 0.0413. In FIG. 4 the relative occurrence of 1 mer motifs (5'-X-3'), 2mer motifs (5'-XX-3', 5'-X*X-3', 5'-X**X-3') and 3mer motifs (5'-XXX-3', 5'-XX*X-3', 5'-X*XX-3') within the two groups is shown. A significant overrepresentation or underrepresentation of a given motif was analyzed using a chi-square test. The null hypothesis of equal distribution within both groups was rejected when the calculated p-value was below 0.05 (significant differences in distribution are indicated by "*" in FIG. 4).

Example 5

Calculating an Individual IFN-α Score for 1mer-, 2mer- and 3mer-motifs

Figure 5A:
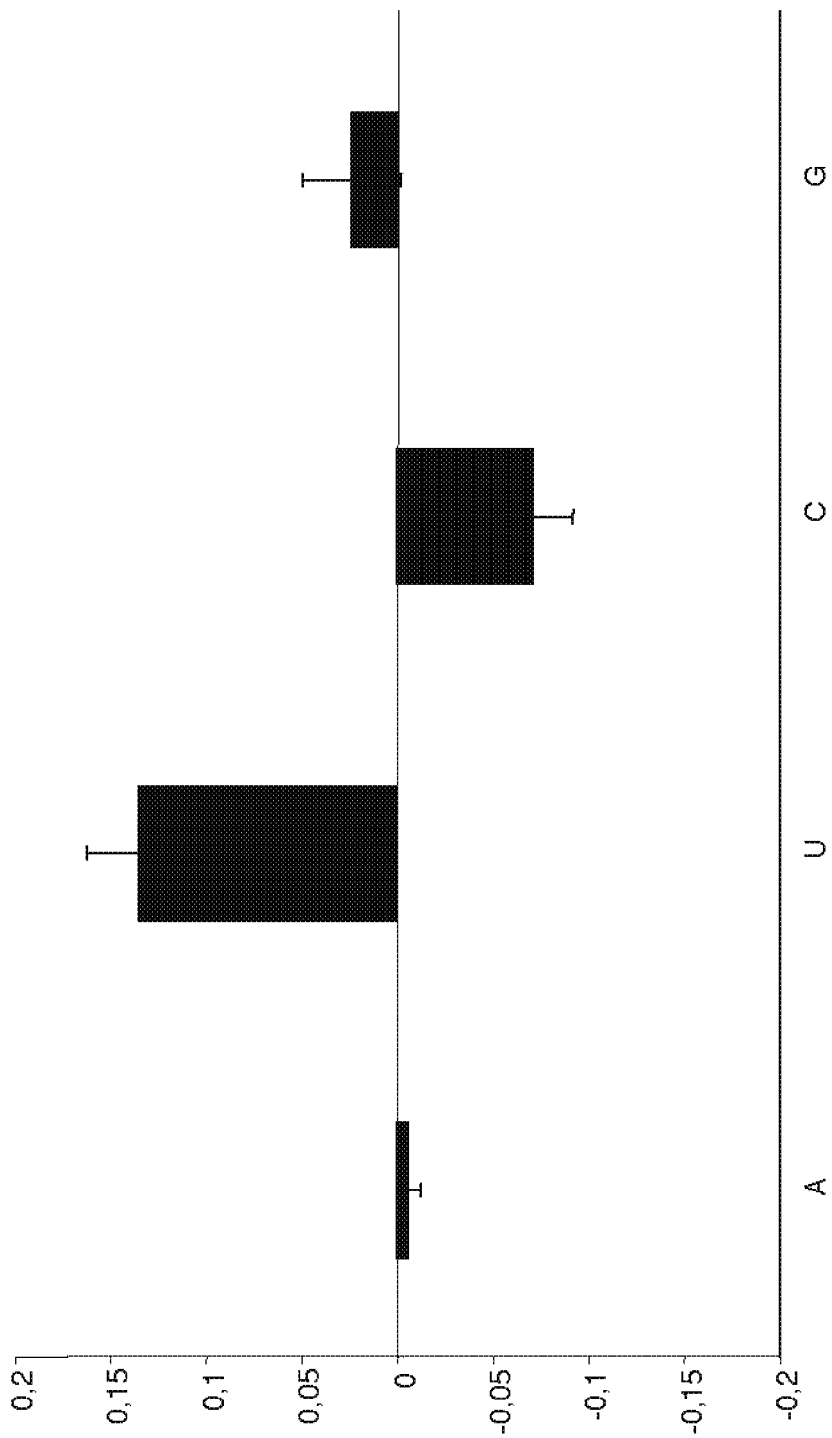
FIG. 5: For all possible 1mer motifs (5'-X-3'), 2mer motifs (5'-XX-3', 5'-X*X-3', 5'-X**X-3') or 3mer motifs (5'-XXX-3', 5'-XX*X-3', 5'-X*XX-3') a mean IFN-a index was assigned by calculating a mean IFN-α index of all ssRNA oligonucleotides containing the corresponding motifs (=IFN-a score of a given motif). The IFN-α score of all possible motifs is depicted in FIG. 5 ±SEM: 1mer motifs 5'-X-3' (FIG. 5A); 2mer motifs 5'-XX-3' (FIG. 5B1), 5'-X*X-3' Figure (FIG. 5B2), 5'-X**X-3' (FIG. 5B3) and 3mer motifs 5'-XXX-3' (FIG. 5C1-5C4), 5'-XX*X-3' (FIG. 5C5-5C8), 5'-X*XX-3' (FIG. 5C9-5C12).

A mean IFN-α index for all possible 1mer motifs (5'-X-3'), 2mer motifs (5'-XX-3', 5'-X*X-3', 5'-X**X-3') or 3mer motifs (5'-XXX-3', 5'-XX*X-3', 5'-X*XX-3') was obtained by calculating a mean IFN-α index of all ssRNA oligonucleotides containing the corresponding motifs. This mean IFN-a index is referred to as the IFN-α score of a given motif. For example the 3mer motif 5'-GUC-3' was contained in ssRNA oligonucleotides ANP 35, 83, 131, 137, 138, 139 and 179 with respective adjusted IFN-α indices of 1.33, 0.68, 0.93, 0.79, 0.44, 0.84, 0.73. The IFN-α score of the 3mer motif 5'-GUC-3' was thus calculated to be 0.82 with a standard error of mean of 0.11. The calculation of the IFN-α score of a motif did not account for the position of the motif within the sequence of the corresponding ssRNA oligonucleotides. Multiple occurrences of one motif within the same ssRNA oligonucleotide was accounted for by adding the corresponding IFN-α index times the number of its occurrence within the oligonucleotide to the calculation of the corresponding IFN-α score of the motif. Consequently an IFN-α score could be assigned to all possible 1 mer motifs (5'-X-3'), 2mer motifs (5'-XX-3', 5'-X*X-3', 5'-X**X-3') or 3mer motifs (5'-XXX-3', 5'-XX*X-3', 5'-X*XX-3') (FIG. 5).

Example 6

Predicting the IFN-α Index of ssRNA Oligonucleotides Using the IFN-α Score of 1 mer-, 2mer- and 3mer-motifs Next we tested the predictive value of the calculated 1 mer-, 2mer- and 3mer-motif IFN-α scores to predict ssRNA oligonucleotides with a low or high IFN-α index. Thus for each ssRNA oligonucleotide the occurrence of a set of motifs was tested and the respective IFN-a scores were assigned to the ssRNA. For example for the panel of 3mer motifs with unspaced sequences (5'-XXX-3') the ssRNA oligonucleotide ANP 35 (5'-AAAAAAAAGUCAAAAAAAA-3') was analyzed the following way:

| 3mer motif (5'-XXX-3') | IFN-α score | Occurrences within the ssRNA oligonucleotide ANP 35 | Assigned IFN-α score |
|---|---|---|---|
| 5'-AAA-3' | −0.0041 | 12 | −0.0503 |
| 5'-AAG-3' | +0.0990 | 1 | +0.0990 |
| 5'-AGU-3' | +0.5796 | 1 | +0.5796 |
| 5'-GUC-3' | +0.8115 | 1 | +0.8115 |
| 5'-UCA-3' | +0.3668 | 1 | +0.3668 |
| 5'-CAA-3' | +0.0033 | 1 | +0.0033 |
| overall | | | +1.8099 |

Figure 6A:
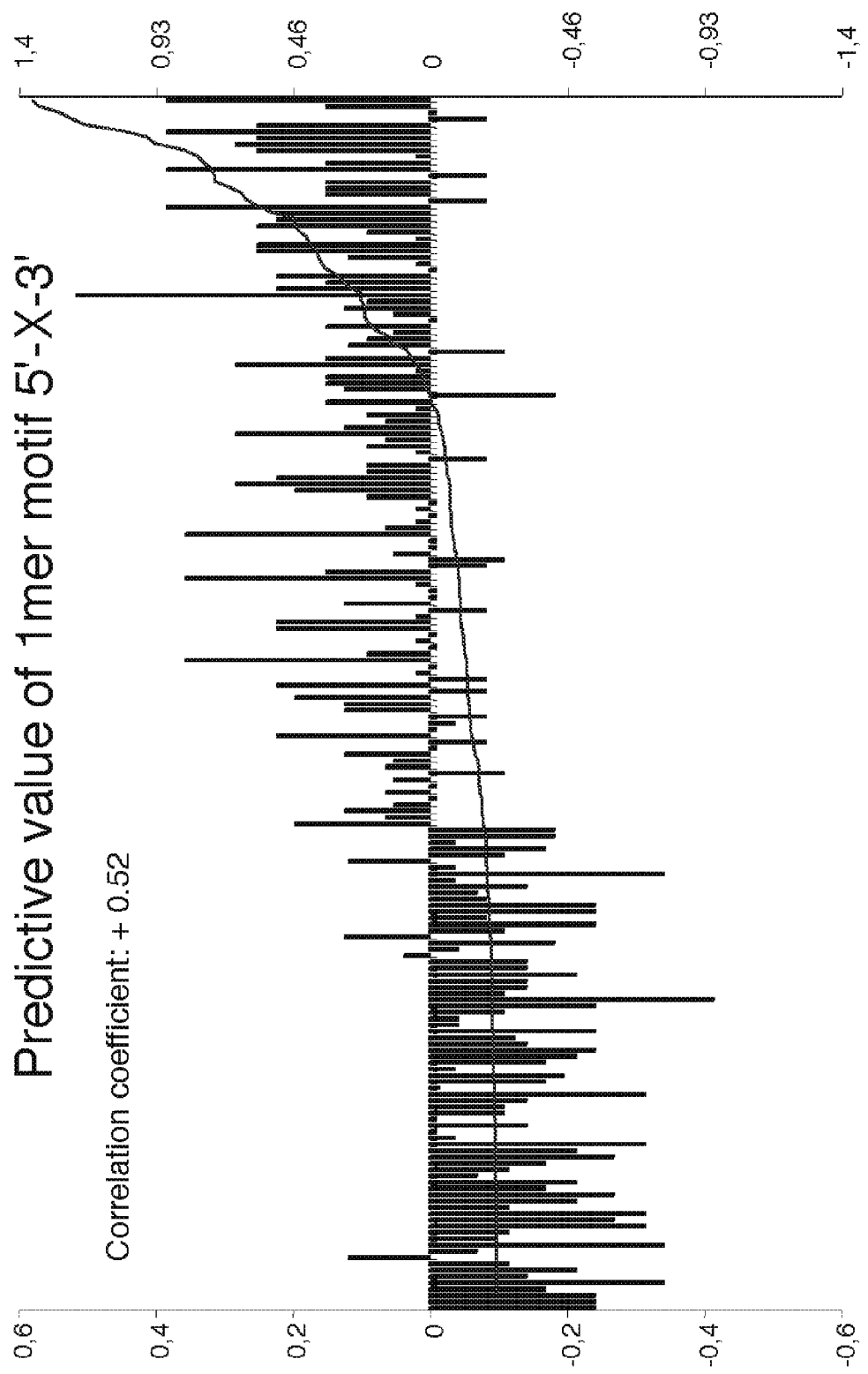
FIG. 6: A calculated IFN-α index was assigned to each oligonucleotide by using the obtained motif-IFN-a scores. For each set of motifs [1mer motifs (5'-X-3'), 2mer motifs (5'-XX-3', 5'-X*X-3', 5'-X**X-3') or 3mer motifs (5'-XXX-3', 5'-XX*X-3', 5'-X*XX-3'] a predicted IFN-a index was calculated for each ssRNA oligonucleotide. Next, the obtained predicted IFN-a indices were compared to the actual adjusted IFN-α indices. Data are depicted the following way: For all ssRNA oligonucleotides the predicted IFN-α indices are shown as a black bars, whereas data are sorted in ascending order according to the actual IFN-α score that is depicted as a red index line. The y-axis on the left side depicts the scale for the predicted IFN-α score, while the y-axis on the right side depicts the scale for the actual IFN-α score.

All ssRNA oligonucleotides were assigned an individual IFN-a score for all possible motif-combinations (1mer-, 2mer- and 3mer-motifs). Next, the prediction that was obtained by using the assigned IFN-α scores was compared to the actual adjusted IFN-α indices for all ssRNA oligonucleotides and for each motif combination. Data were sorted in ascending order according to the adjusted IFN-α indices. For all predictions, the correlation coefficient was calculated: Using the IFN-α scores of 1mer motifs (5'-X-3') to predict the actual adjusted IFN-α indices off all ssRNA oligonucleotides a correlation coefficient of 0.53 was obtained (FIG. 6A). When 2mer motifs were used to predict the adjusted IFN-α indices a correlation coefficient of 0.77 was obtained for 5'-XX-3'-motifs, a correlation coefficient of 0.58 for 5'-X*X-3'-motifs and a correlation coefficient of 0.60 for 5'-X**X-3'-motifs (FIG. 6B). Using 3mer motifs to predict the adjusted IFN-α indices, a correlation coefficient of 0.87 was calculated for 5'-XXX-3'-motifs, of 0.80 for 5'-XX*X-3'-motifs and of 0.80 for 5'-X*XX-3'-motifs.

Figure 6D:
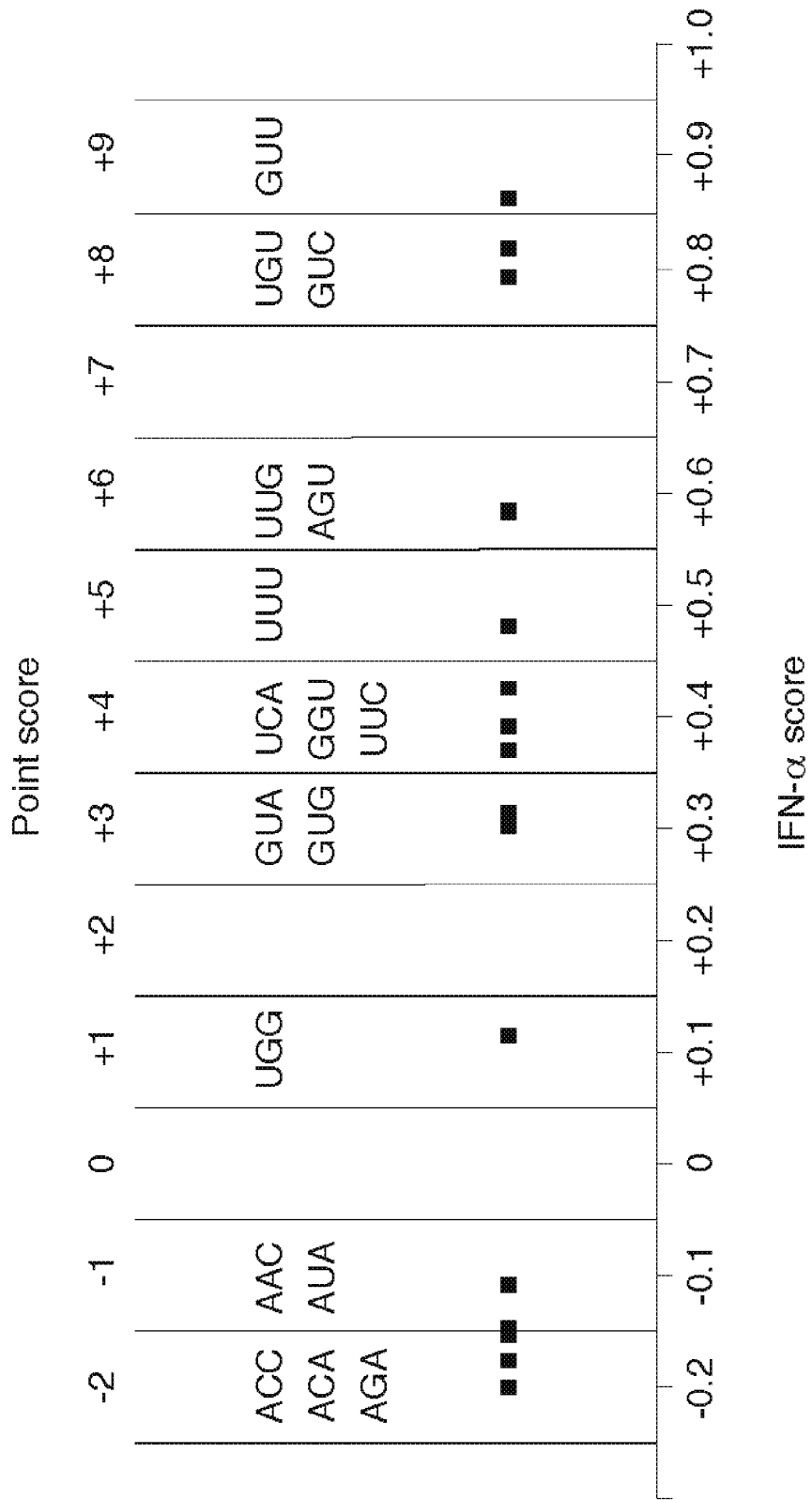
Figure 6E:
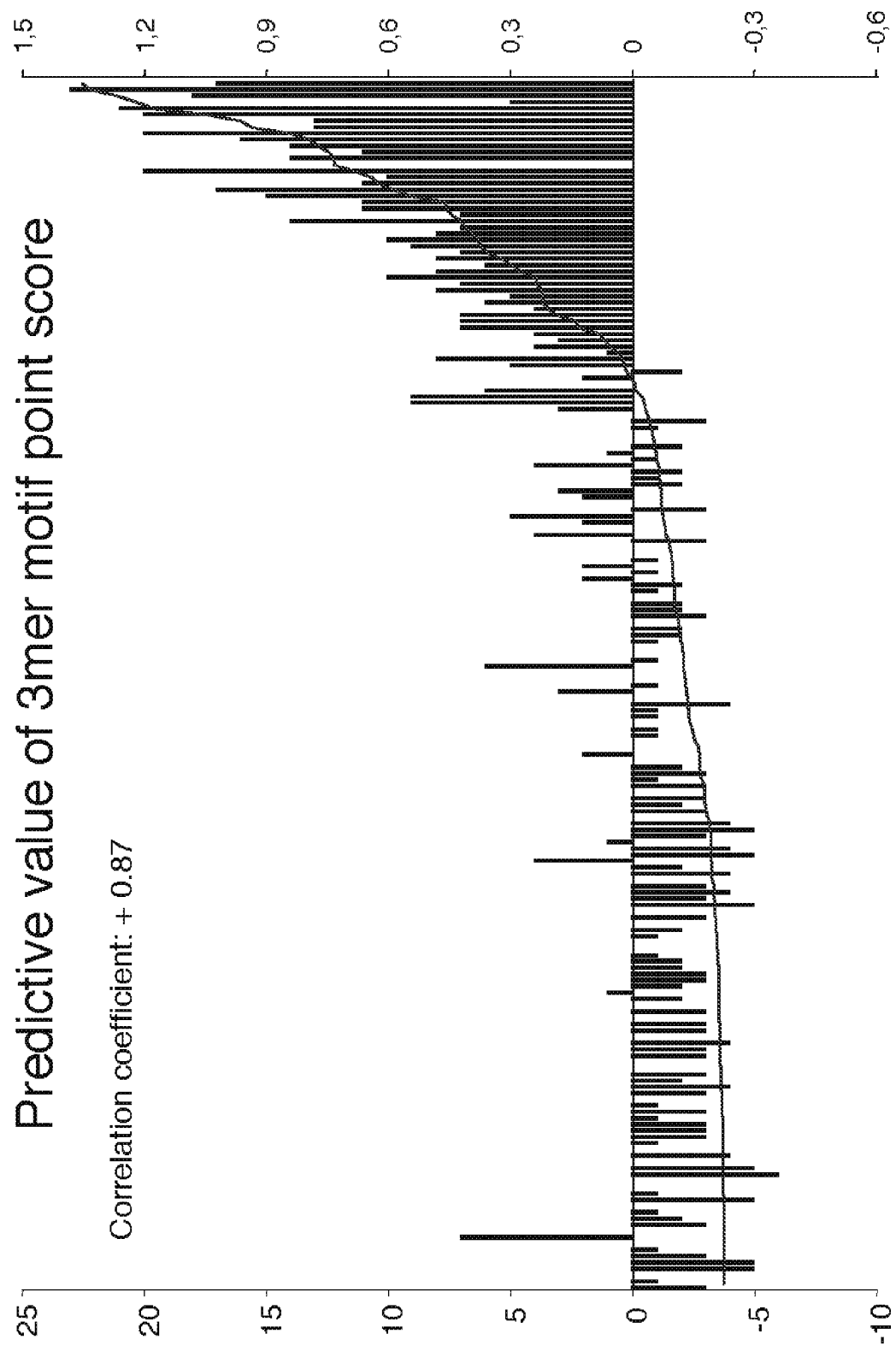

Next, the most accurate prediction algorithm (using the individual IFN-α scores of the 5'-XXX-3'-motifs) was translated into a point score system. The matrix of the 64 different 3mer motifs (5'-XXX-3') was reduced to encompass only the motifs that were significantly over- or underrepresented in either group 1 or group 2 ssRNA oligonucleotides. Even though only 17 3mer motifs (5'-XXX-3') were left in this matrix, a correlation coefficient of 0.87 could still be calculated when using the respective IFN-α scores to predict the IFN-α indices of the complete ssRNA oligonucleotide library (data not shown). In addition, the respective IFN-α scores of the reduced 3mer motif matrix was translated in into a point score system by assigning a point score to each 3mer motif (FIG. 6D). Using this point score system, a prediction of the measured IFN-α indices of all 193 ssRNA oligonucleotides was calculated with a corresponding correlation coefficient of 0.87 (FIG. 6E).

Example 7

Influence of the Positioning and the Flanking Bases on the IFN-α-Inducing Activity of a Potent 4mer Motif Within a 19mer ssRNA Oligonucleotide Next we sought to address the impact of moving a potent 4mer motif to either the 5' or the 3' end within a 19mer ssRNA oligonucleotide. A panel of ssRNA oligonucleotides was designed that included the potent 4mer motif 5'-GUCA-3' within a 19mer poly-A ssRNA oligonucleotide (table 4). The positioning of the 4mer motif was chosen to be either 2, 6, 8, 10 or 14 bases from the 5'-end of the ssRNA oligonucleotide. PBMC were stimulated with the respective ssRNA oligonucleotides and IFN-α production was assessed 44 hours after stimulation. Positioning the 4mer motif two bases from the 5'-end of the ssRNA oligonucleotide slightly decreased IFN-α induction by 13%, when compared to the center positioning (8 bases from the 5'-end). A higher decrease in IFN-α production (29%) was seen, when the 4mer motif was positioned on the 3'-end of the ssRNA oligonucleotide (14 bases from the 5'-end). Nevertheless all ssRNA oligonucleotides tested were still more potent in terms of IFN-α induction than the positive control 9.2sense (FIG. 7A).

Figure 7C:
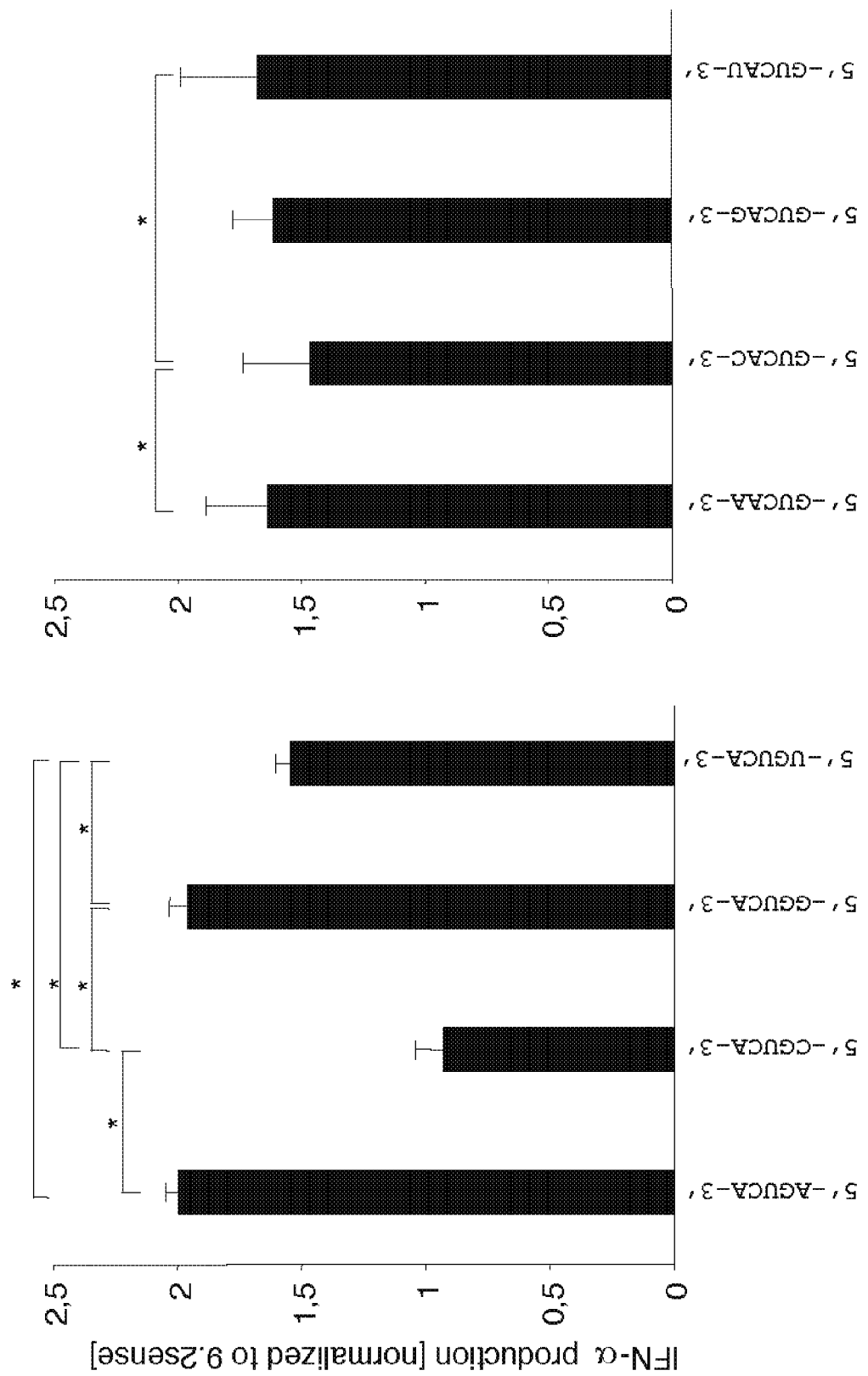

In addition, we addressed the influence of flanking bases on the stimulatory activity of the potent 4mer motif 5'-GUCA-3'. A panel of 16 ssRNA oligonucleotides, which included all possible oligonucleotides with permutated bases at the flanking positions to the 5'- and the 3'-end of the central 5'-GUCA-3'-motif (table 5), was tested (FIG. 7B). As soon as the 5'-GUCA-3'-motif was modified with a preceding 5'-C-3', a significant decrease to less than 50% of the original activity was obtained (FIG. 7C). In addition, when a 5'-U-3' preceded the 5'-GUCA-3'-motif, a significant decrease to about 77% of the original activity was observed (FIG. 7C). In contrast, changing the preceding base to a 5'-G-3' did not impact on the stimulatory activity of the 5'-GUCA-3'-motif. The modification of the flanking base to the 3'-end had little impact on the stimulatory activity of the 5'-GUCA-3'-motif. Nevertheless, a slight, yet significant decrease in activity was detected, as soon as the base to the 3'-end was changed into a 5'-C-3'.

Example 8

Predicting the Immunostimulatory Activity of Complex 19mer ssRNA Oligonucleotides Using the 3mer Motif 5'-XXX-3' Based IFN-α Point Score Matrix Next, we employed the IFN-α point score matrix to predict the potency of complex (i.e., no longer on a poly A backbone) 19mer ssRNA oligonucleotides in terms of IFN-α induction. Modified versions of RNA9.2sense that have been previously described (Hornung et al. 2005, Nat Med 11:263-270) were used to stimulate PBMC; IFN-α production was measured 44 h after stimulation. In addition, respective sequences were analyzed using the above-described algorithm that is based on the IFN-α score of 3mer motifs 5'-XXX-3'. Both the measured and the predicted data were normalized to the ssRNA oligonucleotide RNA9.2sense (set to 100%). In FIG. 8A both measured data and predicted data are depicted. The correlation coefficient for this analysis was calculated to be 0.84.

Example 9

Validation of the Method of Prediction

Our method of predicting the immunostimulatory activity of an RNA oligonucleotide is further validated by data disclosed in various publications. To date, four publications describe IFN-α induction by RNA oligonucleotides in the human system: Heil F et al. 2004, Science 303: 1526-1529; Sioud M et al. 2005, J Mol Biol 348: 1079-1090; Hornung V et al. 2005, Nat Med 11: 263-270; Judge A D et al. 2005, Nat Biotechnol 2005. 23: 457-462.

Heil and colleagues (Heil F et al. 2004, Science 303: 1526-1529) found that when added to human PBMC as a complex with cationic lipid DOTAP, RNA40 (5'-GCC CGU CUG UUG UGU GAC UC-3', HIV-1 U5 region nt 108-127) but not RNA41 (U-A replacement of RNA40) or RNA42 (G-A replacement of RNA40) induced IFN-α, and that the source of IFN-α was PDC. In contrast, both RNA40 and RNA42, but not RNA41 induced TNF-α, IL-6 and IL-12p40; TNF-α was produced by CD11c+ cells. Similar results were found with isolated murine PDC and macrophages. RNA33 (5-GUAGU-GUGUG-3') and RNA34 (5'-GUCUGUUGUGUG-3'), both containing one phosphorothioate linkage at the 3' end, induced the same cytokine profile as RNA40 in the mouse system. Heil et al. stated that a sequence motif responsible for the IFN-α a inducing activity of the RNA oligonucleotides tested could not be identified; subsequently, the activity was attributed to the high GU content of the sequence. Our analysis of the results of Heil et al. reveals that RNA40 contains a 4mer motif, GUUG, which is the fourth most potent motif in inducing IFN-α production in our matrix. Furthermore, our 3mer-based algorithm predicts high IFN-α-inducing activity for RNA40, RNA33 and RNA34, but not for RNA41 and RNA42, which is in agreement with the experimental data (FIG. 8D).

Another publication on ssRNA and IFN-α in the human system is from our own group (Hornung V et al. 2005, Nat Med 11: 263-270). In this publication, we identified a 9mer sequence motif which was responsible for the immunostimulatory activity of the ssRNA oligonucleotide RNA9.2 sense (5'-AGC UUA ACC UGU CCU UCA A-3', 9mer motif underlined). No motif shorter than the 9mer motif was characterized. The analysis of our previously published results reveals that the previously identified 9mer motif contains GUCC which is the tenth most potent immunostimulatory 4mer in our matrix. Furthermore, our 3mer-based IFN-α point score matrix predicts RNA9.2 sense to be a highly active IFN-α-inducing sequence. Moreover, our 3mer-based IFN-α point score matrix offers a prediction of the IFN-α-inducing activities of other sequences tested in Hornung et al.; our prediction correlates very well with the published experimental data.

Another study in the human system was published by Sioud and colleagues (Sioud M et al. 2005, J Mol Biol 348: 1079-1090). The authors examined a panel of 32 siRNAs for their ability to induce TNF-α and IL-6 in PBMC. The most active sequence was number 27 (sense: 5'-GUCCGGGCAG-GUCUACUUUTT-3') either as siRNA (double-stranded) or as the sense strand. As negative control, number 32 (sense: 5'-GCUGGAGAUCCUGAAGAACTT-3') was used. Of note, the whole panel was not screened for IFN-α-inducing activity; only sequence 27 was assayed for IFN-α induction in PBMC. Both the number 27 siRNA and the corresponding sense strand were found to induce IFN-α. DOTAP was used for transfection. Our analysis of the panel of 32 siRNAs reveals that only oligonucleotide number 27, but none of the other oligonucleotides of the panel, contains the motif GUCC, which is ranked number 10 on our most potent immunostimulatory 4mer list and which is also contained in the 9mer motif of our earlier paper (Hornung V et al. 2005, *Nat Med* 11: 263-270) discussed above. Furthermore, our 3mer-based IFN-α point score matrix predicts potent IFN-α-inducing activity for siRNA number 27. However, since siRNA number 27 was the only sequence examined for IFN-α-inducing activity in Sioud et al, a comprehensive analysis of the whole panel of siRNAs could not be carried out.

Besides our own previous publication (Hornung V et al. 2005, *Nat Med* 11: 263-270), Judge and colleagues are the only ones who proposed a sequence motif (UGUGU) for the IFN-α-inducing activity of RNA oligonucleotides (Judge A D et al. 2005, *Nat Biotechnol* 2005. 23: 457-462). Although most of their work was done with siRNA (double-stranded), for one of their potent immunostimulatory sequences, βP-Gal control, both the sense and the antisense strand were tested. The sense strand, but not the antisense strand, was found to be active to inducing IFN-α in human PBMC. The sense strand (5'-UUGAUGUGUUUAGUCGCUA-3') contained the proposed UGUGU motif, while the antisense strand (5'-UAGC-GACUAAACACAUCAA-3') did not. The introduction of one (UGCGU) or two (UGCGC) mismatches in the sense strand sequence of the β-Gal control siRNA led to the loss of IFN-a-inducing activity. On the other hand, the creation of the UGUGU motif, starting from UGGCU, in a primarily non-stimulatory siRNA, BP1, led to an enhanced IFN-α-inducing activity. Furthermore, Judge and colleagues showed that they could select non-stimulatory siRNA sequences by avoiding U-rich sequences and GUGU motifs. Indeed, in our 4mer matrix, GUGU is the 7th most active motif, and UGUG is the 20th most active motif. Furthermore, the relative IFN-α-inducing activities of β-Gal control siRNA, BP1 siRNA and their derivatives predicated by our 3mer-based IFN-α point score matrix correlates extremely well with the experimental data of Judge et al. (FIG. 8B).

Additional publication reports the induction of IFN-α by RNA oligonucleotides in the mouse system.

Barchet W et al. (2005, *Eur J Immunol* 35: 236-242) reports IFN-α induction by RNA oligonucleotides in murine PDC. In this study, the RNA sequences examined were derived from the 5' and 3' untranslated regions (UTR) of Influenza virus. The following sequences were used:

```
5' UTR:
5'-AGUAGAAACAAGGUAGUUU-3'  (19 mer)

3' UTR:
5'-UUAACUACCUGCUUUUGCU-3'  (19 mer)

5'3' UTR:
5'-AGUAGAAACAAGGUAGUUUUUGUUAACUACCUGCUUUUGCU-3'

(42 mer),

5' UTR U-C replacement:
5'-AGCAGAAACAAGGCAGCCC-3'  (19 mer)

5' UTR G-C replacement:
5'-ACUACAAACAACCUACUUU-3'  (19 mer)
```

5'UTR, 3'UTR and 5'3'UTR oligonucleotides all induced IFN-α production from murine PDC. The activity of 5'UTR was significantly reduced when the Gs were replaced by Cs, and abolished when the Us were replaced by Cs. No motif responsible for the IFN-α-inducing activity was defined in this study. According to our 4mer motif matrix, 5'UTR contains the 5th active motif GUUU, and 3'UTR contains the motif UUUU which is above average. The activity levels of the oligonucleotides used in Barchet et al. predicted by our 3mer-based IFN-α point score matrix correlates with the experimental data of Barchet et al.

It should be noted that in some studies double stranded RNA oligonucleotides were used. In such cases, a mean value for the individually analyzed single strands was calculated. Nevertheless, using the prediction algorithm, a good estimate of the actual IFN-α data could be obtained.

All of the publications discussed above validate the use of our 4mer matrix and algorithms for predicting the immunostimulatory activity of RNA oligonucleotides. The teaching in the prior art with regard to the prediction of IFN-α-inducing activity of RNA oligonucleotides has been limited. The only criteria available so far are the content of G and U (Heil et al. 2004, *Science* 303: 1526-1529), and the presence of the GUGU motif (Judge et al. 2005, *Nat Biotechnol* 2005. 23: 457-462). With our 3mer-based IFN-α point score matrix, we now can predict the immunostimulatory activity of any RNA oligonucleotide reliably.

Example 10

Determining the Threshold for High and Low Immunostimulatory Activity

The immunostimulatory activity of any given RNA oligonucleotide can be predicted using the 3mer-based IFN-α point score matrix as described previously (i.e., the "addition method". For research and drug discovery and development purposes, two groups of RNA oligonucleotide are of interest: Group A oligonucleotides which have high or maximal IFN-α-inducing activity, and Group B oligonucleotides which have low or minimal IFN-α-inducing activity. Among all possible ssRNA oligonucleotides of a certain length, 1% of the oligonucleotides with the highest IFN-α scores are assigned to Group A; where as 1% of the oligonucleotides with the lowest IFN-α scores are assigned to Group B. The cut-off IFN-α score for Group A oligonucleotide is the threshold for high or maximal immunostimulatory activity; the cut-off IFN-α score for Group B oligonucleotide is the threshold for low or minimal immunostimulatory activity.

The IFN-α score thresholds for high/maximal and low/minimal immunostimulatory activity for 19mer ssRNA oligonucleotides are determined as follows:

A pool of all possible sequences of 19mer RNA oligonucleotides consists of $4^{19}=274{,}877{,}906{,}944$ oligonucleotides. The IFN-α score for every single RNA oligonucleotide in the pool is calculated using the 3mer-based IFN-α point score matrix. All $4^{19}$ oligonucleotides are ranked based on their calculated predicted IFN-α scores. The threshold for group A is determined to be $$1.4909 \times n + 22.014$$

(n=length of the ssRNA oligonucleotide, and n>9).

All ssRNA oligonucleotides with a calculated IFN-α score above the threshold value are grouped into Group A. The Group A threshold for 19mer ssRNA oligonucleotides is 50.3411. Non-limiting examples of Group A 19mer ssRNA oligonucleotides include the following:

| Sequence (5'-->3') | Predicted IFN-α score |
|---|---|
| GUUUGUUGCUUUGAUUGCC | 60 |
| UUGUAGUUCGUUGCUAGUG | 60 |

| Sequence (5'-->3')      | Predicted IFN-α score |
|-------------------------|-----------------------|
| AGUUCAUGGUGGGUUGUAC     | 62                    |
| UGUUUAAGUUGUUCUACCC     | 62                    |
| AAGUUUUGAUUUUUCAGUA     | 63                    |
| AGGCGUUUGUGUUCGGGUU     | 65                    |
| AGAUGUUGUAGGGUGUUUU     | 66                    |
| UAGUGUGUGUCAGUGUGAC     | 71                    |
| GGUUGCGUGUGGAGUUGUU     | 72                    |
| UGUAGUUUUGUUAGAGUCA     | 75                    |
| GUGUGGUUGCUGUUGUCAA     | 77                    |

The threshold for Group B oligonucleotides is determined to be:

$$(0.005 \times n^2) - (0.2671 \times n) - 3.5531$$

(n=length of the ssRNA oligonucleotide, and X>9)

All ssRNA oligonucleotides with a calculated IFN-α score below the threshold value are grouped into Group B. The Group B threshold for 19mer ssRNA oligonucleotide is −6.823. Non-limiting examples of Group B 19mer oligonucleotide include the following:

| Sequence (5'-->3')      | Predicted IFN-α score |
|-------------------------|-----------------------|
| GGGACCGAAAGACCAGACC     | −10                   |
| UAAGACUAGAAGAGACAGA     | −10                   |
| AGAUCCGAACCACCGACCA     | −9                    |
| GAACCAGAAAAUAGAGCAG     | −8                    |
| CAUAUAAGAAGACCAGCCA     | −8                    |
| UAAGAACCAACUGCUAGAA     | −8                    |
| CCCCUACAGACAGAAUACC     | −7                    |
| CUGGCAGAUAGAUAGAAGC     | −7                    |
| CUAGACCAGAACAAUCUCG     | −7                    |
| UUAGAGACAUAACAACAUU     | −7                    |
| GGACCAAACCUCUCGACAU     | −7                    |

For ssRNA oligonucleotides between 3 and 9 nucleotides in length, the Group A and Group B threshold values are given below in Table 8:

TABLE 8

Threshold IFN-α scores for Group A and Group B oligonucleotides 3-9 nucleotides in length.

| | The predicted IFN-α score (using the IFN-α point score matrix) | |
|---|---|---|
| ssRNA oligonucleotide length | Threshold for GROUP B ssRNA oligonucleotides | Threshold for GROUP A ssRNA oligonucelotides |
| 3 | −2 | 9 |
| 4 | −2 | 15 |
| 5 | −3 | 20 |
| 6 | −4 | 23 |
| 7 | −4 | 26 |
| 8 | −5 | 28 |
| 9 | −5 | 30 |

Example 11

Designing siRNA with High or Low Immunostimulatory Activity

The threshold for Group A siRNA is $$1.4909 \times n + 31.014$$

(n=length of the ssRNA oligonucleotide and n>9) according to the "addition method".

An siRNA is considered a Group A siRNA, i.e., an siRNA with high or maximal immunostimulatory activity, if at least one of the strands, preferably the sense strand, has an IFN-α score above the threshold.

In order to maximize the chance of identifying at least one siRNA with optimized gene silencing as well as immunostimulatory activity, at least ten siRNA molecules need to be identified whose sense strands have an IFN-α score above the threshold for Group A siRNA. When fewer than ten siRNA can be identified that fit the above criteria, the threshold for Group A siRNA is decrease by 1 in a stepwise manner until ten siRNA can be identified.

Most commonly used siRNA are at least 19 nucleotides in length. The threshold for Group A siRNA for a 19mer is 59.3411.

The following example demonstrates the identification of Group A siRNA for mRNA of human cyclophilin B (hCyPB) (Accession No. M6087).

For hCyPB, 833 putative or potential siRNA duplexes (19mer) can be identified. The IFN-α score is calculated for both the sense and the antisense strand of all possible 833 19mer siRNA using the IFN-α point score matrix. All siRNA duplexes which contain at least one strand with an IFN-α score higher than 59.3411 are put into Group A. 11 siRNA duplexes are assigned to Group A because the IFN-α scores of their sense strands are above the threshold; 24 siRNA duplexes are assigned to Group A because the IFN-α scores of their antisense strands are above the threshold. The Group A hCyPB siRNA are listed in Table 9:

| Sense strand (5'→3') | IFN-α score | Antisene strand (5'→3') | IFN-α score |
|---|---|---|---|
| UAACAAACUCCUACCAACA | −9 | UGUUGGUAGGAGUUUGUUA | 74 |
| AACAAACUCCUACCAACAC | −9 | GUGUUGGUAGGAGUUUGUU | 77 |
| UACCAACACUGACCAAUAA | −8 | UUAUUGGUCAGUGUUGGUA | 63 |

-continued

| Sense strand (5'→3') | IFN-α score | Antisene strand (5'→3') | IFN-α score |
|---|---|---|---|
| CUACCAACACUGACCAAUA | -8 | UAUUGGUCAGUGUUGGUAG | 63 |
| ACCAACACUGACCAAUAAA | -8 | UUUAUUGGUCAGUGUUGGU | 65 |
| ACAAACUCCUACCAACACU | -8 | AGUGUUGGUAGGAGUUUGU | 74 |
| ACUCCUACCAACACUGACC | -7 | GGUCAGUGUUGGUAGGAGU | 62 |
| CCUACCAACACUGACCAAU | -7 | AUUGGUCAGUGUUGGUAGG | 63 |
| UCCUACCAACACUGACCAA | -7 | UUGGUCAGUGUUGGUAGGA | 63 |
| AAACUCCUACCAACACUGA | -6 | UCAGUGUUGGUAGGAGUUU | 64 |
| CCAACACUGACCAAUAAAA | -6 | UUUUAUUGGUCAGUGUUGG | 66 |
| CAAACUCCUACCAACACUG | -6 | CAGUGUUGGUAGGAGUUUG | 66 |
| AACUCCUACCAACACUGAC | -6 | GUCAGUGUUGGUAGGAGUU | 67 |
| AACACUGACCAAUAAAAAA | -6 | UUUUUUAUUGGUCAGUGUU | 69 |
| CAACACUGACCAAUAAAAA | -6 | UUUUUAUUGGUCAGUGUUG | 70 |
| GCUACAAAAACAGCAAAUU | -5 | AAUUUGCUGUUUUUGUAGC | 60 |
| GGCUACAAAAACAGCAAAU | -5 | AUUUGCUGUUUUUGUAGCC | 60 |
| ACACUGACCAAUAAAAAAA | -5 | UUUUUUUAUUGGUCAGUGU | 65 |
| UGGCUACAAAAACAGCAAA | -4 | UUUGCUGUUUUUGUAGCCA | 60 |
| GUAACAAACUCCUACCAAC | -4 | GUUGGUAGGAGUUUGUUAC | 66 |
| CACUGACCAAUAAAAAAAA | -3 | UUUUUUUUAUUGGUCAGUG | 62 |
| ACUGACCAAUAAAAAAAAA | -3 | UUUUUUUUUAUUGGUCAGU | 64 |
| UACAAAAACAGCAAAUUCC | -1 | GGAAUUUGCUGUUUUUGUA | 60 |
| CUACAAAAACAGCAAAUUC | -1 | GAAUUUGCUGUUUUUGUAG | 60 |
| AAAAUGUGGGUUUUUUUUU | 60 | AAAAAAAAACCCACAUUUU | 5 |
| UGUGGUGUUUGGCAAAGUU | 63 | AACUUUGCCAAACACCACA | 3 |
| AAAUGUGGGUUUUUUUUUU | 65 | AAAAAAAAAACCCACAUUU | 0 |
| GUUUUUUUUUUUUUUAAUA | 68 | UAUUAAAAAAAAAAAAAAC | -1 |
| AAUGUGGGUUUUUUUUUUU | 70 | AAAAAAAAAAACCCACAUU | -5 |
| GGUUUUUUUUUUUUUUAAU | 73 | AUUAAAAAAAAAAAAAACC | -3 |
| GGGUUUUUUUUUUUUUUAA | 73 | UUAAAAAAAAAAAAAACCC | -3 |
| UGGGUUUUUUUUUUUUUUA | 74 | UAAAAAAAAAAAAAACCCA | -3 |
| AUGUGGGUUUUUUUUUUUU | 75 | AAAAAAAAAAAACCCACAU | -5 |
| GUGGGUUUUUUUUUUUUUU | 77 | AAAAAAAAAAAAAACCCAC | -3 |
| UGUGGGUUUUUUUUUUUUU | 80 | AAAAAAAAAAAAACCCACA | -5 |

The IFN-α score threshold for a Group B siRNA is $$0.6075\times n-9.9484$$

($n$=length of the ssRNA oligonucleotide and $n>13$) according to the "addition method".

Both the sense and the antisense strands of an siRNA have to have an IFN-α score below the threshold for the siRNA to be assigned to Group B. In order to maximize the chance of identifying at least one siRNA with optimal gene silencing activity but minimal immunostimulatory activity, at least ten Group B siRNA duplexes should be identified for a given target mRNA. Should this condition not be met, the threshold IFN-α score is increased by 1 in a stepwise manner until ten Group B siRNA are identified.

The IFN-α score threshold for Group B 19mer siRNA duplexes is 1.5941.

None of the 833 potential hCyPB siRNA have an IFN-α score of lower than 1.5491 for both strands. When the threshold was increased to 2.5491, one siRNA is identified. In order to identify at least ten siRNA duplexes, the threshold IFN-α score has to be increased by 3 to 4.5491. The Group B siRNA thus identified are listed in Table 10:

exceeded the control oligonucleotide by 1.43-fold in terms of IFN-α induction. A considerable amount of IFN-α, yet significantly less, was induced by the second best motif combination 5'-GUU-3' (88% of control).

| Sense strand (5'→3') | IFN-α score | Antisense strand (5'→3') | IFN-α score |
|---|---|---|---|
| AAGAUCGAGGUGGAGAAGC | 4 | GCUUCUCCACCUCGAUCUU | 2 |
| AGAUCGAGGUGGAGAAGCC | 4 | GGCUUCUCCACCUCGAUCU | 2 |
| CCGCCGCCCUCAUCGCGGG | 4 | CCCGCGAUGAGGGCGGCGG | 0 |
| CCUUCUGCGGCCGAUGAGA | 2 | UCUCAUCGGCCGCAGAAGG | 2 |
| CGCCGCCCUCAUCGCGGGG | 4 | CCCCGCGAUGAGGGCGGCG | 0 |
| CUUCCUGCUGCUGCCGGGA | 4 | UCCCGGCAGCAGCAGGAAG | 0 |
| GAGCGCUUCCCCGAUGAGA | 2 | UCUCAUCGGGGAAGCGCUC | 4 |
| GCCGCCGCCCUCAUCGCGG | 4 | CCGCGAUGAGGGCGGCGGC | 0 |
| GGCAAGAUCGAGGUGGAGA | 4 | UCUCCACCUCGAUCUUGCC | 4 |
| UCUUCCUGCUGCUGCCGGG | 4 | CCCGGCAGCAGCAGGAAGA | -2 |
| UGCCGCCGCCCUCAUCGCG | 4 | CGCGAUGAGGGCGGCGGCA | 0 |

Example 12

Rational Identification of a Potent 4mer ssRNA Motif with Maximal IFN-α Induction in PBMC Previous experiments have shown that a minimal length of 19 bases is required for maximal IFN-α induction by ssRNA oligonucleotides. Since poly A oligonucleotides proved to be inactive in terms of IFN-α induction, we decided to analyze sequence requirements for IFN-α induction in PBMC by placing putative motifs into the center of poly A RNA oligonucleotides. RNA9.2sense (5'-AGCUUAACCUGUCCUU-CAA-3') was used as an established positive control. We started by analyzing the impact of a single nucleotide exchange in the center of a poly A RNA oligonucleotide.

As expected, little IFN-α induction could be elicited by these oligonucleotides, yet a consistent induction was seen for the ssRNA oligonucleotide containing a Uracil (U) in the center of the poly-A chain (FIG. 9A).

Based on these data, a panel of ssRNA oligonucleotides was designed that contained a U in the center of a 19mer poly A oligonucleotide including all possible single base permutations to either the 5' or the 3' end (FIG. 9B). Compared to the 1mer motifs, a considerable increase in IFN-α induction by the tested 2mer motifs could be seen. A wide distribution with an approximately 100-fold difference between the weakest and the strongest motif was observed: 5'-CU-3', 0.24% of control vs. 5'-GU-3', 24.63% of control. Among all 2mer motifs tested, 5'-GU-3' turned out to be the most potent motif with a mean IFN-α induction of 24.63% of the control oligonucleotide 9.2 sense.

Figure 9C:
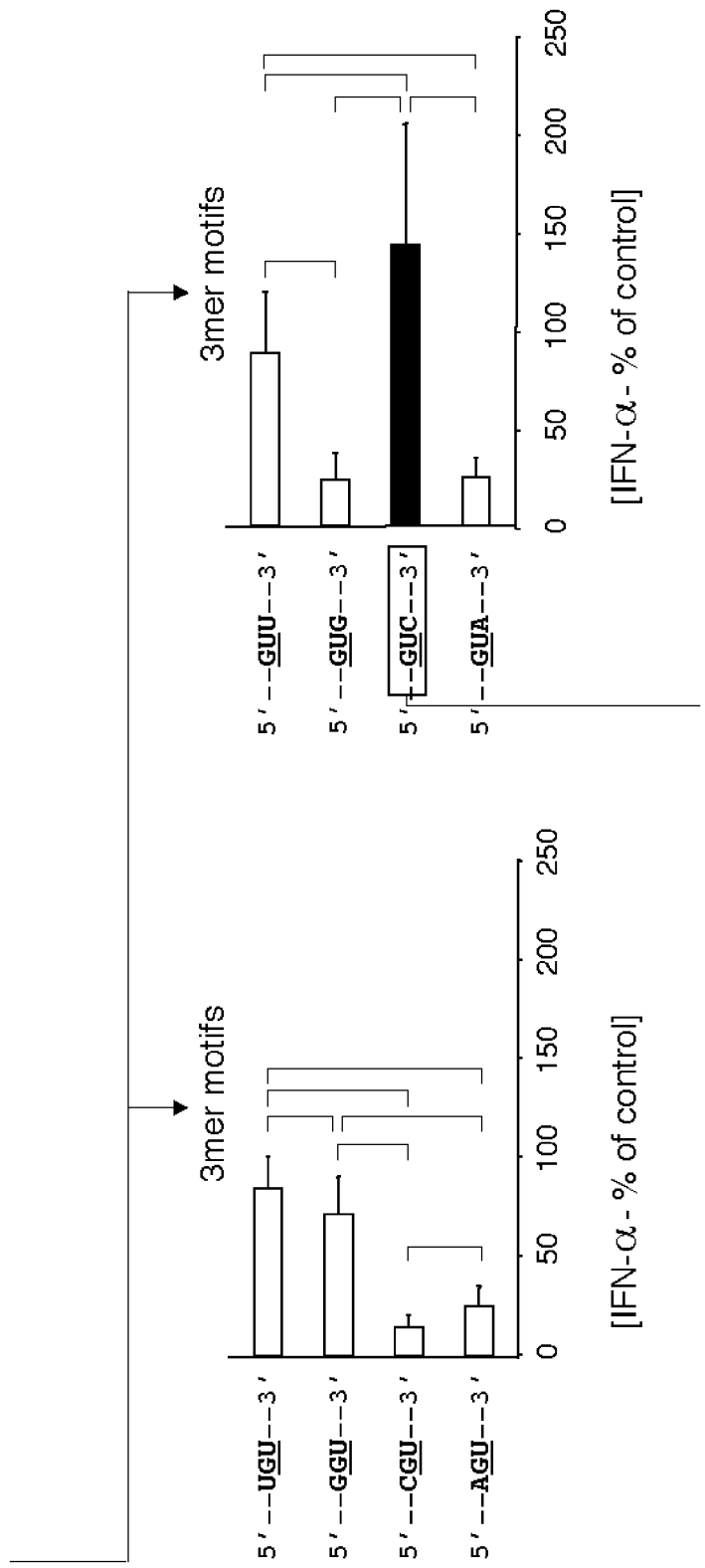
FIG. 9: PBMC from individual healthy donors were isolated and stimulated with poly-L-arginine complexed ssRNA-oligonucleotides in duplicates. For a detailed list of all tested oligonucleotides see Table 1. 44 hours after stimulation IFN-α production was assessed in supernatant via ELISA. For all tested ssRNA-oligonucleotides, the mean values of the measured duplicates were normalized to the positive control ssRNA-oligonucleotide 9.2sense (5'-AGCUUAACCUGUCCUUCAA) by dividing the mean value of tested oligonucleotide by the mean value of 9.2sense (=100%). Data from nine different (A-D) donors or three different donors (E) were summarized and are presented as mean values±SEM.
Figure 9D:
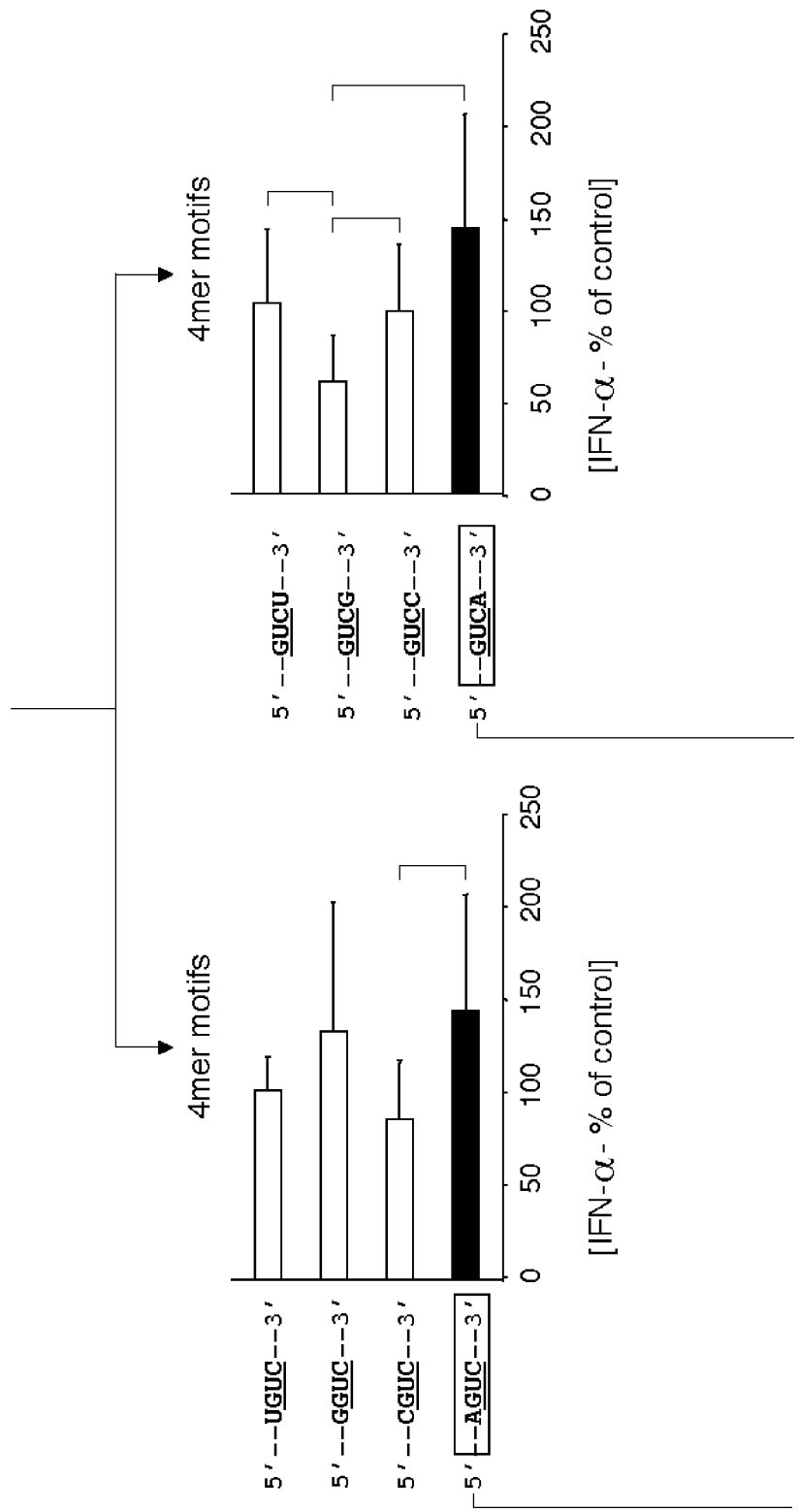
Figure 9E:
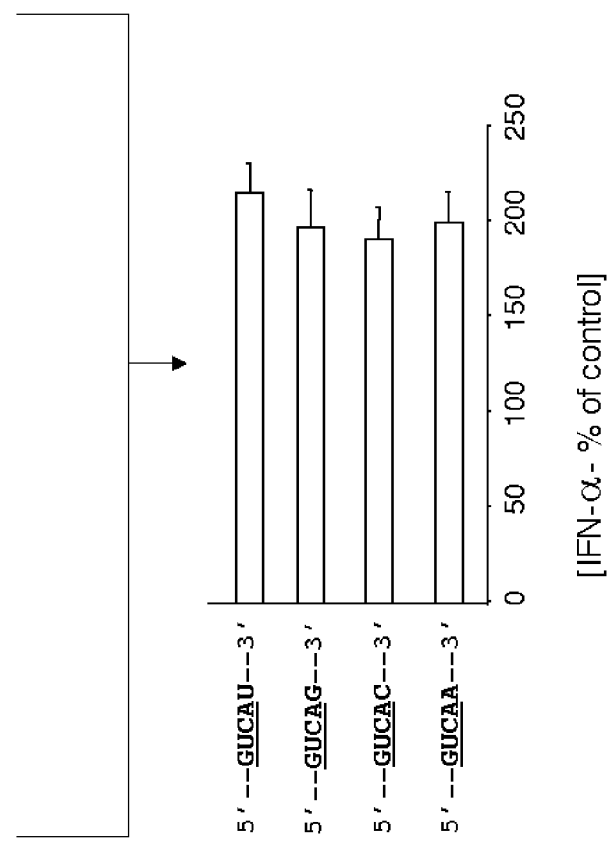

Following these results, oligonucleotides were designed that contained the 5'-GU-3' motif in the center of a 19mer poly A oligonucleotide while again all possible single base permutations to either the 5' end of the central motif were tested (FIG. 9C). Compared to 5'-GU-3', an almost 6-fold increase in IFN-α induction was seen for the most potent oligonucleotide that minimally contained the sequence 5'-GUC-3' as the central motif. This oligonucleotide Based on these data, we again designed oligonucleotides that contained the identified minimal 3mer motif 5'-GUC-3' with single base permutations to either the 5' or the 3' end. While the transition from 1 mer motifs to 2mer motifs and from 2mer motifs to 3mer motifs had resulted in a strong increase in IFN-α induction, no additional enhancement in IFN-α induction was seen with the elongation of the central motif to a 4mer motif (FIG. 9D). Nevertheless, these data indicated that A was required at the 3' end of the 5'-GUC-3' motif for maximal IFN-α induction. Placing either C or U at the 3' end of the 5'-GUC-3' motif resulted in a reduction of approximately one third in IFN-α induction, whereas the addition of G resulted in an almost two third decrease in IFN-α production. No further increase in IFN-α induction was seen when the position to the 5' end of the 5'-GUC-3' motif was permutated. While changing the A to G resulted in a slight, yet not significant decrease in IFN-α induction, a decrease of approximately one third was obtained when either U or C were positioned at the 5' end. Altogether these data identified the 4mer sequence 5'-GUCA-3' as a potent motif for the induction of IFN-α in PBMC. Additional modification of the 3' end by single base permutations did not result in an increase in IFN-α induction (FIG. 9E), thereby indicating the maximal requirement of a 4mer motif for potent IFN-α induction.

Example 13

The Effect of Position and Number of 4mer Motifs on Immunostimulatory Activity

The position of the 4mer motif within the poly A backbone had little impact on the immunostimulatory activity of the respective oligonucleotide (FIG. 7). Only a slight decrease (12.6%) in IFN-α induction was seen, when the 4mer motif was moved to 5' end of the oligonucleotide, while positioning of the 4mer motif at the 3' end resulted in a decrease of 28.8% in IFN-α induction. Moving the motif two nucleotides to the 5' end from the center position resulted in an almost identical IFN-α inducing activity.

Figure 10:
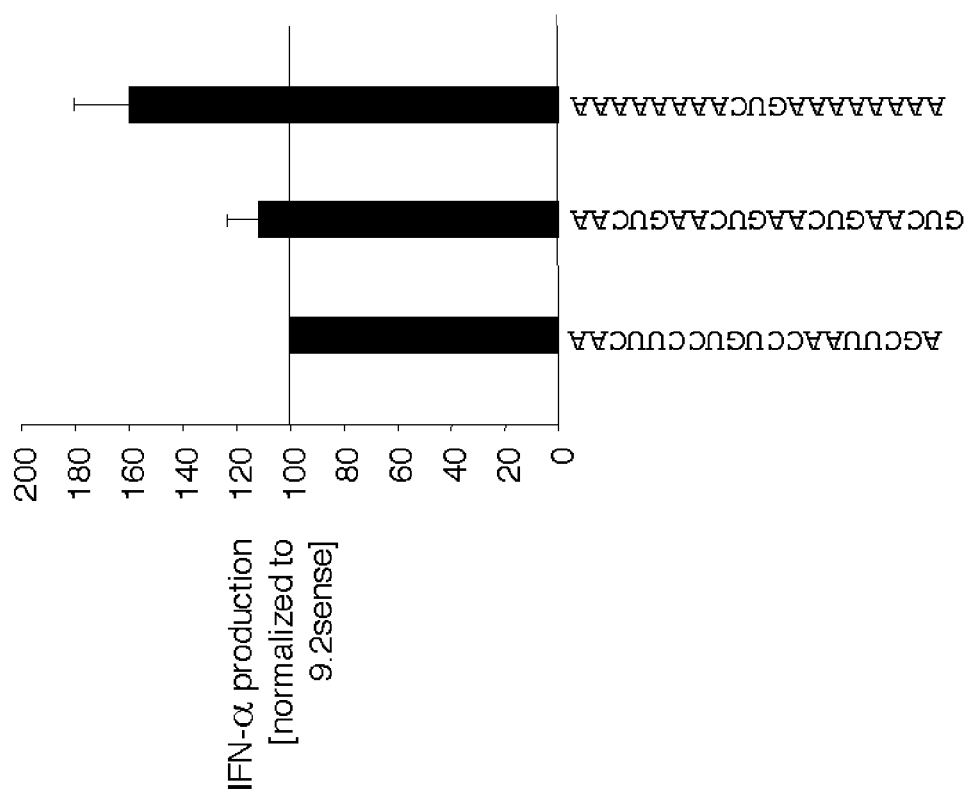
FIG. 10: PBMC from individual healthy donors were isolated and stimulated with poly-L-arginine complexed ssRNA-oligonucleotides in duplicates. For a detailed list of all tested oligonucleotides see Table 13. 44 hours after stimulation IFN-α production was assessed in supernatant via ELISA. For all tested ssRNA-oligonucleotides, the mean values of the measured duplicates were normalized to the positive control ssRNA-oligonucleotide 9.2sense (5'-AGCU- UAACCUGUCCUUCAA) by dividing the mean value of tested oligonucleotide by the mean value of 9.2sense (=100%). Data from two different donors were summarized and are presented as mean values±SEM.

Moreover, no inhibitory effect was seen, when non-stimulatory motifs were introduced into ssRNA oligonucleotides that contained the 4mer motif 5'-GUCA-3' (data not shown). More importantly, when additional 5'-GUCA-3' motifs were introduced into a ssRNA oligonucleotide, no further increase in IFN-α induction could be observed (FIG. 10).

Example 14

Identification of G-U-Pyrimidine as the Optimal IFN-α Inducing RNA Motif Using a ssRNA Oligonucleotide Library Encompassing all Possible 4mer Motifs The approach of gradually refining a stimulatory motif by permutation of the adjoining bases is based on the assumption that the exact succession of specific bases is critical for the stimulatory capacity of the sequence. The toleration of per se "non-stimulatory inserts" into an active sequence cannot be accounted for by this experimental setup. Moreover, this approach would miss stimulatory motifs if the sequential combination of several by itself non-stimulatory bases could synergize to render a potent motif. To test for these possibilities a library of ssRNA oligonucleotides was designed that encompassed all possible 4mer motifs in the centre of a poly A oligonucleotide. In view of the fact that flanking A residues can be part of a 4mer RNA sequence motif, only 193 ssRNA oligonucleotides (Table 1) were needed to cover all 256 possible 4mer motifs.

Figures 3, 5B:
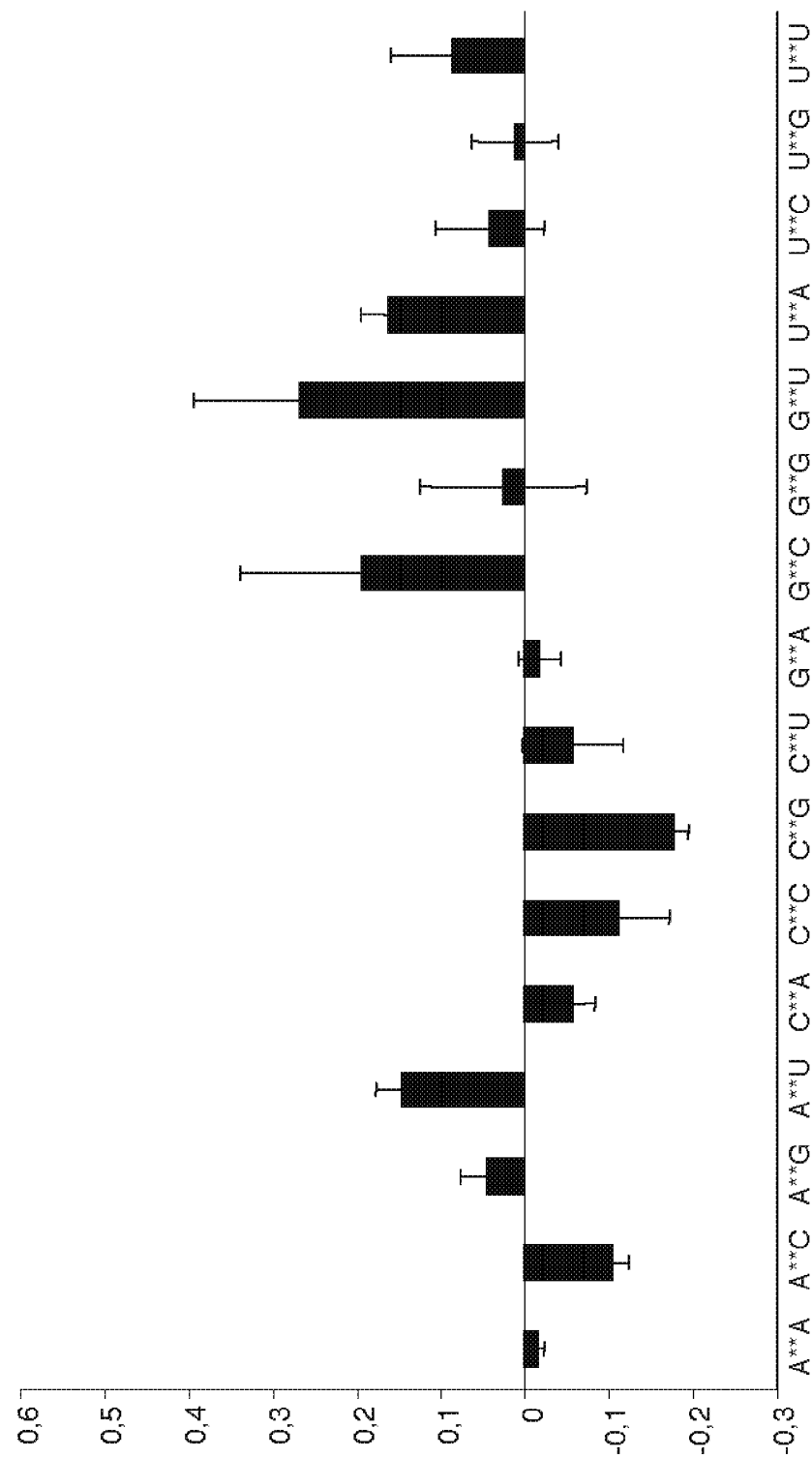
Figure 11B:
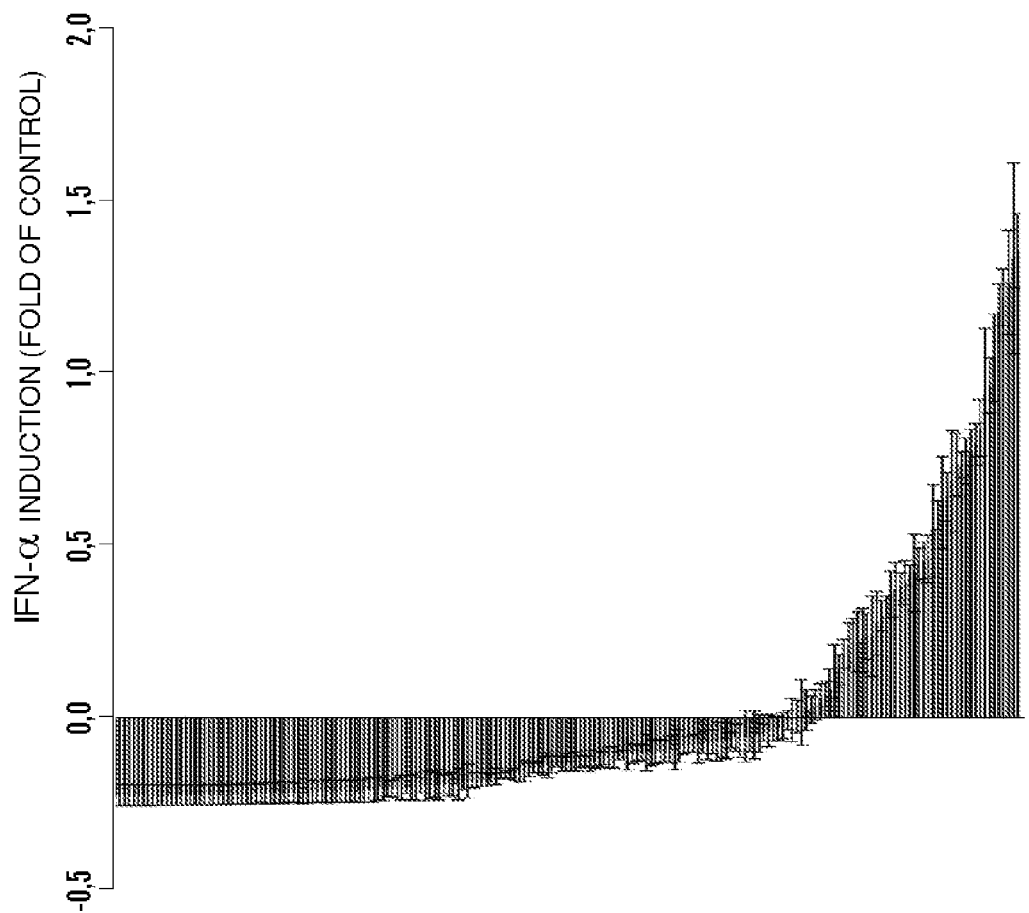
FIG. 11: PBMC of six different healthy donors were isolated and stimulated with poly-L-arginine complexed ssRNA-oligonucleotides in duplicates. 44 hours after stimulation IFN-α production was assessed in supernatant via ELISA. For all tested ssRNA-oligonucleotides, the mean values of the measured duplicates were normalized to the positive control ssRNA-oligonucleotide 9.2sense (5'-AGCUUAACCUGUCCUUCAA) by dividing the mean value of tested oligonucleotide by the mean value of 9.2sense. Next, for each individual donor a global normalization to the mean was performed by subtracting the mean of all data from a particular donor from the individual raw data. Data from six individual donors were visualized using tree view and are depicted in ascending order (A). In addition all individual data were summarized as mean values±SEM and are depicted in ascending order (B).
Figure 11A:
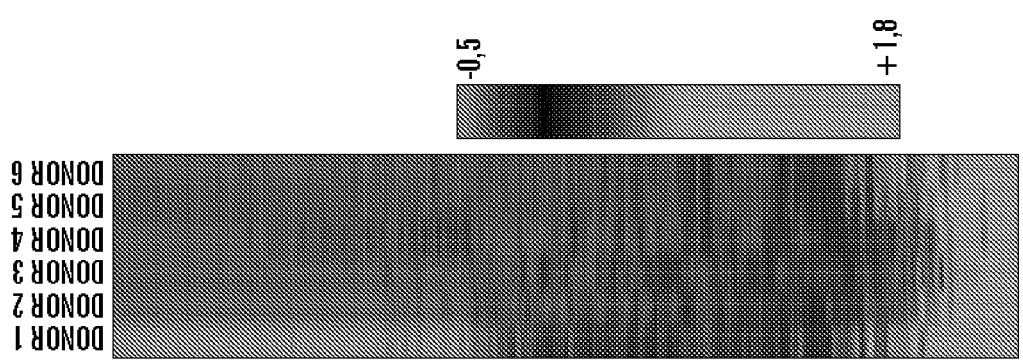

All 193 ssRNA oligonucleotides were tested on PBMC from six individual healthy donors. RNA9.2sense (5'-AGCUUAACCUGUCCUUCAA-3') was included as a positive control on all cell culture plates and was used as a reference for the oligonucleotides tested (RNA9.2sense=1, all data are expressed as fold values). As typically performed for large data sets such as gene array data, a global normalization to the mean was performed for each individual donor by subtracting the mean of all data from a particular donor from the individual raw data. This allowed to control for the observed inter individual variability between the donors and made it possible to summarize all donors as mean values±SEM. Thus due to the normalization, a negative value was obtained for all oligonucleotides that were below the immunostimulatory activity of the mean of all oligonucleotides, whereas for all oligonucleotides that were above the immunostimulatory activity of the mean a positive value was obtained. A colored output was chosen to give an overview on all obtained data in one graph in ascending order (FIG. 11A), while the corresponding mean values are depicted next to it (FIG. 11B). A complete list of all data with the respective sequence information is depicted in FIG. 3. Confirming the validity of our prior approach, the 4mer motif 5'-GUCA-3' turned out to be the second highest hit in the obtained data set, whereas only the motif 5'-GUUC-3' turned out to be more active in terms of IFN-α induction.

To systematically identify motifs or patterns that were associated with high or low IFN-α induction, a statistical analysis was performed by analyzing the occurrence of all possible 3mer motifs within the tested oligonucleotide library. For all 3mer motifs the mean level of IFN-α induction was calculated by grouping all oligonucleotides that contained the respective 3mer motif.

For example the 3mer motif 5'-GUC-3' was contained in ssRNA oligonucleotides ANP 35, 83, 131, 137, 138, 139 and 179 with respective IFN-α induction levels of 1.33, 0.68, 0.93, 0.79, 0.44, 0.84 and 0.73. The mean IFN-α induction level of the 3mer motif 5'-GUC-3' was thus calculated to be 0.82 with a standard error of mean of 0.10.

3mer motifs that were gapped by one nucleotide between either the first and the second nucleotide position or the second and third nucleotide position were also included in this analysis. A two-tailed T-Test was used to identify motifs that were either significantly higher or lower in IFN-α induction than the particular motif analyzed.

Figure 12:
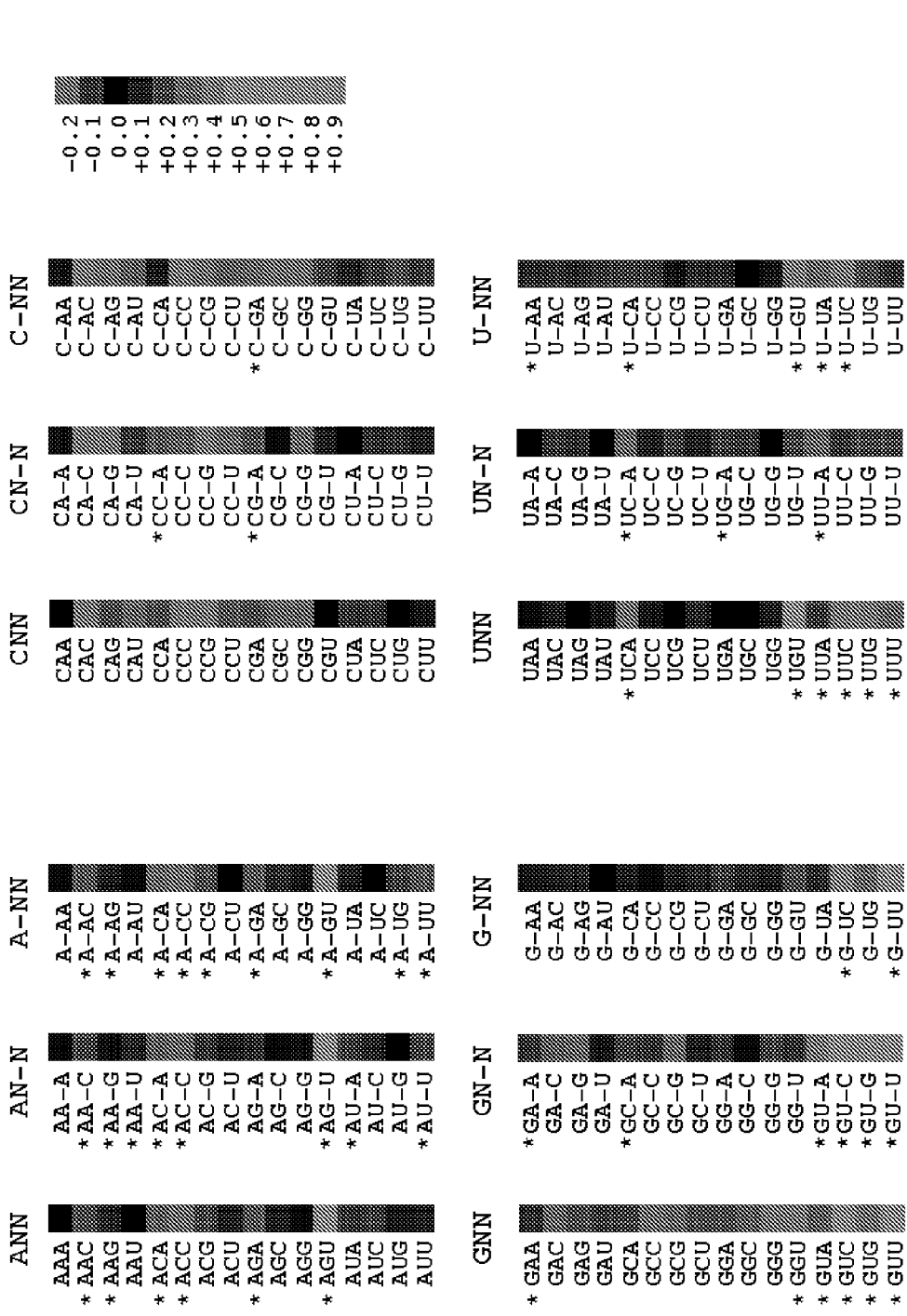
FIG. 12: The occurrence of 3mer motifs in all ssRNA-oligonucleotides was analyzed. The mean level of IFN-α induction was calculated by grouping all oligonucleotides that contained a respective 3mer motif. For example the 3mer motif 5'-GUC-3' was contained in ssRNA oligonucleotides ANP 35, 83, 131, 137, 138, 139 and 179 with respective IFN-α induction levels of 1.33, 0.68, 0.93, 0.79, 0.44, 0.84 and 0.73. The mean IFN-α induction level of the 3mer motif 5'-GUC-3' was thus calculated to be 0.82 with a standard error of mean of 0.10. 3mer motifs that were gapped by one nucleotide between either the first and the second nucleotide position (5'-N—NN-3') or the second and third nucleotide position (5'-NN—N-3') were also included in the analysis. A two-tailed T-Test was used to identify motifs that were either significantly higher or lower in IFN-α induction than the residual motifs. For all motifs analyzed, the mean IFN-α induction level was visualized using tree view. The data were assorted according to the first nucleotide position of the motif in four groups. (p-value <0.05 is indicated by *).

For ungapped 3mer motifs, the highest mean level of IFN-α induction was obtained for the motif 5'-GUU-3' (0.87) followed by the motif 5'-GUC-3' (0.82). Within 3mer motifs that contained a nucleotide gap between the first and second position 5'-GNUC-3' (0.87) and 5'-GNUU-3' (0.72) were the two highest hits, where N represents any one nucleotide A, G, U or C. Correspondingly 5'-GUNU-3' (0.83) and 5'-GUNC-3' (0.72) were the two most potent 3mer motifs within the group of 3mer motifs, which had a nucleotide gap between the second and the third base position (FIG. 12). A detailed list of all motifs and the respective mean levels of IFN-α induction is given in Table 12.

Figure 13:
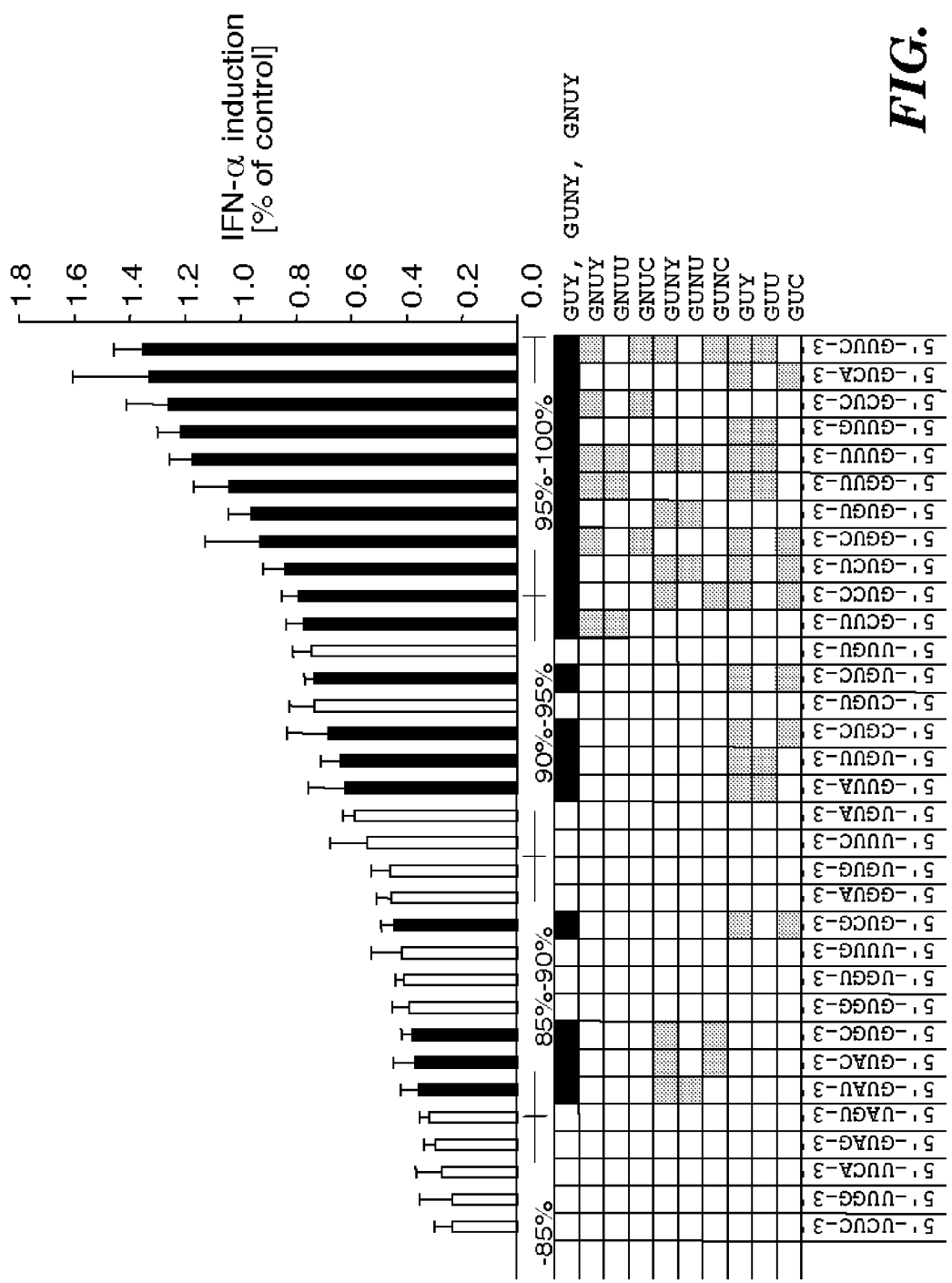
FIG. 13: The top 15 percent of all ssRNA oligonucleotides and the respective mean IFN-α induction levels are shown in ascending order. The presence of the identified potent 3mer motifs 5'GUY-3' (5'-GUC-3', 5'-GUU-3'), 5'-GUNY-3' (5'-GUNC-3', 5'-GUNU-3') and 5'-GNUY-3' (5'-GNUC-3', 5'-GNUU-3') is indicated by a grey box. All ssRNA oligonucleotides that contain any of the above motifs are indicated by a black box.

Among the top 5% of the tested ssRNA oligonucleotide library, all oligonucleotides contained at least one of the above-mentioned most potent motifs and this was also true for 79% of all top 10% oligonucleotides (FIG. 13). The mean level of IFN-α induction for all oligonucleotides that contained at least one of the above motifs was calculated to be 0.72±0.09 compared to −0.09±0.01 for the rest of the oligonucleotides. Altogether this analysis was able to identify the motif G-U-Pyrimidine with a one-gap tolerance between either the first and the second or the second and the third position as a potent motif for RNA-mediated IFN-α induction in the human system.

Example 15

Comparison of Immunostimulatory Activity

Figure 14:
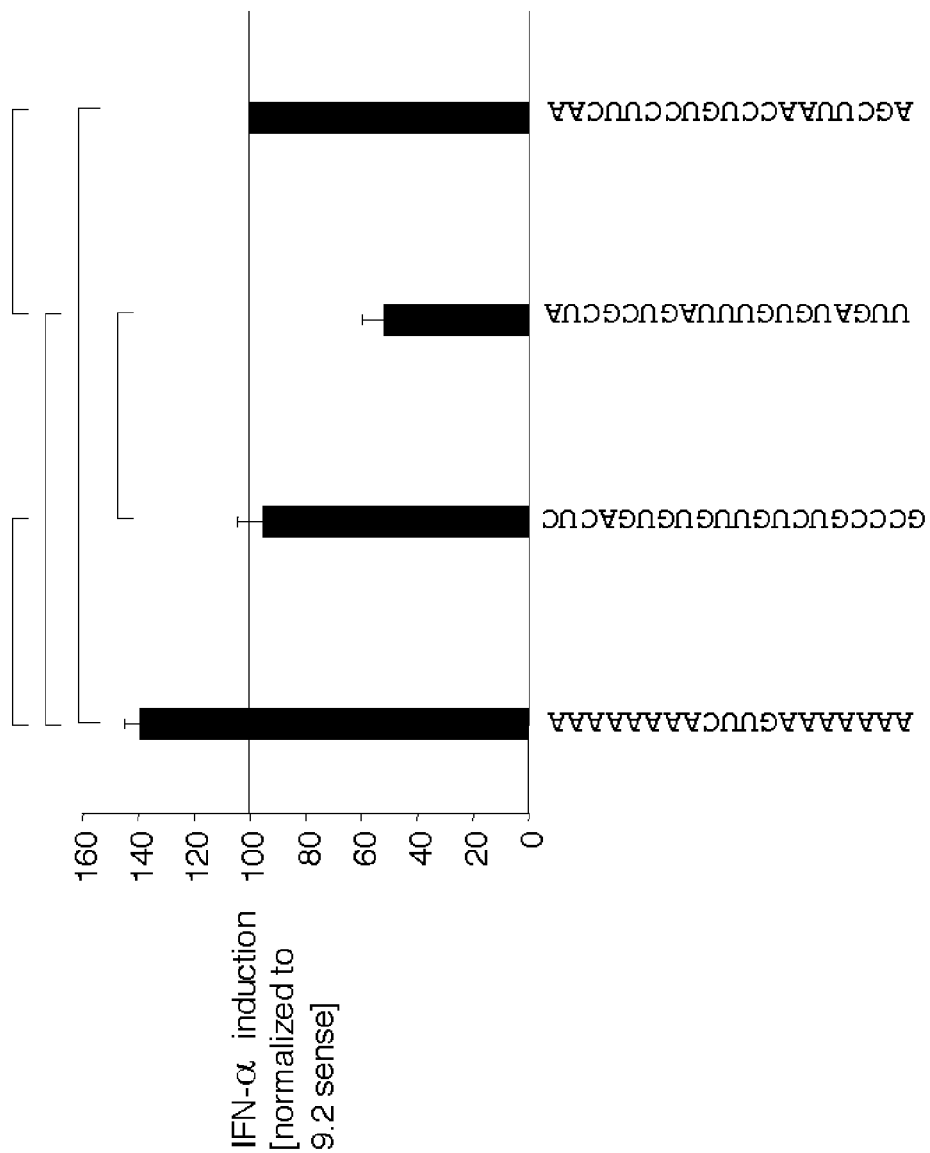
FIG. 14: PBMC of four different healthy donors were isolated and stimulated with the following poly-L-arginine complexed ssRNA-oligonucleotides: ANP143 (5'-AAAAAAAGUUCAAAAAAAA-3'), RNA40 (5'-GCCCGUCUGUUGUGUGACUC-3'), β-Gal control sense (5'-UUGAUGUGUUUAGUCGCUA-3') and 9.2sense (5'-AGCUUAACCUGUCCUUCAA-3'). 44 hours after stimulation IFN-a production was assessed in supernatant via ELISA. All tested ssRNA-oligonucleotides were normalized to the positive control ssRNA-oligonucleotide 9.2sense by dividing the mean value of tested oligonucleotide by the mean value of 9.2sense. Significant differences were analyzed using a two-tailed T-Test.

Comparing the motif 5'-GUUC-3' on a poly A backbone to previously published ssRNA oligonucleotides with high IFN-α inducing activity revealed an almost 1.4 fold higher level of IFN-α induction than 9.2sense 5'-AGCUUAACCUGUCCUUCAA-3' (Hornung et al. *Nat Med* 11:263:270), 1.5 fold higher level than RNA40 5'-GCCCGUCUGUUGUGUGACUC-3' (Heil et al. *Science* 303:1526-1529) and a more than 2.5 fold higher activity than β-Gal control sense 5'-UUGAUGUGUUUAGUCGCUA-3' (Judge et al. *Nat Biotech* 23:457-462) (FIG. 14).

Example 16

Using the Obtained Motif Information to Predict Low or High IFN-α Inducing ssRNA Oligonucleotides An analysis of published ssRNA oligonucleotides that were described to induce IFN-α indicated a good correlation with our motif information. To systematically predict the IFN-α inducing activity of a ssRNA oligonucleotide, an algorithm was established based on the occurrence of 3mer motifs 5'-NNN-3'. Since above data had indicated that the major IFN-α inducing activity of a ssRNA oligonucleotide was independent of the position of the stimulatory motif and the presence of additional stimulatory or inhibitory motifs, an algorithm was developed that predicted the IFN-α inducting activity by accounting for the highest stimulatory motif within the oligonucleotide independent of its position. Only motifs that had been shown to significantly correlate with high or low IFN-α inducing activity were included in the algorithm: 18 ungapped 3mer motifs (5'-NNN-3'), indicated by "*" or "**" in Table 12A. Thus for a given oligonucleotide, a predicted IFN-α inducing activity was calculated by analyzing the occurrence of all 3mer motifs within this oligonucleotide and subsequently by assigning the highest obtained mean IFN-α induction level to this respective oligonucleotide.

Figure 15:
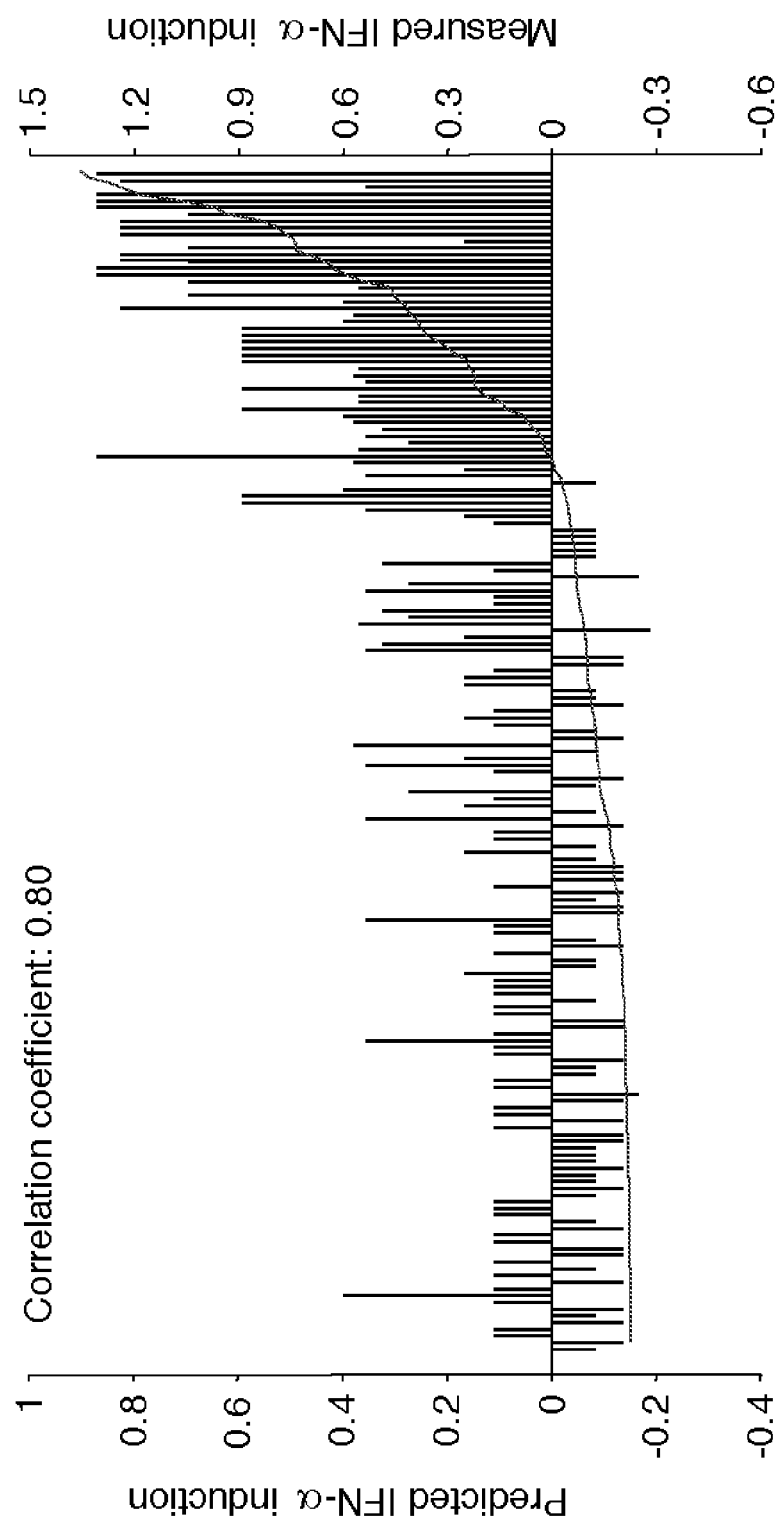
FIG. 15: The occurrence of 3mer motifs was analyzed in the 193 oligonucleotide library. For each oligonucleotide the 3mer motif with the highest calculated mean IFN-α induction level was identified and assigned to the respective oligonucleotide. The predicted data are depicted in ascending order (black bars) according to the corresponding measured IFN-α induction levels (black line). In addition, the correlation coefficient for the two data sets was determined.

Applying this algorithm (i.e., the "simplified method") to our own data set resulted in a correlation coefficient of 0.80 for the comparison of the predicted and the measured data (FIG. 15).

Figure 16:
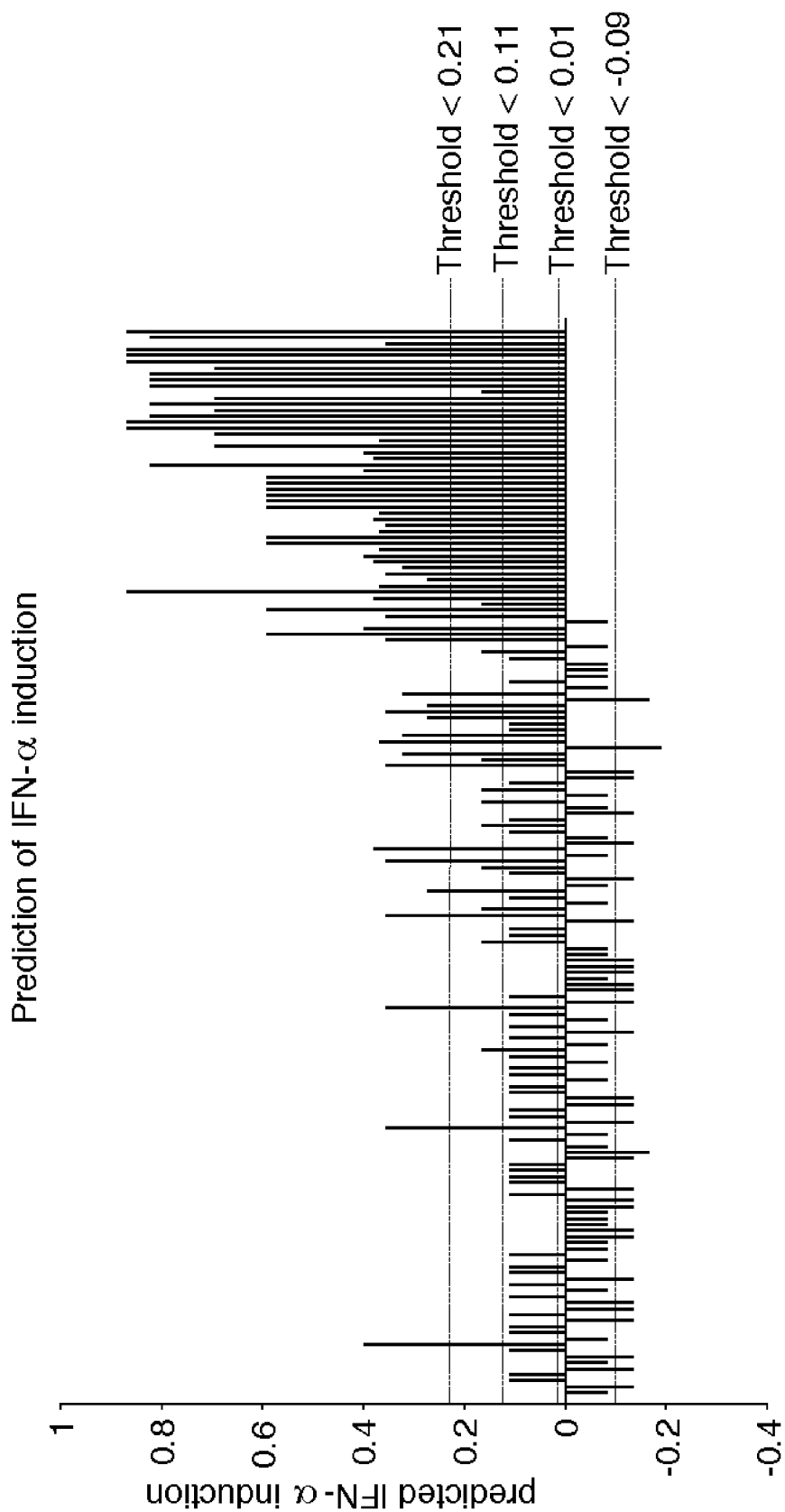
FIG. 16: The occurrence of 3mer motifs was analyzed in the 193 oligonucleotide library. For each oligonucleotide the 3mer motif with the highest calculated mean IFN-α induction level was identified and assigned to the respective oligonucleotide. The predicted data are depicted in ascending order. Various threshold levels (dotted lines) were tested for both for the positive predictive value and the sensitivity to identify oligonucleotides below the IFN-α induction level of 0 (A). For each threshold level, data were then regrouped according to the predicted IFN-α induction level (selected oligonucleotides: left group, eliminated oligonucleotides: right group). For each group, the mean level of IFN-α induction ±SEM is depicted in the lower panel. The positive predictive value and the sensitivity for each threshold is indicated in the upper left.
Figure 16:
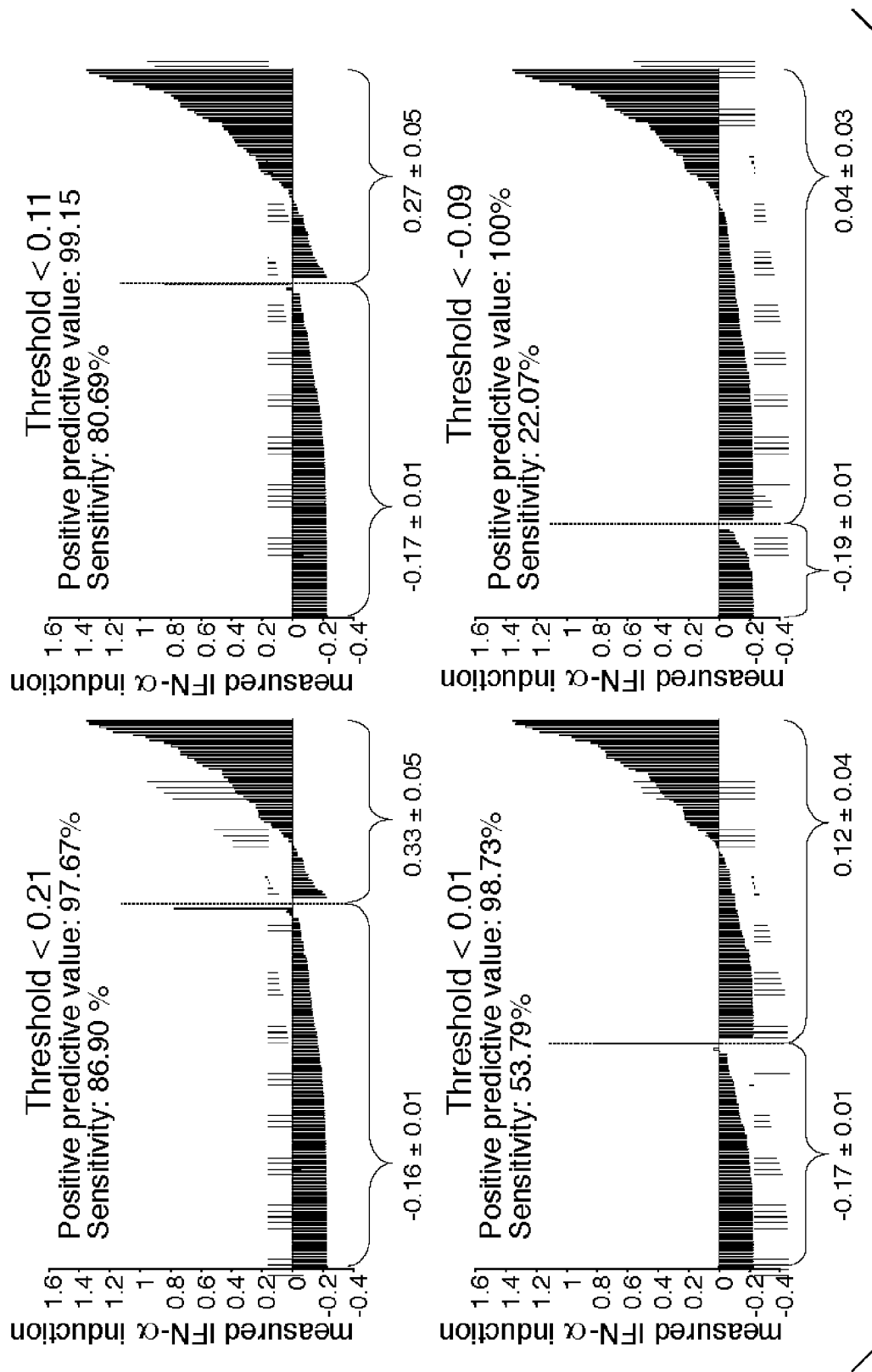

The predictive quality of this algorithm to define low IFN-α inducing ssRNA oligonucleotides was then tested on the 193 oligo data set. Low inducing oligonucleotides were predefined by an IFN-α induction level below the mean of all oligonucleotides. Various threshold levels for the prediction algorithm were tested for both for the positive predictive value and the sensitivity to identify ssRNA oligonucleotides below the mean IFN-α of all oligonucleotides (FIG. 16). A high positive predictive value and a yet high sensitivity was obtained when the threshold of the prediction algorithm was set at 0.11 (FIG. 16B, upper right panel). 118 oligonucleotides had a calculated predicted IFN-α induction level below the threshold of 0.11 and 117 of these oligonucleotides had the expected measured IFN-α level below 0 (positive predictive value of 99.15%). Only 28 oligonucleotides of a total of 145 oligonucleotides were not detected using the prediction (sensitivity of 80.69%). Using the prediction algorithm with the threshold of 0.11 therefore allowed to predict a large percentage of oligonucleotides that would be below the desired level of 0 with high accuracy.

Applying this algorithm to more complex oligonucleotides resulted in a considerable lower percentage of oligonucleotides that met the above criteria. Approximately 10% of a random pool of 19mer oligonucleotides fell below the threshold of 0.11 when analyzed using the IFN-α prediction algorithm (data not shown). When a random pool of 19mer duplexes was analyzed, approximately 1% of all duplexes were comprised of single stranded RNA oligonucleotides that were both below the threshold of 0.11.

Example 17

Preparing siRNA with High or Low Immunostimulatory Activity

Figure 17A:
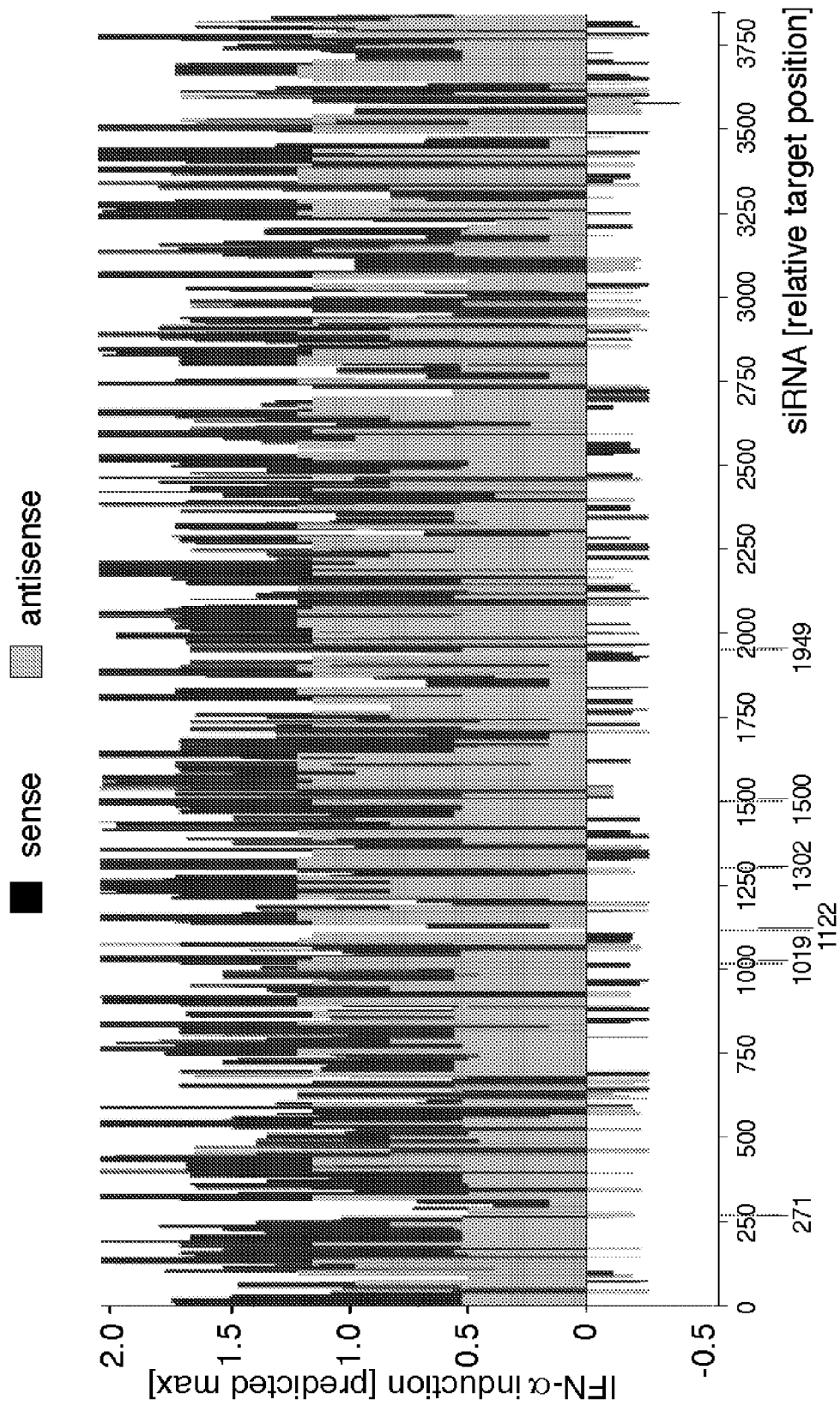
FIG. 17: The prediction algorithm was used to analyze all possible siRNA duplexes targeting the mRNA of human TLR9 (NM_017442). For the 3868 bp long mRNA of TLR9 all possible 19mer siRNA duplexes were considered and the IFN-α prediction algorithm was applied on both the sense and the antisense strand of each siRNA duplex. The predicted IFN-α induction levels are depicted in stacked columns for the sense (upper columns in black) and the antisense strand (lower column in grey). The relative targeting position of the siRNA duplex is given on the y-axis, whereas the predicted IFN-α induction is depicted on the x-axis (A). In addition, six selected regions of the TLR9 mRNA and the respective predicted IFN-α induction levels are depicted in detail in B.
Figure 17B:
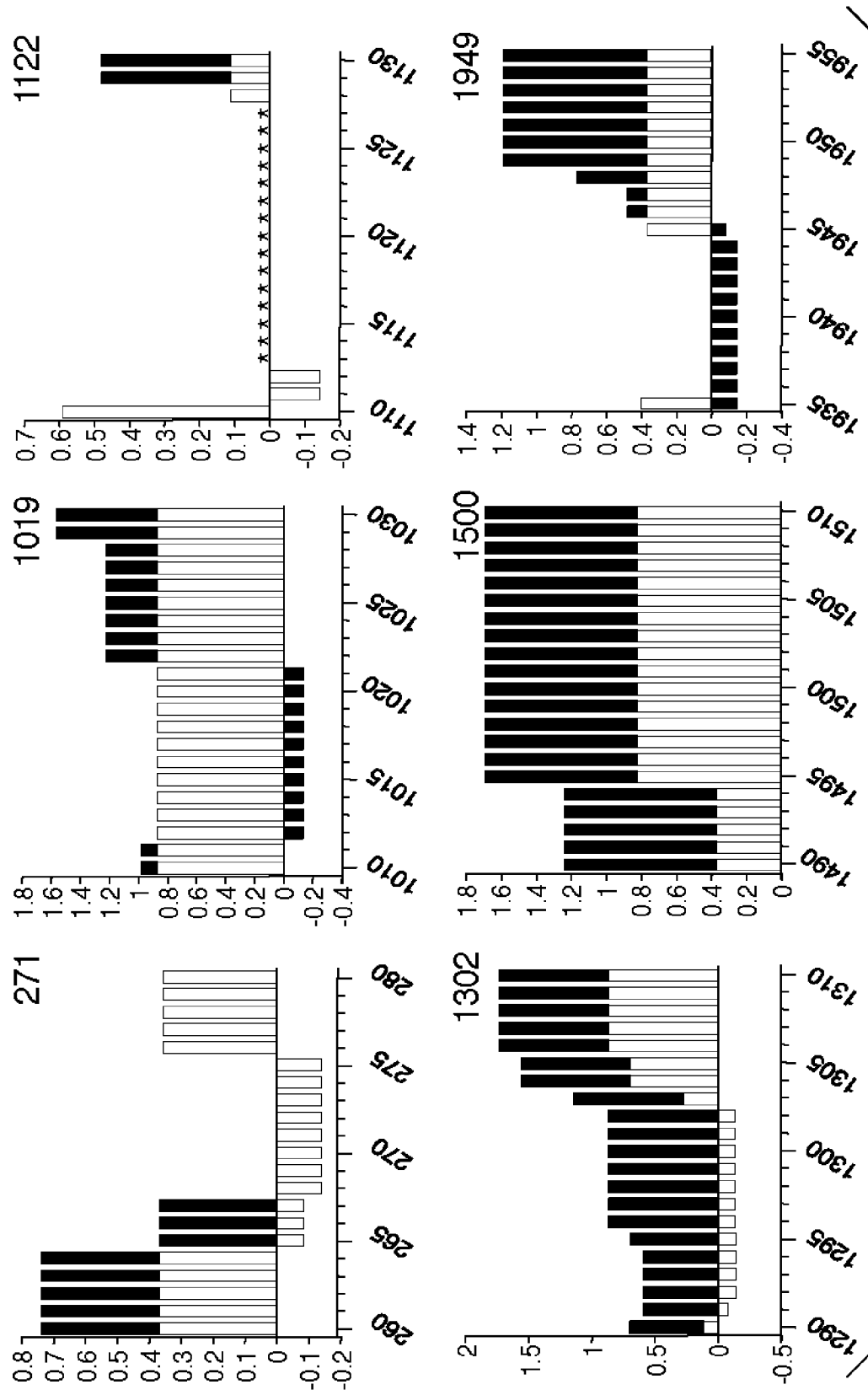

To address the applicability of this algorithm for the identification of non-stimulatory RNA oligonucleotides, a panel of siRNA duplexes was designed to target the mRNA of human TLR9. From a total pool of 3850 siRNA duplexes that were considered, 116 could be identified (3.01%) that had a calculated predicted IFN-α induction below the threshold of 0.11 according to the "simplified method". These 116 predicted siRNA duplexes were distributed over 21 different target sites within in the mRNA, whereas seven major sites could be identified that could be targeted by more than five consecutive siRNA duplexes. Three different siRNA duplexes were chosen to target TLR9 using the above described algorithm with putatively low IFN-α induction (TLR9_271, TLR9_1122 and TLR9_1949), whereas three different siRNA duplexes were picked that contained at least one strand with predicted high IFN-α induction (TLR9_1019, TLR9_1302 and TLR9_1949). Altogether eight ssRNA oligonucleotides with presumably low IFN-α induction (TLR9_271 sense, TLR9_271 antisense, TLR9_1019 sense, TLR9_1122 sense, TLR9_1122 antisense, TLR9_1302 antisense, TLR9_1949 sense, TLR9_1949 antisense) and four ssRNA oligonucleotides with high IFN-α induction (TLR9_1019 antisense, TLR9_1302 sense, TLR9_1500 sense anf TLR9_1500 antisense) were contained in this selection (FIG. 17).

Figure 18A:
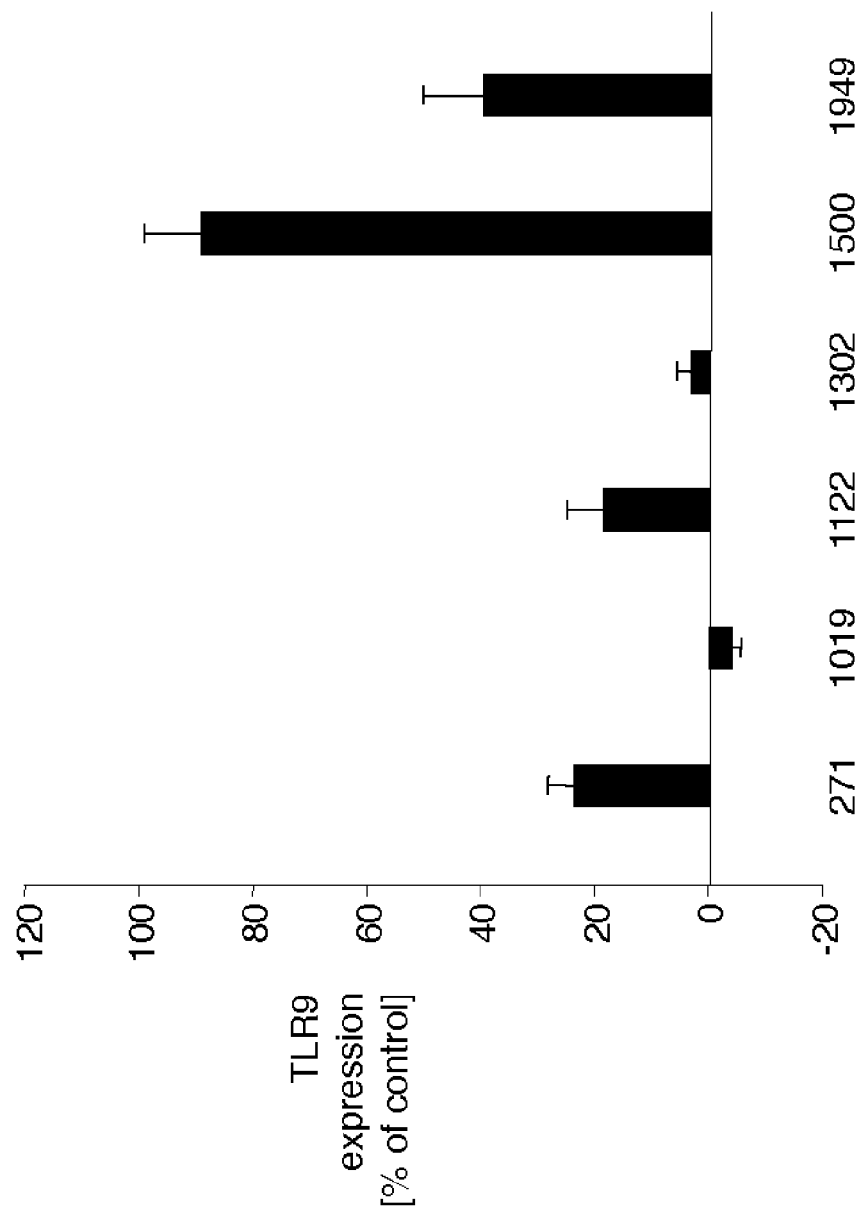
FIG. 18: HEK 293 cells were transfected with an expression plasmid coding for human TLR9 with a C-terminal YFP-tag. Various siRNA-duplices targeting human TLR9 mRNA were cotransfected. The starting base of the individual siRNA is given in the lower panel. 20 hours after transfection, TLR9 expression was analyzed by flow cytometry. Data are depicted as percentage of TLR9-expression referring to an irrelevant control siRNA as 100% and siRNA_sb1647 as 0%. Results are shown as mean values±SEM (n=3) (A). In addition, above siRNA duplexes and the respective single stranded components were used to transfect human PBMC from five individual donors. 40 hours after transfection IFN-α induction was measured via ELISA. Data are depicted as mean values±SEM (B).
Figure 18B:
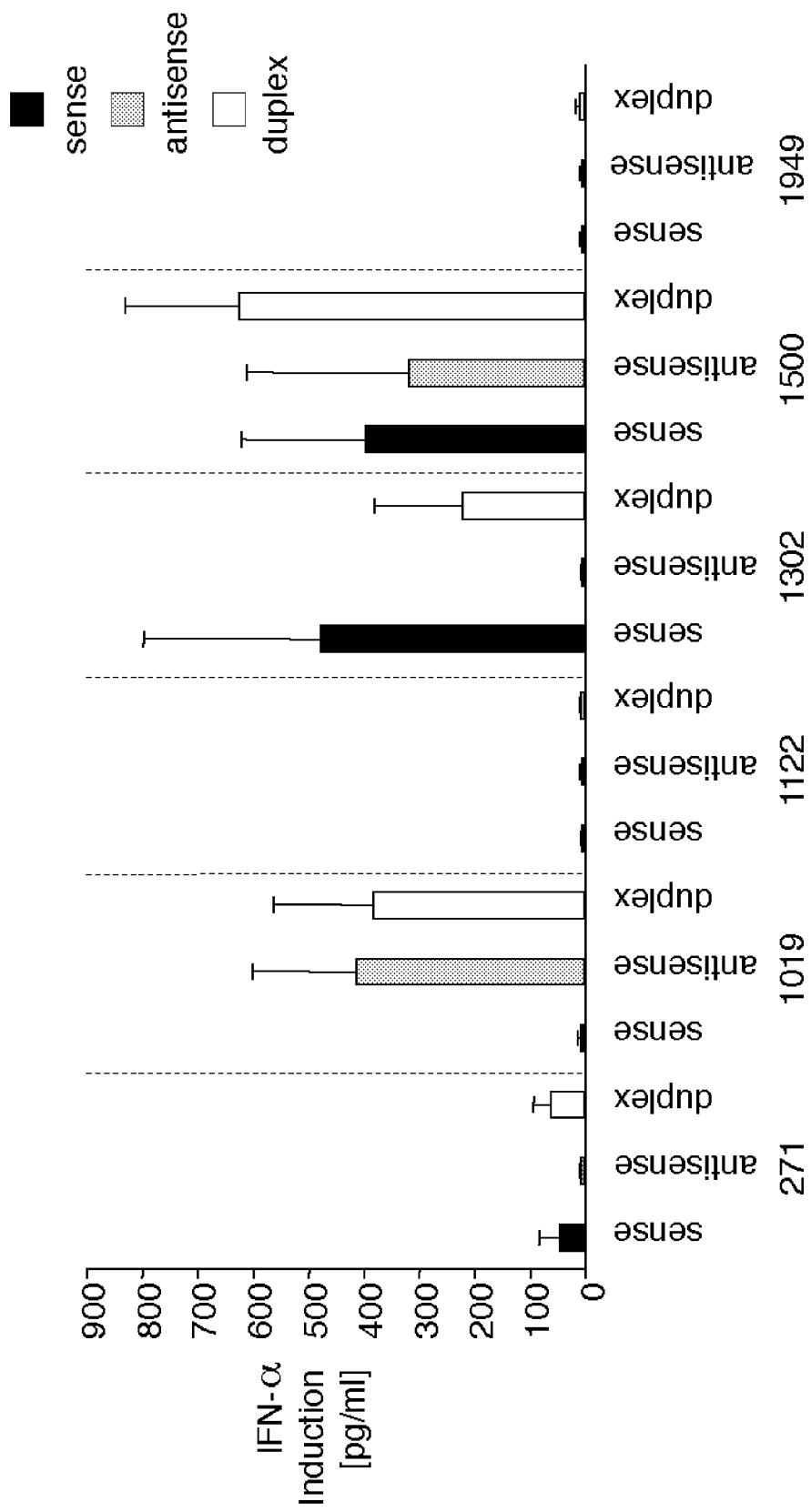

The functionality of theses siRNA duplexes in terms of posttranscriptional gene silencing was assessed by analyzing the knock down activity of TLR9 expression (FIG. 18). Two siRNA duplexes with good knock down activity could be identified within both groups of siRNA duplexes.

When analyzing the IFN-α induction of both the single stranded components and the respective siRNA duplexes, a high accuracy of the IFN-α prediction algorithm could be seen. Of all eight ssRNA oligonucleotides predicted to be low in IFN-α induction, seven oligonucleotides (TLR9_271 antisense, TLR9_1019 sense, TLR9_1122 sense, TLR9_1122 antisense, TLR9_1302 antisense, TLR9_1949 sense, TLR9_1949 antisense) showed negligible to absent IFN-α induction, whereas one oligonucleotide (TLR9_271 sense) showed minimal IFN-α induction. This was also true for the respective siRNA duplexes: TLR9_1122 and TLR9_1949 duplexes showed negligible to absent IFN-α induction, and TLR9_271 duplex showed minimal IFN-α induction. Likewise, all ssRNA oligonucleotides predicted to be high in IFN-α induction showed a strong IFN-α response (TLR9_1019 antisense, TLR9_1302 sense, TLR9_1500 sense anf TLR9_1500 antisense). As described previously, within a siRNA duplex, the strong induction of IFN-α by either one component dictated the immunostimulatory activity of the whole siRNA duplex. TLR9_1019, TLR9_1032 and TLR9_1500 duplexes all showed high IFN-α induction.

Altogether these results indicated that using a motif-based algorithm we are able to rationally design both stimulatory and non-stimulatory functional siRNA duplexes.

Example 18

Systematic and Automated Identification of siRNA with Desired Immunolostimulatory Activity Based on the algorithm described in example 17 (i.e., the "simplified method"), a computer program was written that applies the algorithm to all possible siRNA duplexes targeting all human RNA transcripts (50421 as of September 2006) as published by the National Center for Biotechnology Information (NCBI). Each entry into the NCBI database (ftp://ftp.ncbi.nih.gov/refseq/H_sapiens/mRNA_Prot/human-.rna.fna.gz) of all listed human RNA transcripts was analyzed the following way: A list of all possible 19mer siRNA duplexes targeting a given RNA transcript was generated. Of all siRNA duplexes the IFN-α induction of both the sense and the antisense strand was predicted using the method described in example 17. The obtained data is stored in a database (CD-ROM) and can be retrieved by a search engine. Using the search interface, the user can pick the transcript of interest (alphabetical index of all RNA transcripts targeted by siRNAs) and then adjust the level of threshold to identify siRNA duplexes that are of either low, intermediate or high in immunostimulatory activity (FIG. 19A). For example, using the threshold of 0.11 as described in example 17, a set of siRNA duplexes was identified for Homo sapiens vascular endothelial growth factor (VEGF) transcript variant 1 mRNA (NM_001025366.1) with low immunostimulatory activity for both the sense and the antisense strand (FIG. 19B).

TABLE 1 ssRNA oligonucleotides containing all possible 4 mer motifs on the poly a backbone.

| Name | Sequence |
| --- | --- |
| ANP-Oligo 001 | AAAAAAAAAAAAAAAAA |
| ANP-Oligo 002 | AAAAAAAACAAAAAAAA |
| ANP-Oligo 003 | AAAAAAAAGAAAAAAAA |
| ANP-Oligo 004 | AAAAAAAAUAAAAAAAA |
| ANP-Oligo 005 | AAAAAAAACCAAAAAAA |
| ANP-Oligo 006 | AAAAAAAACGAAAAAAA |
| ANP-Oligo 007 | AAAAAAAACUAAAAAAA |
| ANP-Oligo 008 | AAAAAAAAGCAAAAAAA |
| ANP-Oligo 009 | AAAAAAAAGGAAAAAAA |
| ANP-Oligo 010 | AAAAAAAAGUAAAAAAA |
| ANP-Oligo 011 | AAAAAAAAUCAAAAAAA |
| ANP-Oligo 012 | AAAAAAAAUGAAAAAAA |
| ANP-Oligo 013 | AAAAAAAAUUAAAAAAA |
| ANP-Oligo 014 | AAAAAAAACACAAAAAAA |
| ANP-Oligo 015 | AAAAAAAACAGAAAAAAA |
| ANP-Oligo 016 | AAAAAAAACAUAAAAAAA |
| ANP-Oligo 017 | AAAAAAAACCCAAAAAAA |
| ANP-Oligo 018 | AAAAAAAACCGAAAAAAA |
| ANP-Oligo 019 | AAAAAAAACCUAAAAAAA |
| ANP-Oligo 020 | AAAAAAAACGCAAAAAAA |
| ANP-Oligo 021 | AAAAAAAACGGAAAAAAA |
| ANP-Oligo 022 | AAAAAAAACGUAAAAAAA |
| ANP-Oligo 023 | AAAAAAAACUCAAAAAAA |
| ANP-Oligo 024 | AAAAAAAACUGAAAAAAA |
| ANP-Oligo 025 | AAAAAAAACUUAAAAAAA |
| ANP-Oligo 026 | AAAAAAAAGACAAAAAAA |
| ANP-Oligo 027 | AAAAAAAAGAGAAAAAAA |
| ANP-Oligo 028 | AAAAAAAAGAUAAAAAAA |
| ANP-Oligo 029 | AAAAAAAAGCCAAAAAAA |
| ANP-Oligo 030 | AAAAAAAAGCGAAAAAAA |
| ANP-Oligo 031 | AAAAAAAAGCUAAAAAAA |
| ANP-Oligo 032 | AAAAAAAAGGCAAAAAAA |
| ANP-Oligo 033 | AAAAAAAAGGGAAAAAAA |
| ANP-Oligo 034 | AAAAAAAAGGUAAAAAAA |
| ANP-Oligo 035 | AAAAAAAAGUCAAAAAAA |
| ANP-Oligo 036 | AAAAAAAAGUGAAAAAAA |
| ANP-Oligo 037 | AAAAAAAAGUUAAAAAAA |
| ANP-Oligo 038 | AAAAAAAAUACAAAAAAA |
| ANP-Oligo 039 | AAAAAAAAUAGAAAAAAA |
| ANP-Oligo 040 | AAAAAAAAUAUAAAAAAA |
| ANP-Oligo 041 | AAAAAAAAUCCAAAAAAA |
| ANP-Oligo 042 | AAAAAAAAUCGAAAAAAA |
| ANP-Oligo 043 | AAAAAAAAUCUAAAAAAA |
| ANP-Oligo 044 | AAAAAAAAUGCAAAAAAA |
| ANP-Oligo 045 | AAAAAAAAUGGAAAAAAA |
| ANP-Oligo 046 | AAAAAAAAUGUAAAAAAA |
| ANP-Oligo 047 | AAAAAAAAUUCAAAAAAA |
| ANP-Oligo 048 | AAAAAAAAUUGAAAAAAA |
| ANP-Oligo 049 | AAAAAAAAUUUAAAAAAA |
| ANP-Oligo 050 | AAAAAAACAACAAAAAAA |
| ANP-Oligo 051 | AAAAAAACAAGAAAAAAA |
| ANP-Oligo 052 | AAAAAAACAAUAAAAAAA |
| ANP-Oligo 053 | AAAAAAACACCAAAAAAA |
| ANP-Oligo 054 | AAAAAAACACGAAAAAAA |
| ANP-Oligo 055 | AAAAAAACACUAAAAAAA |
| ANP-Oligo 056 | AAAAAAACAGCAAAAAAA |
| ANP-Oligo 057 | AAAAAAACAGGAAAAAAA |
| ANP-Oligo 058 | AAAAAAACAGUAAAAAAA |
| ANP-Oligo 059 | AAAAAAACAUCAAAAAAA |
| ANP-Oligo 060 | AAAAAAACAUGAAAAAAA |
| ANP-Oligo 061 | AAAAAAACAUUAAAAAAA |
| ANP-Oligo 062 | AAAAAAACCACAAAAAAA |
| ANP-Oligo 063 | AAAAAAACCAGAAAAAAA |
| ANP-Oligo 064 | AAAAAAACCAUAAAAAAA |
| ANP-Oligo 065 | AAAAAAACCCCAAAAAAA |
| ANP-Oligo 066 | AAAAAAACCCGAAAAAAA |
| ANP-Oligo 067 | AAAAAAACCCUAAAAAAA |
| ANP-Oligo 068 | AAAAAAACCGCAAAAAAA |
| ANP-Oligo 069 | AAAAAAACCGGAAAAAAA |
| ANP-Oligo 070 | AAAAAAACCGUAAAAAAA |
| ANP-Oligo 071 | AAAAAAACCUCAAAAAAA |
| ANP-Oligo 072 | AAAAAAACCUGAAAAAAA |
| ANP-Oligo 073 | AAAAAAACCUUAAAAAAA |
| ANP-Oligo 074 | AAAAAAACGACAAAAAAA |
| ANP-Oligo 075 | AAAAAAACGAGAAAAAAA |

TABLE 1-continued ssRNA oligonucleotides containing all possible 4 mer motifs on the poly a backbone.

| Name | Sequence |
| --- | --- |
| ANP-Oligo 076 | AAAAAAACGAUAAAAAAAA |
| ANP-Oligo 077 | AAAAAAACGCCAAAAAAAA |
| ANP-Oligo 078 | AAAAAAACGCGAAAAAAAA |
| ANP-Oligo 079 | AAAAAAACGCUAAAAAAAA |
| ANP-Oligo 080 | AAAAAAACGGCAAAAAAAA |
| ANP-Oligo 081 | AAAAAAACGGGAAAAAAAA |
| ANP-Oligo 082 | AAAAAAACGGUAAAAAAAA |
| ANP-Oligo 083 | AAAAAAACGUCAAAAAAAA |
| ANP-Oligo 084 | AAAAAAACGUGAAAAAAAA |
| ANP-Oligo 085 | AAAAAAACGUUAAAAAAAA |
| ANP-Oligo 086 | AAAAAAACUACAAAAAAAA |
| ANP-Oligo 087 | AAAAAAACUAGAAAAAAAA |
| ANP-Oligo 088 | AAAAAAACUAUAAAAAAAA |
| ANP-Oligo 089 | AAAAAAACUCCAAAAAAAA |
| ANP-Oligo 090 | AAAAAAACUCGAAAAAAAA |
| ANP-Oligo 091 | AAAAAAACUCUAAAAAAAA |
| ANP-Oligo 092 | AAAAAAACUGCAAAAAAAA |
| ANP-Oligo 093 | AAAAAAACUGGAAAAAAAA |
| ANP-Oligo 094 | AAAAAAACUGUAAAAAAAA |
| ANP-Oligo 095 | AAAAAAACUUCAAAAAAAA |
| ANP-Oligo 096 | AAAAAAACUUGAAAAAAAA |
| ANP-Oligo 097 | AAAAAAACUUUAAAAAAAA |
| ANP-Oligo 098 | AAAAAAAGAACAAAAAAAA |
| ANP-Oligo 099 | AAAAAAAGAAGAAAAAAAA |
| ANP-Oligo 100 | AAAAAAAGAAUAAAAAAAA |
| ANP-Oligo 101 | AAAAAAAGACCAAAAAAAA |
| ANP-Oligo 102 | AAAAAAAGACGAAAAAAAA |
| ANP-Oligo 103 | AAAAAAAGACUAAAAAAAA |
| ANP-Oligo 104 | AAAAAAAGAGCAAAAAAAA |
| ANP-Oligo 105 | AAAAAAAGAGGAAAAAAAA |
| ANP-Oligo 106 | AAAAAAAGAGUAAAAAAAA |
| ANP-Oligo 107 | AAAAAAAGAUCAAAAAAAA |
| ANP-Oligo 108 | AAAAAAAGAUGAAAAAAAA |
| ANP-Oligo 109 | AAAAAAAGAUUAAAAAAAA |
| ANP-Oligo 110 | AAAAAAAGCACAAAAAAAA |
| ANP-Oligo 111 | AAAAAAAGCAGAAAAAAAA |
| ANP-Oligo 112 | AAAAAAAGCAUAAAAAAAA |
| ANP-Oligo 113 | AAAAAAAGCCCAAAAAAAA |
| ANP-Oligo 114 | AAAAAAAGCCGAAAAAAAA |
| ANP-Oligo 115 | AAAAAAAGCCUAAAAAAAA |
| ANP-Oligo 116 | AAAAAAAGCGCAAAAAAAA |
| ANP-Oligo 117 | AAAAAAAGCGGAAAAAAAA |
| ANP-Oligo 118 | AAAAAAAGCGUAAAAAAAA |
| ANP-Oligo 119 | AAAAAAAGCUCAAAAAAAA |
| ANP-Oligo 120 | AAAAAAAGCUGAAAAAAAA |
| ANP-Oligo 121 | AAAAAAAGCUUAAAAAAAA |
| ANP-Oligo 122 | AAAAAAAGGACAAAAAAAA |
| ANP-Oligo 123 | AAAAAAAGGAGAAAAAAAA |
| ANP-Oligo 124 | AAAAAAAGGAUAAAAAAAA |
| ANP-Oligo 125 | AAAAAAAGGCCAAAAAAAA |
| ANP-Oligo 126 | AAAAAAAGGCGAAAAAAAA |
| ANP-Oligo 127 | AAAAAAAGGCUAAAAAAAA |
| ANP-Oligo 128 | AAAAAAAGGGCAAAAAAAA |
| ANP-Oligo 129 | AAAAAAAGGGGAAAAAAAA |
| ANP-Oligo 130 | AAAAAAAGGGUAAAAAAAA |
| ANP-Oligo 131 | AAAAAAAGGUCAAAAAAAA |
| ANP-Oligo 132 | AAAAAAAGGUGAAAAAAAA |
| ANP-Oligo 133 | AAAAAAAGGUUAAAAAAAA |
| ANP-Oligo 134 | AAAAAAAGUACAAAAAAAA |
| ANP-Oligo 135 | AAAAAAAGUAGAAAAAAAA |
| ANP-Oligo 136 | AAAAAAAGUAUAAAAAAAA |
| ANP-Oligo 137 | AAAAAAAGUCCAAAAAAAA |
| ANP-Oligo 138 | AAAAAAAGUCGAAAAAAAA |
| ANP-Oligo 139 | AAAAAAAGUCUAAAAAAAA |
| ANP-Oligo 140 | AAAAAAAGUGCAAAAAAAA |
| ANP-Oligo 141 | AAAAAAAGUGGAAAAAAAA |
| ANP-Oligo 142 | AAAAAAAGUGUAAAAAAAA |
| ANP-Oligo 143 | AAAAAAAGUUCAAAAAAAA |
| ANP-Oligo 144 | AAAAAAAGUUGAAAAAAAA |
| ANP-Oligo 145 | AAAAAAAGUUUAAAAAAAA |
| ANP-Oligo 146 | AAAAAAAUAACAAAAAAAA |
| ANP-Oligo 147 | AAAAAAAUAAGAAAAAAAA |
| ANP-Oligo 148 | AAAAAAAUAAUAAAAAAAA |
| ANP-Oligo 149 | AAAAAAAUACCAAAAAAAA |

TABLE 1-continued ssRNA oligonucleotides containing all possible 4 mer motifs on the poly a backbone.

| Name | Sequence |
|---|---|
| ANP-Oligo 150 | AAAAAAAUACGAAAAAAAA |
| ANP-Oligo 151 | AAAAAAAUACUAAAAAAAA |
| ANP-Oligo 152 | AAAAAAAUAGCAAAAAAAA |
| ANP-Oligo 153 | AAAAAAAUAGGAAAAAAAA |
| ANP-Oligo 154 | AAAAAAAUAGUAAAAAAAA |
| ANP-Oligo 155 | AAAAAAAUAUCAAAAAAAA |
| ANP-Oligo 156 | AAAAAAAUAUGAAAAAAAA |
| ANP-Oligo 157 | AAAAAAAUAUUAAAAAAAA |
| ANP-Oligo 158 | AAAAAAAUCACAAAAAAAA |
| ANP-Oligo 159 | AAAAAAAUCAGAAAAAAAA |
| ANP-Oligo 160 | AAAAAAAUCAUAAAAAAAA |
| ANP-Oligo 161 | AAAAAAAUCCCAAAAAAAA |
| ANP-Oligo 162 | AAAAAAAUCCGAAAAAAAA |
| ANP-Oligo 163 | AAAAAAAUCCUAAAAAAAA |
| ANP-Oligo 164 | AAAAAAAUCGCAAAAAAAA |
| ANP-Oligo 165 | AAAAAAAUCGGAAAAAAAA |
| ANP-Oligo 166 | AAAAAAAUCGUAAAAAAAA |
| ANP-Oligo 167 | AAAAAAAUCUCAAAAAAAA |
| ANP-Oligo 168 | AAAAAAAUCUGAAAAAAAA |
| ANP-Oligo 169 | AAAAAAAUCUUAAAAAAAA |
| ANP-Oligo 170 | AAAAAAAUGACAAAAAAAA |
| ANP-Oligo 171 | AAAAAAAUGAGAAAAAAAA |
| ANP-Oligo 172 | AAAAAAAUGAUAAAAAAAA |
| ANP-Oligo 173 | AAAAAAAUGCCAAAAAAAA |
| ANP-Oligo 174 | AAAAAAAUGCGAAAAAAAA |
| ANP-Oligo 175 | AAAAAAAUGCUAAAAAAAA |
| ANP-Oligo 176 | AAAAAAAUGGCAAAAAAAA |
| ANP-Oligo 177 | AAAAAAAUGGGAAAAAAAA |
| ANP-Oligo 178 | AAAAAAAUGGUAAAAAAAA |
| ANP-Oligo 179 | AAAAAAAUGUCAAAAAAAA |
| ANP-Oligo 180 | AAAAAAAUGUGAAAAAAAA |
| ANP-Oligo 181 | AAAAAAAUGUUAAAAAAAA |
| ANP-Oligo 182 | AAAAAAAUUACAAAAAAAA |
| ANP-Oligo 183 | AAAAAAAUUAGAAAAAAAA |
| ANP-Oligo 184 | AAAAAAAUUAUAAAAAAAA |
| ANP-Oligo 185 | AAAAAAAUUCCAAAAAAAA |
| ANP-Oligo 186 | AAAAAAAUUCGAAAAAAAA |
| ANP-Oligo 187 | AAAAAAAUUCUAAAAAAAA |
| ANP-Oligo 188 | AAAAAAAUUGCAAAAAAAA |
| ANP-Oligo 189 | AAAAAAAUUGGAAAAAAAA |
| ANP-Oligo 190 | AAAAAAAUUGUAAAAAAAA |
| ANP-Oligo 191 | AAAAAAAUUUCAAAAAAAA |
| ANP-Oligo 192 | AAAAAAAUUUGAAAAAAAA |
| ANP-Oligo 193 | AAAAAAAUUUUAAAAAAAA |

TABLE 2

Group 1 ssRNA-Oligonucleotides

| Name | Sequence 5'→3' | adjusted IFN-α index | SEM |
|---|---|---|---|
| ANP-Oligo 018 | AAAAAAAACCGAAAAAAAA | −0, 23 | 0, 03 |
| ANP-Oligo 020 | AAAAAAAACGCAAAAAAAA | −0, 23 | 0, 03 |
| ANP-Oligo 029 | AAAAAAAAGCCAAAAAAAA | −0, 23 | 0, 03 |
| ANP-Oligo 051 | AAAAAAACAAGAAAAAAAA | −0, 23 | 0, 03 |
| ANP-Oligo 053 | AAAAAAACACCAAAAAAAA | −0, 23 | 0, 03 |
| ANP-Oligo 075 | AAAAAAACGAGAAAAAAAA | −0, 23 | 0, 03 |
| ANP-Oligo 080 | AAAAAAACGGCAAAAAAAA | −0, 23 | 0, 03 |
| ANP-Oligo 128 | AAAAAAAGGGCAAAAAAAA | −0, 23 | 0, 03 |
| ANP-Oligo 130 | AAAAAAAGGGUAAAAAAAA | −0, 23 | 0, 03 |
| ANP-Oligo 009 | AAAAAAAAGGAAAAAAAAA | −0, 23 | 0, 03 |
| ANP-Oligo 017 | AAAAAAAACCCAAAAAAAA | −0, 23 | 0, 03 |
| ANP-Oligo 003 | AAAAAAAAGAAAAAAAAAA | −0, 23 | 0, 03 |
| ANP-Oligo 081 | AAAAAAACGGGAAAAAAAA | −0, 23 | 0, 03 |
| ANP-Oligo 113 | AAAAAAAGCCCAAAAAAAA | −0, 23 | 0, 03 |
| ANP-Oligo 014 | AAAAAAAACACAAAAAAAA | −0, 23 | 0, 03 |
| ANP-Oligo 077 | AAAAAAACGCCAAAAAAAA | −0, 23 | 0, 03 |
| ANP-Oligo 126 | AAAAAAAGGCGAAAAAAAA | −0, 23 | 0, 03 |
| ANP-Oligo 125 | AAAAAAAGGCCAAAAAAAA | −0, 23 | 0, 03 |
| ANP-Oligo 050 | AAAAAAACAACAAAAAAAA | −0, 23 | 0, 03 |
| ANP-Oligo 015 | AAAAAAAACAGAAAAAAAA | −0, 22 | 0, 03 |
| ANP-Oligo 114 | AAAAAAAGCCGAAAAAAAA | −0, 22 | 0, 03 |
| ANP-Oligo 027 | AAAAAAAAGAGAAAAAAAA | −0, 22 | 0, 03 |
| ANP-Oligo 117 | AAAAAAAGCGGAAAAAAAA | −0, 22 | 0, 03 |
| ANP-Oligo 006 | AAAAAAAACGAAAAAAAAA | −0, 22 | 0, 03 |
| ANP-Oligo 005 | AAAAAAAACCAAAAAAAAA | −0, 22 | 0, 03 |

TABLE 2-continued

Group 1 ssRNA-Oligonucleotides

| Name | Sequence 5'→3' | adjusted IFN-α index | SEM |
|---|---|---|---|
| ANP-Oligo 069 | AAAAAAACCGGAAAAAAAA | -0,22 | 0,03 |
| ANP-Oligo 066 | AAAAAAACCCGAAAAAAAA | -0,22 | 0,03 |
| ANP-Oligo 007 | AAAAAAAACUAAAAAAAA | -0,22 | 0,03 |
| ANP-Oligo 060 | AAAAAAACAUGAAAAAAAA | -0,22 | 0,03 |
| ANP-Oligo 021 | AAAAAAACGGAAAAAAAA | -0,22 | 0,03 |
| ANP-Oligo 042 | AAAAAAAAUCGAAAAAAAA | -0,22 | 0,03 |
| ANP-Oligo 086 | AAAAAAACUACAAAAAAAA | -0,22 | 0,03 |
| ANP-Oligo 064 | AAAAAAACCAUAAAAAAAA | -0,22 | 0,03 |
| ANP-Oligo 102 | AAAAAAAGACGAAAAAAAA | -0,22 | 0,03 |
| ANP-Oligo 068 | AAAAAAACCGCAAAAAAAA | -0,22 | 0,03 |
| ANP-Oligo 129 | AAAAAAAGGGGAAAAAAAA | -0,22 | 0,03 |
| ANP-Oligo 008 | AAAAAAAAGCAAAAAAAA | -0,22 | 0,03 |
| ANP-Oligo 002 | AAAAAAAACAAAAAAAA | -0,22 | 0,03 |
| ANP-Oligo 038 | AAAAAAAAUACAAAAAAAA | -0,22 | 0,03 |
| ANP-Oligo 026 | AAAAAAAAGACAAAAAAAA | -0,22 | 0,03 |
| ANP-Oligo 116 | AAAAAAAGCGCAAAAAAAA | -0,22 | 0,03 |
| ANP-Oligo 054 | AAAAAAACACGAAAAAAAA | -0,22 | 0,03 |
| ANP-Oligo 057 | AAAAAAACAGGAAAAAAAA | -0,22 | 0,03 |
| ANP-Oligo 001 | AAAAAAAAAAAAAAAAA | -0,21 | 0,03 |
| ANP-Oligo 074 | AAAAAAACGACAAAAAAAA | -0,21 | 0,03 |
| ANP-Oligo 033 | AAAAAAAAGGGAAAAAAAA | -0,21 | 0,03 |
| ANP-Oligo 123 | AAAAAAAGGAGAAAAAAAA | -0,21 | 0,03 |
| ANP-Oligo 059 | AAAAAAACAUCAAAAAAAA | -0,21 | 0,03 |
| ANP-Oligo 110 | AAAAAAAGCACAAAAAAAA | -0,21 | 0,03 |
| ANP-Oligo 065 | AAAAAAACCCAAAAAAAA | -0,21 | 0,03 |
| ANP-Oligo 055 | AAAAAAACACUAAAAAAAA | -0,21 | 0,03 |
| ANP-Oligo 122 | AAAAAAAGGACAAAAAAAA | -0,21 | 0,03 |
| ANP-Oligo 104 | AAAAAAAGAGCAAAAAAAA | -0,21 | 0,03 |
| ANP-Oligo 078 | AAAAAAACGCGAAAAAAAA | -0,21 | 0,03 |
| ANP-Oligo 032 | AAAAAAAAGGCAAAAAAAA | -0,21 | 0,04 |
| ANP-Oligo 030 | AAAAAAAAGCGAAAAAAAA | -0,21 | 0,03 |
| ANP-Oligo 004 | AAAAAAAAUAAAAAAAA | -0,21 | 0,03 |
| ANP-Oligo 105 | AAAAAAAGAGGAAAAAAAA | -0,21 | 0,03 |
| ANP-Oligo 161 | AAAAAAAUCCCAAAAAAAA | -0,21 | 0,02 |
| ANP-Oligo 061 | AAAAAAACAUUAAAAAAAA | -0,2 | 0,02 |
| ANP-Oligo 041 | AAAAAAAAUCCAAAAAAAA | -0,2 | 0,03 |
| ANP-Oligo 063 | AAAAAAACCAGAAAAAAAA | -0,2 | 0,04 |
| ANP-Oligo 072 | AAAAAAACCUGAAAAAAAA | -0,2 | 0,02 |
| ANP-Oligo 101 | AAAAAAAGACCAAAAAAAA | -0,2 | 0,04 |
| ANP-Oligo 056 | AAAAAAACAGCAAAAAAAA | -0,2 | 0,04 |
| ANP-Oligo 162 | AAAAAAAUCCGAAAAAAAA | -0,2 | 0,02 |
| ANP-Oligo 099 | AAAAAAAGAAGAAAAAAAA | -0,2 | 0,05 |
| ANP-Oligo 111 | AAAAAAAGCAGAAAAAAAA | -0,2 | 0,04 |
| ANP-Oligo 011 | AAAAAAAAUCAAAAAAAA | -0,2 | 0,04 |
| ANP-Oligo 062 | AAAAAAACCACAAAAAAAA | -0,19 | 0,04 |
| ANP-Oligo 016 | AAAAAAAACAUAAAAAAAA | -0,19 | 0,03 |
| ANP-Oligo 177 | AAAAAAAUGGGAAAAAAAA | -0,19 | 0,03 |
| ANP-Oligo 019 | AAAAAAAACCUAAAAAAAA | -0,19 | 0,03 |
| ANP-Oligo 098 | AAAAAAAGAACAAAAAAAA | -0,19 | 0,05 |
| ANP-Oligo 052 | AAAAAAACAAUAAAAAAAA | -0,19 | 0,02 |
| ANP-Oligo 089 | AAAAAAACUCCAAAAAAAA | -0,18 | 0,05 |
| ANP-Oligo 067 | AAAAAAACCCUAAAAAAAA | -0,18 | 0,02 |
| ANP-Oligo 040 | AAAAAAAAUAUAAAAAAAA | -0,18 | 0,02 |
| ANP-Oligo 039 | AAAAAAAAUAGAAAAAAAA | -0,18 | 0,02 |
| ANP-Oligo 043 | AAAAAAAAUCUAAAAAAAA | -0,18 | 0,02 |
| ANP-Oligo 073 | AAAAAAACCUUAAAAAAAA | -0,18 | 0,01 |
| ANP-Oligo 024 | AAAAAAAACUGAAAAAAAA | -0,17 | 0,02 |
| ANP-Oligo 028 | AAAAAAAAGAUAAAAAAAA | -0,17 | 0,01 |
| ANP-Oligo 103 | AAAAAAAGACUAAAAAAAA | -0,17 | 0,01 |
| ANP-Oligo 091 | AAAAAAACUCUAAAAAAAA | -0,17 | 0,01 |
| ANP-Oligo 158 | AAAAAAAUCACAAAAAAAA | -0,17 | 0,02 |
| ANP-Oligo 012 | AAAAAAAAUGAAAAAAAA | -0,16 | 0,02 |
| ANP-Oligo 163 | AAAAAAAUCCUAAAAAAAA | -0,15 | 0,03 |
| ANP-Oligo 025 | AAAAAAAACUUAAAAAAAA | -0,15 | 0,02 |
| ANP-Oligo 112 | AAAAAAAGCAUAAAAAAAA | -0,15 | 0,01 |
| ANP-Oligo 070 | AAAAAAACCGUAAAAAAAA | -0,14 | 0,02 |
| ANP-Oligo 172 | AAAAAAAUGAUAAAAAAAA | -0,14 | 0,03 |
| ANP-Oligo 150 | AAAAAAAUACGAAAAAAAA | -0,14 | 0,04 |
| ANP-Oligo 146 | AAAAAAAUAACAAAAAAAA | -0,14 | 0,03 |
| ANP-Oligo 115 | AAAAAAAGCCUAAAAAAAA | -0,14 | 0,01 |
| ANP-Oligo 160 | AAAAAAAUCAUAAAAAAAA | -0,13 | 0,02 |
| ANP-Oligo 151 | AAAAAAAUACUAAAAAAAA | -0,13 | 0,03 |
| ANP-Oligo 013 | AAAAAAAAUUAAAAAAAA | -0,13 | 0,03 |
| ANP-Oligo 090 | AAAAAAACUCGAAAAAAAA | -0,13 | 0,03 |

TABLE 2-continued

Group 1 ssRNA-Oligonucleotides

| Name | Sequence 5'→3' | adjusted IFN-α index | SEM |
|---|---|---|---|
| ANP-Oligo 048 | AAAAAAAAUUGAAAAAAAA | -0,13 | 0,02 |
| ANP-Oligo 092 | AAAAAAACUGCAAAAAAAA | -0,13 | 0,02 |
| ANP-Oligo 093 | AAAAAAACUGGAAAAAAAA | -0,13 | 0,03 |
| ANP-Oligo 031 | AAAAAAAAGCUAAAAAAAA | -0,13 | 0,02 |
| ANP-Oligo 157 | AAAAAAAUAUUAAAAAAAA | -0,12 | 0,02 |
| ANP-Oligo 108 | AAAAAAAGAUGAAAAAAAA | -0,12 | 0,02 |
| ANP-Oligo 076 | AAAAAAACGAUAAAAAAAA | -0,12 | 0,03 |
| ANP-Oligo 165 | AAAAAAAUCGGAAAAAAAA | -0,11 | 0,03 |
| ANP-Oligo 087 | AAAAAAACUAGAAAAAAAA | -0,11 | 0,01 |
| ANP-Oligo 109 | AAAAAAAGAUUAAAAAAAA | -0,11 | 0,01 |
| ANP-Oligo 183 | AAAAAAAUUAGAAAAAAAA | -0,11 | 0,05 |
| ANP-Oligo 127 | AAAAAAAGGCUAAAAAAAA | -0,11 | 0,03 |
| ANP-Oligo 079 | AAAAAAACGCUAAAAAAAA | -0,1 | 0,02 |
| ANP-Oligo 088 | AAAAAAACUAUAAAAAAAA | -0,1 | 0,03 |
| ANP-Oligo 159 | AAAAAAAUCAGAAAAAAAA | -0,1 | 0,05 |
| ANP-Oligo 152 | AAAAAAAUAGCAAAAAAAA | -0,1 | 0,04 |
| ANP-Oligo 084 | AAAAAAACGUGAAAAAAAA | -0,1 | 0,03 |
| ANP-Oligo 184 | AAAAAAAUUAUAAAAAAAA | -0,1 | 0,03 |
| ANP-Oligo 175 | AAAAAAAUGCUAAAAAAAA | -0,1 | 0,03 |
| ANP-Oligo 164 | AAAAAAAUCGCAAAAAAAA | -0,09 | 0,04 |
| ANP-Oligo 149 | AAAAAAAUACCAAAAAAAA | -0,09 | 0,06 |
| ANP-Oligo 185 | AAAAAAAUUCCAAAAAAAA | -0,08 | 0,05 |
| ANP-Oligo 044 | AAAAAAAAUGCAAAAAAAA | -0,08 | 0,03 |
| ANP-Oligo 022 | AAAAAAAACGUAAAAAAAA | -0,08 | 0,02 |
| ANP-Oligo 049 | AAAAAAAAUUUAAAAAAAA | -0,08 | 0,02 |
| ANP-Oligo 147 | AAAAAAAUAAGAAAAAAAA | -0,07 | 0,06 |
| ANP-Oligo 120 | AAAAAAAGCUGAAAAAAAA | -0,07 | 0,03 |
| ANP-Oligo 107 | AAAAAAAGAUCAAAAAAAA | -0,07 | 0,05 |
| ANP-Oligo 118 | AAAAAAAGCGUAAAAAAAA | -0,07 | 0,03 |
| ANP-Oligo 170 | AAAAAAAUGACAAAAAAAA | -0,07 | 0,06 |
| ANP-Oligo 124 | AAAAAAAGGAUAAAAAAAA | -0,07 | 0,05 |
| ANP-Oligo 148 | AAAAAAAUAAUAAAAAAAA | -0,07 | 0,05 |
| ANP-Oligo 097 | AAAAAAACUUUAAAAAAAA | -0,07 | 0,02 |
| ANP-Oligo 156 | AAAAAAAUAUGAAAAAAAA | -0,06 | 0,04 |
| ANP-Oligo 045 | AAAAAAAAUGGAAAAAAAA | -0,06 | 0,06 |
| ANP-Oligo 171 | AAAAAAAUGAGAAAAAAAA | -0,05 | 0,08 |
| ANP-Oligo 173 | AAAAAAAUGCCAAAAAAAA | -0,05 | 0,05 |

TABLE 2-continued

Group 1 ssRNA-Oligonucleotides

| Name | Sequence 5'→3' | adjusted IFN-α index | SEM |
|---|---|---|---|
| ANP-Oligo 174 | AAAAAAAUGCGAAAAAAAA | -0,05 | 0,07 |
| ANP-Oligo 153 | AAAAAAAUAGGAAAAAAAA | -0,05 | 0,05 |
| ANP-Oligo 100 | AAAAAAAGAAUAAAAAAAA | -0,04 | 0,02 |
| ANP-Oligo 169 | AAAAAAAUCUUAAAAAAAA | -0,04 | 0,05 |
| ANP-Oligo 155 | AAAAAAAUAUCAAAAAAAA | -0,03 | 0,04 |
| ANP-Oligo 010 | AAAAAAAAGUAAAAAAAAA | -0,03 | 0,04 |
| ANP-Oligo 036 | AAAAAAAAGUGAAAAAAAA | -0,02 | 0,04 |
| ANP-Oligo 082 | AAAAAAACGGUAAAAAAAA | -0,01 | 0,03 |
| ANP-Oligo 168 | AAAAAAAUCUGAAAAAAAA | -0,01 | 0,06 |

TABLE 3

Group 2 ssRNA-Oligonucleotides

| Name | Sequence 5'→3' | adjusted IFN-α index | SEM |
|---|---|---|---|
| ANP-Oligo 071 | AAAAAAACCUCAAAAAAAA | 0 | 0,05 |
| ANP-Oligo 182 | AAAAAAAUUACAAAAAAAA | 0,01 | 0,1 |
| ANP-Oligo 096 | AAAAAAACUUGAAAAAAAA | 0,02 | 0,06 |
| ANP-Oligo 085 | AAAAAAACGUUAAAAAAAA | 0,02 | 0,04 |
| ANP-Oligo 176 | AAAAAAAUGGCAAAAAAAA | 0,04 | 0,04 |
| ANP-Oligo 187 | AAAAAAAUUCUAAAAAAAA | 0,05 | 0,04 |
| ANP-Oligo 166 | AAAAAAAUCGUAAAAAAAA | 0,07 | 0,04 |
| ANP-Oligo 023 | AAAAAAAACUCAAAAAAAA | 0,08 | 0,06 |
| ANP-Oligo 193 | AAAAAAAUUUUAAAAAAAA | 0,13 | 0,08 |
| ANP-Oligo 188 | AAAAAAAUUUGCAAAAAAAA | 0,14 | 0,04 |
| ANP-Oligo 132 | AAAAAAAGGUGAAAAAAAA | 0,18 | 0,04 |
| ANP-Oligo 106 | AAAAAAAGAGUAAAAAAAA | 0,21 | 0,07 |
| ANP-Oligo 095 | AAAAAAACUUCAAAAAAAA | 0,22 | 0,07 |
| ANP-Oligo 186 | AAAAAAAUUCGAAAAAAAA | 0,22 | 0,09 |
| ANP-Oligo 058 | AAAAAAACAGUAAAAAAAA | 0,22 | 0,09 |
| ANP-Oligo 167 | AAAAAAAUCUCAAAAAAAA | 0,23 | 0,07 |
| ANP-Oligo 189 | AAAAAAAUUGGAAAAAAAA | 0,24 | 0,12 |
| ANP-Oligo 047 | AAAAAAAAUUCAAAAAAAA | 0,27 | 0,09 |
| ANP-Oligo 135 | AAAAAAAGUAGAAAAAAAA | 0,3 | 0,04 |
| ANP-Oligo 154 | AAAAAAAUAGUAAAAAAAA | 0,32 | 0,03 |
| ANP-Oligo 136 | AAAAAAAGUAUAAAAAAAA | 0,36 | 0,07 |
| ANP-Oligo 134 | AAAAAAAGUACAAAAAAAA | 0,37 | 0,08 |

TABLE 3-continued

Group 2 ssRNA-Oligonucleotides

| Name | Sequence 5'→3' | adjusted IFN-α index | SEM |
|---|---|---|---|
| ANP-Oligo 140 | AAAAAAAGUGCAAAAAAAA | 0, 38 | 0, 04 |
| ANP-Oligo 141 | AAAAAAAGUGGAAAAAAAA | 0, 39 | 0, 06 |
| ANP-Oligo 178 | AAAAAAAUGGAAAAAAAA | 0, 41 | 0, 03 |
| ANP-Oligo 192 | AAAAAAAUUUGAAAAAAAA | 0, 42 | 0, 11 |
| ANP-Oligo 138 | AAAAAAAGUCGAAAAAAAA | 0, 44 | 0, 05 |
| ANP-Oligo 034 | AAAAAAAAGGUAAAAAAAA | 0, 46 | 0, 05 |
| ANP-Oligo 180 | AAAAAAAUGUGAAAAAAAA | 0, 46 | 0, 07 |
| ANP-Oligo 191 | AAAAAAAUUUCAAAAAAAA | 0, 54 | 0, 13 |
| ANP-Oligo 046 | AAAAAAAAUGUAAAAAAAA | 0, 59 | 0, 04 |
| ANP-Oligo 037 | AAAAAAAAGUUAAAAAAAA | 0, 62 | 0, 13 |
| ANP-Oligo 181 | AAAAAAAUGUUAAAAAAAA | 0, 64 | 0, 07 |
| ANP-Oligo 083 | AAAAAAACGUCAAAAAAAA | 0, 68 | 0, 15 |
| ANP-Oligo 094 | AAAAAAACUGUAAAAAAAA | 0, 73 | 0, 09 |
| ANP-Oligo 179 | AAAAAAAUGUCAAAAAAAA | 0, 73 | 0, 04 |
| ANP-Oligo 190 | AAAAAAAUUGUAAAAAAAA | 0, 74 | 0, 07 |
| ANP-Oligo 121 | AAAAAAAGCUUAAAAAAAA | 0, 77 | 0, 07 |
| ANP-Oligo 137 | AAAAAAAGUCCAAAAAAAA | 0, 79 | 0, 06 |
| ANP-Oligo 139 | AAAAAAAGUCUAAAAAAAA | 0, 84 | 0, 08 |
| ANP-Oligo 131 | AAAAAAAGGUCAAAAAAAA | 0, 93 | 0, 2 |
| ANP-Oligo 142 | AAAAAAAGUGUAAAAAAAA | 0, 96 | 0, 08 |
| ANP-Oligo 133 | AAAAAAAGGUUAAAAAAAA | 1, 04 | 0, 13 |
| ANP-Oligo 145 | AAAAAAAGUUUAAAAAAAA | 1, 17 | 0, 08 |
| ANP-Oligo 144 | AAAAAAAGUUGAAAAAAAA | 1, 22 | 0, 08 |
| ANP-Oligo 119 | AAAAAAAGCUCAAAAAAAA | 1, 26 | 0, 15 |
| ANP-Oligo 035 | AAAAAAAAGUCAAAAAAAA | 1, 33 | 0, 28 |
| ANP-Oligo 143 | AAAAAAAGUUCAAAAAAAA | 1, 35 | 0, 11 |

TABLE 4 ssRNA oligonucleotides-FIG. 7A

| Name | Sequence 5'→3' |
|---|---|
| ANP-Oligo 194 | AAGUCAAAAAAAAAAAAA |
| ANP-Oligo 195 | AAAAAAGUCAAAAAAAAA |
| ANP-Oligo 035 | AAAAAAAAGUCAAAAAAAA |
| ANP-Oligo 196 | AAAAAAAAAAGUCAAAAA |
| ANP-Oligo 197 | AAAAAAAAAAAAAAGUCAA |

TABLE 5 ssRNA oligonucleotides-FIG. 7B

| Name | Sequence 5'→3' |
|---|---|
| ANP-Oligo 035 | AAAAAAAAGUCAAAAAAAA |
| ANP-Oligo 198 | AAAAAAAAGUCACAAAAAA |
| ANP-Oligo 199 | AAAAAAAAGUCAGAAAAAA |
| ANP-Oligo 200 | AAAAAAAAGUCAUAAAAAA |
| ANP-Oligo 083 | AAAAAAACGUCAAAAAAAA |
| ANP-Oligo 201 | AAAAAAACGUCACAAAAAA |
| ANP-Oligo 202 | AAAAAAACGUCAGAAAAAA |
| ANP-Oligo 203 | AAAAAAACGUCAUAAAAAA |
| ANP-Oligo 131 | AAAAAAAGGUCAAAAAAAA |
| ANP-Oligo 204 | AAAAAAAGGUCACAAAAAA |
| ANP-Oligo 205 | AAAAAAAGGUCAGAAAAAA |
| ANP-Oligo 206 | AAAAAAAGGUCAUAAAAAA |
| ANP-Oligo 179 | AAAAAAAUGUCAAAAAAAA |
| ANP-Oligo 207 | AAAAAAAUGUCACAAAAAA |
| ANP-Oligo 208 | AAAAAAAUGUCAGAAAAAA |
| ANP-Oligo 209 | AAAAAAAUGUCAUAAAAAA |

TABLE 6 ssRNA oligonucleotides--FIG. 8A

| Oligo-name | Sequence 5'→3' |
|---|---|
| 9.2 sense | AGCUUAACCUGUCCUUCAA |
| L7A | AAAAAAACCUGUCCUUCAA |
| L8A | AAAAAAAACUGUCCUUCAA |
| L9A | AAAAAAAAAUGUCCUUCAA |
| L10A | AAAAAAAAAAGUCCUUCAA |
| L11A | AAAAAAAAAAAUCCUUCAA |
| L12A | AAAAAAAAAAAACCUUCAA |
| R9A | AGCUUAACCUAAAAAAAAA |
| R8A | AGCUUAACCUGAAAAAAAA |
| R7A | AGCUUAACCUGUAAAAAAA |
| R6A | AGCUUAACCUGUCAAAAAA |
| R5A | AGCUUAACCUGUCCAAAAA |
| R4A | AGCUUAACCUGUCCUAAAA |
| R3A | AGCUUAACCUGUCCUUAAA |

TABLE 12

3mer motifs and their mean levels of IFN-α induction
A. 3mer motifs 5'-NNN-3'

| Motif | Occurrences | Mean (IFN-α point score) | Sem | p-value |
|---|---|---|---|---|
| AAA | 2192 | 0.00 | 0.01 | 0.389 |
| AAC | 67 | −0.14 | 0.02 | **0.001 |
| AAG | 67 | 0.11 | 0.06 | **0.009 |
| AAU | 67 | 0.01 | 0.03 | 0.841 |
| ACA | 31 | −0.17 | 0.02 | **0.007 |
| ACC | 19 | −0.19 | 0.01 | *0.017 |
| ACG | 19 | −0.12 | 0.05 | 0.128 |
| ACU | 19 | −0.07 | 0.05 | 0.407 |
| AGA | 31 | −0.14 | 0.02 | *0.021 |
| AGC | 19 | −0.05 | 0.09 | 0.508 |
| AGG | 19 | −0.01 | 0.09 | 0.877 |
| AGU | 19 | 0.59 | 0.10 | **<0.001 |
| AUA | 31 | −0.10 | 0.02 | 0.118 |
| AUC | 19 | −0.11 | 0.03 | 0.176 |
| AUG | 19 | 0.08 | 0.07 | 0.318 |
| AUU | 19 | 0.09 | 0.06 | 0.253 |
| CAA | 67 | 0.00 | 0.05 | 0.913 |
| CAC | 7 | −0.21 | 0.01 | 0.11 |
| CAG | 7 | −0.13 | 0.06 | 0.313 |
| CAU | 7 | −0.19 | 0.01 | 0.143 |
| CCA | 19 | −0.14 | 0.05 | 0.077 |
| CCC | 7 | −0.21 | 0.01 | 0.102 |
| CCG | 7 | −0.21 | 0.01 | 0.11 |
| CCU | 7 | −0.15 | 0.03 | 0.252 |
| CGA | 19 | −0.14 | 0.04 | 0.082 |
| CGC | 7 | −0.19 | 0.02 | 0.155 |
| CGG | 7 | −0.18 | 0.03 | 0.172 |
| CGU | 7 | 0.05 | 0.11 | 0.678 |
| CUA | 19 | −0.09 | 0.05 | 0.251 |
| CUC | 7 | 0.16 | 0.19 | 0.229 |
| CUG | 7 | 0.00 | 0.12 | 0.979 |
| CUU | 7 | 0.08 | 0.12 | 0.529 |
| GAA | 67 | −0.08 | 0.03 | *0.044 |
| GAC | 7 | −0.19 | 0.02 | 0.153 |
| GAG | 7 | −0.13 | 0.06 | 0.306 |
| GAU | 7 | −0.11 | 0.01 | 0.385 |
| GCA | 19 | −0.12 | 0.04 | 0.114 |
| GCC | 7 | −0.19 | 0.03 | 0.149 |
| GCG | 7 | −0.17 | 0.03 | 0.184 |
| GCU | 7 | 0.22 | 0.21 | 0.094 |
| GGA | 19 | −0.13 | 0.04 | 0.111 |
| GGC | 7 | −0.17 | 0.04 | 0.194 |
| GGG | 7 | −0.22 | 0.00 | 0.095 |
| GGU | 7 | 0.40 | 0.18 | **0.002 |
| GUA | 19 | 0.27 | 0.08 | **<0.001 |
| GUC | 7 | 0.82 | 0.10 | **<0.001 |
| GUG | 7 | 0.32 | 0.13 | *0.014 |
| GUU | 7 | 0.87 | 0.18 | **<0.001 |
| UAA | 67 | 0.06 | 0.04 | 0.135 |
| UAC | 7 | −0.06 | 0.08 | 0.647 |
| UAG | 7 | 0.01 | 0.08 | 0.94 |
| UAU | 7 | −0.03 | 0.07 | 0.793 |
| UCA | 19 | 0.35 | 0.12 | **<0.001 |
| UCC | 7 | −0.03 | 0.14 | 0.794 |
| UCG | 7 | 0.02 | 0.09 | 0.848 |
| UCU | 7 | 0.10 | 0.13 | 0.421 |
| UGA | 19 | 0.04 | 0.08 | 0.611 |
| UGC | 7 | 0.01 | 0.07 | 0.91 |
| UGG | 7 | 0.10 | 0.09 | 0.448 |
| UGU | 7 | 0.69 | 0.06 | **<0.001 |
| UUA | 19 | 0.17 | 0.10 | *0.036 |
| UUC | 7 | 0.37 | 0.18 | **0.005 |
| UUG | 7 | 0.38 | 0.18 | **0.004 |
| UUU | 7 | 0.32 | 0.17 | *0.013 |

| Motif | Occurences | Mean | Sem | p-value |
|---|---|---|---|---|
| B. 3mer motifs 5'-NN-N-3' | | | | |
| AANA | 1864 | −0.01 | 0.01 | 0.096 |
| AANC | 112 | −0.12 | 0.02 | **0.001 |
| AANG | 112 | 0.07 | 0.04 | *0.021 |
| AANU | 112 | 0.11 | 0.03 | **0.001 |
| ACNA | 40 | −0.17 | 0.02 | **0.002 |
| ACNC | 16 | −0.18 | 0.02 | *0.035 |
| ACNG | 16 | −0.10 | 0.06 | 0.244 |
| ACNU | 16 | −0.05 | 0.06 | 0.533 |
| AGNA | 40 | −0.09 | 0.03 | 0.111 |
| AGNC | 16 | 0.06 | 0.12 | 0.46 |
| AGNG | 16 | −0.02 | 0.09 | 0.805 |
| AGNU | 16 | 0.52 | 0.15 | **<0.001 |
| AUNA | 40 | −0.11 | 0.02 | *0.038 |
| AUNC | 16 | −0.07 | 0.04 | 0.398 |
| AUNG | 16 | 0.05 | 0.07 | 0.556 |
| AUNU | 16 | 0.19 | 0.08 | *0.027 |
| CANA | 76 | −0.02 | 0.04 | 0.668 |
| CANC | 4 | −0.22 | 0.01 | 0.209 |
| CANG | 4 | −0.22 | 0.00 | 0.201 |
| CANU | 4 | −0.10 | 0.11 | 0.577 |
| CCNA | 28 | −0.16 | 0.04 | *0.015 |
| CCNC | 4 | −0.16 | 0.05 | 0.365 |
| CCNG | 4 | −0.21 | 0.01 | 0.216 |
| CCNU | 4 | −0.18 | 0.02 | 0.295 |
| CGNA | 28 | −0.14 | 0.03 | *0.036 |
| CGNC | 4 | 0.00 | 0.23 | 0.981 |
| CGNG | 4 | −0.19 | 0.03 | 0.268 |
| CGNU | 4 | −0.05 | 0.03 | 0.765 |
| CUNA | 28 | 0.01 | 0.07 | 0.896 |
| CUNC | 4 | −0.08 | 0.10 | 0.649 |
| CUNG | 4 | −0.09 | 0.04 | 0.616 |
| CUNU | 4 | 0.10 | 0.21 | 0.567 |
| GANA | 76 | −0.09 | 0.03 | *0.017 |
| GANC | 4 | −0.17 | 0.03 | 0.324 |
| GANG | 4 | −0.19 | 0.02 | 0.281 |
| GANU | 4 | −0.03 | 0.08 | 0.87 |
| GCNA | 28 | −0.13 | 0.03 | *0.044 |
| GCNC | 4 | 0.15 | 0.37 | 0.38 |
| GCNG | 4 | −0.18 | 0.04 | 0.298 |
| GCNU | 4 | 0.10 | 0.22 | 0.548 |
| GGNA | 28 | −0.10 | 0.04 | 0.131 |
| GGNC | 4 | 0.07 | 0.29 | 0.697 |
| GGNG | 4 | −0.12 | 0.10 | 0.492 |
| GGNU | 4 | 0.16 | 0.30 | 0.353 |
| GUNA | 28 | 0.38 | 0.08 | **<0.001 |
| GUNC | 4 | 0.72 | 0.23 | **<0.001 |
| GUNG | 4 | 0.59 | 0.21 | **<0.001 |
| GUNU | 4 | 0.83 | 0.17 | **<0.001 |
| UANA | 76 | 0.06 | 0.04 | 0.15 |
| UANC | 4 | −0.09 | 0.02 | 0.599 |
| UANG | 4 | −0.08 | 0.02 | 0.641 |
| UANU | 4 | 0.00 | 0.11 | 0.999 |
| UCNA | 28 | 0.30 | 0.10 | **<0.001 |
| UCNC | 4 | −0.06 | 0.10 | 0.738 |
| UCNG | 4 | −0.11 | 0.04 | 0.541 |
| UCNU | 4 | −0.07 | 0.05 | 0.706 |
| UGNA | 28 | 0.17 | 0.07 | **0.008 |
| UGNC | 4 | 0.16 | 0.19 | 0.351 |
| UGNG | 4 | 0.04 | 0.14 | 0.817 |
| UGNU | 4 | 0.20 | 0.19 | 0.239 |
| UUNA | 28 | 0.30 | 0.09 | **<0.001 |
| UUNC | 4 | 0.15 | 0.14 | 0.377 |
| UUNG | 4 | 0.19 | 0.11 | 0.267 |
| UUNU | 4 | 0.21 | 0.18 | 0.228 |
| C. 3mer motifs 5'-N-NN-3' | | | | |
| ANAA | 1864 | −0.01 | 0.01 | 0.107 |
| ANAC | 76 | −0.14 | 0.02 | **0.001 |
| ANAG | 76 | 0.09 | 0.05 | *0.019 |
| ANAU | 76 | −0.01 | 0.03 | 0.78 |
| ANCA | 40 | −0.18 | 0.01 | **0.001 |
| ANCC | 28 | −0.20 | 0.01 | **0.003 |
| ANCG | 28 | −0.13 | 0.03 | *0.048 |
| ANCU | 28 | 0.02 | 0.07 | 0.767 |
| ANGA | 40 | −0.16 | 0.01 | **0.004 |
| ANGC | 28 | −0.08 | 0.06 | 0.207 |
| ANGG | 28 | −0.04 | 0.07 | 0.533 |
| ANGU | 28 | 0.57 | 0.08 | **<0.001 |
| ANUA | 40 | −0.05 | 0.03 | 0.366 |
| ANUC | 28 | 0.06 | 0.07 | 0.334 |
| ANUG | 28 | 0.18 | 0.07 | **0.007 |

TABLE 12-continued

3mer motifs and their mean levels of IFN-α induction
A. 3mer motifs 5'-NNN-3'

| | | | | |
|---|---|---|---|---|
| ANUU | 28 | 0.27 | 0.08 | **<0.001 |
| CNAA | 112 | −0.04 | 0.03 | 0.218 |
| CNAC | 4 | −0.21 | 0.01 | 0.215 |
| CNAG | 4 | −0.19 | 0.03 | 0.265 |
| CNAU | 4 | −0.16 | 0.03 | 0.361 |
| CNCA | 16 | −0.05 | 0.09 | 0.537 |
| CNCC | 4 | −0.21 | 0.01 | 0.218 |
| CNCG | 4 | −0.20 | 0.02 | 0.258 |
| CNCU | 4 | −0.17 | 0.02 | 0.334 |
| CNGA | 16 | −0.18 | 0.02 | *0.039 |
| CNGC | 4 | −0.19 | 0.02 | 0.262 |
| CNGG | 4 | −0.20 | 0.02 | 0.251 |
| CNGU | 4 | 0.20 | 0.19 | 0.244 |
| CNUA | 16 | −0.07 | 0.06 | 0.389 |
| CNUC | 4 | 0.17 | 0.19 | 0.318 |
| CNUG | 4 | −0.13 | 0.06 | 0.464 |
| CNUU | 4 | −0.11 | 0.05 | 0.538 |
| GNAA | 112 | −0.04 | 0.03 | 0.186 |
| GNAC | 4 | −0.06 | 0.14 | 0.717 |
| GNAG | 4 | −0.08 | 0.12 | 0.649 |
| GNAU | 4 | 0.02 | 0.11 | 0.89 |
| GNCA | 16 | 0.10 | 0.13 | 0.243 |
| GNCC | 4 | 0.03 | 0.25 | 0.842 |
| GNCG | 4 | −0.06 | 0.17 | 0.745 |
| GNCU | 4 | 0.11 | 0.24 | 0.534 |
| GNGA | 16 | −0.11 | 0.05 | 0.203 |
| GNGC | 4 | −0.07 | 0.15 | 0.688 |
| GNGG | 4 | −0.07 | 0.15 | 0.706 |
| GNGU | 4 | 0.22 | 0.26 | 0.207 |
| GNUA | 16 | 0.13 | 0.10 | 0.14 |
| GNUC | 4 | 0.87 | 0.33 | **<0.001 |
| GNUG | 4 | 0.30 | 0.31 | 0.08 |
| GNUU | 4 | 0.72 | 0.29 | **<0.001 |
| UNAA | 112 | 0.14 | 0.04 | **<0.001 |
| UNAC | 4 | −0.09 | 0.04 | 0.603 |
| UNAG | 4 | −0.08 | 0.01 | 0.626 |
| UNAU | 4 | −0.11 | 0.02 | 0.522 |
| UNCA | 16 | 0.18 | 0.11 | *0.032 |
| UNCC | 4 | −0.11 | 0.03 | 0.528 |
| UNCG | 4 | −0.04 | 0.09 | 0.807 |
| UNCU | 4 | −0.08 | 0.05 | 0.634 |
| UNGA | 16 | 0.14 | 0.09 | 0.113 |
| UNGC | 4 | −0.01 | 0.06 | 0.975 |
| UNGG | 4 | −0.03 | 0.09 | 0.86 |
| UNGU | 4 | 0.39 | 0.14 | *0.025 |
| UNUA | 16 | 0.29 | 0.12 | **0.001 |
| UNUC | 4 | 0.37 | 0.17 | *0.032 |
| UNUG | 4 | 0.20 | 0.14 | 0.24 |
| UNUU | 4 | 0.15 | 0.17 | 0.375 |

TABLE 13

RNA oligonucleotide containing multiple copies of GUCA

| Oligo-name | Sequence 5' → 3' |
|---|---|
| 9.2 sense | AGCUUAACCUGUCCUUCAA |
| Poly GUCA | GUCAAGUCAAGUCAAGUCAA |
| ANP35 | AAAAAAAAGUCAAAAAAAA |

---

The invention claimed is:

1. A method for determining the immunostimulatory activity of an RNA oligonucleotide, comprising the steps of:
    (a) complexing the RNA oligonucleotide with a complexation agent;
    (b) contacting a cell with the complexed RNA oligonucleotide, wherein the cell expresses TLR7, TLR8, or both TLR7 and TLR8; and
    (c) determining the amount of IFN-α produced by the cell of step (b), an increase of IFN-α production indicating immunostimulatory activity of the RNA oligonucleotide, wherein the RNA oligonucleotide has an IFN-α score of at least $1.4909 \times n + 31.014$, where n is length of the RNA oligonucleotide and IFN-α score is calculated by the method comprising the steps of:
    (a) identifying all possible 3-nucleotide (3mer) motifs contained in the oligonucleotide;
    (b) assigning an IFN-α point score for each individual 3mer motif:
        (i) for a 3mer motif which appears in Table 7, assigning an IFN-α point score according to Table 7;
        (ii) for a 3mer motif which does not appear in Table 7, assigning an IFN-α point score of 0; and
    (c) assigning the sum of the IFN-α point scores of individual 3mer motifs as the IFN-α score of the oligonucleotide.

2. The method of claim 1, wherein the complexation agent is poly-L-arginine (poly-L-Arg).

3. The method of claim 1, wherein the cell is a plasmacytoid dendritic cell (PDC).

4. The method of claim 1, wherein the RNA oligonucleotide has gene silencing activity.

5. The method of claim 1, wherein the RNA oligonucleotide is double-stranded or partially double-stranded.

6. The method of claim 1, wherein the RNA oligonucleotide is single-stranded.

7. The method of claim 1, wherein the RNA oligonucleotide comprises a 2'-modified ribose.

8. The method of claim 1, wherein the RNA oligonucleotide comprises a phosphorothioate linkage.

9. The method of claim 1, wherein the RNA oligonucleotide is conjugated with a ligand.

10. The method of claim 9, wherein the ligand is an antigen.

11. The method of claim 1, wherein the RNA oligonucleotide is 5'-phosphorylated.

12. The method of claim 1, wherein the RNA oligonucleotide is an siRNA, shRNA, or antisense RNA.

13. The method of claim 1, wherein the RNA oligonucleotide is between 6 and 64 nucleotides in length.

14. The method of claim 1, wherein the RNA oligonucleotide is at least 80% complementary to a target mRNA.

15. The method of claim 2, wherein poly-L-arginine is of molecular weight 5,000-15,000.

16. The method of claim 2, wherein 14.8 µg/ml of the RNA oligonucleotide is complexed with 24 µg/ml of poly-L-arginine.

* * * * *

UNITED STATES PATENT AND TRADEMARK OFFICE
CERTIFICATE OF CORRECTION

| | |
|---|---|
| PATENT NO. | : 8,076,068 B2 |
| APPLICATION NO. | : 12/066903 |
| DATED | : December 13, 2011 |
| INVENTOR(S) | : Hartmann |

It is certified that error appears in the above-identified patent and that said Letters Patent is hereby corrected as shown below:

At column 4, line 58, "IFN-a" should read --IFN-α--

At column 4, line 64, "IFN-a" should read --IFN-α--

At column 4, line 65, "IFN-a" should read --IFN-α--

At column 4, line 66, "IFN-a" should read --IFN-α--

At column 4, line 67, "IFN-a indices from the individual IFN-a" should read --IFN-α indices from the individual IFN-α--

At column 5, line 1, "IFN-a" should read --IFN-α--

At column 5, line 7, "off" should read --of--

At column 5, line 14, "IFN-a index below the mean IFN-a" should read --IFN-α index below the mean IFN-α--

At column 5, line 34, "IFN-a" should read --IFN-α--

At column 5, line 36, "IFN-a" should read --IFN-α--

At column 5, line 44, "IFN-a" should read --IFN-α--

At column 5, line 47, "IFN-a" should read --IFN-α--

At column 5, line 49, "IFN-a" should read --IFN-α--

At column 5, line 59, "IFN-a" should read --IFN-α--

Signed and Sealed this
Twenty-third Day of October, 2012

David J. Kappos
*Director of the United States Patent and Trademark Office*

CERTIFICATE OF CORRECTION (continued)
U.S. Pat. No. 8,076,068 B2

At column 6, line 8, "IFN-a" should read --IFN-α--

At column 6, line 18, "IFN-a" should read --IFN-α--

At column 7, line 56, "IFN-a" should read --IFN-α--

At column 42, line 14, "IFN-a" should read --IFN-α--

At column 42, line 32, "were" should read --was--

At column 43, line 36, "CO2" should read --$CO_2$--

At column 43, line 42, "IFN-a the IFN-a" should read --IFN-α the IFN-α--

At column 43, line 57, "IFN-a" should read --IFN-α--

At column 44, line 2, "IFN-a" should read --IFN-α--

At column 44, line 5, "IFN-a" should read --IFN-α--

At column 44, line 30, "IFN-a" should read --IFN-α--

At column 44, line 33, "IFN-a" should read --IFN-α--

At column 44, line 34, "IFN-a index (one value of IFN-a" should read --IFN-α index (one value of IFN-α--

At column 44, line 49, "IFN-a" should read --IFN-α--

At column 44, line 50, "IFN-a" should read --IFN-α--

At column 44, line 55, "IFN-a" should read --IFN-α--

At column 44, line 66, "IFN-a" should read --IFN-α--

At column 45, line 17, "IFN-a index below the mean IFN-a" should read --IFN-α index below the mean IFN-α--

At column 45, line 53, "IFN-a" should read --IFN-α--

At column 45, line 64, "was" should read --were--

At column 46, line 16, "IFN-a" should read --IFN-α--

CERTIFICATE OF CORRECTION (continued)
U.S. Pat. No. 8,076,068 B2

At column 46, line 35, "IFN-a" should read --IFN-α--

At column 46, line 65, "was" should read --were--, and "in" should be deleted

At column 48, line 11, "Judge A D" should read --Judge AD--

At column 48, line 27, "a" should be deleted

At column 48, line 42, "5'-AGC UUA ACC UGU CCU UCA A-3'" should read --5'-AGC UUA ACC U<u>GU CCU UCA A</u>-3'--

At column 49, lines 13-14, "Judge A D" should read --Judge AD--

At column 49, line 16, "βP-Gal" should read --β-Gal--

At column 49, line 25, "IFN-a-inducing" should read --IFN-α-inducing--

At column 58, line 60, "Since above" should read --Since the above--

At column 60, line 4, "anf" should read --and--

At column 60, line 6, "theses" should read --these--

At column 60, line 27, "anf" should read --and--